US008911738B2

(12) United States Patent
Throsby et al.

(10) Patent No.: US 8,911,738 B2
(45) Date of Patent: Dec. 16, 2014

(54) HOST CELL SPECIFIC BINDING MOLECULES CAPABLE OF NEUTRALIZING VIRUSES AND USES THEREOF

(75) Inventors: Mark Throsby, Utrecht (NL); Cornelis A. de Kruif, De Bilt (NL)

(73) Assignee: Crucell Holland B.V., Leiden (NL)

( * ) Notice: Subject to any disclaimer, the term of this patent is extended or adjusted under 35 U.S.C. 154(b) by 653 days.

(21) Appl. No.: 13/199,348

(22) Filed: Aug. 25, 2011

(65) Prior Publication Data

US 2012/0076794 A1 Mar. 29, 2012

Related U.S. Application Data

(62) Division of application No. 11/919,265, filed as application No. PCT/EP2006/062250 on May 11, 2006, now Pat. No. 8,052,974.

(30) Foreign Application Priority Data

May 12, 2005 (WO) ................. PCT/EP2005/052160
Jun. 8, 2005 (WO) ................. PCT/EP2005/052648
Jun. 23, 2005 (WO) ................. PCT/EP2005/052946
Aug. 15, 2005 (WO) ................. PCT/EP2005/054002

(51) Int. Cl.
*A61K 39/42* (2006.01)
*A61K 39/12* (2006.01)
*C07K 16/10* (2006.01)

(52) U.S. Cl.
CPC .................................. *C07K 16/1081* (2013.01)
USPC .......................... 424/147.1; 424/218.1; 435/5

(58) Field of Classification Search
None
See application file for complete search history.

(56) References Cited

U.S. PATENT DOCUMENTS 5,494,671 A 2/1996 Lai et al.
5,514,375 A 5/1996 Paoletti et al.
5,696,108 A 12/1997 Heath, Jr. et al.
5,744,140 A 4/1998 Paoletti et al.
5,744,141 A 4/1998 Paoletti et al.
6,184,024 B1 2/2001 Lai et al.
6,258,788 B1 7/2001 Schmaljohn
6,265,150 B1 7/2001 Terstappen et al.
6,306,899 B1 10/2001 Cheng et al.
6,331,415 B1 12/2001 Cabilly et al.
6,416,763 B1 7/2002 McDonnel et al.
6,432,411 B1 8/2002 Ivy et al.
6,455,509 B1 9/2002 Kochel et al.
6,685,948 B1 2/2004 Zeng et al.
6,875,433 B2 4/2005 Hart et al.
6,946,125 B2 9/2005 Rahal
7,074,555 B2 7/2006 Esty et al.
7,153,513 B2 12/2006 Chu
7,244,430 B2 7/2007 Throsby et al.
7,329,530 B2 2/2008 Houtzager et al.
7,425,437 B2 9/2008 Uytdehaag et al.
7,491,516 B2 2/2009 Collinson et al.
7,537,764 B2 5/2009 Throsby et al.
7,579,446 B2 8/2009 Bakker et al.
7,696,330 B2 4/2010 ter Meulen et al.
7,740,852 B2 6/2010 Bakker et al.
7,858,086 B2 12/2010 Geuijen et al.
7,901,919 B2 3/2011 Houtzager et al.
7,960,518 B2 6/2011 Throsby et al.
7,968,092 B2 6/2011 Throsby et al.
8,241,631 B2 8/2012 Throsby et al.
8,628,776 B2 1/2014 Throsby et al.
2003/0148261 A1 8/2003 Fikrig et al.
2004/0009178 A1 1/2004 Bowdish et al.
2004/0077086 A1 4/2004 Reiter et al.
2004/0197769 A1 10/2004 Wong et al.
2004/0258699 A1 12/2004 Bowdish et al.
2006/0057149 A1 3/2006 Johnson et al.
2006/0067940 A1 3/2006 Diamond et al.
2006/0115837 A1 6/2006 Fremont et al.
2006/0115896 A1 6/2006 Wong et al.
2006/0269571 A1 11/2006 Hall et al.
2007/0025992 A1 2/2007 Takayama et al.
2007/0287163 A1 12/2007 Geuijen et al.
2008/0014204 A1 1/2008 ter Meulen et al.
2008/0070799 A1 3/2008 Bakker et al.
2009/0017068 A1 1/2009 UytdeHaag et al.
2009/0054254 A1 2/2009 Throsby et al.
2009/0104204 A1 4/2009 Throsby et al.
2009/0130652 A1 5/2009 Throsby et al.
2009/0311265 A1 12/2009 van den Brink et al.
2010/0069614 A1 3/2010 Houtzager et al.
2010/0146647 A1 6/2010 Logtenberg et al.

(Continued)

FOREIGN PATENT DOCUMENTS

EP 0 102 228 A 3/1984
EP 0 869 184 A 10/1998

(Continued)

OTHER PUBLICATIONS

Bae et al., "Production of Hantaan Virus from Human Immortalized Retina Cell and Its Immunogenicity," J. Microbiol. Biotechnol., Dec. 20, 2002, pp. 882-889, vol. 12, No. 6.

(Continued)

*Primary Examiner* — Stacy B Chen
(74) *Attorney, Agent, or Firm* — TraskBritt, P.C.

(57) ABSTRACT

Provided are human binding molecules that specifically bind to a host cell protein and have virus neutralizing activity, nucleic acid molecules encoding such human binding molecules, compositions comprising the human binding molecules, and methods of identifying or producing the human binding molecules. The human binding molecules can be used in the diagnosis, prophylaxis and/or treatment of viral infections.

5 Claims, 5 Drawing Sheets

(56) References Cited

U.S. PATENT DOCUMENTS

2010/0172917 A1 7/2010 ter Meulen et al.
2010/0272724 A1 10/2010 Bakker et al.
2010/0297153 A1 11/2010 Geuijen et al.
2010/0303801 A1 12/2010 Throsby et al.
2010/0310572 A1 12/2010 Bakker et al.
2014/0099320 A1 4/2014 Throsby et al.

FOREIGN PATENT DOCUMENTS

EP 0 872 553 A 10/1998
EP 0 947 581 10/1999
WO WO 84/03564 9/1984
WO WO 93/09872 5/1993
WO WO 98/15833 4/1998
WO WO 98/37911 9/1998
WO WO 99/26653 6/1999
WO WO 99/63095 12/1999
WO WO 00/10991 3/2000
WO WO 00/12128 3/2000
WO WO 00/14245 3/2000
WO WO 00/63403 10/2000
WO WO 01/03729 1/2001
WO WO 01/38362 5/2001
WO WO 01/39802 6/2001
WO WO 01/60315 8/2001
WO WO 01/60847 8/2001
WO WO 02/15664 2/2002
WO WO 02/072036 A2 9/2002
WO WO 02/103012 A1 12/2002
WO WO 2004/042042 A1 5/2004
WO WO 2005/007800 A2 1/2005
WO WO 2005/106483 A1 11/2005
WO WO 2005/123774 12/2005
WO WO 2006/067122 A2 6/2006

OTHER PUBLICATIONS

Beasley et al., Identification of Neutralizing Epitopes within Structural Domain III of the West Nile Envelope Protein, Journal of Virology, Dec. 2002, pp. 13097-13100, vol. 76, No. 24.

Blitvich et al., Epitope-Blocking Enzyme-Linked Immunosorbent Assays for the Detection of Serum Antibodies to West Nile Virus in Multiple Avian Species, Journal of Clinical Microbiology, Mar. 2003, pp. 1041-1047, vol. 41, No. 3.

Bao et al., "Flavivirus Induces MHC Antigen on Human Myoblasts: A Model of Autoimmune Myositis?" Muscle and Nerve, Nov. 1992, pp. 1271-1277, vol. 15, No. 11.

Boel et al., Functional human monoclonal antibodies of all isotypes constructed from phage display library-derived single-chain Fv antibody fragments, Journal of Immunological Methods, 2000, pp. 153-166, vol. 239.

Chen et al., Preparation of monoclonal antibodies against West Nile virus envelope protein domain, Chinese J. Exp. Clin Virol., Sep. 2006, pp. 213-215, vol. 20, No. 3.

Chung et al., Antibodies against West Nile Virus Nonstructural Protein NSI Prevent Lethal Infection through Fc gamma Receptor-Dependent and -Independent Mechanisms, Journal of Virology, Feb. 2006, pp. 1340-1351, vol. 80, No. 3.

Fields et al., Virology (Third Ed.), excerpt. pp. 931-932, 1996.

Gallimore et al., Transformation of Human Embryo Retinoblasts with Simian Virus 40, Adenovirus and ras Oncogenes, Anticancer Research, May 3, 1986, pp. 499-508, vol. 6, No. 3.

Goncalvez et al., Chimpanzee Fab Fragments and a Derived Humanized Immunoglobulin G1 Antibody That Efficiently Cross-Neutralize Dengue Type 1 and Type 2 Viruses, Journal of Virology, Dec. 2004, pp. 12910-12918, vol. 78. No. 23.

Jia et al., "Genetic analysis of West Nile Virus New York 1999 encephalitis virus," The Lancet, Dec. 4, 1999, pp. 1971-1972, vol. 354, No. 9196.

Leibl et al., "Adjuvant/carrier activity of inactivated tick-borne encephalitis virus," Vaccine, 1998, pp. 340-345, vol. 16, No. 4.

Malkinson et al, "Use of Live and Inactivated Vaccines in the Control of West Nile Virus in Domestic Geese," Annals of the New York Academy of Sciences, 2001, pp. 255-261.

Marks et al., By-passing Immunization: Building High Affinity Human Antibodies by Chain Shuffling, Bio/Technology, Jul. 1992, pp. 779-783, vol. 10.

Mehlhop et al., Complement Activation Is Required for Induction of a Protective Antibody Response against West Nile Virus Infection, Journal of Virology, Jun. 2005, pp. 7466-7477, vol. 79, No. 12.

Niedrig et al., Monoclonal Antibodies Directed Against Tick-Borne Encephalitis Virus with Neutralizing Activity In Vivo, Acta virologica, 1994, pp. 141-149, vol. 38.

Nybakken et al., Structural basis of West Nile virus neutralization by a therapeutic antibody, Nature, Sep. 29, 2005, pp. 764-768, vol. 437.

Pau et al., "The human cell line PER.C6 provides a new manufacturing system for the production of influenza vaccines," Vaccine, 2001, pp. 2716-2721, vol. 19.

PCT International Preliminary Examination Report, PCT/EP2003/50806, dated Feb. 17, 2005.

PCT International Preliminary Report on Patentability, PCT/EP2006/063463, dated Sep. 10, 2007, 10 pages.

PCT International Search Report, PCT/EP2003/50806, dated Apr. 26, 2004.

PCT International Search Report, PCT/EP2006/063463, dated Oct. 6, 2006.

PCT International Preliminary Report on Patentability, International Application No. PCT/EP2006/062250, dated Oct. 1, 2007.

PCT International Search Report, International Application No. PCT/EP2006/062250, dated May 3, 2007.

Razumov et al., Neutralizing Monoclonal Antibodies Against Russian Strain of the West Nile Virus, Viral Immunology, 2005, pp. 558-568, vol. 18, No. 3.

Roehrig et al., Antibody Prophylaxis and Therapy for Flavivirus Encephalitis Infections, Ann. N. Y. Acad. Sci., Dec. 2001, pp. 286-297, vol. 951.

Rudikoff et al., PNAS USA, 1982, 79:1979-1983.

Sanchez et al., Characterization of neutralizing antibodies to West Nile virus, Virology, 2005, pp. 70-82, vol. 336.

Shen et al., "Early Induction of Interferon-Independent Virus-Specific ICAM-1 (CD54) Expression by Flavivirus in Quiescent but Not Proliferating Fibroblasts—Implications for Virus-Host Interactions," Virology, 1995, pp. 437-449, vol. 208, No. 2.

Shi et al., "Infectious cDNA Clone of the Epidemic West Nile Virus from New York City," J. of Virology, Jun. 2002, pp. 5847-5856, vol. 76, No. 12.

Yamshchikov et al., "An Infectious Clone of the West Nile Flavivirus," Virology, Mar. 15, 2001, pp. 294-304, vol. 281, No. 2.

Burton D.R., et al., Human antibodies from combinatorial libraries, Adv. Immunol., 1994, pp. 191-280, vol. 57.

Clackson T., et al., Making antibody fragments using phage display libraries, Nature, 1991, pp. 624-628, vol. 352.

De Kruif J., et al., Rapid selection of cell subpopulation-specific human monoclonal antibodies from a synthetic phage antibody library. Proc. Natl. Acad. Sci., 1995a, p. 3938, vol. 92.

De Kruif J., et al., Selection and application of human single-chain Fv antibody fragments from a semi-synthetic phage antibody display library with designed CDR3 regions, J. Mol. Biol, 1995b, pp. 97-105, vol. 248.

Hayes, West Nile Fever; in Arboviruses: Epidemiology and Ecology, ed. T. P. Monath, CRC press, Boca Raton, FL, 1988, p. 59-88.

Huls G., et al., Antitumor immune effector mechanisms recruited by phage display-derived fully human IgG1 and IgA1 monoclonal antibodies, Cancer Res., 1999, pp. 5778-5784, vol. 59.

Lanciotti et al., Virology, Jun. 20, 2002, pp. 96-105, vol. 298.

Lazar et al., Developments in Biological Standardization, 1985, pp. 315-323, vol. 66.

Marks J.D., et al., Bypassing immunisation: high affinity human antibodies by chain shuffling, Bio/Technology, 1992, pp. 779-783, vol. 10.

(56) References Cited

OTHER PUBLICATIONS

Engle et al., Antibody Prophylaxis and Therapy against West Nile Virus Infection in Wild-Type and Immunodeficient Mice, Journal of Virology, Dec. 2003, pp. 12941-12949, vol. 77, No. 24.

Gould et al., Protective and Theraupeutic Capacity of Human Single-Chain Fv-Fc Fusion proteins against West Nile Virus, Journal of Virology, Dec. 2005, pp. 14606-14613, vol. 79, No. 23.

Holt et al., Domain antibodies: proteins for therapy, Trends in Biotechnology, Nov. 2003, pp. 484-490, vol. 21, No. 11.

Kramer et al., The human antibody repertoire specific for rabies virus glycoprotein as selected from immune libraries, European Journal of Immunology, 2005, pp. 2131-2145, vol. 35.

Oliphant et al., Development of a humanized monoclonal antibody with therapeutic potential against West Nile virus, Nature Medicine, May 2005, pp. 522-530, vol. 11, No. 5.

Throsby et al., Isolation and Characterization of Human Monoclonal Antibodies from Individuals Infected with West Nile Virus, Journal of Virology, 2006, pp. 6982-6992, vol. 80, No. 14.

Vogt et al., Journal of Virology, Jul. 2009, pp. 6494-6507, vol. 83, No. 13.

Ben-Nathan et al., BMC Infectious Diseases, 2009, vol. 9, No. 18, eight pages.

U.S. Appl. No. 13/068,784, filed May 19, 2011, Throsby et al., Human Binding Molecules Having Killing Activity Against Enterococci and Uses Thereof.

HOST CELL SPECIFIC BINDING MOLECULES CAPABLE OF NEUTRALIZING VIRUSES AND USES THEREOF

CROSS-REFERENCE TO RELATED APPLICATION

This application is a divisional of U.S. patent application Ser. No. 11/919,265, filed Oct. 24, 2007, now U.S. Pat. No. 8,052,974, issued Nov. 8, 2011, which is a national phase entry under 35 U.S.C. §371 of International Patent Application PCT/EP2006/062250, filed May 11, 2006, published in English as International Patent Publication WO 2006/120230 A2 on Nov. 16, 2006, which claims the benefit under Article 8 of the Patent Cooperation Treaty to International Patent Application Serial No. PCT/EP2005/054002, filed Aug. 15, 2005, to International Patent Application Serial No. PCT/EP2005/052946, filed Jun. 23, 2005, to International Patent Application Serial No. PCT/EP2005/052648, filed Jun. 8, 2005, and to International Patent Application Serial No. PCT/EP2005/052160, filed May 12, 2005, the disclosure of each of which is hereby incorporated herein by this reference in its entirety.

TECHNICAL FIELD

The invention relates to medicine. In particular, the invention relates to the diagnosis, prophylaxis and/or treatment of viral infections.

STATEMENT ACCORDING TO 37 C.F.R. §1.52(e)(5)—SEQUENCE LISTING SUBMITTED ON COMPACT DISC

Pursuant to 37 C.F.R. §1.52(e)(1)(ii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "Sequence Listing as submitted.txt" which is 260 KB and created on Aug. 24, 2011.

BACKGROUND

Several viruses assemble their core proteins and genomic material in the cytoplasm of a host cell and exit the cell by budding from the plasma membrane. Studies of these viruses, e.g., HIV-1 viruses, have shown that in addition to proteins encoded by the virus, host cell proteins can be found in viruses. While some of these proteins may be taken into the viruses simply because of their proximity to the viral assembly and budding sites, other host cell proteins are likely to be included in viruses as a result of their interaction with viral proteins during assembly and release. Additionally, some host cell proteins may be incorporated to provide a function for the virus during the infection process. Host cell proteins have been found on the surface or the interior of the viruses. Despite their detection on or in viruses, the role and function of host cell proteins in the viral assembly process is poorly understood and still highly speculative.

A variety of agents are presently used to combat viral infection. These agents include anti-viral compounds, compounds suitable for active immunization such as vaccines and compounds suitable for passive immunization such as neutralizing immunoglobulins. The latter group is often focused on neutralizing immunoglobulins that act through specific binding to viral proteins or cell surface receptors involved in viral entry. Due to their binding specificity, such immunoglobulins are however only suitable in the prophylaxis and/or treatment of specific viral diseases and are not broadly applicable in the treatment of viral diseases.

Neutralization of viruses has been described for immunoglobulins directed against virus-incorporated host cell-derived proteins. For instance, HIV-1 has been shown to incorporate the host cell derived protein Intercellular Adhesion Molecule-1 (ICAM-1) and an antibody against ICAM-1 has been shown to neutralize ICAM-1 expressing HIV-1 virions (see Rizzuto and Sodroski, 1997). Disadvantageously, ICAM-1 is also localized on the surface of uninfected host cells, so protection and/or treatment of a viral infection with the immunoglobulin against ICAM-1 may, due to interaction of the immunoglobulin with uninfected host cells, result in serious and unwanted side effects. A further disadvantage of the anti-ICAM-1 immunoglobulin is that its neutralizing activity is, similar to the viral protein-specific and cell surface receptor-specific immunoglobulins, virus (HIV-1) specific.

SUMMARY OF THE INVENTION

Provided are immunoglobulins able to bind an intracellular host cell protein that is incorporated into viruses or expressed at the cell surface. Due to the intracellular localization of the protein in uninfected host cells, fewer unwanted side effects occur upon administration of the immunoglobulins. An advantage of the immunoglobulins is that they are not dependent on specific viral identification and that they interact with a host cell protein that is commonly involved in the viral assembly and budding process and consequently are capable of neutralizing several distinct viruses.

Provided are binding molecules capable of specifically binding to a host cell protein and capable of neutralizing viruses. Also provided are nucleic acid molecules encoding at least the binding region of the binding molecules. Further provided for is the use of the binding molecules hereof in the prophylaxis and/or treatment of a subject having, or at risk of developing, a viral infection. Besides that, the binding molecules hereof may be used in the diagnosis/detection of a viral infection.

Encompassed are binding molecules capable of specifically binding to a host cell protein. Preferably, the host cell protein is an intracellular host cell protein, meaning that the host cell protein is normally (e.g., in an uninfected host cell) not exposed on the outside of the host cell such as, e.g., a cell surface receptor. In one aspect, the host cell protein is a mammalian, preferably a human, host cell protein. In normal (e.g., uninfected) host cells the intracellular host cell protein may have a cytoplasmic localization (is a cytoplasmic protein). Alternatively, it may also be localized on or inside host cell organelles including, but not limited to, mitochondria, the Golgi apparatus, nucleus, vacuoles, vesicles and/or the endoplasmic reticulum. After infection of the host cell with a virus the intracellular host cell protein may travel to the cell membrane and may become localized/incorporated in or on the cell surface of the host cell. In other words, after infection of the host cell with a virus, the intracellular host cell protein may become displayed on the surface of the host cell. The localization of the host cell protein in normal (e.g., uninfected) cells compared to infected cells may therefore differ. The binding molecules hereof may be capable of specifically binding to a host cell, once the intracellular host cell protein is exposed in or on the surface of the cell. The binding molecules hereof may also bind a fragment of a host cell protein, the fragment at least comprising an antigenic determinant recognized by the binding molecules hereof. An "antigenic determinant" as used herein is a moiety, such as a peptide or polypeptide, protein, glycoprotein, analogue or fragment thereof, that is able to bind to a binding molecule of the invention with sufficiently high affinity to form a detectable antigen-binding molecule complex.

In a certain embodiment, the intracellular host cell protein recognized by the binding molecules hereof is Fas-associated factor-1 (FAF-1; for nucleotide sequence see SEQ ID NO:1 of the incorporated SEQUENCE LISTING (nucleotides 278-2230 encode the protein) and for amino acid sequence see SEQ ID NO:2; see also GenBank No. BC067100) or NADH-dehydrogenase (ubiquinone) flavoprotein-1 (NDUFV-1; for nucleotide sequence see SEQ ID NO:3 (nucleotides 34-1428 encode the protein) and for amino acid sequence see SEQ ID NO:4; see also GenBank No. BC015645.2). In an embodiment hereof, naturally occurring truncated or secreted forms, naturally occurring variant forms (e.g., alternatively spliced forms) and naturally occurring allelic variants of FAF-1 or NDUFV-1, particularly the FAF-1 or NDUFV-1 comprising an amino acid sequence as shown in SEQ ID NO:2 and SEQ ID NO:4, respectively, are also a part hereof. A variant form of NDUFV-1 is shown under GenBank No. BC008146.1. This variant form has an amino acid sequence that is identical to SEQ ID NO:4, with the proviso that it lacks amino acids 16-24 of SEQ ID NO:4. Other variant forms of NDUFV-1 can be found under GenBank Nos. S67973.1, CR605492.1, and BC007619.1. A variant form of FAF-1 is shown under GenBank No. NM_131917. This variant form has an amino acid sequence that is identical to SEQ ID NO:2, with the proviso that as a result of the lack of an internal coding sequence it lacks amino acids 189-344 (but has the same N- and C-termini as compared to the full-length form of FAF-1). The amino acids 189-344 have been replaced by amino acids FSSR in this variant form. Binding molecules hereof may also be capable of specifically binding to the variants and alternative forms of FAF-1 or NDUFV-1, as long as the modifications in the variants and alternative forms do not abolish the binding of the binding molecules to them. FAF-1 or NDUFV-1 variants may comprise an amino acid sequence having a homology of at least 95%, preferably at least 97%, more preferably at least 98%, and even more preferably at least 99% with the amino acid sequence of SEQ ID NO:2 or SEQ ID NO:4, respectively. Molecular biological techniques to make variants and forms of FAF-1 or NDUFV-1 recombinantly and/or purify them from a (natural) source are well within the reach of the person skilled in the art and are also contemplated herein.

In a further embodiment, provided is a pharmaceutical composition comprising FAF-1 and/or NDUFV-1 and a pharmaceutically acceptable excipient. Further disclosure of elements concerning pharmaceutical compositions in general is given below. The host cell proteins described herein may be used as vaccine for the prophylaxis and/or treatment of viral diseases including, but not limited to, flavivirus infections such as WNV infections.

Encompassed herein are binding molecules capable of specifically binding to a fragment of FAF-1 or NDUFV-1 or any of the variants or forms described herein. The fragment should at least comprise the antigenic determinant of FAF-1 or NDUFV-1 recognized by the respective binding molecules.

In one aspect, the intracellular host cell protein can be incorporated into a viral membrane. Incorporation can take place inside the host cell, e.g., in the cytoplasm, but may also take place inside or on the surface of one of the host cells organelles. Alternatively, incorporation can also take place near, in or on the host cell surface, e.g., when after infection of the host cell with a virus the intracellular host cell protein is displayed on the surface of the host cell. In other words, the host cell protein may be incorporated into the viral membrane of newly formed viruses after infection of a host cell with a virus. Therefore, the intracellular host cell protein may also be present in or on viruses, virus-like particles (VLP) or other material at least comprising a viral membrane or parts thereof comprising the host cell protein. Consequently, the binding molecules hereof may be capable of specifically binding to viruses, virus-like particles or the other material at least comprising a viral membrane or parts thereof comprising the host cell protein. The viruses comprising the host cell protein may be in activated or inactivated/attenuated form. Methods for inactivating/attenuating viruses are well known in the art and include, but are not limited to, heat inactivation, inactivation by UV irradiation, and inactivation by gamma irradiation. As used herein, "virus-like particle" refers to a virus particle that assembles into intact enveloped viral structures. A virus-like particle does however not contain genetic information sufficient to replicate. Virus-like particles have essentially a similar physical appearance as the wild-type virus, i.e., they are morphologically and antigenically essentially similar to authentic virions. The virus-like particles as used herein may comprise, next to the intracellular host cell protein, wild-type viral amino acid sequences. The virus-like particles may also include functional copies of certain genes. Furthermore, the virus-like particles may also include foreign nucleic acid. The virus-like particles can be naturally or unnaturally occurring viral particles. They may lack functional copies of certain genes of the wild-type virus, and this may result in the virus-like particle being incapable of some function that is characteristic of the wild-type virus, such as replication and/or cell-cell movement. The missing functional copies of the genes can be provided by the genome of a host cell or on a plasmid present in the host cell, thereby restoring the function of the wild-type virus to the virus-like particle when in the host cell. Virus-like particles may display the same cellular tropism as the wild-type virus. The virus-like particle may be non-infectious, but may be infectious. The term "infectious" as used herein means the capacity of the virus-like particle to complete the initial steps of viral cycle that lead to cell entry. In an embodiment hereof, the virus-like particle self assembles. In another embodiment, the virus-like particles are pseudoviruses. Pseudoviruses and their production are well known to the skilled person. Preferably, the pseudoviruses as used herein comprise the intracellular host cell protein on their surface, e.g., incorporated into their viral membrane. Virus-like particles can be produced in suitable host cells such as inter alia mammalian cells. They can be produced intracellularly and/or extracellularly and can be harvested, isolated and/or purified as intact virus-like particles by means known to the skilled person such as inter alia affinity chromatography, gel filtration chromatography, ion-exchange chromatography, and/or density gradient sedimentation. A virus-like particle as herein described, particularly one that comprises an intracellular host cell protein, e.g., FAF-1 and/or NDUFV-1, incorporated into its viral membrane is also part hereof.

In a particular embodiment, the virus-like particle is derived from an enveloped virus, preferably a member of the flavivirus genus such as WNV. In an embodiment, the WNV-derived virus-like particle also comprises WNV E protein. In another embodiment, this virus-like particle further comprises WNV M-protein. By a "WNV E- and M-protein" is meant an envelope and membrane protein, respectively, from any WNV strain. Preferably, the WNV E- and M-protein are derived from a same WNV strain.

In a further aspect, the binding molecules hereof have virus neutralizing activity. Preferably, the binding molecules hereof have virus neutralizing activity against viruses of more than one genus. Preferably, they neutralize viruses of at least two different genera, more preferably at least three different genera, even more preferably at least four different genera, and in particular at least five or more different genera. The viruses may be non-enveloped viruses, but preferably they are enveloped viruses including, but not limited to, Herpes viridae (e.g., Herpes Simplex Virus type 1, 2, 6, 7, 8, cytomegalovirus, varicella-zoster virus, Epstein Barr virus), poxviridae (e.g., Smallpox virus), retroviridae (e.g., HIV1, HIV2, HTLV1, HTLV2), paramyxoviridae (e.g., Mumps virus, measles virus, respiratory syncytial virus, parainfluenza virus), HepaDNAviridae (e.g., Hepatitis B virus), orthomyxoviridae (e.g., Influenza virus A or B), togaviridae (e.g., Rubella), flaviviridae (e.g., Yellow fever virus, Dengue virus, West Nile Virus, Hepatitis C virus, Japanese encephalitis virus, Venezuela encephalitis virus) rhabodiviridae (e.g., Rabies virus), arenaviridae (e.g., Lassa virus, lymphocytic choriomeningitis virus) and coronaviridae (e.g., SARS virus, metapneumoniae virus). Moreover, they may also neutralize viruses not mentioned above, including, but not limited to, Sindbis virus, poliovirus, human papilloma virus, adeno-associated virus, coxsackivirus, enterovirus, Hepatitis A virus, tick-borne encephalitis virus, astrovirus, Ebola virus, Marburg virus, La Crosse virus, California encephalitis virus, Hantaan virus, Crimean-Congo virus, Rift Valley fever, Argentine hemorrhagic fever virus, Bolivian hemorrhagic fever virus, Colorado tick fever, JC virus, BK virus, human adenovirus, and human parvovirus. The binding molecules hereof may have a broad virus neutralizing activity and are capable of neutralizing different, preferably all, viruses within a genus. They may neutralize different, preferably all, strains of a given virus.

In a specific aspect, the binding molecules hereof have flavivirus neutralizing activity, preferably West Nile virus neutralizing activity. The genus flavivirus is a member of the Flaviviridae family. Flaviviruses are small spherical enveloped positive-strand RNA viruses. The flavivirus genus comprises more than 80 highly related viruses including several human pathogens such as inter alia yellow fever virus, Japanese encephalitis virus, St. Louis encephalitis virus, Murray Valley encephalitis virus, tick-borne encephalitis virus, and dengue virus. Other viruses belonging to the genus flavivirus can inter alia be found in Kuno et al. (1998), which is incorporated by reference herein. Preferably, the binding molecules hereof are capable of neutralizing both WNV lineage I variants such as inter alia strain 385-99 and WNV lineage II variants such as inter alia strain H-442. In the most preferred embodiment, the binding molecules hereof are capable of neutralizing essentially all WNV variants and strains currently known. In one embodiment, the binding molecules hereof also neutralize at least one other flavivirus including, but not limited to, yellow fever virus, Japanese encephalitis virus, St. Louis encephalitis virus, Murray Valley encephalitis virus, tick-borne encephalitis virus, and dengue virus, e.g., dengue virus 1, 2, 3, 4. In addition to members of the flavivirus genera, viral members of the pestivirus en hepacivirus such as Hepatitis C virus may be neutralized. Like flavivirus, the Hepatitis C virus assembly and budding takes place in the ER.

In a further aspect, the binding molecules hereof also have rabies virus neutralizing activity. In one aspect, they are also capable of specifically binding to rabies virus. Rabies virus is member of the Lyssavirus genus. In total, the Lyssavirus genus includes eleven genotypes: rabies virus (genotype 1), Lagos bat virus (genotype 2), Mokola virus (genotype 3), Duvenhage virus (genotype 4), European bat lyssavirus 1 (genotype 5), European bat lyssavirus 2 (genotype 6), Australian bat lyssavirus (genotype 7), Aravan virus (genotype 8), Khujand virus (genotype 9), Irkut virus (genotype 10) and West Caucasian virus (genotype 11). Besides binding to rabies virus, the binding molecules hereof may also be able to bind to other genotypes of the Lyssavirus genus. The binding molecules may also be capable of neutralizing other genotypes of the Lyssavirus genus. Furthermore, the binding molecules hereof may be able to bind to and/or neutralizing viruses, other than Lyssaviruses, of the rhabdovirus family. This family includes, but is not limited to, the genera ephemerovirus, lyssavirus, rhabdovirus and vesiculovirus.

In an embodiment, the binding molecules hereof are human binding molecules. The binding molecules hereof can be intact immunoglobulin molecules such as polyclonal or monoclonal antibodies or the binding molecules can be antigen-binding fragments including, but not limited to, Fab, F(ab'), $F(ab')_2$, Fv, dAb, Fd, complementarity determining region (CDR) fragments, single chain antibodies (scFv), bivalent single chain antibodies, single chain phage antibodies, diabodies, triabodies, tetrabodies, and peptide or polypeptides that contain at least a fragment of an immunoglobulin that is sufficient to confer specific antigen binding to the intracellular host cell protein or fragment thereof. In one embodiment, the human binding molecules having virus neutralizing activity are administered in IgG1, IgA, or IgM format.

The binding molecules hereof can be used in non-isolated or isolated form. Furthermore, the binding molecules hereof can be used alone or in a mixture comprising at least one binding molecule (or variant or fragment thereof) hereof. In other words, the binding molecules can be used in combination, e.g., as a pharmaceutical composition comprising two or more binding molecules hereof, variants or fragments thereof. For example, binding molecules having different, but complementary activities can be combined in a single therapy to achieve a desired prophylactic, therapeutic or diagnostic effect, but alternatively, binding molecules having identical activities can also be combined in a single therapy to achieve a desired prophylactic, therapeutic or diagnostic effect. The mixture may further comprise at least one other therapeutic agent. Preferably, the therapeutic agent is useful in the prophylaxis and/or treatment of a viral infection (e.g., WNV infection).

Typically, binding molecules hereof can bind to their binding partners, i.e., the intracellular host cell proteins or fragments thereof, with an affinity constant ($K_d$-value) that is lower than $0.2*10^{-4}$ M, $1.0*10^{-5}$ M, $1.0*10^{-6}$ M, $1.0*10^{-7}$ M, preferably lower than $1.0*10^{-8}$ M, more preferably lower than $1.0*10^{-9}$ M, more preferably lower than $1.0*10^{-10}$ M, even more preferably lower than $1.0*10^{-11}$ M, and in particular lower than $1.0*10^{-12}$ M. The affinity constants can vary for antibody isotypes. For example, affinity binding for an IgM isotype refers to a binding affinity of at least about $1.0*10^{-7}$ M. Affinity constants can for instance be measured using surface plasmon resonance, i.e., an optical phenomenon that allows for the analysis of real-time biospecific interactions by detection of alterations in protein concentrations within a biosensor matrix, for example using the BIACORE system (Pharmacia Biosensor AB, Uppsala, Sweden).

The binding molecules hereof may bind to the intracellular host cell protein or fragment thereof in soluble form such as for instance in a sample or may bind to the intracellular host cell protein or a fragment thereof bound or attached to a carrier or substrate, e.g., microtiter plates, membranes and beads, etc. Carriers or substrates may be made of glass, plastic (e.g., polystyrene), polysaccharides, nylon, nitrocellulose, or Teflon, etc. The surface of such supports may be solid or porous and of any convenient shape. Furthermore, the binding molecules may bind to the intracellular host cell protein in purified/isolated or non-purified/non-isolated form. Consequently, the binding molecules may bind to the intracellular host cell protein when it is incorporated into the host cell and/or viral membrane, such as in an infected host cell, a virus or a virus-like particle.

The binding molecules hereof are capable of neutralizing virus infectivity. This may be achieved by targeting viral specific events wherein the intracellular host cell proteins are involved including, but not limited to, virus attachment to cell membranes and penetration in cells, virus uncoating, virus nucleic acid synthesis, viral protein synthesis and maturation, assembly and release of infectious particles, targeting the membrane of infected cells resulting in a signal that leads to no replication or a lower replication rate of the virus. Neutralization assays for different viruses are known in the art. WNV, yellow fever virus, Japanese encephalitis virus, St. Louis encephalitis virus, dengue virus and rabies virus neutralizing activity can for instance be measured as described herein. Alternative WNV neutralization assays are described in for instance Gollins and Porterfield (1986).

In a certain embodiment, the binding molecules hereof comprise at least a CDR3 region, preferably a heavy chain CDR3 region, comprising the amino acid sequence selected from the group consisting of SEQ ID NO:5 and SEQ ID NO:6. In an embodiment, the binding molecules hereof may comprise two, three, four, five or even all six CDR regions of the binding molecules hereof. The heavy chain CDR1 region, heavy chain CDR2 region, light chain CDR1 region, light chain CDR2 region and light chain CDR3 region of the binding molecules hereof are shown in Table 9. CDR regions are according to Kabat et al. (1991) as described in Sequences of Proteins of Immunological Interest.

In yet another embodiment, the binding molecules hereof comprise a heavy chain comprising the variable heavy chain of the amino acid sequence selected from the group consisting of SEQ ID NO:18 and SEQ ID NO:20. In a further embodiment, the binding molecules hereof comprise a light chain comprising the variable light chain of the amino acid sequence selected from the group consisting of SEQ ID NO:22 and SEQ ID NO:24. Table 8 specifies, next to the heavy chain CDR3 region, the nucleotide and amino acid sequence of the heavy and light chains (and their variable regions) of the single chain antibodies.

In yet a further embodiment, the binding molecules hereof comprise a heavy chain comprising the amino acid sequence selected from the group consisting of SEQ ID NOS:30 and 32, and/or comprise a light chain comprising the amino acid sequence selected from the group consisting of SEQ ID NOS: 34 and 36.

In another embodiment, the binding molecules hereof comprise a heavy chain CDR1 region, heavy chain CDR2 region, heavy chain CDR3 region, light chain CDR1 region, light chain CDR2 region and light chain CDR3 region as shown in SEQ ID NOS:12, 13, 6, 143, 144 and 145, respectively. In yet another embodiment, the binding molecules hereof comprise a heavy chain comprising the variable heavy chain of the amino acid sequence of SEQ ID NO:20 and/or comprise a light chain comprising the variable light chain of the amino acid sequence of SEQ ID NO:74, i.e., amino acids 1-113 of SEQ ID NO:74. In yet a further embodiment, the binding molecules comprise a heavy chain comprising the amino acid sequence of SEQ ID NO 32, and/or comprise a light chain comprising the amino acid sequence of SEQ ID NO:74.

Another aspect includes functional variants of the binding molecules as defined herein. Molecules are considered to be functional variants of a binding molecule according to the invention, if the variants are capable of competing for specifically binding to the intracellular host cell proteins or fragment thereof with the parent binding molecules. The host cell protein can be incorporated into the viral membrane. In other words, when the functional variants are still able to bind to the intracellular host cell proteins or fragment thereof. Furthermore, molecules are considered to be functional variants of a binding molecule hereof, if they have virus neutralizing activity (e.g., WNV-neutralizing activity). Functional variants include, but are not limited to, derivatives that are substantially similar in primary structural sequence, but which contain, e.g., in vitro or in vivo modifications, chemical and/or biochemical, that are not found in the parental binding molecule. Such modifications include inter alia acetylation, acylation, covalent attachment of a nucleotide or nucleotide derivative, covalent attachment of a lipid or lipid derivative, cross-linking, disulfide bond formation, glycosylation, hydroxylation, methylation, oxidation, pegylation, proteolytic processing, phosphorylation, and the like.

Alternatively, functional variants can be binding molecules as defined herein comprising an amino acid sequence containing substitutions, insertions, deletions or combinations thereof of one or more amino acids compared to the amino acid sequences of the parental binding molecules. Furthermore, functional variants can comprise truncations of the amino acid sequence at either or both the amino or carboxyl termini. Functional variants may have the same or different, either higher or lower, binding affinities compared to the parental binding molecule but are still able to bind to the intracellular host cell proteins or fragment thereof. For instance, functional variants may have increased or decreased binding affinities for the intracellular host cell proteins or fragment thereof compared to the parental binding molecules. Preferably, the amino acid sequences of the variable regions, including, but not limited to, framework regions, hypervariable regions, in particular the CDR3 regions, are modified. Generally, the light chain and the heavy chain variable regions comprise three hypervariable regions, comprising three CDRs, and more conserved regions, the so-called framework regions (FRs). The hypervariable regions comprise amino acid residues from CDRs and amino acid residues from hypervariable loops. Functional variants intended to fall within the scope of the invention have at least about 50% to about 99%, preferably at least about 60% to about 99%, more preferably at least about 70% to about 99%, even more preferably at least about 80% to about 99%, most preferably at least about 90% to about 99%, in particular at least about 95% to about 99%, and in particular at least about 97% to about 99% amino acid sequence homology with the parental human binding molecules as defined herein. Computer algorithms such as inter alia Gap or Bestfit known to a person skilled in the art can be used to optimally align amino acid sequences to be compared and to define similar or identical amino acid residues. Functional variants can be obtained by altering the parental binding molecules or parts thereof by general molecular biology methods known in the art including, but not limited to, error prone PCR, oligonucleotide-directed mutagenesis, site-directed mutagenesis and heavy or light chain shuffling. Preferably, the functional variants of the invention have virus neutralizing activity. This neutralizing activity may either be identical, or be higher or lower compared to the parental binding molecules. Furthermore, preferably the functional variants have neutralizing activity against more than one genus, preferably against viruses of at least two, three, four, five, six, etc, different genera. Henceforth, when the term (human) binding molecule is used, this also encompasses functional variants of the (human) binding molecule.

In yet a further aspect, disclosed are immunoconjugates, i.e., molecules comprising at least one binding molecule as defined herein and further comprising at least one tag, such as inter alia a detectable moiety/agent. Also contemplated herein are mixtures of immunoconjugates according to the invention or mixtures of at least one immunoconjugates according to the invention and another molecule, such as a therapeutic agent or another binding molecule or immunoconjugate. In a further embodiment, the immunoconjugates hereof may comprise more than one tag. These tags can be the same or distinct from each other and can be joined/conjugated non-covalently to the binding molecules. The tag(s) can also be joined/conjugated directly to the human binding molecules through covalent bonding. Alternatively, the tag(s) can be joined/conjugated to the binding molecules by means of one or more linking compounds. Techniques for conjugating tags to binding molecules are well known to the skilled artisan.

The tags of the immunoconjugates hereof may be therapeutic agents, but preferably they are detectable moieties/agents. The tags may also be toxins, such as botulinum toxin or functional parts thereof. Immunoconjugates comprising a detectable agent can be used diagnostically to, for example, assess if a subject has been infected with a virus or monitor the development or progression of a virus infection as part of a clinical testing procedure to, e.g., determine the efficacy of a given treatment regimen. However, they may also be used for other detection and/or analytical and/or diagnostic purposes such as detection of viruses or virus-like particles comprising the intracellular host cell protein or host cells that have been infected and as a consequence thereof display the intracellular host cell protein on their surface. Detectable moieties/agents include, but are not limited to, enzymes, prosthetic groups, fluorescent materials, luminescent materials, bioluminescent materials, radioactive materials, positron emitting metals, and non-radioactive paramagnetic metal ions. The tags used to label the binding molecules for detection and/or analytical and/or diagnostic purposes depend on the specific detection/analysis/diagnosis techniques and/or methods used such as inter alia immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., neutralization assays), Western blotting applications, etc. Suitable labels for the detection/analysis/diagnosis techniques and/or methods known in the art are well within the reach of the skilled artisan.

Furthermore, the human binding molecules or immunoconjugates can also be attached to solid supports, which are particularly useful for in vitro immunoassays or purification of the intracellular host cell protein or fragment thereof, host cells displaying the intracellular host cell protein on their surface, or viruses or virus-like particles having the intracellular host cell protein incorporated into the viral membrane. Such solid supports might be porous or nonporous, planar or non-planar. The binding molecules can be fused to marker sequences, such as a peptide to facilitate purification. Examples include, but are not limited to, the hexa-histidine tag, the hemagglutinin (HA) tag, the myc tag or the flag tag. Alternatively, an antibody can be conjugated to a second antibody to form an antibody heteroconjugate. In another aspect, the binding molecules hereof may be conjugated/attached to one or more antigens. Such antigens may be antigens which are recognized by the immune system of a subject to which the binding molecule-antigen conjugate is administered. The antigens may be identical, but may also differ from each other. Conjugation methods for attaching the antigens and binding molecules are well known in the art and include, but are not limited to, the use of cross-linking agents. The binding molecules hereof will bind to the intracellular host cell protein and the antigens attached to the binding molecules will initiate a powerful T-cell attack on the conjugate, which will eventually lead to the destruction of the structure to which the intracellular host cell protein is bound or wherein it is incorporated.

Next to producing immunoconjugates chemically by conjugating, directly or indirectly, via for instance a linker, the immunoconjugates can be produced as fusion proteins comprising the binding molecules hereof and a suitable tag. Fusion proteins can be produced by methods known in the art such as, e.g., recombinantly by constructing nucleic acid molecules comprising nucleotides encoding the binding molecules in frame with nucleotides encoding the suitable tag(s) and then expressing the nucleic acid molecules.

It is another aspect to provide a nucleic acid molecule encoding at least a binding molecule or immunoconjugate hereof. Such nucleic acid molecules can be used as intermediates for cloning purposes, e.g., in the process of affinity maturation as described herein. In one embodiment, the nucleic acid molecules are isolated or purified.

The skilled person will appreciate that functional variants of these nucleic acid molecules are also intended to be a part hereof. Functional variants are nucleic acid molecules that can be directly translated, using the standard genetic code, to provide an amino acid sequence identical to that translated from the parental nucleic acid molecules.

The nucleic acid molecules may encode binding molecules comprising a CDR3 region, preferably a heavy chain CDR3 region, comprising an amino acid sequence selected from the group consisting of SEQ ID NO:5 and SEQ ID NO:6. In a further embodiment, the nucleic acid molecules encode binding molecules comprising two, three, four, five or even all six CDR regions of the binding molecules hereof.

In another embodiment, the nucleic acid molecules encode binding molecules comprising a heavy chain comprising the variable heavy chain of the amino acid sequence selected from the group consisting of SEQ ID NO:18 and SEQ ID NO:20. In another embodiment, the nucleic acid molecules encode binding molecules comprising a light chain comprising the variable light chain of the amino acid sequence selected from the group consisting of SEQ ID NO:22 and SEQ ID NO:24.

In yet a further embodiment, the nucleic acid molecules encode binding molecules comprising a heavy chain comprising the amino acid sequence selected from the group consisting of SEQ ID NOS:30 and 32, and/or comprising a light chain comprising the amino acid sequence selected from the group consisting of SEQ ID NOS:34 and 36.

In another embodiment, the nucleic acid molecules encode binding molecules comprising a heavy chain CDR1 region, heavy chain CDR2 region, heavy chain CDR3 region, light chain CDR1 region, light chain CDR2 region and light chain CDR3 region as shown in SEQ ID NOS:12, 13, 6, 143, 144 and 145, respectively. In yet another embodiment, the nucleic acid molecules encode binding molecules comprising a heavy chain comprising the variable heavy chain of the amino acid sequence of SEQ ID NO:20 and/or comprising a light chain comprising the variable light chain of the amino acid sequence of SEQ ID NO:74, i.e., amino acids 1-113 of SEQ ID NO:74. In yet a further embodiment, the nucleic acid molecules encode binding molecules comprising a heavy chain comprising the amino acid sequence of SEQ ID NO 32, and/or comprising a light chain comprising the amino acid sequence of SEQ ID NO:74.

It is another aspect to provide vectors, i.e., nucleic acid constructs, comprising one or more nucleic acid molecules of the invention. Vectors can be derived from plasmids such as inter alia F, R1, RP1, Col, pBR322, TOL, Ti, etc.; cosmids; phages such as lambda, lambdoid, M13, Mu, P1, P22, Qβ, T-even, T-odd, T2, T4, T7, etc; plant viruses. Vectors can be used for cloning and/or for expression of the binding molecules hereof and might even be used for gene therapy purposes. Vectors comprising one or more nucleic acid molecules according to the invention operably linked to one or more expression-regulating nucleic acid molecules are also covered by the invention. The choice of the vector is dependent on the recombinant procedures followed and the host used. Introduction of vectors in host cells can be effected by inter alia calcium phosphate transfection, virus infection, DEAE-dextran mediated transfection, lipofectamin transfection or electroporation. Vectors may be autonomously replicating or may replicate together with the chromosome into which they have been integrated. The vectors may contain one or more selection markers. The choice of the markers may depend on the host cells of choice, although this is not critical to the invention as is well known to persons skilled in the art. They include, but are not limited to, kanamycin, neomycin, puromycin, hygromycin, Zeocin®, thymidine kinase gene from herpes simplex virus (HSV-TK), dihydrofolate reductase gene from mouse (dhfr). Vectors comprising one or more nucleic acid molecules encoding the human binding molecules as described herein operably linked to one or more nucleic acid molecules encoding proteins or peptides that can be used to isolate the human binding molecules are also covered by the invention. These proteins or peptides include, but are not limited to, glutathione-S-transferase, maltose binding protein, metal-binding polyhistidine, green fluorescent protein, luciferase and beta-galactosidase.

Hosts containing one or more copies of the vectors mentioned above are an additional subject of the invention. Preferably, the hosts are host cells. Host cells include, but are not limited to, cells of mammalian, plant, insect, fungal or bacterial origin. Bacterial cells include, but are not limited to, cells from Gram-positive bacteria such as several species of the genera *Bacillus, Streptomyces* and *Staphylococcus* or cells of Gram-negative bacteria such as several species of the genera *Escherichia*, such as *E. coli*, and *Pseudomonas*. In the group of fungal cells preferably yeast cells are used. Expression in yeast can be achieved by using yeast strains such as inter alia, *Pichia pastoris, Saccharomyces cerevisiae* and *Hansenula polymorpha*. Furthermore, insect cells such as cells from *Drosophila* and Sf9 can be used as host cells. Besides that, the host cells can be plant cells such as inter alia cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example, *Agrobacterium*-mediated gene transfer, transformation of leaf discs, protoplast transformation by polyethylene glycol-induced DNA transfer, electroporation, sonication, microinjection or bolistic gene transfer. Additionally, a suitable expression system can be a baculovirus system. Expression systems using mammalian cells such as Chinese Hamster Ovary (CHO) cells, COS cells, BHK cells or Bowes melanoma cells are preferred herein. Mammalian cells provide expressed proteins with posttranslational modifications that are most similar to natural molecules of mammalian origin. Since the invention deals with molecules that may have to be administered to humans, a completely human expression system would be particularly preferred. Therefore, even more preferably, the host cells are human cells. Examples of human cells are inter alia HeLa, 911, AT1080, A549, 293 and HEK293T cells. In preferred embodiments, the human producer cells comprise at least a functional part of a nucleic acid molecule encoding an adenovirus E1 region in expressible format. In even more preferred embodiments, the host cells are derived from a human retina and immortalized with nucleic acids comprising adenoviral E1 sequences, such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6® is a registered trademark of Crucell Holland B.V.). For the purposes of this application "PER.C6®" refers to cells deposited under number 96022940 or ancestors, passages up-stream or downstream as well as descendants from ancestors of deposited cells, as well as derivatives of any of the foregoing. Production of recombinant proteins in host cells can be performed according to methods well known in the art. The use of the cells marketed under the trademark PER.C6® as a production platform for proteins of interest has been described in WO 00/63403 the disclosure of which is incorporated herein by reference.

A method of producing a binding molecule or an immunoconjugate hereof is an additional part hereof. The method comprises the steps of a) culturing a host according to the invention under conditions conducive to the expression of the binding molecule or immunoconjugate, and b) optionally, recovering the expressed binding molecule or immunoconjugate. The expressed binding molecules or immunoconjugates can be recovered from the cell free extract, but preferably they are recovered from the culture medium. This method of producing can also be used to make functional variants of the binding molecules and immunoconjugates hereof. Methods to recover proteins, such as binding molecules, from cell free extracts or culture medium are well known to the man skilled in the art. Binding molecules or immunoconjugates as obtainable by the aforementioned method are also a part hereof.

Alternatively, next to the expression in hosts, such as host cells, the binding molecules and immunoconjugates hereof can be produced synthetically by conventional peptide synthesizers or in cell-free translation systems using RNA nucleic acid derived from DNA molecules hereof. Binding molecules and immunoconjugates as obtainable by the aforementioned synthetic production methods or cell-free translation systems are also a part hereof.

In yet another embodiment, binding molecules can also be produced in transgenic, non-human, mammals such as inter alia rabbits, goats or cows, and secreted into for instance the milk thereof.

In yet another alternative embodiment, binding molecules, preferably human binding molecules specifically binding to the intracellular host cell protein or fragment thereof, may be generated by transgenic non-human mammals, such as, e.g., transgenic mice or rabbits that express human immunoglobulin genes. Such transgenic non-human mammals may have a genome comprising a human heavy chain transgene and a human light chain transgene encoding all or a portion of the human binding molecules as described herein. The transgenic non-human mammals can be immunized with a purified or enriched preparation of the intracellular host cell protein or fragment thereof. Protocols for immunizing non-human mammals are well established in the art. See Using Antibodies: A Laboratory Manual, Edited by: E. Harlow, D. Lane (1998), Cold Spring Harbor Laboratory, Cold Spring Harbor, N.Y. and Current Protocols in Immunology, edited by J. E. Coligan, A. M. Kruisbeek, D. H. Margulies, E. M. Shevach, W. Strober (2001), John Wiley & Sons Inc., New York, the disclosures of which are incorporated herein by reference. Immunization protocols often include multiple immunizations, either with or without adjuvants such as Freund's complete adjuvant and Freund's incomplete adjuvant, but may also include naked DNA immunizations. In another embodiment, the human binding molecules are produced by B-cells or plasma cells derived from the transgenic animals. In yet another embodiment, the human binding molecules are produced by hybridomas, which are prepared by fusion of B-cells obtained from the aforementioned transgenic non-human mammals to immortalized cells. B-cells, plasma cells and hybridomas as obtainable from the above described transgenic non-human mammals and human binding molecules as obtainable from the aforementioned transgenic non-human mammals, B-cells, plasma cells and hybridomas are also a part hereof.

The intracellular host cell proteins FAF-1 and/or NDUFV-1 may also be produced and purified according to the methods and with the vectors and host cells as described herein. Alternatively, they may also be produced and/or purified from a "native" host cell, e.g., a host cell normally expressing the intracellular host cell protein. Expression in a "native" host cell may be increased by substituting the natural promoter of proteins and/or by adding, substituting and/or mutating expression enhancing elements of proteins. The elements and methods to increase expression are known to the skilled artisan.

In a further aspect, provided is a method of identifying binding molecules hereof such as human binding molecules, e.g., monoclonal antibodies or fragments thereof, specifically binding to a host cell protein or nucleic acid molecules encoding such binding molecules and comprises the steps of a) contacting a collection of binding molecules on the surface of replicable genetic packages with a virus, virus-like particle or fragment thereof under conditions conducive to binding, b) selecting at least once for a replicable genetic package binding to the virus, virus-like particle or fragment thereof, and c) separating and recovering the replicable genetic package binding to the virus, virus-like particle or fragment thereof from replicable genetic packages that do not bind. The host cell protein may be an intracellular host cell protein.

A replicable genetic package as used herein can be prokaryotic or eukaryotic and includes cells, spores, yeasts, bacteria, viruses, (bacterio)phage, ribosomes and polysomes. A preferred replicable genetic package is a phage. The binding molecules, such as for instance single chain Fvs, are displayed on the replicable genetic package, i.e., they are attached to a group or molecule located at an exterior surface of the replicable genetic package. The replicable genetic package is a screenable unit comprising a binding molecule to be screened linked to a nucleic acid molecule encoding the binding molecule. The nucleic acid molecule should be replicable either in vivo (e.g., as a vector) or in vitro (e.g., by PCR, transcription and translation). In vivo replication can be autonomous (as for a cell), with the assistance of host factors (as for a virus) or with the assistance of both host and helper virus (as for a phagemid). Replicable genetic packages displaying a collection of binding molecules is formed by introducing nucleic acid molecules encoding exogenous binding molecules to be displayed into the genomes of the replicable genetic packages to form fusion proteins with endogenous proteins that are normally expressed from the outer surface of the replicable genetic packages. Expression of the fusion proteins, transport to the outer surface and assembly results in display of exogenous binding molecules from the outer surface of the replicable genetic packages.

In one embodiment, the selection step in a method according to the invention is performed in the presence of virus that is inactivated. The inactivation of the virus may be performed by viral inactivation methods well known to the skilled artisan. Methods to test if a virus is still infective or partly or completely inactivated are well known to the person skilled in the art. The virus used in the above method may be non-isolated, e.g., present in serum and/or blood of an infected individual. The virus used may also be isolated either before or after inactivation. Purification may be performed by means of, e.g., well known purification methods suitable for viruses such as for instance centrifugation through a glycerol cushion. The virus contains the (intracellular) host cell protein incorporated into its viral membrane.

Alternatively, the selection step may be performed in the presence of a fragment of the virus such as a fragment comprising the viral membrane or virus-like particles having the (intracellular) host cell protein incorporated into their membranes. The inactivated virus, virus-like particle or fragment thereof may be immobilized to a suitable material before use. In a specific embodiment, the selection can be performed on different materials comprising the (intracellular) host cell proteins. For instance, the first selection round can be performed on (inactivated) virus, while the second selection round can be performed on WNV-like particles. Alternatively, the first selection round can be performed on host cells displaying the (intracellular) host cell protein on their surface, while the second selection round can be performed on (inactivated) virus. Of course, other combinations are also suitable. For instance, the first and second selection round can be performed on identical material such as WNV-like particles. Different materials comprising the (intracellular) host cell protein can also be used during one selection/panning step.

In yet a further aspect, provided is a method of obtaining a binding molecule specifically binding to a host cell protein or a nucleic acid molecule encoding such a binding molecule specifically binding to a host cell protein, wherein the method comprises the steps of a) performing the above described method of identifying binding molecules, and b) isolating from the recovered replicable genetic package the binding molecule and/or the nucleic acid molecule encoding the binding molecule. The collection of binding molecules on the surface of replicable genetic packages can be a collection of scFvs or Fabs. Once a new scFv or Fab has been established or identified with the above mentioned method of identifying binding molecules or nucleic acid molecules encoding the binding molecules, the DNA encoding the scFv or Fab can be isolated from the bacteria or phages and combined with standard molecular biological techniques to make constructs encoding bivalent scFvs or complete human immunoglobulins of a desired specificity (e.g., IgG, IgA or IgM). These constructs can be transfected into suitable cell lines and complete human monoclonal antibodies can be produced (see Huls et al., 1999; Boel et al., 2000).

As mentioned before, the preferred replicable genetic package is a phage. Phage display methods for identifying and obtaining (human) binding molecules, e.g., monoclonal antibodies, are by now well-established methods known by the person skilled in the art. They are, e.g., described in U.S. Pat. No. 5,696,108; Burton and Barbas, 1994; de Kruif et al., 1995b; and Phage Display: A Laboratory Manual, edited by C. F. Barbas, D R Burton, J. K. Scott and G. J. Silverman (2001), Cold Spring Harbor Laboratory Press, Cold Spring Harbor, N.Y. All of these references are herewith incorporated herein in their entirety. For the construction of phage display libraries, collections of human monoclonal antibody heavy and light chain variable region genes are expressed on the surface of bacteriophage, preferably filamentous bacteriophage, particles, in for example single chain Fv (scFv) or in Fab format (see de Kruif et al., 1995b). Large libraries of antibody fragment expressing phages typically contain more than $1.0*10^9$ antibody specificities and may be assembled from the immunoglobulin V-regions expressed in the B-lymphocytes of immunized or non-immunized individuals. In a specific embodiment, the phage library of binding molecules, e.g., scFv phage library, is prepared from RNA isolated from cells obtained from a subject that has been vaccinated or exposed to a virus. RNA can be isolated from inter alia bone marrow or peripheral blood, preferably peripheral blood lymphocytes. The subject can be an animal vaccinated or exposed to a virus, but is preferably a human who has been vaccinated or has been exposed to a virus. Preferably the human subject has recovered from the viral infection. In an embodiment hereof, the virus is a flavivirus such as WNV.

Alternatively, phage display libraries may be constructed from immunoglobulin variable regions that have been partially assembled in vitro to introduce additional antibody diversity in the library (semi-synthetic libraries). For example, in vitro assembled variable regions contain stretches of synthetically produced, randomized or partially randomized DNA in those regions of the molecules that are important for antibody specificity, e.g., CDR regions. Host cell protein specific phage antibodies can be selected from the library by for instance immobilizing target antigens such as viruses, virus-like particles, host cells or host cell proteins, e.g., intracellular host cell proteins, on a solid phase and subsequently exposing the target antigens to a phage library to allow binding of phages expressing antibody fragments specific for the solid phase-bound antigen(s). Unbound phages are removed by washing and bound phages eluted from the solid phase for infection of *E. coli* bacteria and subsequent propagation. Multiple rounds of selection and propagation are usually required to sufficiently enrich for phages binding specifically to the target antigen(s). If desired, before exposing the phage library to target antigens the phage library can first be subtracted by exposing the phage library to non-target antigens bound to a solid phase. Phages may also be selected for binding to complex antigens such as complex mixtures of host cell proteins or peptide or polypeptides, (expression) host cells expressing one or more host cell proteins or peptide or polypeptides, virus-like particles comprising host cell proteins, or whole inactivated viruses. Antigen specific phage antibodies can be selected from the library by incubating a solid phase with bound thereon virus-like particles with the phage antibody library to let for example the scFv or Fab part of the phage bind to the virus-like particle. Of course, in an alternative embodiment, selections and subtractions may also be performed in solution. After incubation and several washes to remove unbound and loosely attached phages, the phages that have bound with their scFv or Fab part to the virus-like particle are eluted and used to infect *E. coli* to allow amplification of the new specificity. Generally, one or more selection rounds are required to separate the phages of interest from the large excess of non-binding phages. Alternatively, the host cell proteins can be expressed in expression host cells, e.g., PER.C6® cells, and these cells can be used for selection of phage antibodies specific for the proteins or peptide or polypeptides. A phage display method using (expression) host cells can be extended and improved by subtracting irrelevant binders during screening by addition of an excess of host cells comprising no target molecules or non-target molecules that are similar, but not identical, to the target, and thereby strongly enhance the chance of finding relevant binding molecules. Of course, the subtraction may also be performed before or after the screening with material comprising the host cell protein or fragment thereof. In an embodiment, the selection can take place on host cells that have been infected with a virus or a virus-like particle. These cells display the normally intracellular located host cell protein after infection on their surface. Subtraction may be performed before, during, or after the selection and may be performed with host cells that have not been infected and thus comprise the intracellular host cell protein in its original cellular location, i.e., inside the host cell. The subtraction process is referred to as the Mabstract® process (MABSTRACT® is a registered trademark of Crucell Holland B.V., see also U.S. Pat. No. 6,265,150, which is incorporated herein by this reference).

In yet another aspect, provided is a method of obtaining a binding molecule potentially having neutralizing activity against a virus and being capable of specifically binding to a host cell protein, wherein the method comprises the steps of a) performing the method of obtaining a binding molecule specifically binding to the host cell protein or a nucleic acid molecule encoding such a binding molecule specifically binding to the host cell protein as described herein, and b) verifying if the binding molecule isolated has neutralizing activity against a virus. Preferably, the host cell protein is an intracellular host cell protein. In an embodiment, the methods described herein are performed with a flavivirus such as WNV. In one embodiment of the method, it is verified if the binding molecule isolated has neutralizing activity against viruses of at least two different genera. More preferably, it is verified if the binding molecules are broadly neutralizing binding molecules and are able to neutralize many different genera. Assays for verifying if a binding molecule has neutralizing activity for a specific virus are well known in the art.

Also described is a host cell protein specific binding molecule obtainable by the methods as described herein. Preferably, the binding molecule has neutralizing activity against at least one virus.

In yet a further aspect, provided are compositions comprising at least one binding molecule, at least one functional variant thereof, at least one immunoconjugate hereof or a combination thereof. Also included are compositions comprising at least two binding molecules, preferably human binding molecules, at least one of which may be a binding molecule hereof. Preferably, both binding molecules have virus neutralizing activity. The activity may be against the same virus, but also against different viruses. In an embodiment, the compositions comprising two or more binding molecules having virus neutralizing activity exhibit synergistic virus neutralizing activity. In an embodiment, the binding molecules acting synergistically in neutralizing one virus may also be capable of neutralizing other viruses synergistically. As used herein, the term "synergistic" means that the combined effect of the binding molecules when used in combination is greater than their additive effects when used individually. A way of calculating synergy is by means of the combination index. The concept of the combination index (CI) has been described by Chou and Talalay, 1984. In an alternative embodiment, the compositions comprise two or more binding molecules having different modes of action. In an embodiment, the binding molecules hereof have flavivirus-, e.g., WNV-, neutralizing activity. In addition to that, the compositions may comprise inter alia stabilizing molecules, such as albumin or polyethylene glycol, or salts. Preferably, the salts used are salts that retain the desired biological activity of the binding molecules and do not impart any undesired toxicological effects. If necessary, the human binding molecules hereof may be coated in or on a material to protect them from the action of acids or other natural or unnatural conditions that may inactivate the binding molecules.

In yet a further aspect, compositions are provided comprising at least one nucleic acid molecule as defined herein. The compositions may comprise aqueous solutions such as aqueous solutions containing salts (e.g., NaCl or salts as described herein), detergents (e.g., SDS), and/or other suitable components.

Furthermore, provided are pharmaceutical compositions comprising at least one binding molecule (or functional fragment or variant thereof), at least one immunoconjugate according to the invention, at least one composition according to the invention, or combinations thereof. The pharmaceutical composition hereof further typically comprises at least one pharmaceutically acceptable excipient. A pharmaceutical composition hereof can further comprise at least one other therapeutic, prophylactic and/or diagnostic agent. Preferably, the pharmaceutical composition comprises at least one other prophylactic and/or therapeutic agent. Preferably, the further therapeutic and/or prophylactic agents are agents capable of preventing and/or treating an infection and/or a condition resulting from a virus, e.g., a flavivirus such as WNV. Therapeutic and/or prophylactic agents include, but are not limited to, anti-viral agents. Such agents can be binding molecules, small molecules, organic or inorganic compounds, enzymes, polynucleotides etc. Agents capable of preventing and/or treating a viral infection and/or a condition resulting from a virus that are in the experimental phase might also be used as other therapeutic and/or prophylactic agents useful herein.

The binding molecules or pharmaceutical compositions hereof can be tested in suitable animal model systems prior to use in humans. Such animal model systems include, but are not limited to, a murine model, a hamster model, and a geese model system.

Typically, pharmaceutical compositions must be sterile and stable under the conditions of manufacture and storage. The binding molecules, immunoconjugates, nucleic acid molecules or compositions hereof can be in powder form for reconstitution in the appropriate pharmaceutically acceptable excipient before or at the time of delivery. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Alternatively, the binding molecules, immunoconjugates, nucleic acid molecules or compositions hereof can be in solution and the appropriate pharmaceutically acceptable excipient can be added and/or mixed before or at the time of delivery to provide a unit dosage injectable form. Preferably, the pharmaceutically acceptable excipient used herein is suitable to high drug concentration, can maintain proper fluidity and, if necessary, can delay absorption.

The choice of the optimal route of administration of the pharmaceutical compositions will be influenced by several factors including the physico-chemical properties of the active molecules within the compositions, the urgency of the clinical situation and the relationship of the plasma concentrations of the active molecules to the desired therapeutic effect. For instance, if necessary, the binding molecules hereof can be prepared with carriers that will protect them against rapid release, such as a controlled release formulation, including implants, transdermal patches, and microencapsulated delivery systems. Biodegradable, biocompatible polymers can inter alia be used, such as ethylene vinyl acetate, polyanhydrides, polyglycolic acid, collagen, polyorthoesters, and polylactic acid. Furthermore, it may be necessary to coat the binding molecules with, or co-administer the binding molecules with, a material or compound that prevents the inactivation of the human binding molecules. For example, the binding molecules may be administered to a subject in an appropriate carrier, for example, liposomes or a diluent.

The routes of administration can be divided into two main categories, oral and parenteral administration. The preferred administration route is intravenous.

Oral dosage forms can be formulated inter alia as tablets, troches, lozenges, aqueous or oily suspensions, dispersible powders or granules, emulsions, hard capsules, soft gelatin capsules, syrups or elixirs, pills, dragees, liquids, gels, or slurries. These formulations can contain pharmaceutically excipients including, but not limited to, inert diluents, granulating and disintegrating agents, binding agents, lubricating agents, preservatives, coloring, flavoring or sweetening agents, vegetable or mineral oils, wetting agents, and thickening agents.

The pharmaceutical compositions hereof can also be formulated for parenteral administration. Formulations for parenteral administration can be inter alia in the form of aqueous or non-aqueous isotonic sterile non-toxic injection or infusion solutions or suspensions. The solutions or suspensions may comprise agents that are non-toxic to recipients at the dosages and concentrations employed such as 1,3-butanediol, Ringer's solution, Hank's solution, isotonic sodium chloride solution, oils, fatty acids, local anesthetic agents, preservatives, buffers, viscosity or solubility increasing agents, water-soluble antioxidants, oil-soluble antioxidants, and metal chelating agents.

In a further aspect, the binding molecules (functional fragments and variants thereof), immunoconjugates, compositions, or pharmaceutical compositions hereof can be used as a medicament. So, a method of treatment and/or prevention of a viral infection using the binding molecules, immunoconjugates, compositions, or pharmaceutical compositions hereof is another part hereof. The above-mentioned molecules can inter alia be used in the diagnosis, prophylaxis, treatment, or combination thereof, of one or more conditions resulting from a virus or viral infection. Preferably, they are broadly applicable to prevent, detect and/or treat several viral infections caused by viruses of different genera and/or strains, including, but not limited to, herpes viridae (e.g., Herpes Simplex Virus type 1, 2, 6, 7, 8, cytomegalovirus, varicella-zoster virus, Epstein Barr virus), Poxviridae (e.g., Smallpox virus), Retroviridae (e.g., HIV 1, HIV2, HTLV1, HTLV2), paramyxoviridae (e.g., mumps virus, measles virus, respiratory syncytial virus, parainfluenza virus), HepaDNAviridae (e.g., Hepatitis B virus), Orthomyxoviridae (e.g., Influenza virus A or B), Togaviridae (e.g., Rubella), Flaviviridae (e.g., Yellow fever virus, Dengue virus, West Nile Virus, Hepatitis C virus, Japanese encephalitis virus, Venezuela encephalitis virus) rhabodiviridae (e.g., rabies virus), Arenaviridae (e.g., Lassa virus, lymphocytic choriomeningitis virus) and Coronaviridae (e.g., SARS virus, metapneumoniae virus). Moreover, they may also be applicable to prevent, detect and/or treat several viral infections caused by viruses not mentioned above including, but not limited to, Sindbis virus, poliovirus, human papilloma virus, adeno-associated virus, coxsackivirus, enterovirus, hepatitis A virus, tick-borne encephalitis virus, astrovirus, Ebola virus, Marburg virus, La Crosse virus, California encephalitis virus, Hantaan virus, Crimean-Congo virus, Rift Valley fever, Argentine hemorrhagic fever virus, Bolivian hemorrhagic fever virus, Colorado tick fever, JC virus, BK virus, human adenovirus, and human parvovirus. In other words, the binding molecules hereof are broad spectrum anti-viral binding molecules. They are suitable for treatment of yet untreated patients suffering from a condition resulting from a virus and patients who have been or are treated from a condition resulting from a virus or a viral infection. They protect against further infection by a virus for approximately one month and/or will retard the onset or progress of the symptoms associated with a virus. They may also be used in post-exposure prophylaxis, when there is a chance of infection but symptoms are absent. They may also be used as prophylaxis in the transplant of infected organs or in other patient populations at high risk of exposure and progression to disease due to inter alia age or immune status. In a specific embodiment, the compounds and compositions are used to treat and/or prevent a flavivirus, e.g., WNV, infection and/or a rabies virus infection.

The above-mentioned molecules or compositions may be employed in conjunction with other molecules useful in diagnosis, prophylaxis and/or treatment. They can be used in vitro, ex vivo or in vivo. For instance, the binding molecules, immunoconjugates or pharmaceutical compositions hereof can be co-administered with a vaccine against the intracellular host cell proteins. Alternatively, the vaccine may also be administered before or after administration of the molecules of the invention. Instead of a vaccine, other anti-viral agents can also be employed in conjunction with the binding molecules of the invention. In an aspect the invention is also directed to the use of an intracellular host cell protein, preferably FAF-1 and/or NDUFV-1, as a vaccine suitable for preventing and/or treating a viral infection, e.g., a flavivirus infection such as WNV infection.

The molecules are typically formulated in the compositions and pharmaceutical compositions hereof in a therapeutically or diagnostically effective amount. Alternatively, they may be formulated and administered separately. For instance the other molecules such as the anti-viral compounds may be applied systemically, while the binding molecules hereof may be applied intrathecally, intraventricularly or intradermally.

Dosage regimens can be adjusted to provide the optimum desired response (e.g., a therapeutic response). A suitable dosage range may for instance be 0.1-100 mg/kg body weight, preferably 0.5-15 mg/kg body weight. Furthermore, for example, a single bolus may be administered, several divided doses may be administered over time or the dose may be proportionally reduced or increased as indicated by the exigencies of the therapeutic situation. The molecules and compositions hereof are preferably sterile. Methods to render these molecules and compositions sterile are well known in the art. The other molecules useful in diagnosis, prophylaxis and/or treatment can be administered in a similar dosage regimen as proposed for the binding molecules hereof. If the other molecules are administered separately, they may be administered to a patient prior to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks before), concomitantly with, or subsequent to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks after) the administration of one or more of the human binding molecules or pharmaceutical compositions hereof. The exact dosing regimen is usually sorted out during clinical trials in human patients.

Human binding molecules and pharmaceutical compositions comprising them are particularly useful, and often preferred, for administration to human beings as in vivo therapeutic agents, since recipient immune response to the administered antibody will often be substantially less than that occasioned by administration of a monoclonal murine, chimeric or humanized binding molecule.

Also described is the use of the human binding molecules or binding molecules (functional fragments and variants thereof), immunoconjugates, nucleic acid molecules, compositions or pharmaceutical compositions described herein in the preparation of a medicament for the diagnosis, prophylaxis, treatment, or combination thereof, of a viral infection and/or a condition resulting thereof.

Next to that, kits comprising at least one binding molecule (functional fragments and variants thereof), at least one immunoconjugate, at least one nucleic acid molecule, at least one composition, at least one pharmaceutical composition, at least one vector, at least one host according to the invention or a combination thereof are also a part hereof. Optionally, the aforementioned components of the kits hereof are packed in suitable containers and labeled for diagnosis, prophylaxis and/or treatment of the indicated conditions. The above-mentioned components may be stored in unit or multi-dose containers as an aqueous, preferably sterile, solution or as a lyophilized, preferably sterile, formulation for reconstitution. The containers may be formed from a variety of materials such as glass or plastic and may have a sterile access port (for example the container may be an intravenous solution bag or a vial having a stopper pierceable by a hypodermic injection needle). The kit may further comprise more containers comprising a pharmaceutically acceptable buffer. It may further include other materials desirable from a commercial and user standpoint, including other buffers, diluents, filters, needles, syringes, culture medium for one or more of the suitable hosts and, possibly, even at least one other therapeutic, prophylactic or diagnostic agent. Associated with the kits can be instructions customarily included in commercial packages of therapeutic, prophylactic or diagnostic products, that contain information about for example the indications, usage, dosage, manufacture, administration, contraindications and/or warnings concerning the use of such therapeutic, prophylactic or diagnostic products.

Further described is a method of detecting an intracellular host cell protein such as FAF-1 and/or NDUFV-1 in a sample, wherein the method comprises the steps of a) contacting a sample with a diagnostically effective amount of a binding molecule (functional fragments and variants thereof) or an immunoconjugate described herein, and b) determining whether the binding molecule or immunoconjugate specifically binds to a molecule of the sample. The sample may be a biological sample including, but not limited to blood, serum, urine, tissue or other biological material from (potentially) infected subjects, or a non-biological sample such as water, drink, etc. The (potentially) infected subjects may be human subjects, but also animals that are suspected as carriers of a virus might be tested for the presence of the virus using the human binding molecules or immunoconjugates hereof. By detecting the intracellular host cell proteins a viral infection (infected host cell and/or virus particle) may be detected. The sample may first be manipulated to make it more suitable for the method of detection. Manipulation means inter alia treating the sample suspected to contain and/or containing a virus in such a way that the virus will disintegrate into antigenic components such as proteins, peptide or polypeptides or other antigenic fragments. Preferably, the human binding molecules or immunoconjugates hereof are contacted with the sample under conditions which allow the formation of an immunological complex between the human binding molecules and intracellular host cell protein or antigenic components thereof that may be present in the sample. The formation of an immunological complex, if any, indicating the presence of a virus in the sample, is then detected and measured by suitable means. Such methods include, inter alia, homogeneous and heterogeneous binding immunoassays, such as radio-immunoassays (RIA), ELISA, immunofluorescence, immunohistochemistry, FACS, BIACORE and Western blot analyses.

Preferred assay techniques, especially for large-scale clinical screening of patient sera and blood and blood-derived products are ELISA and Western blot techniques. ELISA tests are particularly preferred. For use as reagents in these assays, the binding molecules or immunoconjugates hereof are conveniently bonded to the inside surface of microtiter wells. The binding molecules or immunoconjugates hereof may be directly bonded to the microtiter well. However, maximum binding of the binding molecules or immunoconjugates hereof to the wells might be accomplished by pre-treating the wells with poly-lysine prior to the addition of the binding molecules or immunoconjugates hereof. Furthermore, the binding molecules or immunoconjugates hereof may be covalently attached by known means to the wells. Generally, the binding molecules or immunoconjugates are used between 0.01 to 100 μg/ml for coating, although higher as well as lower amounts may also be used. Samples are then added to the wells coated with the binding molecules or immunoconjugates hereof.

Furthermore, binding molecules hereof can be used to identify epitopes of the intracellular host cell proteins such as FAF-1 and/or NDUFV-1. The epitopes can be linear, but also structural and/or conformational. In one embodiment, binding of binding molecules hereof to a series of overlapping peptides, such as 15-mer peptides, of the host cell protein can be analyzed by means of PEPSCAN analysis (see inter alia WO 84/03564, WO 93/09872, Slootstra et al., 1996). The binding of the molecules to each peptide can be tested in a PEPSCAN-based enzyme-linked immunoassay (ELISA). In another embodiment, a random peptide library comprising peptides from the host cell proteins can be screened for peptides able to bind to the binding molecules hereof. In the above assays the use of neutralizing binding molecules may identify one or more neutralizing epitopes. The peptides/epitopes found can be used as vaccines and for the diagnosis of a viral infection.

In a further aspect, provided is a method of screening a binding molecule (or a functional fragment or variant thereof) for specific binding to the same epitope of the intracellular host cell protein, such as FAF-1 and/or NDUFV-1, as the epitope bound by a human binding molecule hereof, wherein the method comprises the steps of a) contacting a binding molecule to be screened, a binding molecule hereof and material comprising the intracellular host cell protein or antigenic fragment thereof, b) measure if the binding molecule to be screened is capable of competing for specifically binding to the intracellular host cell protein comprising material or antigenic fragment thereof with the binding molecule of the invention. The material comprising the intracellular host cell protein or antigenic fragment thereof may be a host cell displaying the protein on its surface, a virus having the protein incorporated into its viral membrane, a virus-like particle having the protein incorporated into the viral membrane or the protein itself in purified or non-purified form. In a further step it may be determined, if the screened binding molecules that are capable of competing for specifically binding to the intracellular host cell protein or antigenic fragment thereof have neutralizing activity. A binding molecule that is capable of competing for specifically binding to the intracellular host cell protein or an antigenic fragment thereof with the binding molecule of the invention is another part hereof. In the aforementioned screening method, "specifically binding to the same epitope" also contemplates specific binding to substantially or essentially the same epitope as the epitope bound by the a binding molecule of the invention. The capacity to block, or compete with, the binding of the binding molecules hereof to the intracellular host cell protein typically indicates that a binding molecule to be screened binds to an epitope or binding site on the intracellular host cell protein that structurally overlaps with the binding site on the intracellular host cell protein that is immunospecifically recognized by the binding molecules hereof. Alternatively, this can indicate that a binding molecule to be screened binds to an epitope or binding site that is sufficiently proximal to the binding site immunospecifically recognized by the binding molecules hereof to sterically or otherwise inhibit binding of the binding molecules hereof to the intracellular host cell protein.

In general, competitive inhibition is measured by means of an assay, wherein an antigen composition, i.e., a composition comprising the intracellular host cell protein or antigenic fragments thereof, is admixed with reference binding molecules, i.e., the binding molecules hereof, and binding molecules to be screened. Usually, the binding molecules to be screened are present in excess. Protocols based upon ELISAs and Western blotting are suitable for use in such simple competition studies. In certain embodiments, one may pre-mix the reference binding molecules with varying amounts of the binding molecules to be screened (e.g., 1:10, 1:20, 1:30, 1:40, 1:50, 1:60, 1:70, 1:80, 1:90 or 1:100) for a period of time prior to applying to the antigen composition. In other embodiments, the reference binding molecules and varying amounts of binding molecules to be screened can simply be admixed during exposure to the antigen composition. In yet another embodiment, the reference binding molecules or binding molecules to be screened are contacted before the binding molecules to be screened or reference binding molecules, respectively, are contacted with the intracellular host cell protein or antigenic fragment thereof. In any event, by using species or isotype secondary antibodies one will be able to detect only the bound reference binding molecules, the binding of which will be reduced by the presence of a binding molecule to be screened that recognizes substantially the same epitope. In conducting a binding molecule competition study between a reference binding molecule and any binding molecule to be screened (irrespective of species or isotype), one may first label the reference binding molecule with a detectable label, such as, e.g., biotin, an enzymatic, a radioactive or other label to enable subsequent identification. In these cases, one would pre-mix or incubate the labeled reference binding molecules with the binding molecules to be screened at various ratios (e.g., 1:10, 1:20, 1:30, 1:40, 1:50, 1:60, 1:70, 1:80, 1:90 or 1:100) and (optionally after a suitable period of time) then assay the reactivity of the labeled reference binding molecules and compare this with a control value in which no potentially competing binding molecule was included in the incubation. The assay may again be any one of a range of immunological assays based upon antibody hybridization, and the reference binding molecules would be detected by means of detecting their label, e.g., using streptavidin in the case of biotinylated reference binding molecules or by using a chromogenic substrate in connection with an enzymatic label (such as 3,3'5,5'-tetramethylbenzidine (TMB) substrate with peroxidase enzyme) or by simply detecting a radioactive label. A binding molecule to be screened that binds to the same epitope as the reference binding molecule will be able to effectively compete for binding and thus will significantly reduce reference binding molecule binding, as evidenced by a reduction in bound label. The reactivity of the (labeled) reference binding molecule in the absence of a completely irrelevant binding molecule would be the control high value. The control low value would be obtained by incubating the labeled reference binding molecule with unlabelled reference binding molecules of exactly the same type, when competition would occur and reduce binding of the labeled reference binding molecule. In a test assay, a significant reduction in labeled reference binding molecule reactivity in the presence of a binding molecule to be screened is indicative of a binding molecule that recognizes the same epitope, i.e., one that "cross-reacts" with the labeled reference binding molecule.

Binding molecules identified by these competition assays ("competitive binding molecules" or "cross-reactive binding molecules") include, but are not limited to, antibodies, antibody fragments and other binding agents that bind to an epitope or binding site bound by the reference binding molecule, i.e., a binding molecule described herein, as well as antibodies, antibody fragments and other binding agents that bind to an epitope or binding site sufficiently proximal to an epitope bound by the reference binding molecule for competitive binding between the binding molecules to be screened and the reference binding molecule to occur. Preferably, competitive binding molecules hereof will, when present in excess, inhibit specific binding of a reference binding molecule to a selected target species by at least 10%, preferably by at least 25%, more preferably by at least 50%, and most preferably by at least 75%-90% or even greater. The identification of one or more competitive binding molecules that bind to about, substantially, essentially or at the same epitope as the binding molecules hereof is a straightforward technical matter. As the identification of competitive binding molecules is determined in comparison to a reference binding molecule, i.e., a binding molecule of the invention, it will be understood that actually determining the epitope to which the reference binding molecule and the competitive binding molecule bind is not required in order to identify a competitive binding molecule that binds to the same or substantially the same epitope as the reference binding molecule.

In a further aspect, disclosed are new leader peptide sequences (also called signal sequences or presequences) and nucleotides encoding the leader peptides. The leader peptides are useful in methods for producing recombinant proteins, e.g., immunoglobulin molecules, from a host cell. The entry of almost all secreted polypeptides to the secretory pathway, in both prokaryotes and eukaryotes, is directed by specific leader peptides at the N terminus of the polypeptide chain. Leader peptides direct nascent polypeptides towards the machinery of the cell that exports polypeptides from the cell into the surrounding medium or, in some cases, into the periplasmic space. The mechanisms by which leader peptides direct nascent polypeptide chains to the secretion pathway and direct the precise and efficient proteolytic cleavage to release mature proteins are incompletely understood. The leader peptide is usually, although not necessarily, located at the N terminus of the primary translation product and is generally, although not necessarily, cleaved off the desired polypeptide during the secretion process, to yield the "mature" polypeptide. The secretion of polypeptides is a dynamic and multi-step process involving several elements of the cellular secretory apparatus and specific sequence elements in the signal peptide. It further involves translation, translocation and post-translational processing, and one or more of these steps may not necessarily be completed before another is either initiated or completed. Signal sequences are indispensible for production of phage antibodies, in which antibody fragments such as scFv or Fab are fused to the phage coat proteins such as pIII or pVIII.

Signal sequences are predominantly hydrophobic in nature, a feature which may be important in directing the nascent peptide to the membrane and transfer of secretory proteins across the inner membrane of prokaryotes or the endoplasmic reticulum membranes of eukaryotes. In mammalian cells, leader peptides are recognized by the 54K protein of the signal recognition particle (SRP), which is believed to hold the nascent chain in a translocation competent conformation until it contacts the endoplasmic reticulum membrane. The SRP consists of a 7S RNA and six different polypeptides. The 7S RNA and the 54K leader peptide-binding protein (SRP54) of mammalian SRP exhibit strong sequence similarity to the 4.5S RNA and P48 protein (Ffh) of *Escherichia coli*, which forms the signal recognition particle in bacteria. It is likely that the various sequences found in different signal peptides interact in unique ways with the secretion apparatus. There are no eukaryotic signal sequences available that result in correct protein processing and high protein expression in bacteria or vice versa.

The antibody phage format or scFv fragment format is often not considered a suitable format in assays of functionalities other than binding, e.g., assays for testing neutralizing activity where bivalent binding is required or where functional Fc regions are required. In for instance assays testing neutralizing activity data obtained with phage antibodies or scFv fragments derived from phage antibodies are not representative of the neutralizing activity of the complete immunoglobulin molecules. Therefore, complete immunoglobulin molecules, e.g., IgG1, are needed to test particular specificities for functional activity. To increase the efficiency by which scFv molecules can be reformatted into IgG1 a new vector system making use of new leader peptides was designed. The new vectors and leader peptides were designed to enable direct shuttling of immunoglobulin heavy chain regions (VH region) and immunoglobulin light chain regions (VL region) from bacterial expression vectors, such as phage display vectors, e.g., PDV, pHEN and vectors derived thereof, into a eukaryotic expression system. This approach has a significant time and cost advantage over the standard systems wherein each VH and VL region had to be PCR amplified, cloned and checked for frequent mutations that occur through the amplification process before being shuttled into eukaryotic expression vectors. In short the procedure is as follows. VH and VL fragment repertoires are cloned into prokaryotic expression vectors such as pHEN1 and PDV-C06 using specific restriction enzymes. These sites are chosen to be outside of the V region encoding sequences because there is too much sequence diversity within the V regions for efficient PCR amplification and cloning of V gene repertoires. Typically, the enzyme recognition site at the 5'-end of the VH antibody fragments is located in the coding region of the prokaryotic leader sequence such as the SfiI site in the PelB leader sequence of pHEN1 or PDV-C06. Therefore, SfiI is one of the available sites for cloning at the 5'-end that is present in all phage display derived scFv clones. When using this site for cloning, the sequence encoded by the SfiI site and the downstream sequence are transferred to the eukaryotic vector; this means that the C-terminal part of the prokaryotic leader is transferred to the eukaryotic vector. Herein, a eukaryotic leader was designed that is functional when the region encoding the C-terminal part of the prokaryotic leader sequence (e.g., PelB) is transferred into the eukaryotic vector. VL antibody fragment repertoires are cloned using a Sail site that is located within the scFv linker sequence. When this site is used for cloning, the sequence encoded by the SalI site is transferred to the eukaryotic vector and will be part of the eukaryotic leader sequence. Therefore, leaders were designed that contain a sequence upstream of the SalI restriction site that together with the SalI restriction site encoded sequence and the sequence downstream of the restriction site after transcription and translation form a functional leader in eukaryotic cells. The VH region is cut from a phage display vector with restriction enzymes and cloned in frame between a "truncated" eukaryotic leader peptide and the hinge and constant domains of an immunoglobulin heavy chain present in the expression vector. In an identical way, the VL region is cloned in frame with a "truncated" eukaryotic leader peptide and the constant domain of the immunoglobulin light (either lambda or kappa) chain. The newly designed leader peptides have a sequence that is recognized by the cellular secretory apparatus and is proteolitically cleaved during secretion of the immunoglobulin chains from host cells, e.g., eukaryotic host cells, resulting in correctly processed mature Ig heavy and light chain proteins. The invention also provides an expression vector (pIG-CHG1) for production of a full length IgG1 heavy chain immunoglobulin molecule and two vectors encoding a complete light chain fragment. One vector (pIG-Ckappa) produces the kappa light chain sub-type and the other (pIG-Clambda) the lambda light chain variant. It is essential to determine beforehand what sub-type the VL region belongs to, so that the right constant light chain domain can be fused to it. Of course, the IgG1 constant domain in the vector can be replaced by an IgG2, IgG3 or IgG4 domain to produce heavy chains of the IgG2, IgG3 or IgG4 format. Other proteins that need a leader sequence in both prokaryotes and eukaryotes can also be made by means of the new leaders. For convenient and efficient cloning the pIG vectors were extended with large stuffer fragments such that double cut vectors are easily separated from linear single cut vectors.

Also disclosed is a eukaryotic leader peptide comprising an amino acid molecule selected from the group consisting of SEQ ID NO:150, SEQ ID NO:152 and SEQ ID NO:154. In a further aspect, provided is a recombinant polypeptide (e.g., recombinant protein) comprising a eukaryotic leader peptide described herein and a polypeptide of interest. The polypeptide of interest can be any recombinant protein, but preferably it is a eukaryotic protein such as a mammalian protein, or more preferably a human protein. In one embodiment, the polypeptide of interest is selected from the group consisting of an immunoglobulin heavy chain, an immunoglobulin light chain, an immunoglobulin heavy chain fragment and an immunoglobulin light chain fragment. Preferred fragments are immunoglobulin variable regions (VH or VL regions). Preferably, the immunoglobulin chains and fragments are human. In one aspect, the leader peptide is used to direct or even enhance the secretion of the recombinant polypeptide produced in a recombinant (i.e., transformed) host organism, e.g., a host cell. In an embodiment, the carboxy terminus of the eukaryotic leader peptide is joined/fused to the amino terminus of the polypeptide of interest. Preferably, the leader peptide comprising SEQ ID NO:150 is fused to an immunoglobulin heavy chain or fragment thereof. This leader peptide is the result of joining a "truncated" eukaryotic leader peptide encoded by the nucleotide sequence of SEQ ID NO:155 to a nucleotide sequence encoding an immunoglobulin heavy chain or fragment thereof, e.g., a heavy chain variable region from plasmid pHEN1 or PDV-C06. The leader peptides comprising SEQ ID NO:152 and SEQ ID NO:154 are joined to an immunoglobulin kappa and lambda light chain or fragment thereof, respectively. These leader peptides are the result of joining a "truncated" eukaryotic leader peptide encoded by the nucleotide sequence of SEQ ID NO:156 or SEQ ID NO:157 to a nucleotide sequence encoding an immunoglobulin kappa or lambda light chain or fragment thereof, e.g., a kappa or lambda light chain variable region from plasmid pHEN1 or PDV-C06. Thus, provided is a fusion polypeptide comprising a leader peptide sequence of the invention and a recombinant protein sequence. The fusion polypeptide may be designed such that there are additional amino acids present between the leader peptide and the recombinant protein. In these instances, cleavage of the leader peptide from the fusion polypeptide may produce a modified recombinant protein having additional amino acids at the N terminus. Alternatively, the fusion polypeptide may be designed such that the site for cleavage of the leader peptide occurs a few amino acids into the sequence of the recombinant protein. In these instances, a modified recombinant protein may be produced which has an altered N terminus.

In another aspect, provided is a nucleic acid molecule encoding a eukaryotic leader peptide described herein. The eukaryotic leader peptides according to the invention comprise nucleotides GGCCCAGCCGGCC (SEQ ID NO:158), i.e., a SfiI-site, or nucleotides TCGAC (SEQ ID NO:159), i.e., a combined XhoI/SalI-site, within the nucleic acid molecule encoding the leader peptides. The combined XhoI/SalI-site is made by ligating the XhoI-site in a prokaryotic leader into a eukaryotic vector that has been digested with the restriction enzyme SalI. The sites may be located within the carboxy terminal part of the leader peptide encoding sequences. In one embodiment, the nucleic acid molecule encoding the new leader peptides according to the invention comprise a nucleic acid molecule selected from the group consisting of SEQ ID NO:149, SEQ ID NO:151 and SEQ ID NO:153. The nucleic acid molecule may further comprise a nucleic acid molecule encoding a polypeptide of interest. Suitable polypeptides of interest are mentioned herein. The nucleic acid molecule encoding the leader peptides and the nucleic acid molecule encoding the polypeptides of interest can form a so-called fusion construct. By "fusion construct" is intended a nucleic acid comprising the coding sequence for a leader peptide and the coding sequence, with or without introns, for a recombinant protein, in which the coding sequences are adjacent and in the same reading frame such that, when the fusion construct is transcribed and translated in a host cell, a protein is produced in which the C terminus of the leader peptide is joined to the N terminus of the recombinant protein. The protein product of the fusion construct may be referred to herein as "fusion polypeptide." Nucleic acid encoding the leader peptide can be operably joined/linked to nucleic acid containing the coding region of the recombinant protein in such manner that the leader peptide coding region is upstream of (that is, 5' of) and in the same reading frame with the recombinant protein coding region to provide a fusion construct. Typically, the 3'-end of the nucleic acid encoding the leader peptide is joined to the 5'-end of the nucleic acid encoding the recombinant protein. The two coding regions are joined such that they are in the same reading frame. In this way, the fusion construct will encode a single protein, having the leader peptide at the N terminal end followed by the recombinant protein at the C terminal end. The leader peptide and the recombinant protein may be joined directly or there may be one or several amino acids connecting them. Certain amino acids are well known to interfere with cleavage by signal peptidases and these residues are avoided in designing the cleavage site for the fusion polypeptide. The fusion construct can be expressed in a host cell to provide a fusion polypeptide comprising the leader peptide joined, at its carboxy terminus, to the recombinant protein at its amino terminus. The fusion polypeptide can be secreted from the host cell. Typically, the leader peptide is cleaved from the fusion polypeptide during the secretion process, resulting in the accumulation of secreted recombinant protein in the external cellular environment.

Further provided is an expression vector comprising a nucleic acid molecule of the invention. Preferably, such a nucleic acid molecule comprises a nucleic acid molecule encoding a leader peptide hereof. They may further comprise a nucleic acid molecule encoding the polypeptide of interest. Expression vectors can be prepared containing the nucleic acids encoding the leader peptide or the fusion construct by methods that are well known in the art. In general, the expression vectors will contain nucleic acid encoding the leader peptide, or the fusion construct, under the control of a promoter. In some embodiments, more than one leader peptide or fusion construct may be placed under the control of a single promoter. In such embodiments, the additional fusion construct(s) will be placed downstream of the first fusion construct and separated from the upstream fusion construct by nucleotides. The promoter is chosen so that it is capable of directing transcription in a host of interest. Promoters capable of directing transcription in various host cells are well known. In an embodiment, the promoter is the CMVlong promoter, but any other suitable promoter may also be chosen. In general, a "promoter" will include all nucleotides upstream of the translational start necessary for the transcription of the leader peptide and/or fusion polypeptide coding region. The promoter may include or overlap the sequence of the ribosome binding site. Selection of promoter will often influence the selection of ribosome binding site as well. The expression vector may also contain other expression regulating nucleic acid molecules including selectable marker genes, origins of replication, polyadenylation signal sequences, etc. Other expression regulating nucleic acid molecules and further sequences, e.g., sequences of polypeptides useful for isolation, which can be included in the vectors are mentioned above. The expression vectors may contain one or more selectable marker genes, including ampicillin and/or neomycin, for selection in the host of interest and/or one or more origins of replication, including a pUc ori and/or a SV40 on and/or a fl ori, to provide autonomous replication of the vector in the host. Additionally, they may contain one or more polyadenylation signal sequences including a SV40-polyA signal and/or a BGH-polyA signal. Alternatively, or in addition, the expression vector may contain nucleotides to aid in integration of the vector into the host chromosome. An expression vector according to the invention may further comprise a XhoI-site or a NotI-site. An immunoglobulin heavy and/or light chain variable region may for instance be located between a Sfi-site and a XhoI-site (e.g., in an expression vector for the production of heavy chain (IgG1) immunoglobulin chains), and located between a XhoI-site and a NotI-site (e.g., in an expression vector for the production of light chain (kappa and lambda) immunoglobulin chains). The restriction sites may be located downstream of a nucleic acid molecule encoding the promoter, e.g., the CMVlong promoter, and downstream of the eukaryotic leader peptide of the invention. The sites may be located upstream of a nucleic acid molecule encoding an immunoglobulin constant domain.

Further provided is an expression vector a nucleic acid molecule selected from the group consisting of SEQ ID NO:155, SEQ ID NO:156 and SEQ ID NO:157, i.e., a "truncated" eukaryotic leader peptide. The expression vector comprising the nucleic acid molecule of SEQ ID NO:155 comprises a SfiI-site at its carboxy terminus. The expression vectors comprising the nucleic acid molecule of SEQ ID NO:156 or SEQ ID NO:157 comprise a XhoI-site at their carboxy termini. The vectors may further comprise downstream of the nucleic acid molecule selected from the group consisting of SEQ ID NO:155, SEQ ID NO:156 and SEQ ID NO:157 a XhoI-site (for SEQ ID NO:155) or a NotI-site (for SEQ ID NO:156 and SEQ ID NO:157). They may further comprise a stuffer sequence between the nucleic acid molecule selected from the group consisting of SEQ ID NO:155, SEQ ID NO:156 and SEQ ID NO:157 and the XhoI-site or NotI-site. The nucleic acid molecule selected from the group consisting of SEQ ID NO:155, SEQ ID NO:156 and SEQ ID NO:157, the stuffer sequence and the XhoI-site and NotI-site may be located downstream of a promoter sequence such as a CMVlong promoter sequence. They may be located upstream of an immunoglobulin heavy or light chain constant region. The expression vector may further comprise other expression regulating nucleic acid molecules or other sequences. Examples of suitable expression regulating nucleic acid molecules or other sequences are mentioned above. In an embodiment, the expression vector according to the invention comprises a nucleic acid molecule selected from the group consisting of SEQ ID NO:53, SEQ ID NO:54 and SEQ ID NO:58. These vectors comprise a stuffer sequence.

A host cell comprising at least an expression vector hereof is another aspect of the disclosure. Preferably, the host cell is a human host cell. Other suitable host cells are mentioned above. Furthermore, described is the use of an expression vector hereof and/or a host cell hereof for the production of an immunoglobulin chain and/or molecule.

In yet a further aspect, provided is a method for producing expression vectors. In one embodiment, the expression vector produced is suitable for producing an immunoglobulin heavy chain. The method comprises the steps of: digesting/cutting an expression vector comprising the nucleic acid molecule of SEQ ID NO:155 and downstream thereof an XhoI-site and an immunoglobulin heavy chain constant region with the restriction enzymes SfiI and XhoI, digesting/cutting a phage display vector comprising an immunoglobulin heavy chain variable region with the restriction enzymes SfiI and XhoI, inserting the immunoglobulin heavy chain variable region into the expression vector, and isolating the expression vector. In a specific embodiment, the expression vector comprising the nucleic acid molecule of SEQ ID NO:155 and downstream thereof an XhoI-site and an immunoglobulin heavy chain constant region comprises the nucleic acid molecule of SEQ ID NO:53. In another embodiment, the expression vector produced is suitable for producing an immunoglobulin light chain. The method comprises the steps of digesting/cutting an expression vector comprising the nucleic acid molecule of SEQ ID NO:156 or SEQ ID NO:157 and downstream thereof a NotI-site and an immunoglobulin light chain constant region with the restriction enzymes XhoI and NotI, digesting/cutting a phage display vector comprising an immunoglobulin light chain variable region with the restriction enzymes SalI and NotI, inserting the immunoglobulin light chain variable region into the expression vector, and isolating the expression vector. In a specific embodiment, the expression vector comprising the nucleic acid molecule of SEQ ID NO:156 or SEQ ID NO:157 and downstream thereof an NotI-site and an immunoglobulin light chain constant region comprises the nucleic acid molecule of SEQ ID NO:54 or SEQ ID NO:58, respectively. The phage display vector can be a phagemid but also any other suitable vehicle. It is clear that the digesting/cutting steps can be performed in any order and even concomitantly. It is further to be understood that the variable heavy chain and variable light chain regions in the phage display vector, such as pHEN1 or PDV, are located between the sites SfiI and XhoI and SalI and NotI, respectively. By digesting the display vectors with the respective restriction enzymes the regions are obtained and can be used for insertion into the eukaryotic expression vectors.

Further disclosed is a method for producing an immunoglobulin heavy or light chain, the method comprising the steps of transforming at least one host cell with an expression vector as produced above, culturing the host cell under conditions conducive to the expression of an immunoglobulin chain, and optionally, purifying the immunoglobulin chain from the medium or cellular extract. In an embodiment, the host cell may be transformed with an expression vector suitable for producing a heavy chain and an expression vector suitable for producing a light chain and a complete immunoglobulin may be produced. Many commercially significant proteins are produced by recombinant gene expression in appropriate prokaryotic or eukaryotic host cells. It may be desirable to isolate the expressed protein product after secretion into the culture medium. Secreted proteins are typically soluble and can be separated readily from contaminating host proteins and other cellular components. Method for separation and/or purification are well known in the art.

DETAILED DESCRIPTION

Figure 1:
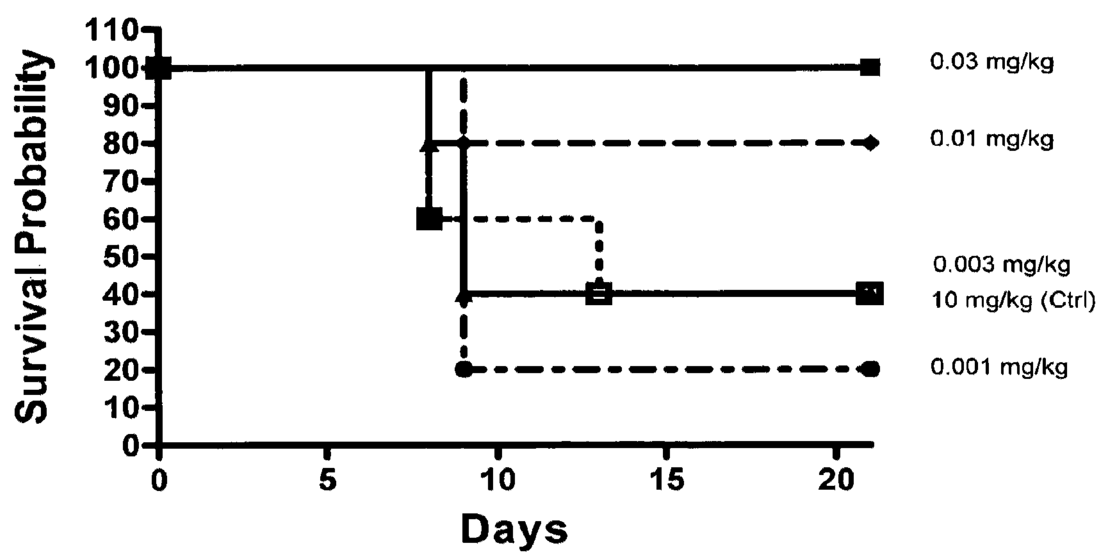
FIG. 1 shows the titration of anti-WNV monoclonal antibody CR4354L4328 in a murine WNV challenge model. From top to bottom titration of anti-WNV monoclonal antibody CR4354L4328 using doses of 0.03, 0.01, 0.003, and 0.001 mg/kg and titration with a control antibody at a concentration of 10 mg/kg are shown. On the X-axis days are shown and on the Y-axis the survival probability (%) is represented.

Here below follow definitions of terms as used herein.

Amino acid sequence. The term "amino acid sequence" (or "amino acid molecule"), as used herein, refers to naturally occurring or synthetic molecules and to a peptide, oligopeptide, polypeptide, or protein sequence.

Binding molecule. As used herein, the term "binding molecule" refers to an intact immunoglobulin including monoclonal antibodies, such as chimeric, humanized or human monoclonal antibodies, or to an antigen-binding and/or variable domain-comprising fragment of an immunoglobulin that competes with the intact immunoglobulin for specific binding to the binding partner of the immunoglobulin, e.g., a host cell protein. Regardless of structure, the antigen-binding fragment binds with the same antigen that is recognized by the intact immunoglobulin. An antigen-binding fragment can comprise a peptide or polypeptide comprising an amino acid sequence of at least two contiguous amino acid residues, at least five contiguous amino acid residues, at least ten contiguous amino acid residues, at least 15 contiguous amino acid residues, at least 20 contiguous amino acid residues, at least 25 contiguous amino acid residues, at least 30 contiguous amino acid residues, at least 35 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least 200 contiguous amino acid residues, or at least contiguous 250 amino acid residues of the amino acid sequence of the binding molecule.

The term "binding molecule," as used herein includes all immunoglobulin classes and subclasses known in the art. Depending on the amino acid sequence of the constant domain of their heavy chains, binding molecules can be divided into the five major classes of intact antibodies: IgA, IgD, IgE, IgG, and IgM, and several of these may be further divided into subclasses (isotypes), e.g., IgA 1, IgA2, IgG 1, IgG2, IgG3 and IgG4.

Antigen-binding fragments include, inter alia, Fab, F(ab'), F(ab')2, Fv, dAb, Fd, complementarity determining region (CDR) fragments, single chain antibodies (scFv), bivalent single chain antibodies, single chain phage antibodies, diabodies, triabodies, tetrabodies, peptide or polypeptides that contain at least a fragment of an immunoglobulin that is sufficient to confer specific antigen binding to the peptide or polypeptide, etc. The above fragments may be produced synthetically or by enzymatic or chemical cleavage of intact immunoglobulins or they may be genetically engineered by recombinant DNA techniques. The methods of production are well known in the art and are described, for example, in Antibodies: A Laboratory Manual, Edited by: E. Harlow and D, Lane (1988), Cold Spring Harbor Laboratory, Cold Spring Harbor, N.Y., which is incorporated herein by reference. A binding molecule or antigen-binding fragment thereof may have one or more binding sites. If there is more than one binding site, the binding sites may be identical to one another or they may be different.

The binding molecule can be a naked or unconjugated binding molecule but can also be part of an immunoconjugate. A naked or unconjugated binding molecule is intended to refer to a binding molecule that is not conjugated, operatively linked or otherwise physically or functionally associated with an effector moiety or tag, such as inter alia a toxic substance, a radioactive substance, a liposome, an enzyme. It will be understood that naked or unconjugated binding molecules do not exclude binding molecules that have been stabilized, multimerized, humanized or in any other way manipulated, other than by the attachment of an effector moiety or tag. Accordingly, all post-translationally modified naked and unconjugated binding molecules are included herewith, including where the modifications are made in the natural binding molecule-producing cell environment, by a recombinant binding molecule-producing cell, and are introduced by the hand of man after initial binding molecule preparation. Of course, the term naked or unconjugated binding molecule does not exclude the ability of the binding molecule to form functional associations with effector cells and/or molecules after administration to the body, as some of such interactions are necessary in order to exert a biological effect. The lack of associated effector group or tag is therefore applied in definition to the naked or unconjugated binding molecule in vitro, not in vivo.

Biological sample. As used herein, the term “biological sample” encompasses a variety of sample types, including blood and other liquid samples of biological origin, solid tissue samples such as a biopsy specimen or tissue cultures, or cells derived thereof and the progeny thereof. The term also includes samples that have been manipulated in any way after their procurement, such as by treatment with reagents, solubilization, or enrichment for certain components, such as proteins or polynucleotides. The term encompasses various kinds of clinical samples obtained from any species, and also includes cells in culture, cell supernatants and cell lysates.

Complementarity determining regions (CDR). The term “complementarity determining regions” as used herein means sequences within the variable regions of binding molecules, such as immunoglobulins, that usually contribute to a large extent to the antigen binding site which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of posttranslational modifications of proteins.

Deletion. The term “deletion,” as used herein, denotes a change in either amino acid or nucleotide sequence in which one or more amino acid or nucleotide residues, respectively, are absent as compared to the parent, often the naturally occurring, molecule.

Expression-regulating nucleic acid molecule. The term “expression-regulating nucleic acid molecule” as used herein refers to polynucleotides necessary for and/or affecting the expression of an operably linked coding sequence in a particular host organism. The expression-regulating nucleic acid molecules, such as inter alia appropriate transcription initiation, termination, promoter, enhancer sequences; repressor or activator sequences; efficient RNA processing signals such as splicing and polyadenylation signals; sequences that stabilize cytoplasmic Mrna; sequences that enhance translation efficiency (e.g., ribosome binding sites); sequences that enhance protein stability; and when desired, sequences that enhance protein secretion, can be any nucleic acid molecule showing activity in the host organism of choice and can be derived from genes encoding proteins, which are either homologous or heterologous to the host organism.

Functional variant. The term “functional variant,” as used herein, refers to a binding molecule that comprises a nucleotide and/or amino acid sequence that is altered by one or more nucleotides and/or amino acids compared to the nucleotide and/or amino acid sequences of the parental binding molecule and that is still capable of competing for binding to the binding partner, e.g., an intracellular host cell protein, with the parental binding molecule. In other words, the modifications in the amino acid and/or nucleotide sequence of the parental binding molecule do not significantly affect or alter the binding characteristics of the binding molecule encoded by the nucleotide sequence or containing the amino acid sequence, i.e., the binding molecule is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis, and may comprise natural as well as unnatural nucleotides and amino acids.

Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cystine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). It will be clear to the skilled artisan that other classifications of amino acid residue families than the one used above can also be employed. Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, inserted, or deleted without abolishing immunological activity may be found using computer programs well known in the art.

A mutation in a nucleotide sequence can be a single alteration made at a locus (a point mutation), such as transition or transversion mutations, or alternatively, multiple nucleotides may be inserted, deleted or changed at a single locus. In addition, one or more alterations may be made at any number of loci within a nucleotide sequence. The mutations may be performed by any suitable method known in the art.

Host. The term “host,” as used herein, is intended to refer to an organism or a cell into which a vector such as a cloning vector or an expression vector has been introduced. The organism or cell can be prokaryotic or eukaryotic. It should be understood that this term is intended to refer not only to the particular subject organism or cell, but to the progeny of such an organism or cell as well. Because certain modifications may occur in succeeding generations due to either mutation or environmental influences, such progeny may not, in fact, be identical to the parent organism or cell, but are still included within the scope of the term “host” as used herein.

Human. The term “human,” when applied to binding molecules as defined herein, refers to molecules that are either directly derived from a human or based upon a human sequence. When a binding molecule is derived from or based on a human sequence and subsequently modified, it is still to be considered human as used throughout the specification. In other words, the term human, when applied to binding molecules is intended to include binding molecules having variable and constant regions derived from human germline immunoglobulin sequences or based on variable or constant regions occurring in a human or human lymphocyte and modified in some form. Thus, the human binding molecules may include amino acid residues not encoded by human germline immunoglobulin sequences, comprise substitutions and/or deletions (e.g., mutations introduced by for instance random or site-specific mutagenesis in vitro or by somatic mutation in vivo). "Based on" as used herein refers to the situation that a nucleic acid molecule may be exactly copied from a template, or with minor mutations, such as by error-prone PCR methods, or synthetically made matching the template exactly or with minor modifications. Semi-synthetic molecules based on human sequences are also considered to be human as used herein.

Insertion. The term "insertion," also known as the term "addition," denotes a change in an amino acid or nucleotide sequence resulting in the addition of one or more amino acid or nucleotide residues, respectively, as compared to the parent sequence.

Isolated. The term "isolated," when applied to binding molecules as defined herein, refers to binding molecules that are substantially free of other proteins or polypeptides, particularly free of other binding molecules having different antigenic specificities, and are also substantially free of other cellular material and/or chemicals. For example, when the binding molecules are recombinantly produced, they are preferably substantially free of culture medium, and when the binding molecules are produced by chemical synthesis, they are preferably substantially free of chemical precursors or other chemicals, i.e., they are separated from chemical precursors or other chemicals that are involved in the synthesis of the protein. The term "isolated" when applied to nucleic acid molecules encoding binding molecules as defined herein, is intended to refer to nucleic acid molecules in which the nucleotides encoding the binding molecules are free of other nucleotides, particularly nucleotides encoding binding molecules that bind binding partners other than host cell proteins. Furthermore, the term "isolated" refers to nucleic acid molecules that are substantially separated from other cellular components that naturally accompany the native nucleic acid molecule in its natural host, e.g., ribosomes, polymerases, or genomic sequences with which it is naturally associated. Moreover, "isolated" nucleic acid molecules, such as Cdna molecules, can be substantially free of other cellular material, or culture medium when produced by recombinant techniques, or substantially free of chemical precursors or other chemicals when chemically synthesized.

Monoclonal antibody. The term "monoclonal antibody" as used herein refers to a preparation of antibody molecules of single molecular composition. A monoclonal antibody displays a single binding specificity and affinity for a particular epitope. Accordingly, the term "human monoclonal antibody" refers to an antibody displaying a single binding specificity that has variable and constant regions derived from or based on human germline immunoglobulin sequences or derived from completely synthetic sequences. The method of preparing the monoclonal antibody is not relevant.

Naturally occurring. The term "naturally occurring" as used herein as applied to an object refers to the fact that an object can be found in nature. For example, a polypeptide or polynucleotide sequence that is present in an organism that can be isolated from a source in nature and which has not been intentionally modified by man in the laboratory is naturally occurring.

Nucleic acid molecule. The term "nucleic acid molecule" as used herein refers to a polymeric form of nucleotides and includes both sense and anti-sense strands of RNA, Cdna, genomic DNA, and synthetic forms and mixed polymers of the above. A nucleotide refers to a ribonucleotide, deoxynucleotide or a modified form of either type of nucleotide. The term also includes single- and double-stranded forms of DNA. In addition, a polynucleotide may include either or both naturally occurring and modified nucleotides linked together by naturally occurring and/or unnaturally occurring nucleotide linkages. The nucleic acid molecules may be modified chemically or biochemically or may contain unnatural or derivatized nucleotide bases, as will be readily appreciated by those of skill in the art. Such modifications include, for example, labels, methylation, substitution of one or more of the naturally occurring nucleotides with an analogue, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hair-pinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid molecule encompasses its complement unless otherwise specified. Thus, a reference to a nucleic acid molecule having a particular sequence should be understood to encompass its complementary strand, with its complementary sequence. The complementary strand is also useful, e.g., for anti-sense therapy, hybridization probes and PCR primers.

Operably linked. The term "operably linked" refers to two or more nucleic acid molecule elements that are usually physically linked and are in a functional relationship with each other. For instance, a promoter is operably linked to a coding sequence, if the promoter is able to initiate or regulate the transcription or expression of a coding sequence, in which case the coding sequence should be understood as being "under the control of" the promoter.

Pharmaceutically acceptable excipient. By "pharmaceutically acceptable excipient" is meant any inert substance that is combined with an active molecule such as a drug, agent, or binding molecule for preparing an agreeable or convenient dosage form. The "pharmaceutically acceptable excipient" is an excipient that is non-toxic to recipients at the dosages and concentrations employed, and is compatible with other ingredients of the formulation comprising the drug, agent or binding molecule.

Specifically Binding. The term "specifically binding," as used herein, in reference to the interaction of a binding molecule, e.g., an antibody, and its binding partner, e.g., an antigen, means that the interaction is dependent upon the presence of a particular structure, e.g., an antigenic determinant or epitope, on the binding partner. In other words, the antibody preferentially binds or recognizes the binding partner even when the binding partner is present in a mixture of other molecules or organisms. The binding may be mediated by covalent or non-covalent interactions or a combination of both. In yet other words, the term "specifically binding" means immunospecifically binding to an antigen or a fragment thereof and not immunospecifically binding to other antigens. A binding molecule that immunospecifically binds to an antigen may bind to other peptides or polypeptides with lower affinity as determined by, e.g., radioimmunoassays (RIA), enzyme-linked immunosorbent assays (ELISA), BIACORE, or other assays known in the art. Binding molecules or fragments thereof that immunospecifically bind to an antigen may be cross-reactive with related antigens. Preferably, binding molecules or fragments thereof that immunospecifically bind to an antigen do not cross-react with other antigens.

Substitutions. A "substitution," as used herein, denotes the replacement of one or more amino acids or nucleotides by different amino acids or nucleotides, respectively.

Therapeutically effective amount. The term "therapeutically effective amount" refers to an amount of the binding molecule as defined herein that is effective for preventing, ameliorating and/or treating a condition resulting from a viral infection.

Treatment. The term "treatment" refers to therapeutic treatment as well as prophylactic or preventative measures to cure or halt or at least retard disease progress. Those in need of treatment include those already inflicted with a condition resulting from a viral infection as well as those in which a viral infection is to be prevented. Subjects partially or totally recovered from a viral infection might also be in need of treatment. Prevention encompasses inhibiting or reducing the spread of a virus or inhibiting or reducing the onset, development or progression of one or more of the symptoms associated with a viral infection.

Vector. The term "vector" denotes a nucleic acid molecule into which a second nucleic acid molecule can be inserted for introduction into a host where it will be replicated, and in some cases expressed. In other words, a vector is capable of transporting a nucleic acid molecule to which it has been linked. Cloning as well as expression vectors are contemplated by the term "vector," as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. A vector containing a second nucleic acid molecule is introduced into a cell by transformation, transfection, or by making use of viral entry mechanisms. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome.

EXAMPLES

To further describe the invention, the following illustrative examples are provided.

Example 1

Construction of a scFv Phage Display Library Using RNA Extracted from Peripheral Blood of WNV Convalescent Donors From three convalescent WNV patients samples of blood were taken 1, 2 and 3 months after infection. Peripheral blood leukocytes were isolated by centrifugation and the blood serum was saved and frozen at −80° C. All donors at all time points had high titers of neutralizing antibodies to WNV as determined using a virus neutralization assay. Total RNA was prepared from the cells using organic phase separation and subsequent ethanol precipitation. The obtained RNA was dissolved in RNAse free water and the concentration was determined by OD 260 nm measurement. Thereafter, the RNA was diluted to a concentration of 100 ng/μl. Next, 1 μg of RNA was converted into cDNA as follows: To 10 μl total RNA, 13 μl DEPC-treated ultrapure water and 1 μl random hexamers (500 ng/μl) were added and the obtained mixture was heated at 65° C. for 5 minutes and quickly cooled on wet-ice. Then, 8 μl 5× First-Strand buffer, 2 μl dNTP (10 mM each), 2 μl DTT (0.1 M), 2 μl Rnase-inhibitor (40 U/μl) and 2 μl Superscript™ III MMLV reverse transcriptase (200 U/μl) were added to the mixture, incubated at room temperature for 5 minutes and incubated for 1 hour at 50° C. The reaction was terminated by heat inactivation, i.e., by incubating the mixture for 15 minutes at 75° C.

The obtained cDNA products were diluted to a final volume of 200 μl with DEPC-treated ultrapure water. The OD 260 nm of a 50 times diluted solution (in 10 mM Tris buffer) of the dilution of the obtained cDNA products gave a value of 0.1.

For each donor 5 to 10 μl of the diluted cDNA products were used as template for PCR amplification of the immunoglobulin gamma heavy chain family and kappa or lambda light chain sequences using specific oligonucleotide primers (see Tables 1-6). PCR reaction mixtures contained, besides the diluted cDNA products, 25 pmol sense primer and 25 pmol anti-sense primer in a final volume of 50 μl of 20 mM Tris-HCl (pH 8.4), 50 mM KCl, 2.5 mM $MgCl_2$, 250 μM dNTPs and 1.25 units Taq polymerase. In a heated-lid thermal cycler having a temperature of 96° C., the mixtures obtained were quickly melted for 2 minutes, followed by 30 cycles of: 30 seconds at 96° C., 30 seconds at 60° C. and 60 seconds at 72° C.

In a first round amplification, each of seventeen light chain variable region sense primers (eleven for the lambda light chain (see Table 1) and six for the kappa light chain (see Table 2) were combined with an anti-sense primer recognizing the C-kappa called HuCk 5'-ACACTCTCCCCTGTTGAAGCTCTT-3' (see SEQ ID NO:37) or C-lambda constant region HuCλ2 5'-TGAACATTCTGTAGGGGCCACTG-3' (see SEQ ID NO:38) and HuCλ7 5'-AGAGCATTCTGCAGGGGCCACTG-3' (see SEQ ID NO:39) (the HuCλ2 and HuCλ7 anti-sense primers were mixed to equimolarity before use), yielding 4 times 17 products of about 600 base pairs. These products were purified on a 2% agarose gel and isolated from the gel using Qiagen gel-extraction columns. 1/10 of each of the isolated products was used in an identical PCR reaction as described herein using the same seventeen sense primers, whereby each lambda light chain sense primer was combined with one of the three Jlambda-region specific anti-sense primers and each kappa light chain sense primer was combined with one of the five Jkappa-region specific anti-sense primers. The primers used in the second amplification were extended with restriction sites (see Table 3) to enable directed cloning in the phage display vector PDV-C06 (see SEQ ID NO:40). This resulted in 4 times 63 products of approximately 350 base pairs that were pooled to a total of 10 fractions. This number of fractions was chosen to maintain the natural distribution of the different light chain families within the library and not to over or under represent certain families. The number of alleles within a family was used to determine the percentage of representation within a library (see Table 4). In the next step, 2.5 μg of pooled fraction and 100 μg PDV-C06 vector were digested with SalI and NotI and purified from gel. Thereafter, a ligation was performed overnight at 16° C. as follows. To 500 ng PDV-C06 vector 70 ng pooled fraction was added in a total volume of 50 μl ligation mix containing 50 mM Tris-HCl (pH 7.5), 10 mM $MgCl_2$, 10 mM DTT, 1 mM ATP, 25 μg/ml BSA and 2.5 μl T4 DNA Ligase (400 U/μl). This procedure was followed for each pooled fraction. The ligation mixes were purified by phenol/chloroform, followed by a chloroform extraction and ethanol precipitation, methods well known to the skilled artisan. The DNA obtained was dissolved in 50 μl ultrapure water and per ligation mix two times 2.5 μl aliquots were electroporated into 40 μl of TG1 competent *E. coli* bacteria according to the manufacturer's protocol (Stratagene). Transformants were grown overnight at 37° C. in a total of 30 dishes (three dishes per pooled fraction; dimension of dish: 240 mm×240 mm) containing 2TY agar supplemented with 50 μg/ml ampicillin and 4.5% glucose. A (sub)library of variable light chain regions was obtained by scraping the transformants from the agar plates. This (sub) library was directly used for plasmid DNA preparation using a QIAGEN™ QIAFilter MAXI prep kit.

For each donor the heavy chain immunoglobulin sequences were amplified from the same cDNA preparations in a similar two round PCR procedure and identical reaction parameters as described herein for the light chain regions with the proviso that the primers depicted in Tables 5 and 6 were used. The first amplification was performed using a set of nine sense directed primers (see Table 5; covering all families of heavy chain variable regions) each combined with an IgG specific constant region anti-sense primer called HuCIgG 5'-GTC CAC CTT GGT GTT GCT GGG CTT-3' (SEQ ID NO:41) yielding four times nine products of about 650 base pairs. These products were purified on a 2% agarose gel and isolated from the gel using Qiagen gel-extraction columns. 1/10 of each of the isolated products was used in an identical PCR reaction as described herein using the same nine sense primers, whereby each heavy chain sense primer was combined with one of the four JH-region specific anti-sense primers. The primers used in the second round were extended with restriction sites (see Table 6) to enable directed cloning in the light chain (sub)library vector. This resulted per donor in 36 products of approximately 350 base pairs. These products were pooled for each donor per used (VH) sense primer into nine fractions. The products obtained were purified using Qiagen PCR purification columns. Next, the fractions were digested with SfiI and XhoI and ligated in the light chain (sub)library vector, which was cut with the same restriction enzymes, using the same ligation procedure and volumes as described herein for the light chain (sub)library. Alternatively, the fractions were digested with NcoI and XhoI and ligated in the light chain vector, which was cut with the same restriction enzymes, using the same ligation procedure and volumes as described herein for the light chain (sub)library. Ligation purification and subsequent transformation of the resulting definitive library was also performed as described herein for the light chain (sub)library and at this point the ligation mixes of each donor were combined per VH pool. The transformants were grown in 27 dishes (three dishes per pooled fraction; dimension of dish: 240 mm×240 mm) containing 2TY agar supplemented with 50 μg/ml ampicillin and 4.5% glucose. All bacteria were harvested in 2TY culture medium containing 50 μg/ml ampicillin and 4.5% glucose, mixed with glycerol to 15% (v/v) and frozen in 1.5 ml aliquots at −80° C. Rescue and selection of each library were performed as described below.

Example 2

Selection of Phages Carrying Single Chain Fv Fragments Specifically Recognizing WNV Envelope (E) Protein Antibody fragments were selected using antibody phage display libraries, general phage display technology and MABSTRACT® technology, essentially as described in U.S. Pat. No. 6,265,150 and in WO 98/15833 (both of which are incorporated by reference herein). The antibody phage libraries used were two different semi-synthetic scFv phage libraries (JK1994 and WT2000) and the immune library prepared as described in Example 1. The first semi-synthetic scFv phage library (JK1994) has been described in de Kruif et al., 1995b, the second one (WT2000) was build essentially as described in de Kruif et al., 1995b. Briefly, the library has a semi-synthetic format whereby variation was incorporated in the heavy and light chain V genes using degenerated oligonucleotides that incorporate variation within CDR regions. Only VH3 heavy chain genes were used, in combination with kappa- and lambda light chain genes. CDR1 and CDR3 of the heavy chain and CDR3 of the light chain were recreated synthetically in a PCR-based approach similar as described in de Kruif et al., 1995b. The thus created V region genes were cloned sequentially in scFv format in a phagemid vector and amplified to generate a phage library as described before. Furthermore, the methods and helper phages as described in WO 02/103012 (incorporated by reference herein) were used herein. For identifying phage antibodies recognizing WNV E protein, phage selection experiments were performed using whole WNV (called strain USA99b or strain 385-99) inactivated by gamma irradiation (50 Gy for 1 hour), recombinantly expressed WNV E protein (strain 382-99), and/or WNV-like particles expressing WNV E protein (strain 382-99) on their surface.

The recombinantly expressed E protein was produced as follows. The nucleotide sequence coding for the preM/M-protein and the full length E protein of WNV strain 382-99 (see SEQ ID NO:42 for the amino acid sequence of a fusion protein comprising both WNV polypeptides) was synthesized. Amino acids 1-93 of SEQ ID NO:42 constitute the WNV preM-protein, amino acids 94-168 of SEQ ID NO:42 constitute the WNV M-protein, amino acids 169-669 of SEQ ID NO:42 constitute the WNV E protein (the soluble WNV E protein (ectodomain) constitutes amino acids 169-574 of SEQ ID NO:42, while the WNV E protein stem and transmembrane region constitutes amino acids 575-669 of SEQ ID NO:42) The synthesized nucleotide sequence was cloned into the plasmid pAdapt and the plasmid obtained was called pAdapt.WNV.prM-E (FL).

To produce a soluble secreted form of the E protein a construct was made lacking the transmembrane spanning regions present in the final 95 amino acids at the carboxyl terminal of the full length E protein (truncated form). For that purpose the full length construct pAdapt.WNV.prM-E (FL) was PCR amplified with the primers CMV-Spe (SEQ ID NO:43) and WNV-E-95 REV (SEQ ID NO:44) and the fragment obtained was cloned into the plasmid pAdapt.myc.his to create the plasmid called pAdapt.WNV-95. Next, the region coding for the preM-protein, the truncated E protein, the Myc tag and His tag were PCR amplified with the primers clefsmaquwnv (SEQ ID NO:45) and reverse WNVmychis (SEQ ID NO:46) and cloned into the vector pSyn-C03 containing the HAVT20 leader peptide using the restriction sites EcoRI and SpeI. The expression construct obtained, pSyn-C03-WNV-E-95, was transfected into 90% confluent HEK293T cells using lipofectamine according to the manufacturer's instructions. The cells were cultured for 5 days in serum-free ultra CHO medium, then the medium was harvested and purified by passage over HisTrap chelating columns (Amersham Bioscience) pre-charged with nickel ions. The truncated E protein was eluted with 5 ml of 250 mM imidazole and further purified by passage over a G-75 gel filtration column equilibrated with phosphate buffered saline (PBS). Fractions obtained were analyzed by SDS-PAGE analysis and Western blotting using the WNV-E protein specific murine antibody 7H2 (Biorelience, see Beasley and Barrett 2002). Three 5 ml fractions containing a single band of ~45 kDa that was immunoreactive with antibody 7H2 were aliquoted and stored at −20° C. until further use. The protein concentration was determined by OD 280 nm.

WNV-like particles were produced as follows. The construct pSyn-C03-WNV-E-95 described herein and pcDNA3.1 (Invitrogen) were digested with the restriction endonucleases MunI and XbaI and the construct pAdapt.WNV.prM-E (FL) described herein was digested with the restriction endonucleases ClaI and XbaI. The resulting fragments were combined in a three-point ligation to produce the construct pSyn-H-preM/E FL. This construct contained the full length E protein and expressed the two structural WNV proteins, protein M and E, required for assembly of an enveloped virion. The construct was transfected into 70% confluent HEK293T cells using lipofectamine according to the manufacturer's instructions. The cells were cultured for three days in serum-free ultra CHO medium, then the medium was harvested, layered on to a 30% glycerol solution at a 2:1 ratio and pelleted by centrifugation for 2 hours at 120,000*g at 4° C. The WNV-like particles were resuspended in PBS, aliquoted and stored at −80° C. Aliquots were analyzed by SDS-PAGE analysis and Western blotting using the WNV E protein specific murine antibody 7H2 (Biorelience).

Before inactivation, whole WNV was purified by pelleting through a 30% glycerol solution as described herein for WNV-like particles. The purified WNV was resuspended in 10 mM Tris/HCl pH 7.4 containing 10 mM EDTA and 200 mM NaCl, the obtained preparation was kept on dry ice during inactivation, tested for infectivity and stored at −80° C. in small aliquots. Aliquots were analyzed by SDS-PAGE analysis and Western blotting using the WNV E protein specific murine antibody 7H2 (Biorelience).

Whole inactivated WNV, WNV-like particles or recombinantly expressed soluble E protein were diluted in PBS. 2-3 ml of the preparation was added to MaxiSorp™ Nunc-Immuno Tubes (Nunc) and incubated overnight at 4° C. on a rotating wheel. An aliquot of a phage library (500 μl, approximately $10^{13}$ cfu, amplified using CT helper phage (see WO 02/103012)) was blocked in blocking buffer (2% Protifar in PBS) for 1-2 hours at room temperature. The blocked phage library was added to the immunotubes, incubated for 2 hours at room temperature, and washed with wash buffer (0.1% v/v Tween-20 in PBS) to remove unbound phages. Bound phages were eluted from the antigen by incubation with 1 ml of 50 mM Glycine-HCl pH 2.2 for 10 minutes at room temperature. Subsequently, the eluted phages were mixed with 0.5 ml of 1 M Tris-HCl pH 7.5 to neutralize the pH. This mixture was used to infect 5 ml of an XL1-Blue *E. coli* culture that had been grown at 37° C. to an OD 600 nm of approximately 0.3. The phages were allowed to infect the XL1-Blue bacteria for 30 minutes at 37° C. Then, the mixture was centrifuged for 10 minutes at 3200*g at room temperature and the bacterial pellet was resuspended in 0.5 ml 2-trypton yeast extract (2TY) medium. The obtained bacterial suspension was divided over two 2TY agar plates supplemented with tetracyclin, ampicillin and glucose. After overnight incubation of the plates at 37° C., the colonies were scraped from the plates and used to prepare an enriched phage library, essentially as described by De Kruif et al. (1995a) and WO 02/103012. Briefly, scraped bacteria were used to inoculate 2TY medium containing ampicillin, tetracycline and glucose and grown at a temperature of 37° C. to an OD 600 nm of ~0.3. CT helper phages were added and allowed to infect the bacteria after which the medium was changed to 2TY containing ampicillin, tetracycline and kanamycin. Incubation was continued overnight at 30° C. The next day, the bacteria were removed from the 2TY medium by centrifugation after which the phages in the medium were precipitated using polyethylene glycol (PEG) 6000/NaCl. Finally, the phages were dissolved in 2 ml of PBS with 1% bovine serum albumin (BSA), filter-sterilized and used for the next round of selection.

Typically, two rounds of selections were performed before isolation of individual phage antibodies. After the second round of selection, individual *E. coli* colonies were used to prepare monoclonal phage antibodies. Essentially, individual colonies were grown to log-phase in 96 well plate format and infected with CT helper phages after which phage antibody production was allowed to proceed overnight. The produced phage antibodies were PEG/NaCl-precipitated and filter-sterilized and tested in ELISA for binding to WNV-like particles purified as described supra.

Example 3

Validation of the WNV Specific Single Chain Phage Antibodies

Selected single chain phage antibodies that were obtained in the screens described herein were validated in ELISA for specificity, i.e., binding to WNV E protein, whole inactivated WNV and WNV-like particles, all purified as described supra. For this purpose, whole inactivated WNV, the WNV E protein, or WNV-like particles were coated to Maxisorp™ ELISA plates. In addition, whole inactivated rabies virus was coated onto the plates as a control. After coating, the plates were blocked in PBS containing 1% Protifar for 1 hour at room temperature. The selected single chain phage antibodies were incubated for 15 minutes in an equal volume of PBS containing 1% Protifar to obtain blocked phage antibodies. The plates were emptied, and the blocked single chain phage antibodies were added to the wells. Incubation was allowed to proceed for one hour, the plates were washed in PBS containing 0.1% v/v Tween-20 and bound phage antibodies were detected (using OD 492 nm measurement) using an anti-M13 antibody conjugated to peroxidase. As a control, the procedure was performed simultaneously without single chain phage antibody, with a negative control single chain phage antibody directed against rabies virus glycoprotein (antibody called SC02-447), with a negative control single chain phage antibody directed against SARS-CoV (antibody called SC03-014) and a positive control single chain phage antibody directed against rabies virus. As shown in Table 7, the selected phage antibodies called SC04-348 and SC04-354 displayed significant binding to immobilized whole inactivated WNV and WNV-like particles. Both single chain phage antibodies were selected when WNV-like particles were used in the first and second round of selection. When the ELISA was performed with recombinantly expressed purified soluble WNV E protein prepared as described supra or rabies virus, the single chain phage antibodies SC04-348 and SC04-354 did not bind, suggesting they either bind to a region not present in the truncated soluble E protein, bind to an unrelated protein on the virion surface, do not bind to the monomeric form of the E protein or do not bind because of the phage antibody format.

Example 4

Characterization of the WNV Specific scFvs

From the selected specific single chain phage antibody (scFv) clones plasmid DNA was obtained and nucleotides were determined according to standard techniques. The nucleotides of the scFvs (including restriction sites for cloning) called SC04-348 and SC04-354 are shown in SEQ ID NO:25 and SEQ ID NO:27, respectively. The amino acid sequences of the scFvs called SC04-348 and SC04-354 are shown in SEQ ID NO:26 and SEQ ID NO:28, respectively.

The VH and VL gene identity (see I. M. Tomlinson, S. C. Williams, O. Ignatovitch, S. J. Corbett, G. Winter. V-BASE Sequence Directory. Cambridge United Kingdom: MRC Centre for Protein Engineering (1997)) and heavy chain CDR3 sequences of the scFvs specifically binding WNV are depicted in Table 8. Table 9 shows the other CDR regions of the WNV specific scFvs.

Example 5

Construction of Fully Human Immunoglobulin Molecules (Human Monoclonal Anti-WNV Antibodies) from the Selected Anti-WNV Single Chain Fvs Heavy and light chain variable regions of the scFv called SC04-354 was PCR-amplified using oligonucleotides to append restriction sites and/or sequences for expression in the IgG expression vectors pSyn-C18-HCγ1 (see SEQ ID NO:47) and pSyn-C04-Cλ (see SEQ ID NO:48). The heavy chain variable region of the scFv called SC04-354 was cloned into the vector pSyn-C18-HCγ1; the light chain variable region of the scFv called SC04-354 was cloned into the vector pSyn-C04-Cλ. The VL lambda gene was first amplified using the following oligonucleotides set: SC04-354, 5L-C (SEQ ID NO:49) and sy3L-Cmod (SEQ ID NO:50) and the PCR product cloned into vector pSyn-C04-Cλ. Nucleotide sequence for the construct was verified according to standard techniques known to the skilled artisan. VH gene was first amplified using the following oligonucleotide set: SC04-354, 5H-A (SEQ ID NO:51) and sy3H-A (SEQ ID NO:52). Thereafter, the PCR product was cloned into vector pSyn-C18-HCγ1 and nucleotide sequence was verified according to standard techniques known to the skilled person in the art.

Heavy and light chain variable region of the scFv called SC04-348 was cloned directly by restriction digest for expression in the IgG expression vectors pIg-C911-HCgammal (see SEQ ID NO:53) and pIg-C909-Ckappa (see SEQ ID NO:54). The heavy chain variable regions of the scFv called SC04-348 was cloned into the vector pIg-C911-HCgammal by restriction digest using the enzymes SfiI and XhoI and the light chain variable region of the scFv called SC04-348 was cloned into the vector pIg-C909-Ckappa by restriction digest using the enzymes SalI and NotI. Thereafter the nucleotide sequence was verified according to standard techniques known to the person skilled in the art.

The resulting expression constructs pgG104-348C911 and pgG104-354C18 encoding the human IgG1 heavy chains and pgG104-348C909 and pgG104-354C04 encoding the human IgG1 light chains were transiently expressed in combination in 293T cells and supernatants containing human IgG1 antibodies were obtained. The nucleotides of the heavy chains of the antibodies called CR4348 and CR4354 are shown in SEQ ID NOS:29 and 31, respectively. The amino acid sequences of the heavy chains of the antibodies called CR4348 and CR4354 are shown in SEQ ID NOS:30 and 32, respectively. The nucleotides of the light chain of antibodies CR4348 and CR4354 are shown in SEQ ID NOS:33 and 35, respectively. The amino acid sequences of the light chain of antibodies CR4348 and CR4354 are shown in SEQ ID NOS:34 and 36, respectively. A person skilled in the art can determine the variable regions of the heavy and light chains of the above antibodies by following Kabat et al. (1991) as described in Sequences of Proteins of Immunological Interest. Alternatively, batches of greater than 1 mg of each antibody were produced and purified using standard procedures. The antibodies were then titrated on a fixed concentration of irradiated West Nile virus and tested in ELISA as described herein. The results are shown in Table 10. As a negative control an anti-rabies virus antibody was used. Both antibodies showed binding to the virus in a dose dependent manner. The antibodies were also able to bind WNV-like particles (data not shown).

Additionally, binding of CR4348 and CR4354L4328 (an optimized variant of antibody CR4354; see Example 8 for selection of this variant) to viral material was tested in a capture ELISA. For this purpose, CR4348, CR4283 (an anti-WNV monoclonal antibody; positive control for the inactivated WNV and WNV-like particle and negative control for rabies virus), CR4354L4328 and CR4104 (an anti-rabies virus monoclonal antibody; positive control for rabies virus and negative control for the inactivated WNV and WNV-like particle) were coated in a concentration of 5 μg/ml to Maxisorp™ ELISA plates. After coating, the plates were blocked in PBS containing 1% Protifar for 1 hour at room temperature. Next, a serial dilution of whole inactivated WNV, WNV-like particles, or rabies virus (BPL-inactivated) was performed in PBS/protifar in a volume of 100 μl until a dilution of 1/2048 was reached. The viral material was allowed to incubate for 1 hour at room temperature. The plates were emptied, and washed 3 times with 100 μl PBS containing 0.1% v/v Tween-20. Next, the mouse monoclonal antibody 7H2 (Bioreliance) was added at a concentration of 1 μg/ml (diluted in PBS/protifar) for detection of the inactivated WNV and WNV-like particles. Moreover, the mouse monoclonal antibody 1112 directed against rabies virus was added in a 1:1000 dilution (diluted in PBS/protifar) for detection of rabies virus. Bound monoclonal antibodies were detected by OD 492 nm measurement with an anti-mouse antibody conjugated to peroxidase (Jackson) in a 1:2000 dilution in PBS/protifar. CR4348, CR4283 and CR4354L4328 showed a very high binding to WNV-like particles with CR4348 binding twice as efficient compared to CR4354L4328 (data not shown). Moreover, CR4348, CR4283 and CR4354L4328 also bound to WNV (data not shown). When the capture ELISA was performed with rabies virus, binding was observed with the positive control CR4104 and antibody CR4348. No binding of antibody CR4354L4328 was observed (data not shown).

Example 6

In Vitro Neutralization of WNV by WNV Specific scFvs and IgGs (Virus Neutralization Assay)

In order to determine whether the selected scFvs are capable of blocking WNV infection, in vitro virus neutralization assays (VNA) are performed. The VNA are performed on Vero cells (ATCC CCL 81). The WNV strain 385-99 which is used in the assay is diluted to a titer of $4\times10^3$ $TCID_{50}$/ml (50% tissue culture infective dose per ml), with the titer calculated according to the method of Spearman and Kaerber. The scFv preparations are serially two-fold-diluted in PBS starting from 1:2 (1:2-1:1024). 25 μl of the respective scFv dilution is mixed with 25 μl of virus suspension (100 $TCID_{50}$/25 μl) and incubated for one hour at 37° C. The suspension is then pipetted twice in triplicate into 96-well plates. Next, 50 μl of a freshly trypsinized and homogenous suspension of Vero cells (1:3 split of the confluent cell monolayer of a T75-flask) resuspended in DMEM with 10% v/v fetal calf serum and antibiotics is added. The inoculated cells are cultured for three to four days at 37° C. and observed daily for the development of cytopathic effect (CPE). CPE is compared to the positive control (WNV inoculated cells) and negative controls (mock-inoculated cells or cells incubated with scFV only). The complete absence of CPE in an individual cell culture is defined as protection (=100% titer reduction). The serum dilution giving protection in 50% percent of wells (i.e., three out of six wells) is defined as the 50% neutralizing antibody titer. The murine-neutralizing antibody 7H2 (Biorelience) is used as a positive control in the assay. A 50% neutralization titer of ≤1:4 (meaning the antibody is diluted four times or more) is regarded as specific evidence of neutralizing activity of the scFv against WNV.

Alternatively, in vitro virus neutralization assays (VNA) were performed in order to determine whether the anti-WNV IgGs were capable of blocking WNV infection. The VNA were performed essentially as described for scFvs, with the proviso that the serum dilution giving protection in 66% percent of wells (i.e., two out of three wells) was defined as the 66% neutralizing antibody titer and a 66% neutralization titer of ≤1:2 was regarded as specific evidence of neutralizing activity of the IgG against WNV.

Supernatants containing the human anti-WNV antibodies called CR4348 and CR354 were expressed as described in Example 5 and subjected to the aforementioned VNA. All antibodies had a neutralizing titer≤1:2. The potency of the antibodies (in μg/ml) is given in Table 11.

Example 7

In Vivo Protection by Monoclonal Antibodies from Lethal WNV Infection in a Murine Challenge Model A murine challenge model was adapted from the literature (see Ben-Nathan et al. 2003; Beasley et al. 2002; Wang et al. 2001). In Ben-Nathan et al. (2003) four-week-old BALB/c mice were used and the animals were inoculated intraperitoneally (i.p.) with 20-times the viral dose resulting in 50% survival ($LD_{50}$) of WNV strain ISR52 ($LD_{50}$ was equivalent to 5 pfu). Under this dosing mice succumbed to infection six to seven days after inoculation and reached 100% mortality after 11 days. In another study, the WNV strain USA99 (used in the experiments described here) was shown to have an $LD_{50}$ of 0.5 pfu. This is ten-fold lower than the $LD_{50}$ of ISR52, which may indicate a higher degree of neuro-invasiveness for this viral strain or differences associated with the mouse strain used (see Beasley et al. 2002).

To determine the i.p., $LD_{50}$ of USA99 in four week BALB/c mice, animals (five per group) were injected with USA99 at $TCID_{50}$ (tissue culture infectious dose) of 100, 30, 10, 3, 1, 0.3, 0.1, 0.03 the 50% in two separate experiments. The $LD_{50}$ calculated from the first experiment was 5.75 $TCID_{50}$ and from the second experiment 13.25 $TCID_{50}$. For the calculation of the viral dose in further experiments the average of the two experiments, i.e., 9.5 $TCID_{50}$, was calculated by probit regression analysis.

The protective capacity of the in vitro neutralizing antibodies CR4348 and CR4354 was tested in the in vivo model. Purified antibodies were injected i.p. into four week BALB/c mice (five animals per group) at a concentration of 15 mg/kg. After 24 hours the WNV strain USA99 was injected i.p. at a dose of 20-times the $LD_{50}$ calculated. The animals were observed for signs of disease over 21 days and sacrificed when symptoms of encephalitis were evident. In the model unprotected animals generally succumbed to infection between day 8 and day 10.

Table 12 shows that the two antibodies, CR4348 and CR4354, are 100% protective in vivo at the dose of 15 mg/kg. The positive control antibody 7H2 (an anti-WNV murine monoclonal) was fully protective and the negative control antibody (binding an irrelevant antigen) showed no protection in the experiment.

To establish a dose protection relationship, the protective antibody CR4348 was titrated in the mouse model using doses of 10, 3, 1, 0.3, 0.1, 0.03, 0.01, 0.003 and 0.001 mg/kg. Using the same doses, an optimized variant of antibody CR4354, i.e., CR4354L4328 (see Example 8 for selection of this variant), was titrated in the mouse model. A negative control antibody binding an irrelevant antigen was included as a control at a dose 10 mg/kg.

FIG. 1 shows that the antibody CR4354L4328 is 100% protective at a dose of 0.03 mg/kg. The doses 10, 3, 1, 0.3 and 0.1 mg/kg were also 100% protective (data not shown). FIG. 1 also shows that there is a direct correlation between dose and protective capacity. The 50% protective dose calculated by probit regression analysis is 0.003 mg/kg.

Figure 2:
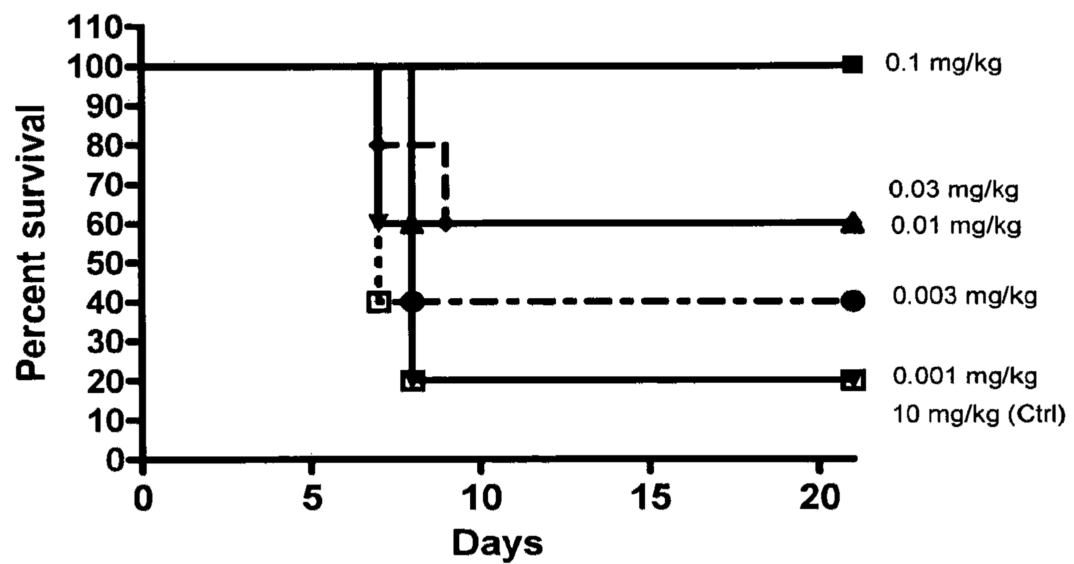
FIG. 2 shows the titration of anti-WNV monoclonal antibody CR4348 in a murine WNV challenge model. From top to bottom titration of anti-WNV monoclonal antibody CR4348 using doses of 0.1, 0.03, 0.01, 0.003, and 0.001 mg/kg and titration with a control antibody at a concentration of 10 mg/kg are shown. On the X-axis days are shown and on the Y-axis the survival probability (%) is represented.

FIG. 2 shows that the antibody CR4348 is 100% protective at a dose of 0.1 mg/kg. The doses 10, 3, 1 and 0.3 mg/kg were also 100% protective (data not shown). FIG. 2 further shows that there is a direct correlation between dose and protective capacity. The 50% protective dose calculated by probit regression analysis is 0.006 mg/kg.

The titration data of the antibodies were compared by probit regression analysis. Values for the Pearson Goodness-of-Fit test (Chi Square=10.38, DF=30, p=1.00) demonstrated that the model was valid and the results of the Parallelism Test (Chi Square=3.47, DF=3, p=0.324) meant that the curves could be reliably compared. The values for the 50% protective dose and 95% protective dose are summarized in Table 13.

Example 8

Selection of Optimized Variants of Neutralizing Monoclonal Antibody CR4354

Monoclonal antibody CR4354 showing to have in vitro WNV-neutralizing activity and being 100% protective in vivo was selected for improving potency and affinity. This was done based on the following hypothesis. The specificity of CR4354 (as determined by the CDR3 region on the heavy chain variable chain) is one that targets a potent neutralizing epitope of WNV, but the light chain that is randomly paired with the heavy chain (through the phage display process) does not optimally recreate the original antigen binding site. Pairing with a more optimally mutated light chain might improve the "fit" of the antibody-binding pocket for the cognate antigen. Thus, replacement of the light chain might be a way of improving the potency and affinity of the antibody.

Analysis of the heavy and light chain of antibody CR4354 showed that they belong to the VH1 1-46 (DP-7) and Vlambda 1 (1c-V1-16) gene family, respectively. Further analysis of WNV specific scFvs selected from the WNV immune library as described in Example 1 revealed 5 scFvs, i.e., SC04-261, SC04-267, SC04-328, SC04-335 and SC04-383 (these scFvs were not included in Table 8), that had light chains having the same gene family as the light chain of CR4354. None of the scFvs or their respective IgGs showed WNV-neutralizing activity. Each of these light chains contained mutations in the CDR and framework regions away from the germline indicating that they had been modified as part of the natural affinity maturation process.

In short, the construction of the antibodies went as follows. CR4354 was prepared as described in Example 5. Heavy chain variable regions of the scFvs called SC04-261, SC04-267, SC04-328 and SC04-335 were PCR-amplified using oligonucleotides to append restriction sites and/or sequences for expression in the IgG expression vector pSyn-C18-HCγ1 and cloned into this vector. Amplification was done using the following oligonucleotide sets: SC04-261, 5H-A (SEQ ID NO:51) and sy3H-A (SEQ ID NO:52); SC04-267, 5H-A (SEQ ID NO:51) and sy3H-C (SEQ ID NO:55); SC04-328, 5H-A (SEQ ID NO:51) and sy3H-A (SEQ ID NO:52); and SC04-335, 5H-C (SEQ ID NO:56) and sy3H-A (SEQ ID NO:52).

The heavy chain variable region of the scFv called SC04-383 was cloned by restriction digest using the enzymes SfiI and XhoI in the IgG expression vector pIg-C911-HCgammal.

The light chain variable region of the scFv called SC04-267 was first amplified using the oligonucleotides SC04-267, 5L-C (SEQ ID NO:49) and sy3L-Amod (SEQ ID NO:57) and the PCR product cloned into vector pSyn-C04-Clambda.

Light chain variable regions of the scFvs called SC04-261, SC04-328, SC04-335, and SC04-383 were cloned directly by restriction digest using the enzymes SalI and NotI for expression in the IgG expression vector pIg-C910-Clambda (SEQ ID NO:58).

Nucleotides for all constructs were verified according to standard techniques known to the skilled artisan.

The resulting expression constructs pgG 104-261 C18, pgG104-267C18, pgG104-328C18, pgG104-335C18 and pgG104-383C911 encoding the anti-WNV human IgG1 heavy chains and pgG104-261C910, pgG104-267C04, pgG104-328C910, pgG104-335C910 and pgG104-383C910 encoding the anti-WNV human IgG1 light chains were transiently expressed in combination in 293T cells and supernatants containing human IgG1 antibodies were obtained.

The nucleotides of the heavy chains of the antibodies called CR4261, CR4267, CR4328, CR4335, CR4354 and CR4383 are shown in SEQ ID NOS:59, 61, 63, 65, 31 and 67, respectively (the variable regions are from nucleotides 1-348; 1-381; 1-348; 1-351; 1-363; and 1-372, respectively). The amino acid sequences of the heavy chains of the antibodies called CR4261, CR4267, CR4328, CR4335, CR4354 and CR4383 are shown in SEQ ID NOS:60, 62, 64, 66, 32 and 68, respectively (the variable regions are from amino acids 1-116; 1-127; 1-116; 1-117; 1-121; and 1-124, respectively). The nucleotides of the light chain of antibodies CR4261, CR4267, CR4328, CR4335, CR4354 and CR438 are shown in SEQ ID NOS:69, 71, 73, 75, 35 and 77, respectively (the variable regions are from nucleotides 1-342; 1-330; 1-339; 1-339; 1-330; and 1-339, respectively). The amino acid sequences of the light chain of antibodies CR4261, CR4267, CR4328, CR4335, CR4354 and CR4383 are shown in SEQ ID NOS: 70, 72, 74, 76, 36 and 78, respectively (the variable regions are from amino acids 1-114; 1-110; 1-113; 1-113; 1-110; and 1-113, respectively).

The expression construct encoding the heavy chain of CR4354 was combined with the constructs expressing the light chains of the respective antibodies for transfection of HEK293T cells essentially as described in Example 5. The obtained antibodies were designated CR4354L4261, CR4354L4267, CR4354L4328, CR4354L4335 and CR4354L4383. Supernatants were tested for binding by ELISA staining as described in Example 5 and for potency in the in vitro neutralization assay as described in Example 6.

Figure 3:
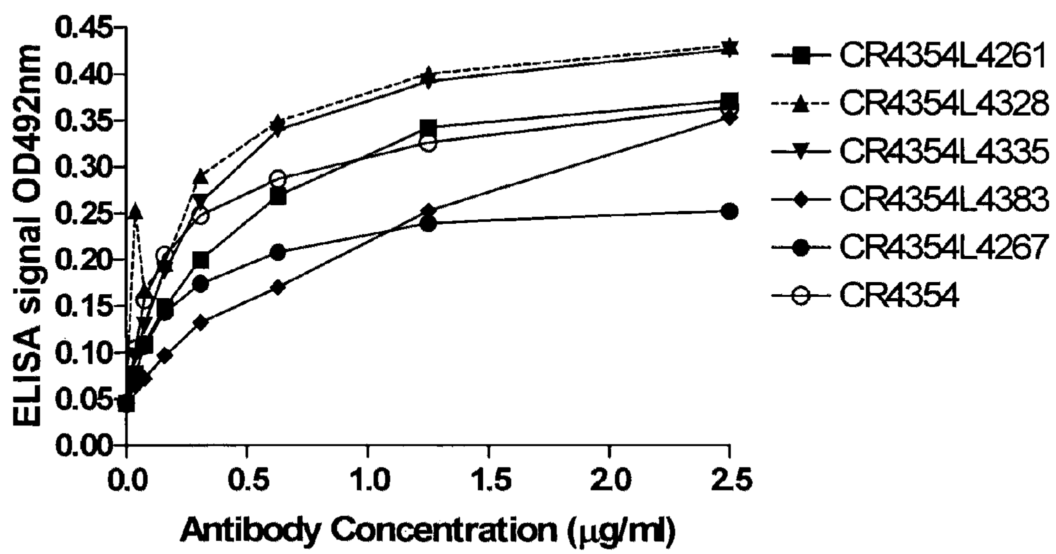
FIG. 3 shows the ELISA binding of dilutions of the optimized antibodies CR4354L4261, CR4354L4267, CR4354L4328, CR4354L4335, CR4354L4383 and the parent antibody CR4354 to WNV. On the Y-axis the absorbance (OD) at 492 nm is shown and on the X-axis the amount of antibody in μg/ml is shown.

The binding data showed that all shuffled variants have specificity for the pre-selected antigen (see FIG. 3).

In terms of functional activity, it was concluded that two chain shuffled variants CR4354L4328 and CR4354L4335 had a higher affinity for WNV compared to CR4354. CR4354L4261 bound the virus with a similar affinity compared to CR4354, while both CR4354L4383 and CR4354L4267 bound with a lower affinity to the virus compared to CR4354 (see FIG. 3).

Furthermore, the antibodies CR4354L4383 and CR4354L4267 did not show any WNV-neutralizing activity, which was consistent with their lower binding affinity. CR4354L4261 had a neutralization endpoint concentration similar to the original antibody CR4534, again consistent with the binding data. CR4354L4335 that bound WNV with a higher affinity compared to CR4354 had a lower neutralizing activity compared to the original antibody CR4534. In contrast, the antibody variant CR4354L4328 that had a higher affinity for WNV compared to CR4354 also had a higher neutralizing activity compared to the original antibody CR4534 (see Table 14). In 4 out of 5 cases there was a direct correlation between binding affinity and neutralization potency of the variants. It was demonstrated that substituting similar light chains can improve a functionality of interest of an antibody, e.g., affinity or neutralizing activity.

Moreover, CR4354 was converted into a fully human IgM format by removing the gamma Fc region from construct pgG104-354C18 by restriction digestion with the endonucleases NheI and XbaI. The vector pCR-IgM (SEQ ID NO:146) containing a mu Fc region was digested with the same restriction enzymes and the obtained mu Fc region was ligated into vector pgG104-354C18 and fused in frame with the variable heavy chain gene derived from SC04-354 to make vector pgM104-354C899. This construct was transiently expressed in combination together with the light chain construct pgG104-354C04 (see above) in 293T cells and supernatants containing human IgM antibodies were obtained. The nucleotide sequence of vector pgM104-354C899 is shown in SEQ ID NO:147. The amino acid sequence of the heavy chain the antibody called CRM4354 is shown in SEQ ID NO:148. The IgM antibody was purified from the supernatant by adding ammonium sulphate to a final concentration of 2.4 M and incubating the mixture overnight on ice, while stirring. The precipitated IgM was recovered by centrifugation at 10,395×g for 30 minutes. The pellet was resuspended in PBS and further purified by gel filtration. A HiLoad 26/60 Superdex 200 prep grade column (GE heathcare) equilibrated with PBS was loaded with the resuspended IgM and fractions were collected from the column, while being flushed under a constant flow rate with PBS. The first major elution peak, which contained the purified IgM, was collected. Binding activity of the antibody was confirmed by titration on West Nile virus-like particles (VLPs) (data not shown).

Example 9

In Vitro Neutralization Potency by Plaque Reduction Neutralization Test (PRNT)

To further investigate the neutralizing activity of the antibodies of the invention a PRNT was developed. Briefly, Vero- E6 cells were trypsinized and counted. $2.5\times10^5$ cells were added to each well of a 12-well plate and incubated overnight at 37° C. in a humidified $CO_2$ incubator. Serial dilutions (ten-fold) of a titrated stock of West Nile virus USA99b were made in complete medium. Equal volume (250 μl) mixtures of virus (100 pfu) and serial dilutions of purified IgG1 antibodies were incubated in duplicate at 37° C. for 1 hour. Dilutions of both virus and antibodies were done in DMEM medium. The mixture was then added (400 μl) to the 12-well plates containing Vero cell monolayers after careful aspiration of the overnight medium. After the plates had been incubated at 37° C. for 1 hour, an 1.5 ml overlay of CMC carboxymethyl-cellulose medium with 10% FBS (v/v) (CMC: complete medium) was added per well and the plates placed in a humidified $CO_2$ incubator for 3 days at 37° C. One day before staining the CMC:complete medium was removed from the wells and replaced with a mixture of CMC:PBS (1:1; v/v) containing 8.25 mg/ml of neutral red (2 ml neutral red at 3.3 g/l in 80 ml CMC:PBS). Plates were incubated 1 day further at 37° C. in a humidified $CO_2$ incubator, after which the number of visible plaques was quantified.

To analyze the antibody potency data from the PRNT a binary regression model known as probit analysis was used. Probit analysis is valid, if it can be assumed that the probability of neutralizing WNV in vitro follows a normal distribution with regard to the amount of antibodies used. The assumption of normality most likely holds on a logarithmic scale, hence the neutralization of virus was modeled as a function of the logarithm of the amount of antibodies administered. Antibodies were compared directly in the regression model, with significance level alpha set at 0.05. Antibody concentrations yielding 50% and 90% neutralization were estimated from the model, together with 95% confidence intervals. A summary of the final analysis of the antibodies is given in Table 15. By converting CR4354 into IgM format (CRM4354) the in vitro potency was increased dramatically (see Table 15).

Figure 4:
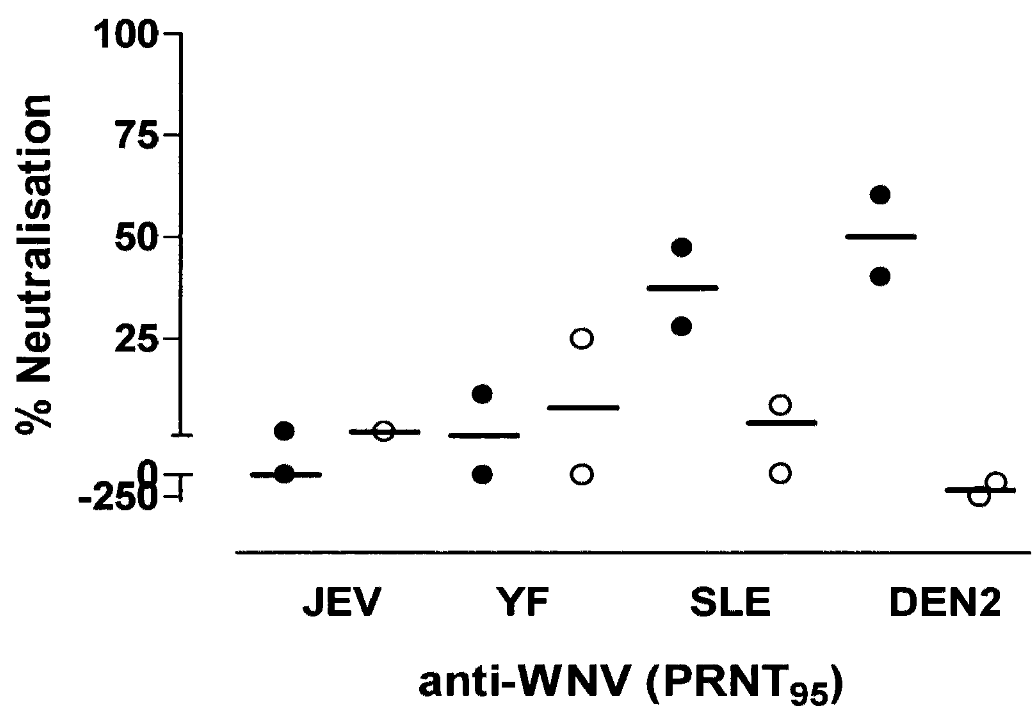
FIG. 4 shows neutralization data of CR4348 (closed circles) and CR4354L4328 (open circles) of the flaviviruses yellow fever virus, Japanese encephalitis virus, St. Louis encephalitis virus and dengue virus 2 in a plaque reduction assay.

Using the assay described herein, the antibodies were tested for their neutralizing potency against other flaviviruses including yellow fever virus, Japanese encephalitis virus, St. Louis encephalitis virus and dengue virus 2. In FIG. 4 is shown that CR4348 had significant neutralizing activity against St. Louis encephalitis virus and dengue virus 2.

Example 10

Identification of the Target Antigens of CR4348 and CR4354L4328

To identify the target antigens of the CR4348 and CR4354L4328 antibodies a human fetal brain protein expression library was screened with the antibodies. The cDNA library was constructed in the bacterial expression vector pQE-30 (Qiagen) for IPTG inducible expression of $(His)_6$-tagged fusion proteins. The library was composed of 38,016 clones with an average insert of 1500 bps and these were printed in duplicate onto the membranes. To identify target antigens CR4348, CR4354L4328 and a negative control antibody (CR4374) were subjected to protein micro-array analysis (RZPD (Heidelberg, Germany)). Two independent experiments were performed with the antibodies. The protein arrays were incubated with the primary antibody and binding was detected with a conjugated anti-human secondary antibody. Clones were considered positive, if duplicate spots appeared that were not present with the secondary antibody alone. The negative control did not show any reactivity, whereas five different clones reacted with CR4348 and four different clones with CR4354L4328. The reactive clones were sequenced and used for database search against the NCBI database using the nucleotide-nucleotide BLAST program. The identity of the clones is depicted in Table 16.

To confirm the protein-array data obtained with CR4348 and CR4354L4328 the different cDNA clones were expressed. The nine different clones and a bacterial clone expressing the E protein of WNV were streaked on an agar plate and grown overnight at 37° C. Next, 10 ml LB volumes were inoculated with the nine different clones and the control WNV E protein clone. The bacteria were grown overnight at 37° C. The next day the cultures were diluted 1:50 and grown until an OD600 nm of 0.6 was reached, subsequently the expression of the protein was induced by adding IPTG and the cells were harvested after 4 hours of induction in three portions of 1 ml. Next, each portion underwent a different extraction procedure that allowed for the extraction of soluble and insoluble proteins. The WNV E protein clone was included as a positive control in the test, since this protein is expressed as a soluble protein and is therefore present in all three extraction procedures. All methods started with a cycle of three freeze-thawings of the pellet. In the first method the pellet was extracted in a volume twice the volume of the cell pellet in a mild extraction buffer (50 mM $Na_2HPO_4$, 300 mM NaCl, 0.05% Tween-20 buffer with lysozyme 1 mg/ml) by incubation of the cell pellet for 30 minutes on ice, next cells were pelleted and the supernatant was stored for analysis (fraction 1). Subsequently, the pellet was extracted with a more stringent buffer (0.2% DOC-1% Triton X-100) and resuspended in a volume twice the volume of the cell pellet. After an incubation period of 30 minutes on ice, cells were pelleted and the supernatant was stored for analysis (fraction 2). In the second method (an adaptation of the colony blot procedure), the pellet was lysed by addition of 10% SDS (twice the volume of the cell pellet). After 10 minutes of incubation at room temperature, the suspension was denatured with an equal volume 0.5 M NaOH containing 1.5 M NaCl for 5 minutes at room temperature. By adding an equal volume of 1.5 M NaCl, 0.5 M Tris pH 7.4 the suspension was neutralized. Next, cell rests were pelleted and the supernatant was stored for analysis (fraction 3). In the third method inclusion bodies were solubilized and the pellet was extracted by addition of 8 M ureum in 100 mM Tris/HCl, 100 mM $NaH_2PO_4$ in a volume twice the volume of the cell pellet. After 30 minutes of incubation at room temperature, cells rests were pelleted and the supernatant was stored for analysis (fraction 4). Proteins extracted with each procedure were spotted on a nitrocellulose filter. Moreover, controls, i.e., purified WNV E protein (negative control) and human IgG (positive control), were spotted. Membranes were blocked overnight with 4% milk powder in TBST at 4° C. Subsequently, the blots were incubated with 5 μg/ml CR4348, CR4354L4328 or the murine anti-WNV E protein monoclonal antibody 7H2. The antibody used for WNV E protein detection recognizes a linear epitope and still reacts with recombinant protein after treatment with denaturing reagents like 8 M urea (method 3). After an incubation period of 1 hour at room temperature in a rolling incubator, the membranes were washed three times for five minutes with TBST. Binding of antibodies was detected with HRP conjugated goat anti-human (Pharmingen) or goat anti-mouse (DAKO) antibodies. Finally, the membranes were washed extensively in TBST followed by a PBS washing step. Reactive proteins were revealed by the ECL chemofluorescence detection system (Amersham).

CR4348 reacted with fractions 1, 2 and 3 of the FAF-1 expression clone (data not shown). CR4354L4328 solely reacted with fraction 3 of the NADH dehydrogenase flavoprotein 1 (NDUFV1) expression clone (data not shown).

This indicates that both antibodies react with a single expression clone. It was further concluded that both antibodies recognize a conformational epitope, since they did not react with protein extracted using 8 M ureum, whereas the anti-WNV antibody that recognizes a linear epitope did react with protein extracted using this procedure (data not shown). In conclusion, CR4348 recognizes an epitope present in the protein FAF-1, while CR4354L4328 recognizes an epitope present in the protein NDUFV-1.

Figure 5:
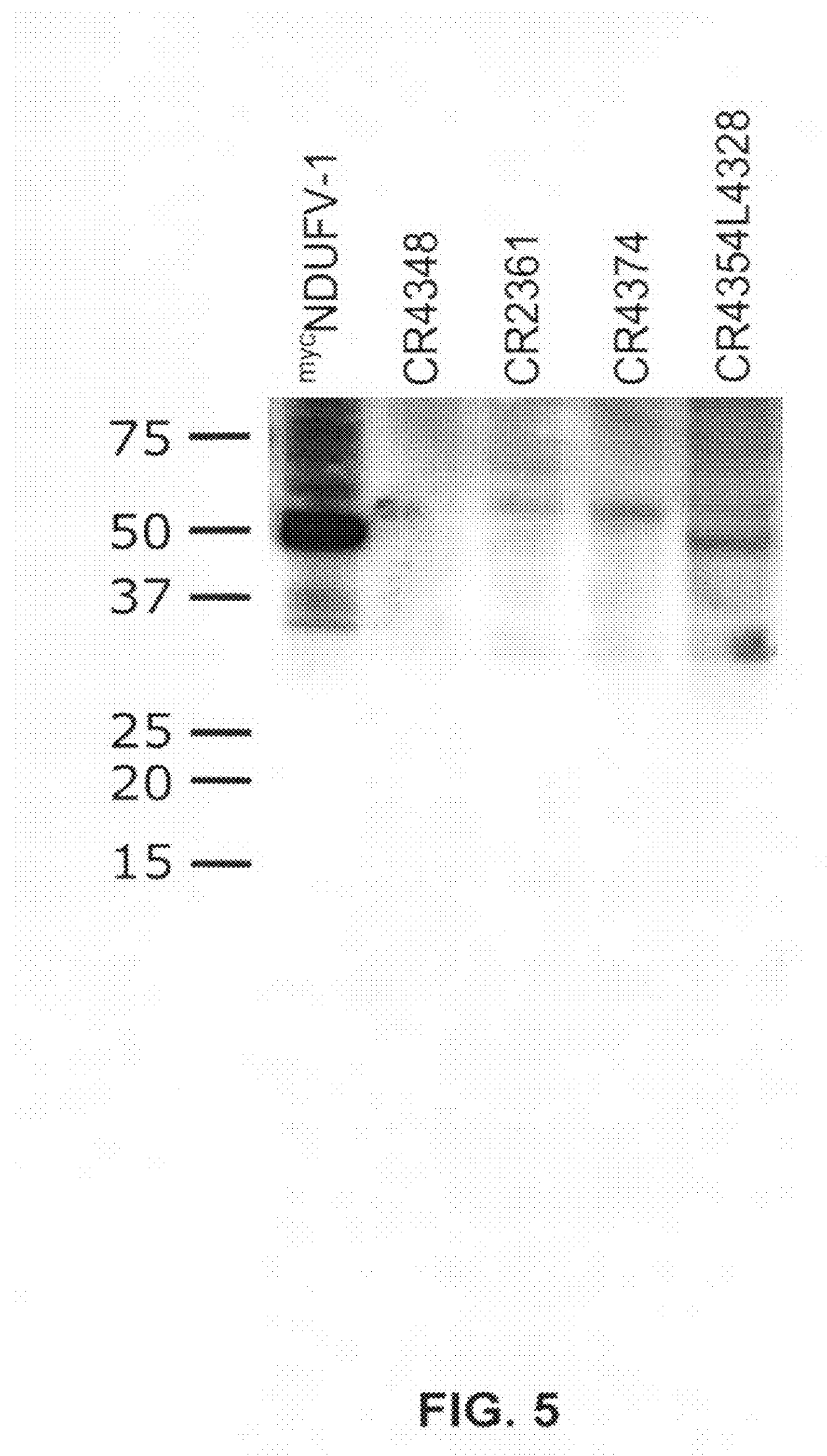
FIG. 5 shows an immunoblot with from left to right mycN-DUFV-1 cell lysate and lysate immunoprecipitated with CR4348, CR4361, CR4374 or CR4354L4328.

To confirm the identification of NDUFV-1 as the target antigen recognized by CR4354L4328, mRNA was extracted from $2*10^7$ 293T cells using the nucleotrap mRNA mini purification kit (Beckton Dickinson) according to protocols provided by the manufacturer. RT-PCR was performed on the isolated mRNA. For the PCR procedure, the following primers were designed: forward primer 5'-ATGAAGGTGACAGCGTGAGGTGAC-3' (SEQ ID NO:160) and reverse primer 5'-ACATGGATAGACGCAGGACAGCAG-3' (SEQ ID NO:161). PCR was performed with Pfu (Promega) in the presence of 5% DMSO and resulted in a 1500 bp product. The resulting fragment was cloned in the pCR4TOPO vector (Invitrogen) and transformed into DH5α cells. The resulting clone, TOPONDUFV1 was verified by sequence analysis and aligned with the sequence present in the database. To simplify the detection of the protein in the subsequent transfection experiments, the protein was fused with a myc tag at the 5' prime end by means of PCR (using the construct as a template). For the 5' myc construct the following primers were designed: forward primer 5'-AAGCTTAGCATGGAACAAAAACTTATTTCT GAAGAAGATCTGCTGGCAACACGGCGGCTGCTCGGCTG-3'(SEQ ID NO:162) and reversed primer 5'-GATATCCTTTATTGTCCAGCATTCCAC-3' (SEQ ID NO:163). PCR was performed using Pfu polymerase and the resulting fragment of the 5' myc tag was cloned in PCRblunt4-TOPO, and subsequently digested with HindIII-EcoRV. The resulting fragment was cloned in the corresponding sites of pcDNA3.1/zeo (Invitrogen) resulting in the mycNDUFV-1 construct. The construct was verified by sequencing. All cloning procedures were performed according to standard molecular techniques. $3*10^5$ 293T cells were seeded in T175 flasks and subjected to a transfection procedure after 72 hours. The expression construct mycNDUFV-1 and a positive control construct ATAD3Amyc were transfected with lipofectamin (Gibco) according to the manufacturer's instructions. 72 hours after transfection, cells were lysed in DOC buffer (1% Triton X-100 and 0.5% w/v desoxycholate in 0.2 M phosphate buffer containing 0.12 M NaCl, pH 7.4 and protease inhibitors (Sigma)). The insoluble material was removed by centrifugation for 30 minutes at 4° C. at 20,000*g. Next, the lysates of the transfected cells were analyzed for the quantity of myc tagged protein expressed. Hereafter, the lysate was pre-cleared with protein A beads (Amersham) for 2 hours at 4° C. In the mean time, 4 μg of CR4354L4328, control antibody CR4374 (negative control, antibody directed against WNV E protein), and control antibody CR2361 IgG1 (positive control; antibody directed against ATAD3A) were coupled to protein A beads at room temperature. Next, the pre-cleared samples were incubated with the IgGs coupled to the beads for 2 hours at 4° C. The protein A beads were washed three times for 5 minutes with 1 ml of DOC lysis buffer and bound complexes were eluted by the addition of sample loading buffer. The samples were subjected to SDS-PAGE under non-reducing conditions. After blotting on PVDF membranes, the myc tagged proteins were detected with the HRP conjugated anti-myc monoclonal antibody 9E10 (Amersham). Immunoblot developed with anti-myc antibody demonstrated that mycNDUFV-1 was only immunoprecipitated by CR4354L4328 and not by the any of the other antibodies (see FIG. 5). In addition, ATAD3Amyc protein was only immunoprecipitated by CR2361 (data not shown).

Example 11

Distribution of the Antigen Recognized by CR4348 and CR4354L4328 on 293T Cells and VLP-Transfected HEK293T Cells as Shown by FACS The distribution of the target antigens recognized by the antibodies CR4348 and CR4354L4328 was analyzed by flow cytometry in three different ways: a) using HEK293T cells in permeabilized format, b) using HEK293T cells in non-permeablized format, and c) using non-permeabilized WNV VLP-transfected HEK293T cells. 293T cells were obtained from the ATCC CRL-11268 and were harvested with trypsin/EDTA. One part of the cells was fixed and permeabilized for intracellular staining with the DakoCytomation IntraStain (K2311) according to the manufacturer's instruction, the other part of the cells was stained extracellularly and was incubated directly after harvest with the antibodies. For each sample, 100.000 cells were incubated with 2.5 μg/ml CR4354L4328, CR4348 or the control antibodies CR2300, CR4374 and CR4104 diluted in PBS containing 1% BSA. CR2300 is a positive control antibody (recognizing CD46 which is present on nucleated cells); CR4374 recognizes WNV E protein and is the positive control antibody for VLP-transfected 293T cells and the negative antibody for non-transfected 293T cells; and CR4104 recognizes rabies glycoprotein and is included as negative control for all stainings. The antibodies were incubated with the cells for 1 hour on ice and the cells were washed three times with PBS/BSA. Binding of the antibodies to the cells was visualized after incubation for 1 hour on ice with goat anti-human phycoerythrin antibody (Pharmingen). The cells were washed twice in PBS/BSA prior to analysis. In the extracellular staining experiment dead or permeable cells were excluded from analysis by staining with 7-AAD, a dye that stains nuclear DNA. VLP-transfected 293T cells were harvested 24 hour after transfection and stained according to the aforementioned method for extracellular staining. Cells were analyzed on a FACS calibur (BD) using CellQuest software. For final analysis of the extracellular stained cells, cells were gated based on forward scatter versus low 7-AAD signal. A sample was considered positive if the mean fluorescence intensity was more than two times the signal obtained with the negative control antibody. As is shown in Table 17, CR4348 and CR4354L4328 both recognized an intracellular target antigen that is not expressed at the cell surface under normal culturing conditions. However, after transfection with the DNA construct for WNV-VLP production the target antigens of CR4348 and CR4354L4328 were detected at the cell surface. The antibodies specifically reacted with antigens expressed after WNV-VLP transfection, since they did not bind the cell surface of mock-transfected cells (data not shown). When the antibodies were applied in a serial dilution, they bound the target antigens in a dose dependent way (data not shown).

From these combined expression data it was concluded that the antigens recognized by CR4348 and CR4354L4328 are located intracellularly in healthy, normal cells. However, after mimicking a WNV-infection by introducing a WNV-VLP construct in the cells the antigens became expressed at the cellular surface.

Example 12

Intracellular Location of the Target Antigens of CR4354L4328 and CR4348 Demonstrated by Immunofluorescence The intracellular location of the CR4354L4328 and CR4348 target antigens was analyzed by immunofluorescent staining of cells. VERO cells and 293T cells were seeded at a confluency of 20% in four-well LAB-TEK chambers (Nunc). 24 Hours after seeding of the cells one part of the VERO cells was infected with 8.1E-3 TCID50/cell of WNV strain 385-99. One part of the 293T cells was transfected with the WNV-VLP construct. The VERO and 293T cells that were not used for infection or transfection were allowed to grow for an additional 24 hours. 24 Hours after infection or transfection all VERO and 293T cells were fixed with 2% formaldehyde in PBS for 15 minutes at room temperature. Thereafter they were kept in PBS until the staining procedure. To allow the antibodies to react with the intracellular antigens in the cell, the cells were permeabilized with 0.2% Triton X-100 in PBS for 5 minutes at room temperature and rinsed for 15 minutes. Next, the cells were blocked with 2% BSA in PBS for 1 hour at room temperature. Subsequently, different stainings were performed. Dual stainings: CR4354L4328, CR4348, CR4104 and CR4283 antibodies were applied at a concentration of 5 μg/ml in 2% BSA for 1 hour at room temperature. After 3 washes of 5 minutes in PBS the antibodies were visualized by adding Alexa fluor 488 goat anti-human antibody at a concentration of 5 μg/ml in 2% BSA containing 5 units of phalloidin bodipy (Molecular probes) to stain the cytoskeletal structure. The cells were incubated for 1 hour at room temperature in the dark. Next, three washes of 5 minutes were performed with PBS and anti fading agent was added (Vectashield) to prevent bleaching of the fluorescent signal. Then, a glass cover slip was glued on top with opaque nail polish (Miss Helen, HEMA). Triple stainings were performed to analyze co-localization of CR4348 and CR4354L4328 with their target antigens FAF-1 and NDUFV1. Slides were viewed under a Leica TCS-NT confocal laser scanning microscope. Staining of uninfected VERO cells with CR4348 demonstrated a network like pattern consisting of tiny vesicles. After infection with WNV, bigger vesicles appeared that were scattered throughout the cytoplasm. Staining of uninfected VERO cells with CR4354L4328 demonstrated a bright nuclear staining. After infection of VERO cells with WNV, densely packed vesicles appeared throughout the cytoplasm and staining of the nucleus disappeared. In 293T cells the target for CR4348 was localized in vesicle-like structures close to the cellular membrane. After transfection with the VLP construct a brighter staining pattern appeared and vesicles were also localized throughout the cytoplasm. In 293T cells CR4354L4328 stains small vesicles that were localized throughout the cytoplasm in densely packed structures. After transfection of the VLP construct the appearance of the vesicles the densely packed structures disappeared and the vesicles became scattered throughout the cell and showed a bright staining pattern.

Example 12

Neutralization of Rabies Virus with CR4354L4328

To investigate the neutralizing activity of CR4354L4328 on other viral species, the antibody was tested in a RFITT experiment for the neutralization of rabies virus. The RFFIT was performed by mixing serial five-fold dilutions of CR4354L4328, CR4374 (negative control; anti-WNV E protein antibody) and CR57 (positive control; anti-rabies virus antibody) with a constant amount of rabies virus (50 FFD50/0.1 ml) in a multi-chambered slide. One unit of virus is determined as the dilution at which 50% of the observed microscopic fields contain one or more foci of infected cells, i.e., the focus forming dose, FFD50. After allowing the mixture to react in a $CO_2$-incubator at 37° C. for 90 minutes, mouse neuroblastoma (MNA) cells in Eagle's minimum essential medium with 10% fetal bovine serum (MEM-10) were added to each monoclonal antibody-virus mixture resulting in a final concentration of $1*10^5$ cells/ml. The monoclonal antibody-virus-cell cultures were incubated for 20 hours in a $CO_2$-incubator at 37° C. The cultures were removed from the incubator, washed, fixed and then stained with an anti-rabies virus antibody conjugate directed against the nucleoprotein and observed under a fluorescence microscope for the presence of fluorescent cells; 20 microscopic fields (160×-200×) were read for each monoclonal antibody dilution and compared against the virus control (50 FFD50/0.1 ml), which should contain 18 to 20 fields with fluorescent cells. The 50% neutralization endpoint of a particular antibody is defined as the dilution by which 50% or more of the observed microscopic fields contain one or more infected cells and was calculated using the Reed-Muench method. Virus neutralizing antibody titers were normalized to international units (IU) using the NIH US standard human Rabies Immune Globulin reference lot R3 (SRIG). The 50% neutralization point of CR57 was obtained at a concentration of 7.3 ng/ml. The 50% neutralization point of CR4354 was obtained at a concentration of 9.2 μg/ml. The control antibody CR4374 could not neutralize rabies virus at any concentration tested. The results clearly show that CR4354L4328 has rabies virus neutralizing activity.

TABLE 1

Human lambda chain variable region primers (sense).

| Primer name | Primer nucleotide sequence | SEQ ID NO |
|---|---|---|
| HuVλ1A | 5'-CAGTCTGTGCTGACT CAGCCACC-3' | SEQ ID NO: 79 |
| HuVλ1B | 5'-CAGTCTGTGYTGACG CAGCCGCC-3' | SEQ ID NO: 80 |
| HuVλ1C | 5'-CAGTCTGTCGTGACG CAGCCGCC-3' | SEQ ID NO: 81 |
| HuVλ2 | 5'-CARTCTGCCCTGACT CAGCCT-3' | SEQ ID NO: 82 |
| HuVλ3A | 5'-TCCTATGWGCTGACT CAGCCACC-3' | SEQ ID NO: 83 |
| HuVλ3B | 5'-TCTTCTGAGCTGACT CAGGACCC-3' | SEQ ID NO: 84 |
| HuVλ4 | 5'-CACGTTATACTGACT CAACCGCC-3' | SEQ ID NO: 85 |
| HuVλ5 | 5'-CAGGCTGTGCTGACT CAGCCGTC-3' | SEQ ID NO: 86 |
| HuVλ6 | 5'-AATTTTATGCTGACT CAGCCCCA-3' | SEQ ID NO: 87 |

TABLE 1-continued

Human lambda chain variable region primers (sense).

| Primer name | Primer nucleotide sequence | SEQ ID NO |
|---|---|---|
| HuVλ7/8 | 5'-CAGRCTGTGGTGACY CAGGAGCC-3' | SEQ ID NO: 88 |
| HuVλ9 | 5'-CWGCCTGTGCTGACT CAGCCMCC-3' | SEQ ID NO: 89 |

TABLE 2

Human kappa chain variable region primers (sense).

| Primer name | Primer nucleotide sequence | SEQ ID NO |
|---|---|---|
| HuVκ1B | 5'-GACATCCAGWTGACC CAGTCTCC-3' | SEQ ID NO: 90 |

TABLE 2-continued

Human kappa chain variable region primers (sense).

| Primer name | Primer nucleotide sequence | SEQ ID NO |
|---|---|---|
| HuVκ2 | 5'-GATGTTGTGATGACT CAGTCTCC-3' | SEQ ID NO: 91 |
| HuVκ3 | 5'-GAAATTGTGWTGACR CAGTCTCC-3' | SEQ ID NO: 92 |
| HuVκ4 | 5'-GATATTGTGATGACC CACACTCC-3' | SEQ ID NO: 93 |
| HuVκ5 | 5'-GAAACGACACTCACG CAGTCTCC-3' | SEQ ID NO: 94 |
| HuVκ6 | 5'-GAAATTGTGCTGACT CAGTCTCC-3' | SEQ ID NO: 95 |

TABLE 3

Human kappa chain variable region primers extended with SalI restriction sites (sense), human kappa chain J-region primers extended with NotI restriction sites (anti-sense), human lambda chain variable region primers extended with SalI restriction sites (sense) and human lambda chain J-region primers extended with NotI restriction sites (anti-sense).

| Primer name | Primer nucleotide sequence | SEQ ID NO |
|---|---|---|
| HuVκ1B-SalI | 5'-TGAGCACACAGGTCGACGGACATCCAGWTGACCCAG TCTCC-3' | SEQ ID NO: 96 |
| HuVκ2-SalI | 5'-TGAGCACACAGGTCGACGGATGTTGTGATGACTCAGT CTCC-3' | SEQ ID NO: 97 |
| HuVκ3B-SalI | 5'-TGAGCACACAGGTCGACGGAAATTGTGWTGACRCAG TCTCC-3' | SEQ ID NO: 98 |
| HuVκ4B-SalI | 5'-TGAGCACACAGGTCGACGGATATTGTGATGACCCAC ACTCC-3' | SEQ ID NO: 99 |
| HuVκ5-SalI | 5'-TGAGCACACAGGTCGACGGAAACGACACTCACGCAG TCTCC-3' | SEQ ID NO: 100 |
| HuVκ6-SalI | 5'-TGAGCACACAGGTCGACGGAAATTGTGCTGACTCAG TCTCC-3' | SEQ ID NO: 101 |
| HuJκ1-NotI | 5'-GAGTCATTCTCGACTTGCGGCCGCACGTTTGATTTCC ACCTTGGTCCC-3' | SEQ ID NO: 102 |
| HuJκ2-NotI | 5'-GAGTCATTCTCGACTTGCGGCCGCACGTTTGATCTCC AGCTTGGTCCC-3' | SEQ ID NO: 103 |
| HuJκ3-NotI | 5'-GAGTCATTCTCGACTTGCGGCCGCACGTTTGATATCC ACTTTGGTCCC-3' | SEQ ID NO: 104 |
| HuJκ4-NotI | 5'-GAGTCATTCTCGACTTGCGGCCGCACGTTTGATCTCC ACCTTGGTCCC-3' | SEQ ID NO: 105 |
| HuJκ5-NotI | 5'-GAGTCATTCTCGACTTGCGGCCGCACGTTTAATCTCC AGTCGTGTCCC-3' | SEQ ID NO: 106 |
| HuVλ1A-SalI | 5'-TGAGCACACAGGTCGACGCAGTCTGTGCTGACTCAGC CACC-3' | SEQ ID NO: 107 |
| HuVλ1B-SalI | 5'-TGAGCACACAGGTCGACGCAGTCTGTGYTGACGCAG CCGCC-3' | SEQ ID NO: 108 |

TABLE 3-continued

Human kappa chain variable region primers extended with SalI restriction sites (sense), human kappa chain J-region primers extended with NotI restriction sites (anti-sense), human lambda chain variable region primers extended with SalI restriction sites (sense) and human lambda chain J-region primers extended with NotI restriction sites (anti-sense).

| Primer name | Primer nucleotide sequence | SEQ ID NO |
|---|---|---|
| HuVλ1C-SalI | 5'-TGAGCACACAGGTCGACGCAGTCTGTCGTGACGCAG CCGCC-3' | SEQ ID NO: 109 |
| HuVλ2-SalI | 5'-TGAGCACACAGGTCGACGCARTCTGCCCTGACTCAGC CT-3' | SEQ ID NO: 110 |
| HuVλ3A-SalI | 5'-TGAGCACACAGGTCGACGTCCTATGWGCTGACTCAG CCACC-3' | SEQ ID NO: 111 |
| HuVλ3B-SalI | 5'-TGAGCACACAGGTCGACGTCTTCTGAGCTGACTCAGG ACCC-3' | SEQ ID NO: 112 |
| HuVλ4-SalI | 5'-TGAGCACACAGGTCGACGCACGTTATACTGACTCAAC CGCC-3' | SEQ ID NO: 113 |
| HuVλ5-SalI | 5'-TGAGCACACAGGTCGACGCAGGCTGTGCTGACTCAG CCGTC-3' | SEQ ID NO: 114 |
| HuVλ6-SalI | 5'-TGAGCACACAGGTCGACGAATTTTATGCTGACTCAGC CCCA-3' | SEQ ID NO: 115 |
| HuVλ7/8-SalI | 5'-TGAGCACACAGGTCGACGCAGRCTGTGGTGACYCAG GAGCC-3' | SEQ ID NO: 116 |
| HuVλ9-SalI | 5'-TGAGCACACAGGTCGACGCWGCCTGTGCTGACTCAG CCMCC-3' | SEQ ID NO: 117 |
| HuJλ1-NotI | 5'-GAGTCATTCTCGACTTGCGGCCGCACCTAGGACGGTG ACCTTGGTCCC-3' | SEQ ID NO: 118 |
| HuJλ2/3-NotI | 5'-GAGTCATTCTCGACTTGCGGCCGCACCTAGGACGGTC AGCTTGGTCCC-3' | SEQ ID NO: 119 |
| HuJλ4/5-NotI | 5'-GAGTCATTCTCGACTTGCGGCCGCACYTAAAACGGTG AGCTGGGTCCC-3' | SEQ ID NO: 120 |

TABLE 4

Distribution of the different light chain products over the ten fractions.

| Light chain products | Number of alleles | Fraction number | alleles/ fraction |
|---|---|---|---|
| Vk1B/Jk1-5 | 19 | 1 and 2 | 9.5 |
| Vk2/Jk1-5 | 9 | 3 | 9 |
| Vk3B/Jk1-5 | 7 | 4 | 7 |
| Vk4B/Jk1-5 | 1 | 5 | 5 |
| Vk5/Jk1-5 | 1 | | |
| Vk6/Jk1-5 | 3 | | |
| Vλ1A/Jl1-3 | 5 | 6 | 5 |
| Vλ1B/Jl1-3 | | | |
| Vλ1C/Jl1-3 | | | |
| Vλ2/Jl1-3 | 5 | 7 | 5 |
| Vλ3A/Jl1-3 | 9 | 8 | 9 |
| Vλ3B/Jl1-3 | | | |
| Vλ4/Jl1-3 | 3 | 9 | 5 |
| Vλ5/Jl1-3 | 1 | | |

TABLE 4-continued

Distribution of the different light chain products over the ten fractions.

| Light chain products | Number of alleles | Fraction number | alleles/ fraction |
|---|---|---|---|
| Vλ6/Jl1-3 | 1 | | |
| Vλ7/8/Jl1-3 | 3 | 10 | 6 |
| Vλ9/Jl1-3 | 3 | | |

TABLE 5

Human IgG heavy chain variable region primers (sense).

| Primer name | Primer nucleotide sequence | SEQ ID NO |
|---|---|---|
| HuVH1B/7A | 5'-CAGRTGCAGCTGGTG CARTCTGG-3' | SEQ ID NO: 121 |
| HuVH1C | 5'-SAGGTCCAGCTGGTR CAGTCTGG-3' | SEQ ID NO: 122 |
| HuVH2B | 5'-SAGGTGCAGCTGGTG GAGTCTGG-3' | SEQ ID NO: 123 |
| HuVH3B | 5'-SAGGTGCAGCTGGTG GAGTCTGG-3' | SEQ ID NO: 124 |

TABLE 5-continued

| Human IgG heavy chain variable region primers (sense). | | |
|---|---|---|
| Primer name | Primer nucleotide sequence | SEQ ID NO |
| HuVH3C | 5'-GAGGTGCAGCTGGTG GAGWCYGG-3' | SEQ ID NO: 125 |
| HuVH4B | 5'-CAGGTGCAGCTACAG CAGTGGGG-3' | SEQ ID NO: 126 |
| HuVH4C | 5'-CAGSTGCAGCTGCAG GAGTCSGG-3' | SEQ ID NO: 127 |
| HuVH5B | 5'-GARGTGCAGCTGGTG CAGTCTGG-3' | SEQ ID NO: 128 |
| HuVH6A | 5'-CAGGTACAGCTGCAG CAGTCAGG-3' | SEQ ID NO: 129 |

TABLE 7

Binding of single chain (scFv) phage antibodies to West Nile virus (WNV), recombinant WNV E protein, FBS, and rabies virus as measured by ELISA at 492 nm).

| Name phage antibody | WN virus | WNV E protein | WNV-like particle | FBS (5%) | Rabies virus |
|---|---|---|---|---|---|
| SC04-348 | 1.026 | 0.093 | 0.771 | ND | 0.063 |
| SC04-354 | 1.041 | 0.069 | 0.811 | ND | 0.063 |
| SC02-447 | 0.094 | 0.057 | ND | 0.041 | ND |
| SC03-014 | 0.061 | 0.060 | ND | ND | 0.062 |
| Pos. control | 0.067 | 0.056 | 0.062 | ND | 0.991 |

ND means not determined

TABLE 6

| Human IgG heavy chain variable region primers extended with SfiI/NcoI restriction sites (sense) and human IgG heavy chain J-region primers extended with XhoI/BstEII restriction sites(anti-sense). | | |
|---|---|---|
| Primer name | Primer nucleotide sequence | SEQ ID NO |
| HuVH1B/7A-SfiI | 5'-GTCCTCGCAACTGCGGCCCAGCCGGCCATGGCCC AGRTGCAGCTGGTGCARTCTGG-3' | SEQ ID NO: 130 |
| HuVH1C-SfiI | 5'-GTCCTCGCAACTGCGGCCCAGCCGGCCATGGCCSA GGTCCAGCTGGTRCAG TCTGG-3' | SEQ ID NO: 131 |
| HuVH2B-SfiI | 5'-GTCCTCGCAACTGCGGCCCAGCCGGCCATGGCCCA GRTCACCTTGAAGGAGTCTGG-3' | SEQ ID NO: 132 |
| HuVH3B-SfiI | 5'-GTCCTCGCAACTGCGGCCCAGCCGGCCATGGCCSAG GTGCAGCTGGTGGAGTCTGG-3' | SEQ ID NO: 133 |
| HuVH3C-SfiI | 5'-GTCCTCGCAACTGCGGCCCAGCCGGCCATGGCCGA GGTGCAGCTGGTGGAGWCYGG-3' | SEQ ID NO: 134 |
| HuVH4B-SfiI | 5'-GTCCTCGCAACTGCGGCCCAGCCGGCCATGGCCCA GGTGCAGCTACAGCAGTGGGG-3' | SEQ ID NO: 135 |
| HuVH4C-SfiI | 5'-GTCCTCGCAACTGCGGCCCAGCCGGCCATGGCCC AGSTGCAGCTGCAGGAGTCSGG-3' | SEQ ID NO: 136 |
| HuVH5B-SfiI | 5'-GTCCTCGCAACTGCGGCCCAGCCGGCCATGGCCG ARGTGCAGCTGGTGCAGTCTGG-3' | SEQ ID NO: 137 |
| HuVH6A-SfiI | 5'-GTCCTCGCAACTGCGGCCCAGCCGGCCATGGCCC AGGTACAGCTGCAGCAGTCAGG-3' | SEQ ID NO: 138 |
| HuJH1/2-XhoI | 5'-GAGTCATTCTCGACTCGAGACGGTGACCAGGGT GCC-3' | SEQ ID NO: 139 |
| HuJH3-XhoI | 5'-GAGTCATTCTCGACTCGAGACGGTGACCATTGT CCC-3' | SEQ ID NO: 140 |
| HuJH4/5-XhoI | 5'-GAGTCATTCTCGACTCGAGACGGTGACCAGGGTT CC-3' | SEQ ID NO: 141 |
| HuJH6-XhoI | 5'-GAGTCATTCTCGACTCGAGACGGTGACCGTGGTC CC-3' | SEQ ID NO: 142 |

TABLE 8

| Data of the WNV specific single chain Fvs. | | | | | |
|---|---|---|---|---|---|
| Name scFv | SEQ ID NO of nucl. sequence | SEQ ID NO of amino acid sequence* | HCDR3 (SEQ ID NO:) | VH-locus | VL-locus |
| SC04-348 | 25 | 26 (Vh 1-124; Vl 143-250) | DKSYYYGSGTSGG WFDP (SEQ ID NO: 5) | 3-09 (DP-31) | Vk I (O12/O2-DPK9) |
| SC04-354 | 27 | 28 (Vh 1-121; Vl 140-250) | DWGSNYVWGSYP KY (SEQ ID NO: 6) | 1-46 (DP-7) | Vl 1 (1c - V1-16) |

*between brackets the amino acids making up the heavy chain variable region (VH) and the light chain variable region (VL) is shown

TABLE 9

| Data of the CDR regions of the WNV specific single chain Fvs. | | | | | |
|---|---|---|---|---|---|
| Name scFv | HCDR1 (SEQ ID NO:) | HCDR2 (SEQ ID NO:) | LCDR1 (SEQ ID NO:) | LCDR2 (SEQ ID NO:) | LCDR3 (SEQ ID NO:) |
| SC04-348 | 7 | 8 | 9 | 10 | 11 |
| SC04-354 | 12 | 13 | 14 | 15 | 16 |

TABLE 13

| Probit analysis of the protective activity of human IgG1 in a murine lethal WNV challenge model | | |
|---|---|---|
| Antibody | 50% protection (μg/kg) | 95% protection (μg/kg) |
| CR4354L4328 | 2.74 | 57.4 |
| CR4348 | 6.26 | 131 |

TABLE 10

| Binding of IgG1 antibodies to WNV as measured by ELISA (OD 492 nm). | | | | | | | | | | | |
|---|---|---|---|---|---|---|---|---|---|---|---|
| | Antibody Concentration (μg/ml) | | | | | | | | | | |
| Ab | 20.000 | 10.000 | 5.000 | 2.500 | 1.250 | 0.630 | 0.310 | 0.160 | 0.078 | 0.039 | 0.000 |
| CR4348 | ND | 0.370 | 0.343 | 0.300 | 0.251 | 0.192 | 0.143 | 0.122 | 0.104 | 0.085 | 0.003 |
| CR4354 | 0.291 | 0.262 | 0.217 | 0.167 | 0.151 | 0.106 | 0.067 | 0.034 | 0.014 | 0.010 | 0.003 |
| Neg. control | 0.051 | ND | ND | ND | ND | ND | ND | ND | ND | ND | ND |

ND means not determined

TABLE 11

| Potency of the anti-WNV antibodies in the 66% neutralizing antibody titer assay. | |
|---|---|
| Antibody name | μg/ml |
| CR4348 | 1.97 |
| CR4354 | 0.48 |

TABLE 12

| Protection from lethal WNV challenge in mice by monoclonal antibodies. | |
|---|---|
| Antibody (15 mg/kg) | Surviving animals |
| CR4348 | 5/5 |
| CR4354 | 5/5 |
| 7H2 | 5/5 |
| Negative Control IgG1 | 0/5 |

TABLE 14

| Percentage difference in 66% neutralization concentration of IgG1 variants of CR4354 against WNV as measured by VNA. | |
|---|---|
| Antibody | Potency (%)* |
| CR4354 | 100 |
| CR4354L4261 | 106 |
| CR4354L4267 | Below detection |
| CR4354L4328 | 286 |
| CR4354L4335 | 60 |
| CR4354L4383 | Below detection |

*Potency is represented in comparison to original antibody CR4354 (the 66% neutralizing concentration of which was set at 100%) and was calculated by dividing the 66% neutralizing concentration (in μg/ml) of CR4354 by the 66% neutralizing concentration (in μg/ml) of the chain shuffled variants and multiplying the resulting number by 100%.

TABLE 15

| Neutralizing potency against West Nile virus strain USA99b as measured by PRNT. | | |
|---|---|---|
| Antibody | PRNT50 (95% CI) (μg/ml) | PRNT90 (95% CI) (μg/ml) |
| CR4348 | 3.72 (3.21-4.27) | 65.2 (52.3-84.1) |
| CR4354L4328 | 21.2 (10.1-53.4) | 1602 (397-20000) |
| CRM4354 | 0.17 (0.11-0.25) | 4.3 (2.85-7.29) |

TABLE 16

Clones reactive with CR4348 and CR4354L4328 as recognized by protein micro-array analysis.

| Antibody | Reactive clone | Blast | Target (*Homo sapiens*) |
|---|---|---|---|
| CR4348 | MPMGp800B14568 | gi\|19528653\|ref\|NM__007051.2\| | Fas(TNFRSF6) associated factor 1 (FAF1) |
| CR4348 | MPMGp800G07549Q170 | gi\|27924136\|gb\|BC044933.1\| | clone IMAGE: 4540326, mRNA, partial cds |
| CR4348 | MPMGp800O05569Q170 | gi\|54607125\|ref\|NM__013364.2\| | paraneoplastic antigen MA3 (PNMA3), mRNA |
| CR4348 | MPMGp800E02577Q | gi\|34364672\|emb\|BX640642.1 | mRNA; cDNA DKFZp686K01114 |
| CR4348 | MPMGp800M04560Q183 | gi\|39761682\|gb\|AY405708.1\| | CYLN2 gene, VIRTUAL TRANSCRIPT |
| CR4354L4328 | MPMGp800J14549Q | gi\|14198175\|gb\|BC008146.1\| | NADH dehydrogenase (ubiquinone) flavoprotein 1 |
| CR4354L4328 | MPMGp800K13552Q | gi\|62087473\|dbj\|AB208947.1\| | mRNA for chordin isoform a variant protein |
| CR4354L4328 | MPMGp800A02549Q | gi\|17149812\|ref\|NM__057161.2\| | kelch domain containing 3 (KLHDC3) |
| CR4354L4328 | MPMGp800I05513Q | gi\|4753262\|gb\|AC006360.2 | PAC clone RP5-1140N14 from 14q24.3 |

TABLE 17

Mean fluorescence measured after incubation with 2.5 μg/ml antibody.

| Antibody | 293T extracellular | 293T intracellular | 293T-VLP extracellular |
|---|---|---|---|
| CR4348 | 16 | 225 | 15 |
| CR4354L4328 | 16 | 840 | 11 |
| CR4104 | 15 | 55 | 4 |
| CR4374 | 15 | 57 | 19 |
| CR2300 | 484 | 236 | 10 |

REFERENCES

Beasley D. W. and A. D. Barrett (2002), Identification of neutralizing epitopes within structural domain III of the West Nile virus envelope protein. *J. Virol.* 76:13097-13100.

Beasley D. W., L. Li, M. T. Suderman, and A. D. Barrett (2002), Mouse neuroinvasive phenotype of West Nile virus strains varies depending upon virus genotype. Virology 296:17-23.

Ben-Nathan D., S. Lustig, G. Tam, S. Robinzon, S. Segal and B. Rager-Zisman (2003), Prophylactic and therapeutic efficacy of human intravenous immunoglobulin in treating WNV infection in mice. *J. Infect. Dis.* 188:5-12.

Boel E., S. Verlaan, M. J. Poppelier, N. A. Westerdaal, J. A. Van Strijp and T. Logtenberg (2000), Functional human monoclonal antibodies of all isotypes constructed from phage display library-derived single chain Fv antibody fragments. *J. Immunol. Methods* 239:153-166.

Burton D. R. and C. F. Barbas (1994), Human antibodies from combinatorial libraries. *Adv. Immunol.* 57:191-280.

Chou, T. C. and P. Talalay (1984), Quantitative analysis of dose-effect relationships: the combined effects of multiple drugs or enzyme inhibitors. *Adv. Enzyme Regul.* 22:27-55.

De Kruif J., L. Terstappen, E. Boel and T. Logtenberg (1995a), Rapid selection of cell subpopulation-specific human monoclonal antibodies from a synthetic phage antibody library. Proc. Natl. Acad. Sci. USA 92:3938.

De Kruif J., E. Boel and T. Logtenberg (1995b), Selection and application of human single chain Fv antibody fragments from a semi-synthetic phage antibody display library with designed CDR3 regions. *J. Mol. Biol.* 248:97-105.

Gollins S. W. and J. S. Porterfield (1986), A new mechanism for the neutralization of enveloped viruses by antiviral antibody. *Nature* 321:244-246.

Huls G., I. J. Heijnen, E. Cuomo, J. van der Linden, E. Boel, J. van de Winkel and T. Logtenberg (1999), Antitumor immune effector mechanisms recruited by phage display-derived fully human IgG 1 and IgA1 monoclonal antibodies. *Cancer Res.* 59:5778-5784.

Kuno G., G. J. Chang, K. R. Tsuchiya, N. Karabatsos and C. B. Cropp (1998), Phylogeny of the genus Flavivirus. *J. Virol.* 72:73-83.

Rizzuto C. D. and J. G. Sodroski (1997), Contribution of virion ICAM-1 to human immunodeficiency virus infectivity and sensitivity to neutralization. *J. Virol.* 71:4847-4851.

Slootstra J. W., W. C. Puijk, G. J. Ligtvoet, J. P. Langeveld, and R. H. Meloen (1996), Structural aspects of antibody-antigen interaction revealed through small random peptide libraries. *Mol. Divers.* 1:87-96.

Wang T., J. F. Anderson, L. A. Magnarelli, S. J. Wong, R. A. Koski and E. Fikrig (2001), Immunization of mice against West Nile virus with recombinant envelope protein. *J. Immunol.* 167:5273-5277.

What is claimed is:

1. A composition comprising a monoclonal antibody comprising a heavy and a light chain, wherein the heavy chain comprises the CDR1 region of SEQ ID NO:12, the CDR2 region of SEQ ID NO:13, and the CDR3 region of SEQ ID NO:6; and the light chain comprises:

the CDR1 region of SEQ ID NO:14, the CDR2 region of SEQ ID NO:15, and the CDR3 region of SEQ ID NO:16, or the sequence of SEQ ID NO:74.

2. The composition of claim 1 further comprising at least one tag.

3. A nucleic acid molecule encoding a monoclonal antibody comprising a heavy and a light chain, wherein the heavy chain comprises the CDR1 region of SEQ ID NO:12, the CDR2 region of SEQ ID NO:13, and the CDR3 region of SEQ ID NO:6; and the light chain comprises:

the CDR1 region of SEQ ID NO:14, the CDR2 region of SEQ ID NO:15, and the CDR3 region of SEQ ID NO:16, or the sequence of SEQ ID NO:74.

4. The composition of claim 1, further comprising at least one pharmaceutically acceptable excipient.

5. In a method of diagnosing and/or treating an infection caused by a flavivirus in a subject, the improvement comprising:

utilizing the composition of claim 1 in the diagnosis and/or treatment of the flavivirus infection in the subject, wherein said flavivirus is a West Nile Virus.

* * * * *

SEQUENCE LISTING

```
<160> NUMBER OF SEQ ID NOS: 163

<210> SEQ ID NO 1
<211> LENGTH: 2424
<212> TYPE: DNA
<213> ORGANISM: Homo sapiens
<220> FEATURE:
```

```
<221> NAME/KEY: CDS
<222> LOCATION: (278)..(2230)
<223> OTHER INFORMATION: Fas-associated factor-1

<400> SEQUENCE: 1

cccacatcca gaccaatctt cctgtccggg ctgctgcgac gcgggctccg caggttgcag      60

gcgggcggcc ggggcgcctg aaggttaccg agtgcatgag cgcctagcgc ttcccgcgct     120

gccccgcccg ctggcccgcc gacccgcccg ccggctcgcc cgccagcccc tcggcgcccg     180

gcggcggcgg cggcggtggc ggcgacggtc gcaggaggtg ccgtctgcct cccaggtgcg     240

cgcttcgctc ccggagccgc ggaactcggc ggccgcc atg gcg tcc aac atg gac      295
                                        Met Ala Ser Asn Met Asp
                                        1               5

cgg gag atg atc ctg gcg gat ttt cag gca tgt act ggc att gaa aac       343
Arg Glu Met Ile Leu Ala Asp Phe Gln Ala Cys Thr Gly Ile Glu Asn
            10                  15                  20

att gac gaa gct att aca ttg ctt gaa caa aat aat tgg gac tta gtg       391
Ile Asp Glu Ala Ile Thr Leu Leu Glu Gln Asn Asn Trp Asp Leu Val
        25                  30                  35

gca gct atc aat ggt gta ata cca cag gaa aat ggc att cta caa agt       439
Ala Ala Ile Asn Gly Val Ile Pro Gln Glu Asn Gly Ile Leu Gln Ser
    40                  45                  50

gaa tat gga ggt gag acc ata cca gga cct gca ttt aat cca gca agt       487
Glu Tyr Gly Gly Glu Thr Ile Pro Gly Pro Ala Phe Asn Pro Ala Ser
55                  60                  65                  70

cat cca gct tca gct cct act tcc tct tct tct tca gcg ttt cga cct       535
His Pro Ala Ser Ala Pro Thr Ser Ser Ser Ser Ser Ala Phe Arg Pro
                75                  80                  85

gta atg cca tcc agg cag att gta gaa agg caa cct cgg atg ctg gac       583
Val Met Pro Ser Arg Gln Ile Val Glu Arg Gln Pro Arg Met Leu Asp
            90                  95                  100

ttc agg gtt gaa tac aga gac aga aat gtt gat gtg gta ctt gaa gac       631
Phe Arg Val Glu Tyr Arg Asp Arg Asn Val Asp Val Val Leu Glu Asp
        105                 110                 115

acc tgt act gtt gga gag att aaa cag att cta gaa aat gaa ctt cag       679
Thr Cys Thr Val Gly Glu Ile Lys Gln Ile Leu Glu Asn Glu Leu Gln
    120                 125                 130

ata cct gtg tcc aaa atg ctg tta aaa ggc tgg aag acg gga gat gtg       727
Ile Pro Val Ser Lys Met Leu Leu Lys Gly Trp Lys Thr Gly Asp Val
135                 140                 145                 150

gaa gac agt acg gtc cta aaa tct cta cac ttg cca aaa aac aac agt       775
Glu Asp Ser Thr Val Leu Lys Ser Leu His Leu Pro Lys Asn Asn Ser
                155                 160                 165

ctt tat gtc ctt aca cca gat ttg cca cca cct tca tca tct agt cat       823
Leu Tyr Val Leu Thr Pro Asp Leu Pro Pro Pro Ser Ser Ser Ser His
            170                 175                 180

gct ggt gcc ctg cag gag tca tta aat caa aac ttc atg ctg atc atc       871
Ala Gly Ala Leu Gln Glu Ser Leu Asn Gln Asn Phe Met Leu Ile Ile
        185                 190                 195

acc cac cga gaa gtc cag cgg gag tac aac ctg aac ttc tca gga agc       919
Thr His Arg Glu Val Gln Arg Glu Tyr Asn Leu Asn Phe Ser Gly Ser
    200                 205                 210

agt act att caa gag gta aag aga aat gtg tat gac ctt aca agt atc       967
Ser Thr Ile Gln Glu Val Lys Arg Asn Val Tyr Asp Leu Thr Ser Ile
215                 220                 225                 230

ccc gtt cgc cac caa tta tgg gag ggc tgg cca act tct gct aca gac      1015
Pro Val Arg His Gln Leu Trp Glu Gly Trp Pro Thr Ser Ala Thr Asp
                235                 240                 245

gac tca atg tgt ctt gct gaa tca ggg ctc tct tat ccc tgc cat cga      1063
```

-continued

```
Asp Ser Met Cys Leu Ala Glu Ser Gly Leu Ser Tyr Pro Cys His Arg
            250                 255                 260

ctt aca gtg gga aga aga tct tca cct gca cag acc cgg gaa cag tcg      1111
Leu Thr Val Gly Arg Arg Ser Ser Pro Ala Gln Thr Arg Glu Gln Ser
        265                 270                 275

gaa gaa caa atc acc gat gtt cat atg gtt agt gat agc gat gga gat      1159
Glu Glu Gln Ile Thr Asp Val His Met Val Ser Asp Ser Asp Gly Asp
    280                 285                 290

gac ttt gaa gat gct aca gaa ttt ggg gtg gat gat gga gaa gta ttt      1207
Asp Phe Glu Asp Ala Thr Glu Phe Gly Val Asp Asp Gly Glu Val Phe
295                 300                 305                 310

ggc atg gcg tca tct gcc ttg aga aaa tct cca atg atg cca gaa aac      1255
Gly Met Ala Ser Ser Ala Leu Arg Lys Ser Pro Met Met Pro Glu Asn
                315                 320                 325

gca gaa aat gaa gga gat gcc tta tta caa ttt aca gca gag ttt tct      1303
Ala Glu Asn Glu Gly Asp Ala Leu Leu Gln Phe Thr Ala Glu Phe Ser
            330                 335                 340

tca aga tat ggt gat tgc cat cct gta ttt ttt att ggc tca tta gaa      1351
Ser Arg Tyr Gly Asp Cys His Pro Val Phe Phe Ile Gly Ser Leu Glu
        345                 350                 355

gct gct ttt caa gag gcc ttc tat gtg aaa gcc cga gat aga aag ctt      1399
Ala Ala Phe Gln Glu Ala Phe Tyr Val Lys Ala Arg Asp Arg Lys Leu
    360                 365                 370

ctt gct atc tac ctc cac cat gat gaa agt gtg tta acc aac gtg ttc      1447
Leu Ala Ile Tyr Leu His His Asp Glu Ser Val Leu Thr Asn Val Phe
375                 380                 385                 390

tgc tca caa atg ctt tgt gct gaa tcc att gtt tct tat ctg agt caa      1495
Cys Ser Gln Met Leu Cys Ala Glu Ser Ile Val Ser Tyr Leu Ser Gln
                395                 400                 405

aat ttt ata acc tgg gct tgg gat ctg aca aag gac tcc aac aga gca      1543
Asn Phe Ile Thr Trp Ala Trp Asp Leu Thr Lys Asp Ser Asn Arg Ala
            410                 415                 420

aga ttt ctc act atg tgc aat aga cac ttt ggc agt gtt gtg gca caa      1591
Arg Phe Leu Thr Met Cys Asn Arg His Phe Gly Ser Val Val Ala Gln
        425                 430                 435

acc att cgg act caa aaa acg gat cag ttt ccg ctt ttc ctg att att      1639
Thr Ile Arg Thr Gln Lys Thr Asp Gln Phe Pro Leu Phe Leu Ile Ile
    440                 445                 450

atg gga aag cga tca tct aat gaa gtg ttg aat gtg ata caa ggg aac      1687
Met Gly Lys Arg Ser Ser Asn Glu Val Leu Asn Val Ile Gln Gly Asn
455                 460                 465                 470

aca aca gta gat gag tta atg atg aga ctc atg gct gca atg gag atc      1735
Thr Thr Val Asp Glu Leu Met Met Arg Leu Met Ala Ala Met Glu Ile
                475                 480                 485

ttc aca gcc caa caa cag gaa gat ata aag gac gag gat gaa cgt gaa      1783
Phe Thr Ala Gln Gln Gln Glu Asp Ile Lys Asp Glu Asp Glu Arg Glu
            490                 495                 500

gcc aga gaa aat gtg aag aga gag caa gat gag gcc tat cgc ctt tca      1831
Ala Arg Glu Asn Val Lys Arg Glu Gln Asp Glu Ala Tyr Arg Leu Ser
        505                 510                 515

ctt gag gct gac aga gca aag agg gaa gct cac gag aga gag atg gca      1879
Leu Glu Ala Asp Arg Ala Lys Arg Glu Ala His Glu Arg Glu Met Ala
    520                 525                 530

gaa cag ttt cgt ttg gag cag att cgc aaa gaa caa gaa gag gaa cgt      1927
Glu Gln Phe Arg Leu Glu Gln Ile Arg Lys Glu Gln Glu Glu Glu Arg
535                 540                 545                 550

gag gcc atc cgg ctg tcc tta gag caa gcc ctg cct cct gag cca aag      1975
Glu Ala Ile Arg Leu Ser Leu Glu Gln Ala Leu Pro Pro Glu Pro Lys
                555                 560                 565
```

```
gaa gaa aat gct gag cct gtg agc aaa ctg cgg atc cgg acc ccc agt     2023
Glu Glu Asn Ala Glu Pro Val Ser Lys Leu Arg Ile Arg Thr Pro Ser
            570                 575                 580

ggc gag ttc ttg gag cgg cgt ttc ctg gcc agc aac aag ctc cag att     2071
Gly Glu Phe Leu Glu Arg Arg Phe Leu Ala Ser Asn Lys Leu Gln Ile
        585                 590                 595

gtc ttt gat ttt gta gct tcc aaa gga ttt cca tgg gat gag tac aag     2119
Val Phe Asp Phe Val Ala Ser Lys Gly Phe Pro Trp Asp Glu Tyr Lys
    600                 605                 610

tta ctg agc acc ttt cct agg aga gac gta act caa ctg gac cca aat     2167
Leu Leu Ser Thr Phe Pro Arg Arg Asp Val Thr Gln Leu Asp Pro Asn
615                 620                 625                 630

aaa tca tta ttg gag gta aag ttg ttc cct caa gaa acc ctt ttc ctt     2215
Lys Ser Leu Leu Glu Val Lys Leu Phe Pro Gln Glu Thr Leu Phe Leu
            635                 640                 645

gaa gca aaa gag taa acacggccca gcggtggaac cagccattcc ttgacaagcc     2270
Glu Ala Lys Glu
            650

agcagcctgc gtcaggagaa gggctcctcg ccaacccacc cacacgctcg tctcactcaa   2330

ttcaatgtca cacttctgcc tcttgcaaaa ttgctggaaa aagtaataat aaatatagct   2390

acttaaaaaa aaaaaaaaaa aaaaaaaaaa aaaa                               2424


<210> SEQ ID NO 2
<211> LENGTH: 650
<212> TYPE: PRT
<213> ORGANISM: Homo sapiens

<400> SEQUENCE: 2

Met Ala Ser Asn Met Asp Arg Glu Met Ile Leu Ala Asp Phe Gln Ala
1               5                   10                  15

Cys Thr Gly Ile Glu Asn Ile Asp Glu Ala Ile Thr Leu Leu Glu Gln
            20                  25                  30

Asn Asn Trp Asp Leu Val Ala Ala Ile Asn Gly Val Ile Pro Gln Glu
        35                  40                  45

Asn Gly Ile Leu Gln Ser Glu Tyr Gly Gly Glu Thr Ile Pro Gly Pro
    50                  55                  60

Ala Phe Asn Pro Ala Ser His Pro Ala Ser Ala Pro Thr Ser Ser Ser
65                  70                  75                  80

Ser Ser Ala Phe Arg Pro Val Met Pro Ser Arg Gln Ile Val Glu Arg
                85                  90                  95

Gln Pro Arg Met Leu Asp Phe Arg Val Glu Tyr Arg Asp Arg Asn Val
            100                 105                 110

Asp Val Val Leu Glu Asp Thr Cys Thr Val Gly Glu Ile Lys Gln Ile
        115                 120                 125

Leu Glu Asn Glu Leu Gln Ile Pro Val Ser Lys Met Leu Leu Lys Gly
    130                 135                 140

Trp Lys Thr Gly Asp Val Glu Asp Ser Thr Val Leu Lys Ser Leu His
145                 150                 155                 160

Leu Pro Lys Asn Asn Ser Leu Tyr Val Leu Thr Pro Asp Leu Pro Pro
                165                 170                 175

Pro Ser Ser Ser Ser His Ala Gly Ala Leu Gln Glu Ser Leu Asn Gln
            180                 185                 190

Asn Phe Met Leu Ile Ile Thr His Arg Glu Val Gln Arg Glu Tyr Asn
        195                 200                 205

Leu Asn Phe Ser Gly Ser Ser Thr Ile Gln Glu Val Lys Arg Asn Val
    210                 215                 220
```

```
Tyr Asp Leu Thr Ser Ile Pro Val Arg His Gln Leu Trp Glu Gly Trp
225                 230                 235                 240

Pro Thr Ser Ala Thr Asp Asp Ser Met Cys Leu Ala Glu Ser Gly Leu
                245                 250                 255

Ser Tyr Pro Cys His Arg Leu Thr Val Gly Arg Arg Ser Ser Pro Ala
            260                 265                 270

Gln Thr Arg Glu Gln Ser Glu Glu Gln Ile Thr Asp Val His Met Val
        275                 280                 285

Ser Asp Ser Asp Gly Asp Asp Phe Glu Asp Ala Thr Glu Phe Gly Val
    290                 295                 300

Asp Asp Gly Glu Val Phe Gly Met Ala Ser Ser Ala Leu Arg Lys Ser
305                 310                 315                 320

Pro Met Met Pro Glu Asn Ala Glu Asn Glu Gly Asp Ala Leu Leu Gln
                325                 330                 335

Phe Thr Ala Glu Phe Ser Ser Arg Tyr Gly Asp Cys His Pro Val Phe
            340                 345                 350

Phe Ile Gly Ser Leu Glu Ala Ala Phe Gln Glu Ala Phe Tyr Val Lys
        355                 360                 365

Ala Arg Asp Arg Lys Leu Leu Ala Ile Tyr Leu His His Asp Glu Ser
    370                 375                 380

Val Leu Thr Asn Val Phe Cys Ser Gln Met Leu Cys Ala Glu Ser Ile
385                 390                 395                 400

Val Ser Tyr Leu Ser Gln Asn Phe Ile Thr Trp Ala Trp Asp Leu Thr
                405                 410                 415

Lys Asp Ser Asn Arg Ala Arg Phe Leu Thr Met Cys Asn Arg His Phe
            420                 425                 430

Gly Ser Val Val Ala Gln Thr Ile Arg Thr Gln Lys Thr Asp Gln Phe
        435                 440                 445

Pro Leu Phe Leu Ile Ile Met Gly Lys Arg Ser Ser Asn Glu Val Leu
    450                 455                 460

Asn Val Ile Gln Gly Asn Thr Thr Val Asp Glu Leu Met Met Arg Leu
465                 470                 475                 480

Met Ala Ala Met Glu Ile Phe Thr Ala Gln Gln Gln Glu Asp Ile Lys
                485                 490                 495

Asp Glu Asp Glu Arg Glu Ala Arg Glu Asn Val Lys Arg Glu Gln Asp
            500                 505                 510

Glu Ala Tyr Arg Leu Ser Leu Glu Ala Asp Arg Ala Lys Arg Glu Ala
        515                 520                 525

His Glu Arg Glu Met Ala Glu Gln Phe Arg Leu Glu Gln Ile Arg Lys
    530                 535                 540

Glu Gln Glu Glu Glu Arg Glu Ala Ile Arg Leu Ser Leu Glu Gln Ala
545                 550                 555                 560

Leu Pro Pro Glu Pro Lys Glu Glu Asn Ala Glu Pro Val Ser Lys Leu
                565                 570                 575

Arg Ile Arg Thr Pro Ser Gly Glu Phe Leu Glu Arg Arg Phe Leu Ala
            580                 585                 590

Ser Asn Lys Leu Gln Ile Val Phe Asp Phe Val Ala Ser Lys Gly Phe
        595                 600                 605

Pro Trp Asp Glu Tyr Lys Leu Leu Ser Thr Phe Pro Arg Arg Asp Val
    610                 615                 620

Thr Gln Leu Asp Pro Asn Lys Ser Leu Leu Glu Val Lys Leu Phe Pro
625                 630                 635                 640
```

```
Gln Glu Thr Leu Phe Leu Glu Ala Lys Glu
                645                 650


<210> SEQ ID NO 3
<211> LENGTH: 1529
<212> TYPE: DNA
<213> ORGANISM: Homo sapiens
<220> FEATURE:
<221> NAME/KEY: CDS
<222> LOCATION: (34)..(1428)
<223> OTHER INFORMATION: NADH-dehydrogenase (ubiquinone) flavoprotein-1

<400> SEQUENCE: 3

gacagcgtga ggtgacccat ctggcccgcc gcg atg ctg gca aca cgg cgg ctg      54
                                     Met Leu Ala Thr Arg Arg Leu
                                     1               5

ctc ggc tgg tcg ctt ccc gcg cgg gta tct gtg cgt ttc agc ggc gac     102
Leu Gly Trp Ser Leu Pro Ala Arg Val Ser Val Arg Phe Ser Gly Asp
        10                  15                  20

acg aca gca ccc aag aaa acc tca ttt ggc tcg ctg aag gat gaa gac     150
Thr Thr Ala Pro Lys Lys Thr Ser Phe Gly Ser Leu Lys Asp Glu Asp
    25                  30                  35

cgg att ttc acc aac ctg tac ggc cgc cat gac tgg agg ctg aaa ggt     198
Arg Ile Phe Thr Asn Leu Tyr Gly Arg His Asp Trp Arg Leu Lys Gly
40                  45                  50                  55

tcc ctg agt cga ggt gac tgg tac aag aca aag gag atc ctg ctg aag     246
Ser Leu Ser Arg Gly Asp Trp Tyr Lys Thr Lys Glu Ile Leu Leu Lys
                60                  65                  70

ggg ccc gac tgg atc ctg ggc gag atc aag aca tcg ggt ttg agg ggc     294
Gly Pro Asp Trp Ile Leu Gly Glu Ile Lys Thr Ser Gly Leu Arg Gly
            75                  80                  85

cgt gga ggc gct ggc ttc ccc act ggc ctc aag tgg agc ttc atg aat     342
Arg Gly Gly Ala Gly Phe Pro Thr Gly Leu Lys Trp Ser Phe Met Asn
        90                  95                  100

aag ccc tca gat ggc agg ccc aag tat ctg gtg gtg aac gca gac gag     390
Lys Pro Ser Asp Gly Arg Pro Lys Tyr Leu Val Val Asn Ala Asp Glu
    105                 110                 115

ggg gag ccg ggc acc tgc aag gac cgg gag atc tta cgc cat gat cct     438
Gly Glu Pro Gly Thr Cys Lys Asp Arg Glu Ile Leu Arg His Asp Pro
120                 125                 130                 135

cac aag ctg ctg gaa ggc tgc ctg gtg ggg ggc cgg gcc atg ggc gcc     486
His Lys Leu Leu Glu Gly Cys Leu Val Gly Gly Arg Ala Met Gly Ala
                140                 145                 150

cgc gct gcc tat atc tac atc cga ggg gaa ttc tac aat gag gcc tcc     534
Arg Ala Ala Tyr Ile Tyr Ile Arg Gly Glu Phe Tyr Asn Glu Ala Ser
            155                 160                 165

aat ctg cag gtg gcc atc cga gag gcc tat gag gca ggt ctg att ggc     582
Asn Leu Gln Val Ala Ile Arg Glu Ala Tyr Glu Ala Gly Leu Ile Gly
        170                 175                 180

aag aat gct tgt ggc tct ggc tat gat ttt gac gtg ttt gtg gtg cgc     630
Lys Asn Ala Cys Gly Ser Gly Tyr Asp Phe Asp Val Phe Val Val Arg
    185                 190                 195

ggg gct ggg gcc tac atc tgt gga gag gag aca gcg ctc atc gag tcc     678
Gly Ala Gly Ala Tyr Ile Cys Gly Glu Glu Thr Ala Leu Ile Glu Ser
200                 205                 210                 215

att gag ggc aag cag ggc aag ccc cgc ctg aag ccc ccc ttc ccc gca     726
Ile Glu Gly Lys Gln Gly Lys Pro Arg Leu Lys Pro Pro Phe Pro Ala
                220                 225                 230

gac gtg gga gtg ttt ggc tgc ccc aca act gtg gcc aac gtg gag aca     774
Asp Val Gly Val Phe Gly Cys Pro Thr Thr Val Ala Asn Val Glu Thr
            235                 240                 245
```

```
gtg gca gtg tcc ccc aca atc tgc cgc cgt gga ggt acc tgg ttt gct      822
Val Ala Val Ser Pro Thr Ile Cys Arg Arg Gly Gly Thr Trp Phe Ala
        250                 255                 260

ggc ttt ggc aga gaa cgc aac tca ggc acc aaa cta ttc aac atc tct      870
Gly Phe Gly Arg Glu Arg Asn Ser Gly Thr Lys Leu Phe Asn Ile Ser
    265                 270                 275

ggc cat gtc aac cac cct tgc act gtg gag gag gag atg tct gtg ccc      918
Gly His Val Asn His Pro Cys Thr Val Glu Glu Glu Met Ser Val Pro
280                 285                 290                 295

ttg aaa gaa ctg att gag aag cat gct ggg ggt gtc acg ggc ggc tgg      966
Leu Lys Glu Leu Ile Glu Lys His Ala Gly Gly Val Thr Gly Gly Trp
            300                 305                 310

gac aac ctc ctt gct gtg atc cct ggc ggc tcg tct acc cca ctg atc     1014
Asp Asn Leu Leu Ala Val Ile Pro Gly Gly Ser Ser Thr Pro Leu Ile
            315                 320                 325

ccc aag tct gtg tgt gag acg gtg ctg atg gac ttc gat gcg ctg gtg     1062
Pro Lys Ser Val Cys Glu Thr Val Leu Met Asp Phe Asp Ala Leu Val
        330                 335                 340

cag gca cag aca ggc ctg ggc aca gct gcg gtg atc gtc atg gac cgc     1110
Gln Ala Gln Thr Gly Leu Gly Thr Ala Ala Val Ile Val Met Asp Arg
    345                 350                 355

tcg acg gac atc gtg aaa gcc atc gcc cgc ctc att gag ttc tat aag     1158
Ser Thr Asp Ile Val Lys Ala Ile Ala Arg Leu Ile Glu Phe Tyr Lys
360                 365                 370                 375

cac gag agc tgt ggc cag tgt acc cca tgc cgt gag ggt gtg gac tgg     1206
His Glu Ser Cys Gly Gln Cys Thr Pro Cys Arg Glu Gly Val Asp Trp
            380                 385                 390

atg aac aag gtg atg gca cgt ttc gtg agg ggg gat gcc cgg ccg gcc     1254
Met Asn Lys Val Met Ala Arg Phe Val Arg Gly Asp Ala Arg Pro Ala
            395                 400                 405

gag atc gac tcc ctg tgg gag atc agc aag cag ata gaa ggc cat acg     1302
Glu Ile Asp Ser Leu Trp Glu Ile Ser Lys Gln Ile Glu Gly His Thr
        410                 415                 420

att tgt gct ctg ggt gac ggg gcc gcc tgg cct gtg cag ggt ctg atc     1350
Ile Cys Ala Leu Gly Asp Gly Ala Ala Trp Pro Val Gln Gly Leu Ile
    425                 430                 435

cgc cac ttt cgg ccg gag ctc gag gag cgg atg cag cgg ttt gcc cag     1398
Arg His Phe Arg Pro Glu Leu Glu Glu Arg Met Gln Arg Phe Ala Gln
440                 445                 450                 455

cag cat cag gcc cgg cag gct gcc tct tag cccaccaccc tggcctgctg       1448
Gln His Gln Ala Arg Gln Ala Ala Ser
                460

tcctgcgtct atccatgtgg aatgctggac aataaagcga gtgctgccca ccctccaaaa   1508

aaaaaaaaaa aaaaaaaaaa a                                             1529
```

<210> SEQ ID NO 4
<211> LENGTH: 464
<212> TYPE: PRT
<213> ORGANISM: Homo sapiens

<400> SEQUENCE: 4

```
Met Leu Ala Thr Arg Arg Leu Leu Gly Trp Ser Leu Pro Ala Arg Val
1               5                   10                  15

Ser Val Arg Phe Ser Gly Asp Thr Thr Ala Pro Lys Lys Thr Ser Phe
            20                  25                  30

Gly Ser Leu Lys Asp Glu Asp Arg Ile Phe Thr Asn Leu Tyr Gly Arg
        35                  40                  45

His Asp Trp Arg Leu Lys Gly Ser Leu Ser Arg Gly Asp Trp Tyr Lys
    50                  55                  60
```

```
Thr Lys Glu Ile Leu Leu Lys Gly Pro Asp Trp Ile Leu Gly Glu Ile
65                  70                  75                  80

Lys Thr Ser Gly Leu Arg Gly Arg Gly Gly Ala Gly Phe Pro Thr Gly
                85                  90                  95

Leu Lys Trp Ser Phe Met Asn Lys Pro Ser Asp Gly Arg Pro Lys Tyr
            100                 105                 110

Leu Val Val Asn Ala Asp Glu Gly Glu Pro Gly Thr Cys Lys Asp Arg
        115                 120                 125

Glu Ile Leu Arg His Asp Pro His Lys Leu Leu Glu Gly Cys Leu Val
    130                 135                 140

Gly Gly Arg Ala Met Gly Ala Arg Ala Ala Tyr Ile Tyr Ile Arg Gly
145                 150                 155                 160

Glu Phe Tyr Asn Glu Ala Ser Asn Leu Gln Val Ala Ile Arg Glu Ala
                165                 170                 175

Tyr Glu Ala Gly Leu Ile Gly Lys Asn Ala Cys Gly Ser Gly Tyr Asp
            180                 185                 190

Phe Asp Val Phe Val Val Arg Gly Ala Gly Ala Tyr Ile Cys Gly Glu
        195                 200                 205

Glu Thr Ala Leu Ile Glu Ser Ile Glu Gly Lys Gln Gly Lys Pro Arg
    210                 215                 220

Leu Lys Pro Pro Phe Pro Ala Asp Val Gly Val Phe Gly Cys Pro Thr
225                 230                 235                 240

Thr Val Ala Asn Val Glu Thr Val Ala Val Ser Pro Thr Ile Cys Arg
                245                 250                 255

Arg Gly Gly Thr Trp Phe Ala Gly Phe Gly Arg Glu Arg Asn Ser Gly
            260                 265                 270

Thr Lys Leu Phe Asn Ile Ser Gly His Val Asn His Pro Cys Thr Val
        275                 280                 285

Glu Glu Glu Met Ser Val Pro Leu Lys Glu Leu Ile Glu Lys His Ala
    290                 295                 300

Gly Gly Val Thr Gly Gly Trp Asp Asn Leu Leu Ala Val Ile Pro Gly
305                 310                 315                 320

Gly Ser Ser Thr Pro Leu Ile Pro Lys Ser Val Cys Glu Thr Val Leu
                325                 330                 335

Met Asp Phe Asp Ala Leu Val Gln Ala Gln Thr Gly Leu Gly Thr Ala
            340                 345                 350

Ala Val Ile Val Met Asp Arg Ser Thr Asp Ile Val Lys Ala Ile Ala
        355                 360                 365

Arg Leu Ile Glu Phe Tyr Lys His Glu Ser Cys Gly Gln Cys Thr Pro
    370                 375                 380

Cys Arg Glu Gly Val Asp Trp Met Asn Lys Val Met Ala Arg Phe Val
385                 390                 395                 400

Arg Gly Asp Ala Arg Pro Ala Glu Ile Asp Ser Leu Trp Glu Ile Ser
                405                 410                 415

Lys Gln Ile Glu Gly His Thr Ile Cys Ala Leu Gly Asp Gly Ala Ala
            420                 425                 430

Trp Pro Val Gln Gly Leu Ile Arg His Phe Arg Pro Glu Leu Glu Glu
        435                 440                 445

Arg Met Gln Arg Phe Ala Gln Gln His Gln Ala Arg Gln Ala Ala Ser
    450                 455                 460
```

<210> SEQ ID NO 5
<211> LENGTH: 17

<212> TYPE: PRT
<213> ORGANISM: Artificial sequence
<220> FEATURE:
<223> OTHER INFORMATION: HCDR3

<400> SEQUENCE: 5

Asp Lys Ser Tyr Tyr Tyr Gly Ser Gly Thr Ser Gly Gly Trp Phe Asp
1 5 10 15

Pro

<210> SEQ ID NO 6
<211> LENGTH: 14
<212> TYPE: PRT
<213> ORGANISM: Artificial sequence
<220> FEATURE:
<223> OTHER INFORMATION: HCDR3

<400> SEQUENCE: 6

Asp Trp Gly Ser Asn Tyr Val Trp Gly Ser Tyr Pro Lys Tyr
1 5 10

<210> SEQ ID NO 7
<211> LENGTH: 5
<212> TYPE: PRT
<213> ORGANISM: Artificial sequence
<220> FEATURE:
<223> OTHER INFORMATION: HCDR1

<400> SEQUENCE: 7

Asp Tyr Ala Met His
1 5

<210> SEQ ID NO 8
<211> LENGTH: 17
<212> TYPE: PRT
<213> ORGANISM: Artificial sequence
<220> FEATURE:
<223> OTHER INFORMATION: HCDR2

<400> SEQUENCE: 8

Gly Ile Ser Trp Asn Ser Gly Asn Ile Gly Tyr Ala Asp Ser Val Lys
1 5 10 15

Gly

<210> SEQ ID NO 9
<211> LENGTH: 11
<212> TYPE: PRT
<213> ORGANISM: Artificial sequence
<220> FEATURE:
<223> OTHER INFORMATION: LCDR1

<400> SEQUENCE: 9

Arg Ala Ser Gln Ser Ile Ser Ser Tyr Leu Asn
1 5 10

<210> SEQ ID NO 10
<211> LENGTH: 7
<212> TYPE: PRT
<213> ORGANISM: Artificial sequence
<220> FEATURE:
<223> OTHER INFORMATION: LCDR2

<400> SEQUENCE: 10

Ala Ala Ser Ser Leu Gln Ser
1 5

<210> SEQ ID NO 11
<211> LENGTH: 9
<212> TYPE: PRT
<213> ORGANISM: Artificial sequence
<220> FEATURE:
<223> OTHER INFORMATION: LCDR3

<400> SEQUENCE: 11

Gln Gln Ser Tyr Ser Thr Pro Arg Thr
1 5

<210> SEQ ID NO 12
<211> LENGTH: 5
<212> TYPE: PRT
<213> ORGANISM: Artificial sequence
<220> FEATURE:
<223> OTHER INFORMATION: HCDR1

<400> SEQUENCE: 12

His Tyr Tyr Met His
1 5

<210> SEQ ID NO 13
<211> LENGTH: 17
<212> TYPE: PRT
<213> ORGANISM: Artificial sequence
<220> FEATURE:
<223> OTHER INFORMATION: HCDR2

<400> SEQUENCE: 13

Ile Ile Asn Pro Ser Gly Gly Ser Thr Thr Tyr Ala Gln Lys Leu Gln
1 5 10 15

Gly

<210> SEQ ID NO 14
<211> LENGTH: 13
<212> TYPE: PRT
<213> ORGANISM: Artificial sequence
<220> FEATURE:
<223> OTHER INFORMATION: LCDR1

<400> SEQUENCE: 14

Ser Gly Ser Ser Ser Asn Ile Gly Ser Asn Thr Val Asn
1 5 10

<210> SEQ ID NO 15
<211> LENGTH: 7
<212> TYPE: PRT
<213> ORGANISM: Artificial sequence
<220> FEATURE:
<223> OTHER INFORMATION: LCDR2

<400> SEQUENCE: 15

Ser Asn Asn Gln Arg Pro Ser
1 5

<210> SEQ ID NO 16
<211> LENGTH: 11
<212> TYPE: PRT
<213> ORGANISM: Artificial sequence
<220> FEATURE:
<223> OTHER INFORMATION: LCDR3

<400> SEQUENCE: 16

Ala Ala Trp Asp Asp Ser Leu Asn Gly Pro Val
1 5 10

```
<210> SEQ ID NO 17
<211> LENGTH: 372
<212> TYPE: DNA
<213> ORGANISM: Artificial sequence
<220> FEATURE:
<223> OTHER INFORMATION: Heavy chain variable region 348
<220> FEATURE:
<221> NAME/KEY: CDS
<222> LOCATION: (1)..(372)
<223> OTHER INFORMATION: Heavy chain variable region 348

<400> SEQUENCE: 17

gag gtg cag ctg gtg gag tct ggg gga ggc ttg gta cag cct ggc agg       48
Glu Val Gln Leu Val Glu Ser Gly Gly Gly Leu Val Gln Pro Gly Arg
1               5                   10                  15

tcc ctg aga ctc tcc tgt gca gcc tct gga ttc acc ttt gat gat tat       96
Ser Leu Arg Leu Ser Cys Ala Ala Ser Gly Phe Thr Phe Asp Asp Tyr
            20                  25                  30

gcc atg cac tgg gtc cgg caa gct cca ggg aag ggc ctg gag tgg gtc      144
Ala Met His Trp Val Arg Gln Ala Pro Gly Lys Gly Leu Glu Trp Val
        35                  40                  45

tca ggt att agt tgg aat agt ggt aac ata ggc tat gcg gac tct gtg      192
Ser Gly Ile Ser Trp Asn Ser Gly Asn Ile Gly Tyr Ala Asp Ser Val
    50                  55                  60

aag ggc cga ttc acc atc tcc aga gac aac gcc aag aac tcc ctg tat      240
Lys Gly Arg Phe Thr Ile Ser Arg Asp Asn Ala Lys Asn Ser Leu Tyr
65                  70                  75                  80

ctg caa atg aac agt ctg aga gct gag gac acg gcc ttg tat tac tgt      288
Leu Gln Met Asn Ser Leu Arg Ala Glu Asp Thr Ala Leu Tyr Tyr Cys
                85                  90                  95

gca aaa gat aaa tcg tat tat tat ggt tcg ggg acc tcg gga ggc tgg      336
Ala Lys Asp Lys Ser Tyr Tyr Tyr Gly Ser Gly Thr Ser Gly Gly Trp
            100                 105                 110

ttc gac ccc tgg ggc cag ggc acc ctg gtg acc gtc                      372
Phe Asp Pro Trp Gly Gln Gly Thr Leu Val Thr Val
        115                 120


<210> SEQ ID NO 18
<211> LENGTH: 124
<212> TYPE: PRT
<213> ORGANISM: Artificial sequence
<220> FEATURE:
<223> OTHER INFORMATION: Heavy chain variable region 348

<400> SEQUENCE: 18

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Asn Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Lys Ser Tyr Tyr Tyr Gly Ser Gly Thr Ser Gly Gly Trp
            100                 105                 110

Phe Asp Pro Trp Gly Gln Gly Thr Leu Val Thr Val
```

```
        115                 120


<210> SEQ ID NO 19
<211> LENGTH: 363
<212> TYPE: DNA
<213> ORGANISM: Artificial sequence
<220> FEATURE:
<223> OTHER INFORMATION: Heavy chain variable region 354
<220> FEATURE:
<221> NAME/KEY: CDS
<222> LOCATION: (1)..(363)
<223> OTHER INFORMATION: Heavy chain variable region 354

<400> SEQUENCE: 19

cag gtg cag ctg gtg cag tct ggg gct gag gtg agg aag cct ggg gcc       48
Gln Val Gln Leu Val Gln Ser Gly Ala Glu Val Arg Lys Pro Gly Ala
1               5                   10                  15

tca gtg aag gtt tcc tgc aag gca tct gga tac acc ttc acc cac tat       96
Ser Val Lys Val Ser Cys Lys Ala Ser Gly Tyr Thr Phe Thr His Tyr
            20                  25                  30

tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45

gga ata atc aac cct agt ggt ggt agc aca acc tac gca cag aag ctc      192
Gly Ile Ile Asn Pro Ser Gly Gly Ser Thr Thr Tyr Ala Gln Lys Leu
    50                  55                  60

cag ggc aga gtc acc atg acc agg gac acg tcc acg agc aca gtc tac      240
Gln Gly Arg Val Thr Met Thr Arg Asp Thr Ser Thr Ser Thr Val Tyr
65                  70                  75                  80

atg gag ctg agc agc ctg aga tct gag gac acg gcc gtg tat tac tgt      288
Met Glu Leu Ser Ser Leu Arg Ser Glu Asp Thr Ala Val Tyr Tyr Cys
                85                  90                  95

gcg aga gat tgg ggc tcc aat tac gtt tgg ggg agt tat ccc aag tac      336
Ala Arg Asp Trp Gly Ser Asn Tyr Val Trp Gly Ser Tyr Pro Lys Tyr
            100                 105                 110

tgg ggc cag ggc acc ctg gtc acc gtc                                  363
Trp Gly Gln Gly Thr Leu Val Thr Val
        115                 120


<210> SEQ ID NO 20
<211> LENGTH: 121
<212> TYPE: PRT
<213> ORGANISM: Artificial sequence
<220> FEATURE:
<223> OTHER INFORMATION: Heavy chain variable region 354

<400> SEQUENCE: 20

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr His Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Thr Tyr Ala Gln Lys Leu
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Trp Gly Ser Asn Tyr Val Trp Gly Ser Tyr Pro Lys Tyr
            100                 105                 110
```

```
Trp Gly Gln Gly Thr Leu Val Thr Val
        115                 120


<210> SEQ ID NO 21
<211> LENGTH: 330
<212> TYPE: DNA
<213> ORGANISM: Artificial sequence
<220> FEATURE:
<223> OTHER INFORMATION: Light chain variable region 348
<220> FEATURE:
<221> NAME/KEY: CDS
<222> LOCATION: (1)..(330)
<223> OTHER INFORMATION: Light chain variable region 348

<400> SEQUENCE: 21

tcg acg gac atc cag atg acc cag tct cca tcc tcc ctg tct gca tct       48
Ser Thr Asp Ile Gln Met Thr Gln Ser Pro Ser Ser Leu Ser Ala Ser
1               5                   10                  15

gta gga gac aga gtc acc atc act tgc cgg gca agt cag agc att agc       96
Val Gly Asp Arg Val Thr Ile Thr Cys Arg Ala Ser Gln Ser Ile Ser
            20                  25                  30

agc tat tta aat tgg tat cag cag aaa cca ggg aaa gcc cct aag ctc      144
Ser Tyr Leu Asn Trp Tyr Gln Gln Lys Pro Gly Lys Ala Pro Lys Leu
        35                  40                  45

ctg atc tat gct gca tcc agt ttg caa agt ggg gtc cca tca agg ttc      192
Leu Ile Tyr Ala Ala Ser Ser Leu Gln Ser Gly Val Pro Ser Arg Phe
    50                  55                  60

agt ggc agt gga tct ggg aca gat ttc act ctc acc atc agc agt ctg      240
Ser Gly Ser Gly Ser Gly Thr Asp Phe Thr Leu Thr Ile Ser Ser Leu
65                  70                  75                  80

caa cct gaa gat ttt gca act tac tac tgt caa cag agt tac agt acc      288
Gln Pro Glu Asp Phe Ala Thr Tyr Tyr Cys Gln Gln Ser Tyr Ser Thr
                85                  90                  95

cct cgg acg ttc ggc caa ggg acc aag ctg gag atc aaa cgt              330
Pro Arg Thr Phe Gly Gln Gly Thr Lys Leu Glu Ile Lys Arg
            100                 105                 110


<210> SEQ ID NO 22
<211> LENGTH: 110
<212> TYPE: PRT
<213> ORGANISM: Artificial sequence
<220> FEATURE:
<223> OTHER INFORMATION: Light chain variable region 348

<400> SEQUENCE: 22

Ser Thr Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Thr
                85                  90                  95

Pro Arg Thr Phe Gly Gln Gly Thr Lys Leu Glu Ile Lys Arg
            100                 105                 110


<210> SEQ ID NO 23
<211> LENGTH: 333
```

```
<212> TYPE: DNA
<213> ORGANISM: Artificial sequence
<220> FEATURE:
<223> OTHER INFORMATION: Light chain variable region 354
<220> FEATURE:
<221> NAME/KEY: CDS
<222> LOCATION: (1)..(333)
<223> OTHER INFORMATION: Light chain variable region 354

<400> SEQUENCE: 23

cag tct gtg ttg acg cag ccg ccc tca gtg tct gcg gcc ccc gga cag       48
Gln Ser Val Leu Thr Gln Pro Pro Ser Val Ser Ala Ala Pro Gly Gln
1               5                   10                  15

aag gtc acc atc tcc tgt tct gga agc agc tcc aac atc gga agt aat       96
Lys Val Thr Ile Ser Cys Ser Gly Ser Ser Ser Asn Ile Gly Ser Asn
            20                  25                  30

act gta aac tgg tac cag cag ctc cca gga acg gcc ccc aaa ctc ctc      144
Thr Val Asn Trp Tyr Gln Gln Leu Pro Gly Thr Ala Pro Lys Leu Leu
        35                  40                  45

atc tat agt aat aat cag cgg ccc tca ggg atc cct gac cga ttc tct      192
Ile Tyr Ser Asn Asn Gln Arg Pro Ser Gly Ile Pro Asp Arg Phe Ser
    50                  55                  60

ggc tcc aag tct ggc acc tca gcc tcc ctg gcc atc agt ggg ctc caa      240
Gly Ser Lys Ser Gly Thr Ser Ala Ser Leu Ala Ile Ser Gly Leu Gln
65                  70                  75                  80

tct gaa gat gag gct gat tat tac tgt gca gca tgg gat gac agc ctg      288
Ser Glu Asp Glu Ala Asp Tyr Tyr Cys Ala Ala Trp Asp Asp Ser Leu
                85                  90                  95

aat ggt ccg gtg ttc ggc gga ggg acc aag ctg acc gtc cta ggt          333
Asn Gly Pro Val Phe Gly Gly Gly Thr Lys Leu Thr Val Leu Gly
            100                 105                 110


<210> SEQ ID NO 24
<211> LENGTH: 111
<212> TYPE: PRT
<213> ORGANISM: Artificial sequence
<220> FEATURE:
<223> OTHER INFORMATION: Light chain variable region 354

<400> SEQUENCE: 24

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Ile Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly
            100                 105                 110


<210> SEQ ID NO 25
<211> LENGTH: 750
<212> TYPE: DNA
<213> ORGANISM: Artificial sequence
<220> FEATURE:
<223> OTHER INFORMATION: SC04-348
<220> FEATURE:
<221> NAME/KEY: CDS
```

```
<222> LOCATION: (1)..(750)
<223> OTHER INFORMATION: SC04-348

<400> SEQUENCE: 25

gag gtg cag ctg gtg cag tct ggg gga ggc ttg gta cag cct ggc agg       48
Glu Val Gln Leu Val Gln Ser Gly Gly Gly Leu Val Gln Pro Gly Arg
1               5                   10                  15

tcc ctg aga ctc tcc tgt gca gcc tct gga ttc acc ttt gat gat tat       96
Ser Leu Arg Leu Ser Cys Ala Ala Ser Gly Phe Thr Phe Asp Asp Tyr
            20                  25                  30

gcc atg cac tgg gtc cgg caa gct cca ggg aag ggc ctg gag tgg gtc      144
Ala Met His Trp Val Arg Gln Ala Pro Gly Lys Gly Leu Glu Trp Val
        35                  40                  45

tca ggt att agt tgg aat agt ggt aac ata ggc tat gcg gac tct gtg      192
Ser Gly Ile Ser Trp Asn Ser Gly Asn Ile Gly Tyr Ala Asp Ser Val
    50                  55                  60

aag ggc cga ttc acc atc tcc aga gac aac gcc aag aac tcc ctg tat      240
Lys Gly Arg Phe Thr Ile Ser Arg Asp Asn Ala Lys Asn Ser Leu Tyr
65                  70                  75                  80

ctg caa atg aac agt ctg aga gct gag gac acg gcc ttg tat tac tgt      288
Leu Gln Met Asn Ser Leu Arg Ala Glu Asp Thr Ala Leu Tyr Tyr Cys
                85                  90                  95

gca aaa gat aaa tcg tat tat tat ggt tcg ggg acc tcg gga ggc tgg      336
Ala Lys Asp Lys Ser Tyr Tyr Tyr Gly Ser Gly Thr Ser Gly Gly Trp
            100                 105                 110

ttc gac ccc tgg ggc cag ggc acc ctg gtc acc gtc tcg agc ggt acg      384
Phe Asp Pro Trp Gly Gln Gly Thr Leu Val Thr Val Ser Ser Gly Thr
        115                 120                 125

ggc ggt tca ggc gga acc ggc agc ggc act ggc ggg tcg acg gac atc      432
Gly Gly Ser Gly Gly Thr Gly Ser Gly Thr Gly Gly Ser Thr Asp Ile
    130                 135                 140

cag atg acc cag tct cca tcc tcc ctg tct gca tct gta gga gac aga      480
Gln Met Thr Gln Ser Pro Ser Ser Leu Ser Ala Ser Val Gly Asp Arg
145                 150                 155                 160

gtc acc atc act tgc cgg gca agt cag agc att agc agc tat tta aat      528
Val Thr Ile Thr Cys Arg Ala Ser Gln Ser Ile Ser Ser Tyr Leu Asn
                165                 170                 175

tgg tat cag cag aaa cca ggg aaa gcc cct aag ctc ctg atc tat gct      576
Trp Tyr Gln Gln Lys Pro Gly Lys Ala Pro Lys Leu Leu Ile Tyr Ala
            180                 185                 190

gca tcc agt ttg caa agt ggg gtc cca tca agg ttc agt ggc agt gga      624
Ala Ser Ser Leu Gln Ser Gly Val Pro Ser Arg Phe Ser Gly Ser Gly
        195                 200                 205

tct ggg aca gat ttc act ctc acc atc agc agt ctg caa cct gaa gat      672
Ser Gly Thr Asp Phe Thr Leu Thr Ile Ser Ser Leu Gln Pro Glu Asp
    210                 215                 220

ttt gca act tac tac tgt caa cag agt tac agt acc cct cgg acg ttc      720
Phe Ala Thr Tyr Tyr Cys Gln Gln Ser Tyr Ser Thr Pro Arg Thr Phe
225                 230                 235                 240

ggc caa ggg acc aag ctg gag atc aaa cgt                              750
Gly Gln Gly Thr Lys Leu Glu Ile Lys Arg
                245                 250


<210> SEQ ID NO 26
<211> LENGTH: 250
<212> TYPE: PRT
<213> ORGANISM: Artificial sequence
<220> FEATURE:
<223> OTHER INFORMATION: SC04-348

<400> SEQUENCE: 26
```

```
Glu Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Asn Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Lys Ser Tyr Tyr Tyr Gly Ser Gly Thr Ser Gly Gly Trp
            100                 105                 110

Phe Asp Pro Trp Gly Gln Gly Thr Leu Val Thr Val Ser Ser Gly Thr
        115                 120                 125

Gly Gly Ser Gly Gly Thr Gly Ser Gly Thr Gly Gly Ser Thr Asp Ile
    130                 135                 140

Gln Met Thr Gln Ser Pro Ser Ser Leu Ser Ala Ser Val Gly Asp Arg
145                 150                 155                 160

Val Thr Ile Thr Cys Arg Ala Ser Gln Ser Ile Ser Ser Tyr Leu Asn
                165                 170                 175

Trp Tyr Gln Gln Lys Pro Gly Lys Ala Pro Lys Leu Leu Ile Tyr Ala
            180                 185                 190

Ala Ser Ser Leu Gln Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gln Gln Ser Tyr Ser Thr Pro Arg Thr Phe
225                 230                 235                 240

Gly Gln Gly Thr Lys Leu Glu Ile Lys Arg
                245                 250


<210> SEQ ID NO 27
<211> LENGTH: 750
<212> TYPE: DNA
<213> ORGANISM: Artificial sequence
<220> FEATURE:
<223> OTHER INFORMATION: SC04-354
<220> FEATURE:
<221> NAME/KEY: CDS
<222> LOCATION: (1)..(750)
<223> OTHER INFORMATION: SC04-354

<400> SEQUENCE: 27

gag gtg cag ctg gtg cag tct ggg gct gag gtg agg aag cct ggg gcc       48
Glu Val Gln Leu Val Gln Ser Gly Ala Glu Val Arg Lys Pro Gly Ala
1               5                   10                  15

tca gtg aag gtt tcc tgc aag gca tct gga tac acc ttc acc cac tat       96
Ser Val Lys Val Ser Cys Lys Ala Ser Gly Tyr Thr Phe Thr His Tyr
            20                  25                  30

tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45

gga ata atc aac cct agt ggt ggt agc aca acc tac gca cag aag ctc      192
Gly Ile Ile Asn Pro Ser Gly Gly Ser Thr Thr Tyr Ala Gln Lys Leu
    50                  55                  60

cag ggc aga gtc acc atg acc agg gac acg tcc acg agc aca gtc tac      240
```

```
Gln Gly Arg Val Thr Met Thr Arg Asp Thr Ser Thr Ser Thr Val Tyr
65                  70                  75                  80

atg gag ctg agc agc ctg aga tct gag gac acg gcc gtg tat tac tgt      288
Met Glu Leu Ser Ser Leu Arg Ser Glu Asp Thr Ala Val Tyr Tyr Cys
                85                  90                  95

gcg aga gat tgg ggc tcc aat tac gtt tgg ggg agt tat ccc aag tac      336
Ala Arg Asp Trp Gly Ser Asn Tyr Val Trp Gly Ser Tyr Pro Lys Tyr
            100                 105                 110

tgg ggc cag ggc acc ctg gtc acc gtc tcg agc ggt acg ggc ggt tca      384
Trp Gly Gln Gly Thr Leu Val Thr Val Ser Ser Gly Thr Gly Gly Ser
        115                 120                 125

ggc gga acc ggc agc ggc act ggc ggg tcg acg cag tct gtg ttg acg      432
Gly Gly Thr Gly Ser Gly Thr Gly Gly Ser Thr Gln Ser Val Leu Thr
    130                 135                 140

cag ccg ccc tca gtg tct gcg gcc ccc gga cag aag gtc acc atc tcc      480
Gln Pro Pro Ser Val Ser Ala Ala Pro Gly Gln Lys Val Thr Ile Ser
145                 150                 155                 160

tgt tct gga agc agc tcc aac atc gga agt aat act gta aac tgg tac      528
Cys Ser Gly Ser Ser Ser Asn Ile Gly Ser Asn Thr Val Asn Trp Tyr
                165                 170                 175

cag cag ctc cca gga acg gcc ccc aaa ctc ctc atc tat agt aat aat      576
Gln Gln Leu Pro Gly Thr Ala Pro Lys Leu Leu Ile Tyr Ser Asn Asn
            180                 185                 190

cag cgg ccc tca ggg atc cct gac cga ttc tct ggc tcc aag tct ggc      624
Gln Arg Pro Ser Gly Ile Pro Asp Arg Phe Ser Gly Ser Lys Ser Gly
        195                 200                 205

acc tca gcc tcc ctg gcc atc agt ggg ctc caa tct gaa gat gag gct      672
Thr Ser Ala Ser Leu Ala Ile Ser Gly Leu Gln Ser Glu Asp Glu Ala
    210                 215                 220

gat tat tac tgt gca gca tgg gat gac agc ctg aat ggt ccg gtg ttc      720
Asp Tyr Tyr Cys Ala Ala Trp Asp Asp Ser Leu Asn Gly Pro Val Phe
225                 230                 235                 240

ggc gga ggg acc aag ctg acc gtc cta ggt                              750
Gly Gly Gly Thr Lys Leu Thr Val Leu Gly
                245                 250


<210> SEQ ID NO 28
<211> LENGTH: 250
<212> TYPE: PRT
<213> ORGANISM: Artificial sequence
<220> FEATURE:
<223> OTHER INFORMATION: SC04-354

<400> SEQUENCE: 28

Glu Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr His Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Thr Tyr Ala Gln Lys Leu
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Trp Gly Ser Asn Tyr Val Trp Gly Ser Tyr Pro Lys Tyr
            100                 105                 110

Trp Gly Gln Gly Thr Leu Val Thr Val Ser Ser Gly Thr Gly Gly Ser
```

```
        115                 120                 125

Gly Gly Thr Gly Ser Gly Thr Gly Gly Ser Thr Gln Ser Val Leu Thr
    130                 135                 140

Gln Pro Pro Ser Val Ser Ala Ala Pro Gly Gln Lys Val Thr Ile Ser
145                 150                 155                 160

Cys Ser Gly Ser Ser Ser Asn Ile Gly Ser Asn Thr Val Asn Trp Tyr
                165                 170                 175

Gln Gln Leu Pro Gly Thr Ala Pro Lys Leu Leu Ile Tyr Ser Asn Asn
            180                 185                 190

Gln Arg Pro Ser Gly Ile Pro Asp Arg Phe Ser Gly Ser Lys Ser Gly
        195                 200                 205

Thr Ser Ala Ser Leu Ala Ile Ser Gly Leu Gln Ser Glu Asp Glu Ala
    210                 215                 220

Asp Tyr Tyr Cys Ala Ala Trp Asp Asp Ser Leu Asn Gly Pro Val Phe
225                 230                 235                 240

Gly Gly Gly Thr Lys Leu Thr Val Leu Gly
                245                 250


<210> SEQ ID NO 29
<211> LENGTH: 1368
<212> TYPE: DNA
<213> ORGANISM: Artificial sequence
<220> FEATURE:
<223> OTHER INFORMATION: Heavy chain CR4348
<220> FEATURE:
<221> NAME/KEY: CDS
<222> LOCATION: (1)..(1368)
<223> OTHER INFORMATION: Heavy chain CR4348

<400> SEQUENCE: 29

gag gtg cag ctg gtg gag tct ggg gga ggc ttg gta cag cct ggc agg       48
Glu Val Gln Leu Val Glu Ser Gly Gly Gly Leu Val Gln Pro Gly Arg
1               5                   10                  15

tcc ctg aga ctc tcc tgt gca gcc tct gga ttc acc ttt gat gat tat       96
Ser Leu Arg Leu Ser Cys Ala Ala Ser Gly Phe Thr Phe Asp Asp Tyr
            20                  25                  30

gcc atg cac tgg gtc cgg caa gct cca ggg aag ggc ctg gag tgg gtc      144
Ala Met His Trp Val Arg Gln Ala Pro Gly Lys Gly Leu Glu Trp Val
        35                  40                  45

tca ggt att agt tgg aat agt ggt aac ata ggc tat gcg gac tct gtg      192
Ser Gly Ile Ser Trp Asn Ser Gly Asn Ile Gly Tyr Ala Asp Ser Val
    50                  55                  60

aag ggc cga ttc acc atc tcc aga gac aac gcc aag aac tcc ctg tat      240
Lys Gly Arg Phe Thr Ile Ser Arg Asp Asn Ala Lys Asn Ser Leu Tyr
65                  70                  75                  80

ctg caa atg aac agt ctg aga gct gag gac acg gcc ttg tat tac tgt      288
Leu Gln Met Asn Ser Leu Arg Ala Glu Asp Thr Ala Leu Tyr Tyr Cys
                85                  90                  95

gca aaa gat aaa tcg tat tat tat ggt tcg ggg acc tcg gga ggc tgg      336
Ala Lys Asp Lys Ser Tyr Tyr Tyr Gly Ser Gly Thr Ser Gly Gly Trp
            100                 105                 110

ttc gac ccc tgg ggc cag ggc acc ctg gtg acc gtc tcc agc gct agc      384
Phe Asp Pro Trp Gly Gln Gly Thr Leu Val Thr Val Ser Ser Ala Ser
        115                 120                 125

acc aag ggc ccc agc gtg ttc ccc ctg gcc ccc agc agc aag agc acc      432
Thr Lys Gly Pro Ser Val Phe Pro Leu Ala Pro Ser Ser Lys Ser Thr
    130                 135                 140

agc ggc ggc aca gcc gcc ctg ggc tgc ctg gtg aag gac tac ttc ccc      480
Ser Gly Gly Thr Ala Ala Leu Gly Cys Leu Val Lys Asp Tyr Phe Pro
145                 150                 155                 160
```

```
gag ccc gtg acc gtg agc tgg aac agc ggc gcc ttg acc agc ggc gtg      528
Glu Pro Val Thr Val Ser Trp Asn Ser Gly Ala Leu Thr Ser Gly Val
            165                 170                 175

cac acc ttc ccc gcc gtg ctg cag agc agc ggc ctg tac agc ctg agc      576
His Thr Phe Pro Ala Val Leu Gln Ser Ser Gly Leu Tyr Ser Leu Ser
        180                 185                 190

agc gtg gtg acc gtg ccc agc agc agc ctg ggc acc cag acc tac atc      624
Ser Val Val Thr Val Pro Ser Ser Ser Leu Gly Thr Gln Thr Tyr Ile
    195                 200                 205

tgc aac gtg aac cac aag ccc agc aac acc aag gtg gac aaa cgc gtg      672
Cys Asn Val Asn His Lys Pro Ser Asn Thr Lys Val Asp Lys Arg Val
210                 215                 220

gag ccc aag agc tgc gac aag acc cac acc tgc ccc ccc tgc cct gcc      720
Glu Pro Lys Ser Cys Asp Lys Thr His Thr Cys Pro Pro Cys Pro Ala
225                 230                 235                 240

ccc gag ctg ctg ggc gga ccc tcc gtg ttc ctg ttc ccc ccc aag ccc      768
Pro Glu Leu Leu Gly Gly Pro Ser Val Phe Leu Phe Pro Pro Lys Pro
                245                 250                 255

aag gac acc ctc atg atc agc cgg acc ccc gag gtg acc tgc gtg gtg      816
Lys Asp Thr Leu Met Ile Ser Arg Thr Pro Glu Val Thr Cys Val Val
            260                 265                 270

gtg gac gtg agc cac gag gac ccc gag gtg aag ttc aac tgg tac gtg      864
Val Asp Val Ser His Glu Asp Pro Glu Val Lys Phe Asn Trp Tyr Val
        275                 280                 285

gac ggc gtg gag gtg cac aac gcc aag acc aag ccc cgg gag gag cag      912
Asp Gly Val Glu Val His Asn Ala Lys Thr Lys Pro Arg Glu Glu Gln
    290                 295                 300

tac aac agc acc tac cgg gtg gtg agc gtg ctc acc gtg ctg cac cag      960
Tyr Asn Ser Thr Tyr Arg Val Val Ser Val Leu Thr Val Leu His Gln
305                 310                 315                 320

gac tgg ctg aac ggc aag gag tac aag tgc aag gtg agc aac aag gcc     1008
Asp Trp Leu Asn Gly Lys Glu Tyr Lys Cys Lys Val Ser Asn Lys Ala
                325                 330                 335

ctg cct gcc ccc atc gag aag acc atc agc aag gcc aag ggc cag ccc     1056
Leu Pro Ala Pro Ile Glu Lys Thr Ile Ser Lys Ala Lys Gly Gln Pro
            340                 345                 350

cgg gag ccc cag gtg tac acc ctg ccc ccc agc cgg gag gag atg acc     1104
Arg Glu Pro Gln Val Tyr Thr Leu Pro Pro Ser Arg Glu Glu Met Thr
        355                 360                 365

aag aac cag gtg tcc ctc acc tgt ctg gtg aag ggc ttc tac ccc agc     1152
Lys Asn Gln Val Ser Leu Thr Cys Leu Val Lys Gly Phe Tyr Pro Ser
    370                 375                 380

gac atc gcc gtg gag tgg gag agc aac ggc cag ccc gag aac aac tac     1200
Asp Ile Ala Val Glu Trp Glu Ser Asn Gly Gln Pro Glu Asn Asn Tyr
385                 390                 395                 400

aag acc acc ccc cct gtg ctg gac agc gac ggc agc ttc ttc ctg tac     1248
Lys Thr Thr Pro Pro Val Leu Asp Ser Asp Gly Ser Phe Phe Leu Tyr
                405                 410                 415

agc aag ctc acc gtg gac aag agc cgg tgg cag cag ggc aac gtg ttc     1296
Ser Lys Leu Thr Val Asp Lys Ser Arg Trp Gln Gln Gly Asn Val Phe
            420                 425                 430

agc tgc agc gtg atg cac gag gcc ctg cac aac cac tac acc cag aag     1344
Ser Cys Ser Val Met His Glu Ala Leu His Asn His Tyr Thr Gln Lys
        435                 440                 445

agc ctg agc ctg agc ccc ggc aag                                     1368
Ser Leu Ser Leu Ser Pro Gly Lys
    450                 455
```

<210> SEQ ID NO 30

<211> LENGTH: 456
<212> TYPE: PRT
<213> ORGANISM: Artificial sequence
<220> FEATURE:
<223> OTHER INFORMATION: Heavy chain CR4348

<400> SEQUENCE: 30

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Asn Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Lys Ser Tyr Tyr Tyr Gly Ser Gly Thr Ser Gly Gly Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

```
Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455


<210> SEQ ID NO 31
<211> LENGTH: 1359
<212> TYPE: DNA
<213> ORGANISM: Artificial sequence
<220> FEATURE:
<223> OTHER INFORMATION: Heavy chain CR4354
<220> FEATURE:
<221> NAME/KEY: CDS
<222> LOCATION: (1)..(1359)
<223> OTHER INFORMATION: Heavy chain CR4354

<400> SEQUENCE: 31

cag gtg cag ctg gtg cag tct ggg gct gag gtg agg aag cct ggg gcc       48
Gln Val Gln Leu Val Gln Ser Gly Ala Glu Val Arg Lys Pro Gly Ala
1               5                   10                  15

tca gtg aag gtt tcc tgc aag gca tct gga tac acc ttc acc cac tat       96
Ser Val Lys Val Ser Cys Lys Ala Ser Gly Tyr Thr Phe Thr His Tyr
            20                  25                  30

tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45

gga ata atc aac cct agt ggt ggt agc aca acc tac gca cag aag ctc      192
Gly Ile Ile Asn Pro Ser Gly Gly Ser Thr Thr Tyr Ala Gln Lys Leu
    50                  55                  60

cag ggc aga gtc acc atg acc agg gac acg tcc acg agc aca gtc tac      240
Gln Gly Arg Val Thr Met Thr Arg Asp Thr Ser Thr Ser Thr Val Tyr
65                  70                  75                  80

atg gag ctg agc agc ctg aga tct gag gac acg gcc gtg tat tac tgt      288
Met Glu Leu Ser Ser Leu Arg Ser Glu Asp Thr Ala Val Tyr Tyr Cys
                85                  90                  95

gcg aga gat tgg ggc tcc aat tac gtt tgg ggg agt tat ccc aag tac      336
Ala Arg Asp Trp Gly Ser Asn Tyr Val Trp Gly Ser Tyr Pro Lys Tyr
            100                 105                 110

tgg ggc cag ggc acc ctg gtg acc gtc tcc agc gct agc acc aag ggc      384
Trp Gly Gln Gly Thr Leu Val Thr Val Ser Ser Ala Ser Thr Lys Gly
        115                 120                 125

ccc agc gtg ttc ccc ctg gcc ccc agc agc aag agc acc agc ggc ggc      432
Pro Ser Val Phe Pro Leu Ala Pro Ser Ser Lys Ser Thr Ser Gly Gly
    130                 135                 140

aca gcc gcc ctg ggc tgc ctg gtg aag gac tac ttc ccc gag ccc gtg      480
Thr Ala Ala Leu Gly Cys Leu Val Lys Asp Tyr Phe Pro Glu Pro Val
145                 150                 155                 160

acc gtg agc tgg aac agc ggc gcc ttg acc agc ggc gtg cac acc ttc      528
Thr Val Ser Trp Asn Ser Gly Ala Leu Thr Ser Gly Val His Thr Phe
                165                 170                 175

ccc gcc gtg ctg cag agc agc ggc ctg tac agc ctg agc agc gtg gtg      576
Pro Ala Val Leu Gln Ser Ser Gly Leu Tyr Ser Leu Ser Ser Val Val
            180                 185                 190

acc gtg ccc agc agc agc ctg ggc acc cag acc tac atc tgc aac gtg      624
```

```
Thr Val Pro Ser Ser Ser Leu Gly Thr Gln Thr Tyr Ile Cys Asn Val
        195                 200                 205

aac cac aag ccc agc aac acc aag gtg gac aaa cgc gtg gag ccc aag      672
Asn His Lys Pro Ser Asn Thr Lys Val Asp Lys Arg Val Glu Pro Lys
    210                 215                 220

agc tgc gac aag acc cac acc tgc ccc ccc tgc cct gcc ccc gag ctg      720
Ser Cys Asp Lys Thr His Thr Cys Pro Pro Cys Pro Ala Pro Glu Leu
225                 230                 235                 240

ctg ggc gga ccc tcc gtg ttc ctg ttc ccc ccc aag ccc aag gac acc      768
Leu Gly Gly Pro Ser Val Phe Leu Phe Pro Pro Lys Pro Lys Asp Thr
                245                 250                 255

ctc atg atc agc cgg acc ccc gag gtg acc tgc gtg gtg gtg gac gtg      816
Leu Met Ile Ser Arg Thr Pro Glu Val Thr Cys Val Val Val Asp Val
            260                 265                 270

agc cac gag gac ccc gag gtg aag ttc aac tgg tac gtg gac ggc gtg      864
Ser His Glu Asp Pro Glu Val Lys Phe Asn Trp Tyr Val Asp Gly Val
        275                 280                 285

gag gtg cac aac gcc aag acc aag ccc cgg gag gag cag tac aac agc      912
Glu Val His Asn Ala Lys Thr Lys Pro Arg Glu Glu Gln Tyr Asn Ser
    290                 295                 300

acc tac cgg gtg gtg agc gtg ctc acc gtg ctg cac cag gac tgg ctg      960
Thr Tyr Arg Val Val Ser Val Leu Thr Val Leu His Gln Asp Trp Leu
305                 310                 315                 320

aac ggc aag gag tac aag tgc aag gtg agc aac aag gcc ctg cct gcc     1008
Asn Gly Lys Glu Tyr Lys Cys Lys Val Ser Asn Lys Ala Leu Pro Ala
                325                 330                 335

ccc atc gag aag acc atc agc aag gcc aag ggc cag ccc cgg gag ccc     1056
Pro Ile Glu Lys Thr Ile Ser Lys Ala Lys Gly Gln Pro Arg Glu Pro
            340                 345                 350

cag gtg tac acc ctg ccc ccc agc cgg gag gag atg acc aag aac cag     1104
Gln Val Tyr Thr Leu Pro Pro Ser Arg Glu Glu Met Thr Lys Asn Gln
        355                 360                 365

gtg tcc ctc acc tgt ctg gtg aag ggc ttc tac ccc agc gac atc gcc     1152
Val Ser Leu Thr Cys Leu Val Lys Gly Phe Tyr Pro Ser Asp Ile Ala
    370                 375                 380

gtg gag tgg gag agc aac ggc cag ccc gag aac aac tac aag acc acc     1200
Val Glu Trp Glu Ser Asn Gly Gln Pro Glu Asn Asn Tyr Lys Thr Thr
385                 390                 395                 400

ccc cct gtg ctg gac agc gac ggc agc ttc ttc ctg tac agc aag ctc     1248
Pro Pro Val Leu Asp Ser Asp Gly Ser Phe Phe Leu Tyr Ser Lys Leu
                405                 410                 415

acc gtg gac aag agc cgg tgg cag cag ggc aac gtg ttc agc tgc agc     1296
Thr Val Asp Lys Ser Arg Trp Gln Gln Gly Asn Val Phe Ser Cys Ser
            420                 425                 430

gtg atg cac gag gcc ctg cac aac cac tac acc cag aag agc ctg agc     1344
Val Met His Glu Ala Leu His Asn His Tyr Thr Gln Lys Ser Leu Ser
        435                 440                 445

ctg agc ccc ggc aag                                                 1359
Leu Ser Pro Gly Lys
    450


<210> SEQ ID NO 32
<211> LENGTH: 453
<212> TYPE: PRT
<213> ORGANISM: Artificial sequence
<220> FEATURE:
<223> OTHER INFORMATION: Heavy chain CR4354

<400> SEQUENCE: 32

Gln Val Gln Leu Val Gln Ser Gly Ala Glu Val Arg Lys Pro Gly Ala
1               5                   10                  15
```

```
Ser Val Lys Val Ser Cys Lys Ala Ser Gly Tyr Thr Phe Thr His Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Thr Tyr Ala Gln Lys Leu
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Trp Gly Ser Asn Tyr Val Trp Gly Ser Tyr Pro Lys Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430
```

```
Val Met His Glu Ala Leu His Asn His Tyr Thr Gln Lys Ser Leu Ser
        435                 440                 445

Leu Ser Pro Gly Lys
    450


<210> SEQ ID NO 33
<211> LENGTH: 645
<212> TYPE: DNA
<213> ORGANISM: Artificial sequence
<220> FEATURE:
<223> OTHER INFORMATION: Light chain CR4348
<220> FEATURE:
<221> NAME/KEY: CDS
<222> LOCATION: (1)..(645)
<223> OTHER INFORMATION: Light chain CR4348

<400> SEQUENCE: 33

tcg acg gac atc cag atg acc cag tct cca tcc tcc ctg tct gca tct      48
Ser Thr Asp Ile Gln Met Thr Gln Ser Pro Ser Ser Leu Ser Ala Ser
1               5                   10                  15

gta gga gac aga gtc acc atc act tgc cgg gca agt cag agc att agc      96
Val Gly Asp Arg Val Thr Ile Thr Cys Arg Ala Ser Gln Ser Ile Ser
            20                  25                  30

agc tat tta aat tgg tat cag cag aaa cca ggg aaa gcc cct aag ctc     144
Ser Tyr Leu Asn Trp Tyr Gln Gln Lys Pro Gly Lys Ala Pro Lys Leu
        35                  40                  45

ctg atc tat gct gca tcc agt ttg caa agt ggg gtc cca tca agg ttc     192
Leu Ile Tyr Ala Ala Ser Ser Leu Gln Ser Gly Val Pro Ser Arg Phe
    50                  55                  60

agt ggc agt gga tct ggg aca gat ttc act ctc acc atc agc agt ctg     240
Ser Gly Ser Gly Ser Gly Thr Asp Phe Thr Leu Thr Ile Ser Ser Leu
65                  70                  75                  80

caa cct gaa gat ttt gca act tac tac tgt caa cag agt tac agt acc     288
Gln Pro Glu Asp Phe Ala Thr Tyr Tyr Cys Gln Gln Ser Tyr Ser Thr
                85                  90                  95

cct cgg acg ttc ggc caa ggg acc aag ctg gag atc aaa cgt gcg gcc     336
Pro Arg Thr Phe Gly Gln Gly Thr Lys Leu Glu Ile Lys Arg Ala Ala
            100                 105                 110

gca ccc agc gtg ttc atc ttc ccc ccc tcc gac gag cag ctg aag agc     384
Ala Pro Ser Val Phe Ile Phe Pro Pro Ser Asp Glu Gln Leu Lys Ser
        115                 120                 125

ggc acc gcc agc gtg gtg tgc ctg ctg aac aac ttc tac ccc cgg gag     432
Gly Thr Ala Ser Val Val Cys Leu Leu Asn Asn Phe Tyr Pro Arg Glu
    130                 135                 140

gcc aag gtg cag tgg aag gtg gac aac gcc ctg cag agc ggc aac agc     480
Ala Lys Val Gln Trp Lys Val Asp Asn Ala Leu Gln Ser Gly Asn Ser
145                 150                 155                 160

cag gag agc gtg acc gag cag gac agc aag gac tcc acc tac agc ctg     528
Gln Glu Ser Val Thr Glu Gln Asp Ser Lys Asp Ser Thr Tyr Ser Leu
                165                 170                 175

agc agc acc ctc acc ctg agc aag gcc gac tac gag aag cac aag gtg     576
Ser Ser Thr Leu Thr Leu Ser Lys Ala Asp Tyr Glu Lys His Lys Val
            180                 185                 190

tac gcc tgc gag gtg acc cac cag ggc ctg agc agc ccc gtg acc aag     624
Tyr Ala Cys Glu Val Thr His Gln Gly Leu Ser Ser Pro Val Thr Lys
        195                 200                 205

agc ttc aac cgg ggc gag tgt                                         645
Ser Phe Asn Arg Gly Glu Cys
    210                 215


<210> SEQ ID NO 34
<211> LENGTH: 215
```

<212> TYPE: PRT
<213> ORGANISM: Artificial sequence
<220> FEATURE:
<223> OTHER INFORMATION: Light chain CR4348

<400> SEQUENCE: 34

```
Ser Thr Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Thr
                85                  90                  95

Pro Arg Thr Phe Gly Gln Gly Thr Lys Leu Glu Ile Lys Arg Ala Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 35
<211> LENGTH: 648
<212> TYPE: DNA
<213> ORGANISM: Artificial sequence
<220> FEATURE:
<223> OTHER INFORMATION: Light chain CR4354
<220> FEATURE:
<221> NAME/KEY: CDS
<222> LOCATION: (1)..(648)
<223> OTHER INFORMATION: Light chain CR4354

<400> SEQUENCE: 35

```
cag tcc gtg ctg acc cag cct ccc tca gtg tct gcg gcc ccc gga cag       48
Gln Ser Val Leu Thr Gln Pro Pro Ser Val Ser Ala Ala Pro Gly Gln
1               5                   10                  15

aag gtc acc atc tcc tgt tct gga agc agc tcc aac atc gga agt aat       96
Lys Val Thr Ile Ser Cys Ser Gly Ser Ser Ser Asn Ile Gly Ser Asn
            20                  25                  30

act gta aac tgg tac cag cag ctc cca gga acg gcc ccc aaa ctc ctc      144
Thr Val Asn Trp Tyr Gln Gln Leu Pro Gly Thr Ala Pro Lys Leu Leu
        35                  40                  45

atc tat agt aat aat cag cgg ccc tca ggg atc cct gac cga ttc tct      192
Ile Tyr Ser Asn Asn Gln Arg Pro Ser Gly Ile Pro Asp Arg Phe Ser
    50                  55                  60
```

```
ggc tcc aag tct ggc acc tca gcc tcc ctg gcc atc agt ggg ctc caa      240
Gly Ser Lys Ser Gly Thr Ser Ala Ser Leu Ala Ile Ser Gly Leu Gln
65                  70                  75                  80

tct gaa gat gag gct gat tat tac tgt gca gca tgg gat gac agc ctg      288
Ser Glu Asp Glu Ala Asp Tyr Tyr Cys Ala Ala Trp Asp Asp Ser Leu
                85                  90                  95

aat ggt ccg gtg ttc ggc gga ggc acc aag ctt acc gtg ctg ggc cag      336
Asn Gly Pro Val Phe Gly Gly Gly Thr Lys Leu Thr Val Leu Gly Gln
            100                 105                 110

ccc aag gcc gct ccc agc gtg acc ctg ttc ccc ccc tcc tcc gag gag      384
Pro Lys Ala Ala Pro Ser Val Thr Leu Phe Pro Pro Ser Ser Glu Glu
        115                 120                 125

ctg cag gcc aac aag gcc acc ctg gtg tgc ctc atc agc gac ttc tac      432
Leu Gln Ala Asn Lys Ala Thr Leu Val Cys Leu Ile Ser Asp Phe Tyr
    130                 135                 140

cct ggc gcc gtg acc gtg gcc tgg aag gcc gac agc agc ccc gtg aag      480
Pro Gly Ala Val Thr Val Ala Trp Lys Ala Asp Ser Ser Pro Val Lys
145                 150                 155                 160

gcc ggc gtg gag acc acc acc ccc agc aag cag agc aac aac aag tac      528
Ala Gly Val Glu Thr Thr Thr Pro Ser Lys Gln Ser Asn Asn Lys Tyr
                165                 170                 175

gcc gcc agc agc tac ctg agc ctc acc ccc gag cag tgg aag agc cac      576
Ala Ala Ser Ser Tyr Leu Ser Leu Thr Pro Glu Gln Trp Lys Ser His
            180                 185                 190

cgg agc tac agc tgc cag gtg acc cac gag ggc agc acc gtg gag aag      624
Arg Ser Tyr Ser Cys Gln Val Thr His Glu Gly Ser Thr Val Glu Lys
        195                 200                 205

acc gtg gcc ccc acc gag tgc agc                                      648
Thr Val Ala Pro Thr Glu Cys Ser
    210                 215


<210> SEQ ID NO 36
<211> LENGTH: 216
<212> TYPE: PRT
<213> ORGANISM: Artificial sequence
<220> FEATURE:
<223> OTHER INFORMATION: Light chain CR4354

<400> SEQUENCE: 36

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Ile Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160
```

```
Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 37
<211> LENGTH: 24
<212> TYPE: DNA
<213> ORGANISM: Artificial sequence
<220> FEATURE:
<223> OTHER INFORMATION: Anti-sense primer HuCkappa

<400> SEQUENCE: 37

acactctccc ctgttgaagc tctt                                              24


<210> SEQ ID NO 38
<211> LENGTH: 23
<212> TYPE: DNA
<213> ORGANISM: Artificial sequence
<220> FEATURE:
<223> OTHER INFORMATION: Anti-sense primer HuClambda2

<400> SEQUENCE: 38

tgaacattct gtaggggcca ctg                                               23


<210> SEQ ID NO 39
<211> LENGTH: 23
<212> TYPE: DNA
<213> ORGANISM: Artificial sequence
<220> FEATURE:
<223> OTHER INFORMATION: Anti-sense primer HuClambda7

<400> SEQUENCE: 39

agagcattct gcaggggcca ctg                                               23


<210> SEQ ID NO 40
<211> LENGTH: 4941
<212> TYPE: DNA
<213> ORGANISM: Artificial sequence
<220> FEATURE:
<223> OTHER INFORMATION: Vector PDV-C06

<400> SEQUENCE: 40

aagcttgcat gcaaattcta tttcaaggag acagtcataa tgaaatacct attgcctacg      60

gcagccgctg gattgttatt actcgcggcc cagccggcca tggccgaggt gtttgactaa     120

tggggcgcgc ctcagggaac cctggtcacc gtctcgagcg gtacgggcgg ttcaggcgga     180

accggcagcg gcactggcgg gtcgacggaa attgtgctca cacagtctcc agccaccctg     240

tctttgtctc caggggaaag agccaccctc tcctgcaggg ccagtcagag tgttagcagc     300

tacttagcct ggtaccaaca gaaacctggc caggctccca ggctcctcat ctatgatgca     360

tccaacaggg ccactggcat cccagccagg ttcagtggca gtgggtctgg gacagacttc     420

actctcacca tcagcagcct agagcctgaa gattttgcag tttattactg tcagcagcgt     480

agcaactggc ctccggcttt cggcggaggg accaaggtgg agatcaaacg tgcggccgca     540

catcatcatc accatcacgg ggccgcatat accgatattg aaatgaaccg cctgggcaaa     600
```

```
ggggccgcat agactgttga aagttgttta gcaaaacctc atacagaaaa ttcatttact    660
aacgtctgga aagacgacaa aactttagat cgttacgcta actatgaggg ctgtctgtgg    720
aatgctacag gcgttgtggt ttgtactggt gacgaaactc agtgttacgg tacatgggtt    780
cctattgggc ttgctatccc tgaaaatgag ggtggtggct ctgagggtgg cggttctgag    840
ggtggcggtt ctgagggtgg cggtactaaa cctcctgagt acggtgatac acctattccg    900
ggctatactt atatcaaccc tctcgacggc acttatccgc ctggtactga gcaaaacccc    960
gctaatccta atccttctct tgaggagtct cagcctctta atactttcat gtttcagaat   1020
aataggttcc gaaataggca gggtgcatta actgtttata cgggcactgt tactcaaggc   1080
actgaccccg ttaaaactta ttaccagtac actcctgtat catcaaaagc catgtatgac   1140
gcttactgga acggtaaatt cagagactgc gctttccatt ctggctttaa tgaggatcca   1200
ttcgtttgtg aatatcaagg ccaatcgtct gacctgcctc aacctcctgt caatgctggc   1260
ggcggctctg gtggtggttc tggtggcggc tctgagggtg gcggctctga gggtggcggt   1320
tctgagggtg gcggctctga gggtggcggt tccggtggcg gctccggttc cggtgatttt   1380
gattatgaaa aaatggcaaa cgctaataag ggggctatga ccgaaaatgc cgatgaaaac   1440
gcgctacagt ctgacgctaa aggcaaactt gattctgtcg ctactgatta cggtgctgct   1500
atcgatggtt tcattggtga cgtttccggc cttgctaatg gtaatggtgc tactggtgat   1560
tttgctggct ctaattccca aatggctcaa gtcggtgacg gtgataattc acctttaatg   1620
aataatttcc gtcaatattt accttctttg cctcagtcgg ttgaatgtcg cccttatgtc   1680
tttggcgctg gtaaaccata tgaattttct attgattgtg acaaaataaa cttattccgt   1740
ggtgtctttg cgtttctttt atatgttgcc acctttatgt atgtattttc gacgtttgct   1800
aacatactgc gtaataagga gtcttaataa gaattcactg gccgtcgttt tacaacgtcg   1860
tgactgggaa aaccctggcg ttacccaact taatcgcctt gcagcacatc ccccctttcgc   1920
cagctggcgt aatagcgaag aggcccgcac cgatcgccct tcccaacagt tgcgcagcct   1980
gaatggcgaa tggcgcctga tgcggtattt tctccttacg catctgtgcg gtatttcaca   2040
ccgcatacgt caaagcaacc atagtacgcg ccctgtagcg gcgcattaag cgcggcgggt   2100
gtggtggtta cgcgcagcgt gaccgctaca cttgccagcg ccctagcgcc cgctcctttc   2160
gctttcttcc cttcctttct cgccacgttc gccggctttc cccgtcaagc tctaaatcgg   2220
gggctccctt tagggttccg atttagtgct ttacggcacc tcgaccccaa aaaacttgat   2280
ttgggtgatg gttcacgtag tgggccatcg ccctgataga cggtttttcg ccctttgacg   2340
ttggagtcca cgttctttaa tagtggactc ttgttccaaa ctggaacaac actcaaccct   2400
atctcgggct attcttttga tttataaggg attttgccga tttcggccta ttggttaaaa   2460
aatgagctga tttaacaaaa atttaacgcg aattttaaca aaatattaac gtttacaatt   2520
ttatggtgca ctctcagtac aatctgctct gatgccgcat agttaagcca gccccgacac   2580
ccgccaacac ccgctgacgc gccctgacgg gcttgtctgc tcccggcatc cgcttacaga   2640
caagctgtga ccgtctccgg gagctgcatg tgtcagaggt tttcaccgtc atcaccgaaa   2700
cgcgcgagac gaaagggcct cgtgatacgc ctatttttat aggttaatgt catgataata   2760
atggtttctt agacgtcagg tggcactttt cggggaaatg tgcgcggaac ccctatttgt   2820
ttatttttct aaatacattc aaatatgtat ccgctcatga gacaataacc ctgataaatg   2880
cttcaataat attgaaaaag gaagagtatg agtattcaac atttccgtgt cgcccttatt   2940
cccttttttg cggcattttg ccttcctgtt tttgctcacc cagaaacgct ggtgaaagta   3000
```

```
aaagatgctg aagatcagtt gggtgcacga gtgggttaca tcgaactgga tctcaacagc   3060

ggtaagatcc ttgagagttt tcgccccgaa gaacgttttc caatgatgag cacttttaaa   3120

gttctgctat gtggcgcggt attatcccgt attgacgccg ggcaagagca actcggtcgc   3180

cgcatacact attctcagaa tgacttggtt gagtactcac cagtcacaga aaagcatctt   3240

acggatggca tgacagtaag agaattatgc agtgctgcca taaccatgag tgataacact   3300

gcggccaact tacttctgac aacgatcgga ggaccgaagg agctaaccgc tttttgcac    3360

aacatggggg atcatgtaac tcgccttgat cgttgggaac cggagctgaa tgaagccata   3420

ccaaacgacg agcgtgacac cacgatgcct gtagcaatgg caacaacgtt gcgcaaacta   3480

ttaactggcg aactacttac tctagcttcc cggcaacaat taatagactg gatggaggcg   3540

gataaagttg caggaccact tctgcgctcg gcccttccgg ctggctggtt tattgctgat   3600

aaatctggag ccggtgagcg tgggtctcgc ggtatcattg cagcactggg gccagatggt   3660

aagccctccc gtatcgtagt tatctacacg acggggagtc aggcaactat ggatgaacga   3720

aatagacaga tcgctgagat aggtgcctca ctgattaagc attggtaact gtcagaccaa   3780

gtttactcat atatacttta gattgattta aaacttcatt tttaatttaa aaggatctag   3840

gtgaagatcc tttttgataa tctcatgacc aaaatccctt aacgtgagtt ttcgttccac   3900

tgagcgtcag accccgtaga aaagatcaaa ggatcttctt gagatccttt ttttctgcgc   3960

gtaatctgct gcttgcaaac aaaaaaacca ccgctaccag cggtggtttg tttgccggat   4020

caagagctac caactctttt tccgaaggta actggcttca gcagagcgca gataccaaat   4080

actgtccttc tagtgtagcc gtagttaggc caccacttca agaactctgt agcaccgcct   4140

acatacctcg ctctgctaat cctgttacca gtggctgctg ccagtggcga taagtcgtgt   4200

cttaccgggt tggactcaag acgatagtta ccggataagg cgcagcggtc gggctgaacg   4260

gggggttcgt gcacacagcc cagcttggag cgaacgacct acaccgaact gagataccta   4320

cagcgtgagc tatgagaaag cgccacgctt cccgaaggga gaaaggcgga caggtatccg   4380

gtaagcggca gggtcggaac aggagagcgc acgagggagc ttccaggggg aaacgcctgg   4440

tatctttata gtcctgtcgg gtttcgccac ctctgacttg agcgtcgatt tttgtgatgc   4500

tcgtcagggg ggcggagcct atggaaaaac gccagcaacg cggccttttt acggttcctg   4560

gccttttgct ggccttttgc tcacatgttc tttcctgcgt tatcccctga ttctgtggat   4620

aaccgtatta ccgcctttga gtgagctgat accgctcgcc gcagccgaac gaccgagcgc   4680

agcgagtcag tgagcgagga agcggaagag cgcccaatac gcaaaccgcc tctccccgcg   4740

cgttggccga ttcattaatg cagctggcac gacaggtttc ccgactggaa agcgggcagt   4800

gagcgcaacg caattaatgt gagttagctc actcattagg caccccaggc tttacacttt   4860

atgcttccgg ctcgtatgtt gtgtggaatt gtgagcggat aacaatttca cacaggaaac   4920

agctatgacc atgattacgc c                                              4941
```

<210> SEQ ID NO 41
<211> LENGTH: 24
<212> TYPE: DNA
<213> ORGANISM: Artificial sequence
<220> FEATURE:
<223> OTHER INFORMATION: Anti-sense primer HuCIgG

<400> SEQUENCE: 41

```
gtccaccttg gtgttgctgg gctt                                           24
```

<210> SEQ ID NO 42
<211> LENGTH: 669
<212> TYPE: PRT
<213> ORGANISM: West Nile virus

<400> SEQUENCE: 42

```
Met Val Thr Leu Ser Asn Phe Gln Gly Lys Val Met Met Thr Val Asn
1               5                   10                  15

Ala Thr Asp Val Thr Asp Val Ile Thr Ile Pro Thr Ala Ala Gly Lys
            20                  25                  30

Asn Leu Cys Ile Val Arg Ala Met Asp Val Gly Tyr Met Cys Asp Asp
        35                  40                  45

Thr Ile Thr Tyr Glu Cys Pro Val Leu Ser Ala Gly Asn Asp Pro Glu
    50                  55                  60

Asp Ile Asp Cys Trp Cys Thr Lys Ser Ala Val Tyr Val Arg Tyr Gly
65                  70                  75                  80

Arg Cys Thr Lys Thr Arg His Ser Arg Arg Ser Arg Arg Ser Leu Thr
                85                  90                  95

Val Gln Thr His Gly Glu Ser Thr Leu Ala Asn Lys Lys Gly Ala Trp
            100                 105                 110

Met Asp Ser Thr Lys Ala Thr Arg Tyr Leu Val Lys Thr Glu Ser Trp
        115                 120                 125

Ile Leu Arg Asn Pro Gly Tyr Ala Leu Val Ala Ala Val Ile Gly Trp
    130                 135                 140

Met Leu Gly Ser Asn Thr Met Gln Arg Val Val Phe Val Val Leu Leu
145                 150                 155                 160

Leu Leu Val Ala Pro Ala Tyr Ser Phe Asn Cys Leu Gly Met Ser Asn
                165                 170                 175

Arg Asp Phe Leu Glu Gly Val Ser Gly Ala Thr Trp Val Asp Leu Val
            180                 185                 190

Leu Glu Gly Asp Ser Cys Val Thr Ile Met Ser Lys Asp Lys Pro Thr
        195                 200                 205

Ile Asp Val Lys Met Met Asn Met Glu Ala Ala Asn Leu Ala Glu Val
    210                 215                 220

Arg Ser Tyr Cys Tyr Leu Ala Thr Val Ser Asp Leu Ser Thr Lys Ala
225                 230                 235                 240

Ala Cys Pro Thr Met Gly Glu Ala His Asn Asp Lys Arg Ala Asp Pro
                245                 250                 255

Ala Phe Val Cys Arg Gln Gly Val Val Asp Arg Gly Trp Gly Asn Gly
            260                 265                 270

Cys Gly Leu Phe Gly Lys Gly Ser Ile Asp Thr Cys Ala Lys Phe Ala
        275                 280                 285

Cys Ser Thr Lys Ala Ile Gly Arg Thr Ile Leu Lys Glu Asn Ile Lys
    290                 295                 300

Tyr Glu Val Ala Ile Phe Val His Gly Pro Thr Thr Val Glu Ser His
305                 310                 315                 320

Gly Asn Tyr Ser Thr Gln Val Gly Ala Thr Gln Ala Gly Arg Phe Ser
                325                 330                 335

Ile Thr Pro Ala Ala Pro Ser Tyr Thr Leu Lys Leu Gly Glu Tyr Gly
            340                 345                 350

Glu Val Thr Val Asp Cys Glu Pro Arg Ser Gly Ile Asp Thr Asn Ala
        355                 360                 365

Tyr Tyr Val Met Thr Val Gly Thr Lys Thr Phe Leu Val His Arg Glu
    370                 375                 380
```

```
Trp Phe Met Asp Leu Asn Leu Pro Trp Ser Ser Ala Gly Ser Thr Val
385                 390                 395                 400

Trp Arg Asn Arg Glu Thr Leu Met Glu Phe Glu Glu Pro His Ala Thr
                405                 410                 415

Lys Gln Ser Val Ile Ala Leu Gly Ser Gln Glu Gly Ala Leu His Gln
            420                 425                 430

Ala Leu Ala Gly Ala Ile Pro Val Glu Phe Ser Ser Asn Thr Val Lys
        435                 440                 445

Leu Thr Ser Gly His Leu Lys Cys Arg Val Lys Met Glu Lys Leu Gln
    450                 455                 460

Leu Lys Gly Thr Thr Tyr Gly Val Cys Ser Lys Ala Phe Lys Phe Leu
465                 470                 475                 480

Gly Thr Pro Ala Asp Thr Gly His Gly Thr Val Val Leu Glu Leu Gln
                485                 490                 495

Tyr Thr Gly Thr Asp Gly Pro Cys Lys Val Pro Ile Ser Ser Val Ala
            500                 505                 510

Ser Leu Asn Asp Leu Thr Pro Val Gly Arg Leu Val Thr Val Asn Pro
        515                 520                 525

Phe Val Ser Val Ala Thr Ala Asn Ala Lys Val Leu Ile Glu Leu Glu
    530                 535                 540

Pro Pro Phe Gly Asp Ser Tyr Ile Val Val Gly Arg Gly Glu Gln Gln
545                 550                 555                 560

Ile Asn His His Trp His Lys Ser Gly Ser Ser Ile Gly Lys Ala Phe
                565                 570                 575

Thr Thr Thr Leu Lys Gly Ala Gln Arg Leu Ala Ala Leu Gly Asp Thr
            580                 585                 590

Ala Trp Asp Phe Gly Ser Val Gly Gly Val Phe Thr Ser Val Gly Lys
        595                 600                 605

Ala Val His Gln Val Phe Gly Gly Ala Phe Arg Ser Leu Phe Gly Gly
    610                 615                 620

Met Ser Trp Ile Thr Gln Gly Leu Leu Gly Ala Leu Leu Leu Trp Met
625                 630                 635                 640

Gly Ile Asn Ala Arg Asp Arg Ser Ile Ala Leu Thr Phe Leu Ala Val
                645                 650                 655

Gly Gly Val Leu Leu Phe Leu Ser Val Asn Val His Ala
            660                 665
```

<210> SEQ ID NO 43
<211> LENGTH: 23
<212> TYPE: DNA
<213> ORGANISM: Artificial sequence
<220> FEATURE:
<223> OTHER INFORMATION: Primer CMV-Spe

<400> SEQUENCE: 43

```
ccatgttgac attgattatt gac                                              23
```

<210> SEQ ID NO 44
<211> LENGTH: 26
<212> TYPE: DNA
<213> ORGANISM: Artificial sequence
<220> FEATURE:
<223> OTHER INFORMATION: Primer WNV-E-95 REV

<400> SEQUENCE: 44

```
gctctagact tgccgatgct gctgcc                                           26
```

<210> SEQ ID NO 45
<211> LENGTH: 40
<212> TYPE: DNA
<213> ORGANISM: Artificial sequence
<220> FEATURE:
<223> OTHER INFORMATION: Primer clefsmaquwnv

<400> SEQUENCE: 45
ggaattcagc atggcccagg tgaccctgag caacttccag 40

<210> SEQ ID NO 46
<211> LENGTH: 26
<212> TYPE: DNA
<213> ORGANISM: Artificial sequence
<220> FEATURE:
<223> OTHER INFORMATION: Primer reverse WNVmychis

<400> SEQUENCE: 46
gactagtcaa ctcaatggtg atggtg 26

<210> SEQ ID NO 47
<211> LENGTH: 6760
<212> TYPE: DNA
<213> ORGANISM: Artificial sequence
<220> FEATURE:
<223> OTHER INFORMATION: Vector pSyn-C18-HCgamma1

<400> SEQUENCE: 47
ctagcaccaa gggccccagc gtgttccccc tggcccccag cagcaagagc accagcggcg 60
gcacagccgc cctgggctgc ctggtgaagg actacttccc cgagcccgtg accgtgagct 120
ggaacagcgg cgccttgacc agcggcgtgc acaccttccc cgccgtgctg cagagcagcg 180
gcctgtacag cctgagcagc gtggtgaccg tgcccagcag cagcctgggc acccagacct 240
acatctgcaa cgtgaaccac aagcccagca acaccaaggt ggacaaacgc gtggagccca 300
agagctgcga caagacccac acctgccccc cctgccctgc ccccgagctg ctgggcggac 360
cctccgtgtt cctgttcccc cccaagccca aggacaccct catgatcagc cggacccccg 420
aggtgacctg cgtggtggtg gacgtgagcc acgaggaccc cgaggtgaag ttcaactggt 480
acgtggacgg cgtggaggtg cacaacgcca agaccaagcc ccgggaggag cagtacaaca 540
gcacctaccg ggtggtgagc gtgctcaccg tgctgcacca ggactggctg aacggcaagg 600
agtacaagtg caaggtgagc aacaaggccc tgcctgcccc catcgagaag accatcagca 660
aggccaaggg ccagccccgg gagccccagg tgtacaccct gcccccccagc cgggaggaga 720 tgaccaagaa ccaggtgtcc ctcacctgtc tggtgaaggg cttctacccc agcgacatcg 780
ccgtggagtg ggagagcaac ggccagcccg agaacaacta caagaccacc ccccctgtgc 840
tggacagcga cggcagcttc ttcctgtaca gcaagctcac cgtggacaag agccggtggc 900
agcagggcaa cgtgttcagc tgcagcgtga tgcacgaggc cctgcacaac cactacaccc 960
agaagagcct gagcctgagc cccggcaagt gataatctag agggcccgtt taaacccgct 1020
gatcagcctc gactgtgcct tctagttgcc agccatctgt tgtttgcccc tcccccgtgc 1080
cttccttgac cctggaaggt gccactccca ctgtcctttc ctaataaaat gaggaaattg 1140
catcgcattg tctgagtagg tgtcattcta ttctgggggg tggggtgggg caggacagca 1200
agggggagga ttgggaagac aatagcaggc atgctgggga tgcggtgggc tctatggctt 1260
ctgaggcgga aagaaccagc tggggctcta gggggtatcc ccacgcgccc tgtagcggcg 1320
cattaagcgc ggcgggtgtg gtggttacgc gcagcgtgac cgctacactt gccagcgccc 1380

```
tagcgcccgc tcctttcgct ttcttccctt cctttctcgc cacgttcgcc ggctttcccc   1440
gtcaagctct aaatcggggg ctccctttag ggttccgatt tagtgcttta cggcacctcg   1500
accccaaaaa acttgattag ggtgatggtt cacgtagtgg gccatcgccc tgatagacgg   1560
tttttcgccc tttgacgttg gagtccacgt tctttaatag tggactcttg ttccaaactg   1620
gaacaacact caaccctatc tcggtctatt cttttgattt ataagggatt ttgccgattt   1680
cggcctattg gttaaaaaat gagctgattt aacaaaaatt taacgcgaat taattctgtg   1740
gaatgtgtgt cagttagggt gtggaaagtc cccaggctcc ccagcaggca gaagtatgca   1800
aagcatgcat ctcaattagt cagcaaccag gtgtggaaag tccccaggct ccccagcagg   1860
cagaagtatg caaagcatgc atctcaatta gtcagcaacc atagtcccgc ccctaactcc   1920
gcccatcccg cccctaactc cgcccagttc cgcccattct ccgccccatg gctgactaat   1980
ttttttattt tatgcagagg ccgaggccgc ctctgcctct gagctattcc agaagtagtg   2040
aggaggcttt tttggaggcc taggcttttg caaaaagctc ccgggagctt gtatatccat   2100
tttcggatct gatcaagaga caggatgagg atcgtttcgc atgattgaac aagatggatt   2160
gcacgcaggt tctccggccg cttgggtgga gaggctattc ggctatgact gggcacaaca   2220
gacaatcggc tgctctgatg ccgccgtgtt ccggctgtca gcgcaggggc gcccggttct   2280
ttttgtcaag accgacctgt ccggtgccct gaatgaactg caggacgagg cagcgcggct   2340
atcgtggctg gccacgacgg gcgttccttg cgcagctgtg ctcgacgttg tcactgaagc   2400
gggaagggac tggctgctat tgggcgaagt gccggggcag gatctcctgt catctcacct   2460
tgctcctgcc gagaaagtat ccatcatggc tgatgcaatg cggcggctgc atacgcttga   2520
tccggctacc tgcccattcg accaccaagc gaaacatcgc atcgagcgag cacgtactcg   2580
gatggaagcc ggtcttgtcg atcaggatga tctggacgaa gagcatcagg ggctcgcgcc   2640
agccgaactg ttcgccaggc tcaaggcgcg catgcccgac ggcgaggatc tcgtcgtgac   2700
ccatggcgat gcctgcttgc cgaatatcat ggtggaaaat ggccgctttt ctggattcat   2760
cgactgtggc cggctgggtg tggcggaccg ctatcaggac atagcgttgg ctacccgtga   2820
tattgctgaa gagcttggcg gcgaatgggc tgaccgcttc ctcgtgcttt acggtatcgc   2880
cgctcccgat tcgcagcgca tcgccttcta tcgccttctt gacgagttct tctgagcggg   2940
actctggggt tcgaaatgac cgaccaagcg acgcccaacc tgccatcacg agatttcgat   3000
tccaccgccg ccttctatga aaggttgggc ttcggaatcg ttttccggga cgccggctgg   3060
atgatcctcc agcgcgggga tctcatgctg gagttcttcg cccaccccaa cttgtttatt   3120
gcagcttata atggttacaa ataaagcaat agcatcacaa atttcacaaa taaagcattt   3180
ttttcactgc attctagttg tggtttgtcc aaactcatca atgtatctta tcatgtctgt   3240
ataccgtcga cctctagcta gagcttggcg taatcatggt catagctgtt tcctgtgtga   3300
aattgttatc cgctcacaat tccacacaac atacgagccg gaagcataaa gtgtaaagcc   3360
tggggtgcct aatgagtgag ctaactcaca ttaattgcgt tgcgctcact gcccgctttc   3420
cagtcgggaa acctgtcgtg ccagctgcat taatgaatcg gccaacgcgc ggggagaggc   3480
ggtttgcgta ttgggcgctc ttccgcttcc tcgctcactg actcgctgcg ctcggtcgtt   3540
cggctgcggc gagcggtatc agctcactca aaggcggtaa tacggttatc cacagaatca   3600
ggggataacg caggaaagaa catgtgagca aaaggccagc aaaaggccag gaaccgtaaa   3660
aaggccgcgt tgctggcgtt tttccatagg ctccgccccc ctgacgagca tcacaaaaat   3720
```

```
cgacgctcaa gtcagaggtg gcgaaacccg acaggactat aaagatacca ggcgtttccc   3780
cctggaagct ccctcgtgcg ctctcctgtt ccgaccctgc cgcttaccgg atacctgtcc   3840
gcctttctcc cttcgggaag cgtggcgctt tctcatagct cacgctgtag gtatctcagt   3900
tcggtgtagg tcgttcgctc caagctgggc tgtgtgcacg aaccccccgt tcagcccgac   3960
cgctgcgcct tatccggtaa ctatcgtctt gagtccaacc cggtaagaca cgacttatcg   4020
ccactggcag cagccactgg taacaggatt agcagagcga ggtatgtagg cggtgctaca   4080
gagttcttga agtggtggcc taactacggc tacactagaa gaacagtatt tggtatctgc   4140
gctctgctga agccagttac cttcggaaaa agagttggta gctcttgatc cggcaaacaa   4200
accaccgctg gtagcggttt ttttgtttgc aagcagcaga ttacgcgcag aaaaaaagga   4260
tctcaagaag atcctttgat cttttctacg gggtctgacg ctcagtggaa cgaaaactca   4320
cgttaaggga ttttggtcat gagattatca aaaaggatct tcacctagat ccttttaaat   4380
taaaaatgaa gttttaaatc aatctaaagt atatatgagt aaacttggtc tgacagttac   4440
caatgcttaa tcagtgaggc acctatctca gcgatctgtc tatttcgttc atccatagtt   4500
gcctgactcc ccgtcgtgta gataactacg atacgggagg gcttaccatc tggccccagt   4560
gctgcaatga taccgcgaga cccacgctca ccggctccag atttatcagc aataaaccag   4620
ccagccggaa gggccgagcg cagaagtggt cctgcaactt tatccgcctc catccagtct   4680
attaattgtt gccgggaagc tagagtaagt agttcgccag ttaatagttt gcgcaacgtt   4740
gttgccattg ctacaggcat cgtggtgtca cgctcgtcgt ttggtatggc ttcattcagc   4800
tccggttccc aacgatcaag gcgagttaca tgatccccca tgttgtgcaa aaaagcggtt   4860
agctccttcg gtcctccgat cgttgtcaga agtaagttgg ccgcagtgtt atcactcatg   4920
gttatggcag cactgcataa ttctcttact gtcatgccat ccgtaagatg cttttctgtg   4980
actggtgagt actcaaccaa gtcattctga gaatagtgta tgcggcgacc gagttgctct   5040
tgcccggcgt caatacggga taataccgcg ccacatagca gaactttaaa agtgctcatc   5100
attggaaaac gttcttcggg gcgaaaactc tcaaggatct taccgctgtt gagatccagt   5160
tcgatgtaac ccactcgtgc acccaactga tcttcagcat cttttacttt caccagcgtt   5220
tctgggtgag caaaaacagg aaggcaaaat gccgcaaaaa agggaataag ggcgacacgg   5280
aaatgttgaa tactcatact cttccttttt caatattatt gaagcattta tcagggttat   5340
tgtctcatga gcggatacat atttgaatgt atttagaaaa ataaacaaat aggggttccg   5400
cgcacatttc cccgaaaagt gccacctgac gtcgacggat cgggagatct cccgatcccc   5460
tatggtgcac tctcagtaca atctgctctg atgccgcata gttaagccag tatctgctcc   5520
ctgcttgtgt gttggaggtc gctgagtagt gcgcgagcaa aatttaagct acaacaaggc   5580
aaggcttgac cgacaattgc atgaagaatc tgcttagggt taggcgtttt gcgctgcttc   5640
gctaggtggt caatattggc cattagccat attattcatt ggttatatag cataaatcaa   5700
tattggctat tggccattgc atacgttgta tccatatcat aatatgtaca tttatattgg   5760
ctcatgtcca acattaccgc catgttgaca ttgattattg actagttatt aatagtaatc   5820
aattacgggg tcattagttc atagcccata tatggagttc cgcgttacat aacttacggt   5880
aaatggcccg cctggctgac cgcccaacga cccccgccca ttgacgtcaa taatgacgta   5940
tgttcccata gtaacgccaa tagggacttt ccattgacgt caatgggtgg agtatttacg   6000
gtaaactgcc cacttggcag tacatcaagt gtatcatatg ccaagtacgc cccctattga   6060
cgtcaatgac ggtaaatggc ccgcctggca ttatgcccag tacatgacct tatgggactt   6120
```

```
tcctacttgg cagtacatct acgtattagt catcgctatt accatggtga tgcggttttg   6180
gcagtacatc aatgggcgtg gatagcggtt tgactcacgg ggatttccaa gtctccaccc   6240
cattgacgtc aatgggagtt tgttttggca ccaaaatcaa cgggactttc caaaatgtcg   6300
taacaactcc gccccattga cgcaaatggg cggtaggcgt gtacggtggg aggtctatat   6360
aagcagagct cgtttagtga accgtcagat cgcctggaga cgccatccac gctgttttga   6420
cctccataga agacaccggg accgatccag cctccgcggc cgggaacggt gcattggaag   6480
ctggcctgga tggcctgact ctcttaggta gccttgcaga agttggtcgt gaggcactgg   6540
gcaggtaagt atcaaggtta caagacaggt ttaaggagat caatagaaac tgggcttgtc   6600
gagacagaga agactcttgc gtttctgata ggcacctatt ggtcttactg acatccactt   6660
tgcctttctc tccacaggtg tccactccca gttcaattac agctcgccac catggcctgc   6720
cccggcttcc tgtgggccct ggtgatcagc acctgcctgg                         6760
```

<210> SEQ ID NO 48
<211> LENGTH: 6283
<212> TYPE: DNA
<213> ORGANISM: Artificial sequence
<220> FEATURE:
<223> OTHER INFORMATION: Vector pSyn-C04-Clambda

<400> SEQUENCE: 48

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgttaa ttaacatgaa    180
gaatctgctt agggttaggc gttttgcgct gcttcgctag gtggtcaata ttggccatta    240
gccatattat tcattggtta tatagcataa atcaatattg gctattggcc attgcatacg    300
ttgtatccat atcataatat gtacatttat attggctcat gtccaacatt accgccatgt    360
tgacattgat tattgactag ttattaatag taatcaatta cggggtcatt agttcatagc    420
ccatatatgg agttccgcgt tacataactt acggtaaatg gcccgcctgg ctgaccgccc    480
aacgaccccc gcccattgac gtcaataatg acgtatgttc ccatagtaac gccaataggg    540
actttccatt gacgtcaatg ggtggagtat ttacggtaaa ctgcccactt ggcagtacat    600
caagtgtatc atatgccaag tacgccccct attgacgtca atgacggtaa atggcccgcc    660
tggcattatg cccagtacat gaccttatgg gactttccta cttggcagta catctacgta    720
ttagtcatcg ctattaccat ggtgatgcgg ttttggcagt acatcaatgg gcgtggatag    780
cggtttgact cacggggatt tccaagtctc caccccattg acgtcaatgg gagtttgttt    840
tggcaccaaa atcaacggga ctttccaaaa tgtcgtaaca actccgcccc attgacgcaa    900
atgggcggta ggcgtgtacg gtgggaggtc tatataagca gagctcgttt agtgaaccgt    960
cagatcgcct ggagacgcca tccacgctgt tttgacctcc atagaagaca ccgggaccga   1020
tccagcctcc gcggccggga acggtgcatt ggaatcgatg actctcttag gtagccttgc   1080
agaagttggt cgtgaggcac tgggcaggta agtatcaagg ttacaagaca ggtttaagga   1140
gatcaataga aactgggctt gtcgagacag agaagactct tgcgtttctg ataggcacct   1200
attggtctta ctgacatcca ctttgccttt ctctccacag gtgtccactc ccagttcaat   1260
tacagctcgc caccatggcc tgccccggct tcctgtgggc cctggtgatc agcacctgcc   1320
tcgagatccc cggaccgcgg ccgcaagctt accgtgctgg gccagcccaa ggccgctccc   1380
```

-continued

```
agcgtgaccc tgttcccccc ctcctccgag gagctgcagg ccaacaaggc caccctggtg   1440
tgcctcatca gcgacttcta ccctggcgcc gtgaccgtgg cctggaaggc cgacagcagc   1500
cccgtgaagg ccggcgtgga gaccaccacc cccagcaagc agagcaacaa caagtacgcc   1560
gccagcagct acctgagcct cacccccgag cagtggaaga gccaccggag ctacagctgc   1620
caggtgaccc acgagggcag caccgtggag aagaccgtgg cccccaccga gtgcagctaa   1680
tagacttaag tttaaaccgc tgatcagcct cgactgtgcc ttctagttgc cagccatctg   1740
ttgtttgccc ctcccccgtg ccttccttga ccctggaagg tgccactccc actgtccttt   1800
cctaataaaa tgaggaaatt gcatcgcatt gtctgagtag gtgtcattct attctggggg   1860
gtggggtggg gcaggacagc aagggggagg attgggaaga caatagcagg catgctgggg   1920
atgcggtggg ctctatggct tctgaggcgg aaagaaccag ctggggctct agggggtatc   1980
cccacgcgcc ctgtagcggc gcattaagcg cggcgggtgt ggtggttacg cgcagcgtga   2040
ccgctacact tgccagcgcc ctagcgcccg ctcctttcgc tttcttccct tcctttctcg   2100
ccacgttcgc cggctttccc cgtcaagctc taaatcgggg gctcccttta gggttccgat   2160
ttagtgcttt acggcacctc gaccccaaaa aacttgatta gggtgatggt tcacgtagtg   2220
ggccatcgcc ctgatagacg gtttttcgcc ctttgacgtt ggagtccacg ttctttaata   2280
gtggactctt gttccaaact ggaacaacac tcaaccctat ctcggtctat tcttttgatt   2340
tataagggat tttggccatt tcggcctatt ggttaaaaaa tgagctgatt taacaaaaat   2400
ttaacgcgaa ttaattctgt ggaatgtgtg tcagttaggg tgtggaaagt ccccaggctc   2460
cccagcaggc agaagtatgc aaagcatgca tctcaattag tcagcaacca ggtgtggaaa   2520
gtccccaggc tccccagcag gcagaagtat gcaaagcatg catctcaatt agtcagcaac   2580
catagtcccg cccctaactc cgcccatccc gcccctaact ccgcccagtt ccgcccattc   2640
tccgccccat ggctgactaa ttttttttat ttatgcagag gccgaggccg cctctgcctc   2700
tgagctattc cagaagtagt gaggaggctt ttttggaggc ctaggctttt gcaaaaagct   2760
cccgggagct tgtatatcca ttttcggatc tgatcagcac gtgatgaaaa agcctgaact   2820
caccgcgacg tctgtcgaga agtttctgat cgaaaagttc gacagcgtct ccgacctgat   2880
gcagctctcg gagggcgaag aatctcgtgc tttcagcttc gatgtaggag ggcgtggata   2940
tgtcctgcgg gtaaatagct gcgccgatgg tttctacaaa gatcgttatg tttatcggca   3000
ctttgcatcg gccgcgctcc cgattccgga agtgcttgac attggggaat tcagcgagag   3060
cctgacctat tgcatctccc gccgtgcaca gggtgtcacg ttgcaagacc tgcctgaaac   3120
cgaactgccc gctgttctgc agccggtcgc ggaggccatg gatgcgatcg ctgcggccga   3180
tcttagccag acgagcgggt tcggcccatt cggaccgcaa ggaatcggtc aatacactac   3240
atggcgtgat ttcatatgcg cgattgctga tccccatgtg tatcactggc aaactgtgat   3300
ggacgacacc gtcagtgcgt ccgtcgcgca ggctctcgat gagctgatgc tttgggccga   3360
ggactgcccc gaagtccggc acctcgtgca cgcggatttc ggctccaaca atgtcctgac   3420
ggacaatggc cgcataacag cggtcattga ctggagcgag gcgatgttcg gggattccca   3480
atacgaggtc gccaacatct tcttctggag gccgtggttg gcttgtatgg agcagcagac   3540
gcgctacttc gagcggaggc atccggagct tgcaggatcg ccgcggctcc gggcgtatat   3600
gctccgcatt ggtcttgacc aactctatca gagcttggtt gacggcaatt tcgatgatgc   3660
agcttgggcg cagggtcgat gcgacgcaat cgtccgatcc ggagccggga ctgtcgggcg   3720
tacacaaatc gcccgcagaa gcgcggccgt ctggaccgat ggctgtgtag aagtactcgc   3780
```

```
cgatagtgga aaccgacgcc ccagcactcg tccgagggca aaggaatagc acgtgctacg   3840

agatttcgat tccaccgccg ccttctatga aaggttgggc ttcggaatcg ttttccggga   3900

cgccggctgg atgatcctcc agcgcgggga tctcatgctg gagttcttcg cccaccccaa   3960

cttgtttatt gcagcttata atggttacaa ataaagcaat agcatcacaa atttcacaaa   4020

taaagcattt ttttcactgc attctagttg tggtttgtcc aaactcatca atgtatctta   4080

tcatgtctgt ataccgtcga cctctagcta gagcttggcg taatcatggt catagctgtt   4140

tcctgtgtga aattgttatc cgctcacaat tccacacaac atacgagccg gaagcataaa   4200

gtgtaaagcc tggggtgcct aatgagtgag ctaactcaca ttaattgcgt tgcgctcact   4260

gcccgctttc cagtcgggaa acctgtcgtg ccagctgcat taatgaatcg gccaacgcgc   4320

ggggagaggc ggtttgcgta ttgggcgctc ttccgcttcc tcgctcactg actcgctgcg   4380

ctcggtcgtt cggctgcggc gagcggtatc agctcactca aaggcggtaa tacggttatc   4440

cacagaatca ggggataacg caggaaagaa catgtgagca aaaggccagc aaaaggccag   4500

gaaccgtaaa aaggccgcgt tgctggcgtt tttccatagg ctccgccccc ctgacgagca   4560

tcacaaaaat cgacgctcaa gtcagaggtg gcgaaacccg acaggactat aaagatacca   4620

ggcgtttccc cctggaagct ccctcgtgcg ctctcctgtt ccgaccctgc cgcttaccgg   4680

atacctgtcc gcctttctcc cttcgggaag cgtggcgctt tctcatagct cacgctgtag   4740

gtatctcagt tcggtgtagg tcgttcgctc caagctgggc tgtgtgcacg aaccccccgt   4800

tcagcccgac cgctgcgcct tatccggtaa ctatcgtctt gagtccaacc cggtaagaca   4860

cgacttatcg ccactggcag cagccactgg taacaggatt agcagagcga ggtatgtagg   4920

cggtgctaca gagttcttga agtggtggcc taactacggc tacactagaa gaacagtatt   4980

tggtatctgc gctctgctga agccagttac cttcggaaaa agagttggta gctcttgatc   5040

cggcaaacaa accaccgctg gtagcggttt ttttgtttgc aagcagcaga ttacgcgcag   5100

aaaaaaagga tctcaagaag atcctttgat cttttctacg gggtctgacg ctcagtggaa   5160

cgaaaactca cgttaaggga ttttggtcat gagattatca aaaaggatct tcacctagat   5220

ccttttaaat taaaaatgaa gttttaaatc aatctaaagt atatatgagt aaacttggtc   5280

tgacagttac caatgcttaa tcagtgaggc acctatctca gcgatctgtc tatttcgttc   5340

atccatagtt gcctgactcc ccgtcgtgta gataactacg atacgggagg gcttaccatc   5400

tggccccagt gctgcaatga taccgcgaga cccacgctca ccggctccag atttatcagc   5460

aataaaccag ccagccggaa gggccgagcg cagaagtggt cctgcaactt tatccgcctc   5520

catccagtct attaattgtt gccgggaagc tagagtaagt agttcgccag ttaatagttt   5580

gcgcaacgtt gttgccattg ctacaggcat cgtggtgtca cgctcgtcgt ttggtatggc   5640

ttcattcagc tccggttccc aacgatcaag gcgagttaca tgatccccca tgttgtgcaa   5700

aaaagcggtt agctccttcg gtcctccgat cgttgtcaga agtaagttgg ccgcagtgtt   5760

atcactcatg gttatggcag cactgcataa ttctcttact gtcatgccat ccgtaagatg   5820

cttttctgtg actggtgagt actcaaccaa gtcattctga gaatagtgta tgcggcgacc   5880

gagttgctct tgcccggcgt caatacggga taataccgcg ccacatagca gaactttaaa   5940

agtgctcatc attggaaaac gttcttcggg gcgaaaactc tcaaggatct taccgctgtt   6000

gagatccagt tcgatgtaac ccactcgtgc acccaactga tcttcagcat cttttacttt   6060

caccagcgtt tctgggtgag caaaaacagg aaggcaaaat gccgcaaaaa agggaataag   6120
```

```
ggcgacacgg aaatgttgaa tactcatact cttccttttt caatattatt gaagcattta   6180

tcagggttat tgtctcatga gcggatacat atttgaatgt atttagaaaa ataaacaaat   6240

aggggttccg cgcacatttc cccgaaaagt gccacctgac gtc                     6283


<210> SEQ ID NO 49
<211> LENGTH: 52
<212> TYPE: DNA
<213> ORGANISM: Artificial sequence
<220> FEATURE:
<223> OTHER INFORMATION: Oligonucleotide 5L-C

<400> SEQUENCE: 49

acctgtctcg agttttccat ggctcagtcc gtgctgaccc agcctccctc ag             52


<210> SEQ ID NO 50
<211> LENGTH: 28
<212> TYPE: DNA
<213> ORGANISM: Artificial sequence
<220> FEATURE:
<223> OTHER INFORMATION: Oligonucleotide sy3L-Cmod

<400> SEQUENCE: 50

ccagcacggt aagcttggtg cctccgcc                                        28


<210> SEQ ID NO 51
<211> LENGTH: 47
<212> TYPE: DNA
<213> ORGANISM: Artificial sequence
<220> FEATURE:
<223> OTHER INFORMATION: Oligonucleotide 5H-A

<400> SEQUENCE: 51

acctgtcttg aattctccat ggcccaggtg cagctggtgc agtctgg                   47


<210> SEQ ID NO 52
<211> LENGTH: 47
<212> TYPE: DNA
<213> ORGANISM: Artificial sequence
<220> FEATURE:
<223> OTHER INFORMATION: Oligonucleotide sy3H-A

<400> SEQUENCE: 52

gcccttggtg ctagcgctgg agacggtcac cagggtgccc tggcccc                   47


<210> SEQ ID NO 53
<211> LENGTH: 10515
<212> TYPE: DNA
<213> ORGANISM: Artificial sequence
<220> FEATURE:
<223> OTHER INFORMATION: Vector pIg-C911-HCgamma1
<220> FEATURE:
<221> NAME/KEY: misc_feature
<222> LOCATION: (1326)..(5076)
<223> OTHER INFORMATION: Stuffer

<400> SEQUENCE: 53

tcgacggatc gggagatctc ccgatcccct atggtgcact ctcagtacaa tctgctctga     60

tgccgcatag ttaagccagt atctgctccc tgcttgtgtg ttggaggtcg ctgagtagtg    120

cgcgagcaaa atttaagcta caacaaggca aggcttgacc gacaattgca tgaagaatct    180

gcttagggtt aggcgttttg cgctgcttcg ctaggtggtc aatattggcc attagccata    240

ttattcattg gttatatagc ataaatcaat attggctatt ggccattgca tacgttgtat    300

ccatatcata atatgtacat ttatattggc tcatgtccaa cattaccgcc atgttgacat    360
```

```
tgattattga ctagttatta atagtaatca attacggggt cattagttca tagcccatat    420

atggagttcc gcgttacata acttacggta aatggcccgc ctggctgacc gcccaacgac    480

ccccgcccat tgacgtcaat aatgacgtat gttcccatag taacgccaat agggactttc    540

cattgacgtc aatgggtgga gtatttacgg taaactgccc acttggcagt acatcaagtg    600

tatcatatgc caagtacgcc ccctattgac gtcaatgacg gtaaatggcc cgcctggcat    660

tatgcccagt acatgacctt atgggacttt cctacttggc agtacatcta cgtattagtc    720

atcgctatta ccatggtgat gcggttttgg cagtacatca atgggcgtgg atagcggttt    780

gactcacggg gatttccaag tctccacccc attgacgtca atgggagttt gttttggcac    840

caaaatcaac gggactttcc aaaatgtcgt aacaactccg ccccattgac gcaaatgggc    900

ggtaggcgtg tacggtggga ggtctatata agcagagctc gtttagtgaa ccgtcagatc    960

gcctggagac gccatccacg ctgttttgac ctccatagaa gacaccggga ccgatccagc   1020

ctccgcggcc gggaacggtg cattggaagc tggcctggat atcctgactc tcttaggtag   1080

ccttgcagaa gttggtcgtg aggcactggg caggtaagta tcaaggttac aagacaggtt   1140

taaggagatc aatagaaact gggcttgtcg agacagagaa gactcttgcg tttctgatag   1200

gcacctattg gtcttactga catccacttt gcctttctct ccacaggtgt ccactcccag   1260

ttcaattaca gctcgccacc atgggatgga gctgtatcat cctcttcttg gtactgctgc   1320

tggcccagcc ggccagtgac cttgaccggt gcaccacttt tgatgatgtt caagctccta   1380

attacactca acatacttca tctatgaggg gggtttacta tcctgatgaa atttttagat   1440

cggacactct ttatttaact caggatttat ttcttccatt ttattctaat gttacagggt   1500

ttcatactat taatcatacg tttggcaacc ctgtcatacc ttttaaggat ggtatttatt   1560

ttgctgccac agagaaatca aatgttgtcc gtggttgggt tttggttct accatgaaca   1620

acaagtcaca gtcggtgatt attattaaca attctactaa tgttgttata cgagcatgta   1680

actttgaatt gtgtgacaac cctttctttg ctgtttctaa acccatgggt acacagacac   1740

atactatgat attcgataat gcatttaatt gcactttcga gtacatatct gatgcctttt   1800

cgcttgatgt ttcagaaaag tcaggtaatt ttaaacactt acgagagttt gtgtttaaaa   1860

ataaagatgg gtttctctat gtttataagg gctatcaacc tatagatgta gttcgtgatc   1920

taccttctgg ttttaacact ttgaaaccta tttttaagtt gcctcttggt attaacatta   1980

caaattttag agccattctt acagcctttt cacctgctca agacatttgg ggcacgtcag   2040

ctgcagccta ttttgttggc tatttaaagc caactacatt tatgctcaag tatgatgaaa   2100

atggtacaat cacagatgct gttgattgtt ctcaaaatcc acttgctgaa ctcaaatgct   2160

ctgttaagag ctttgagatt gacaaaggaa tttaccagac ctctaatttc agggttgttc   2220

cctcaggaga tgttgtgaga ttccctaata ttacaaactt gtgtcctttt ggagaggttt   2280

ttaatgctac taaattccct tctgtctatg catgggagag aaaaaaaatt tctaattgtg   2340

ttgctgatta ctctgtgctc tacaactcaa catttttttc aacctttaag tgctatggcg   2400

tttctgccac taagttgaat gatctttgct tctccaatgt ctatgcagat tcttttgtag   2460

tcaagggaga tgatgtaaga caaatagcgc caggacaaac tggtgttatt gctgattata   2520

attataaatt gccagatgat ttcatgggtt gtgtccttgc ttggaatact aggaacattg   2580

atgctacttc aactggtaat tataattata aatataggta tcttagacat ggcaagctta   2640

ggccctttga gagagacata tctaatgtgc ctttctcccc tgatggcaaa ccttgcaccc   2700
```

```
cacctgctct taattgttat tggccattaa atgattatgg tttttacacc actactggca   2760
ttggctacca accttacaga gttgtagtac tttcttttga acttttaaat gcaccggcca   2820
cggtttgtgg accaaaatta tccactgacc ttattaagaa ccagtgtgtc aattttaatt   2880
ttaatggact cactggtact ggtgtgttaa ctccttcttc aaagagattt caaccatttc   2940
aacaatttgg ccgtgatgtt tctgatttca ctgattccgt tcgagatcct aaaacatctg   3000
aaatattaga catttcacct tgctcttttg gggtgtaag tgtaattaca cctggaacaa    3060
atgcttcatc tgaagttgct gttctatatc aagatgttaa ctgcactgat gtttctacag   3120
caattcatgc agatcaactc acaccagctt ggcgcatata ttctactgga aacaatgtat   3180
tccagactca ggcaggctgt cttataggag ctgagcatgt cgacacttct tatgagtgcg   3240
acattcctat tggagctggc atttgtgcta gttaccatac agtttcttta ttacgtagta   3300
ctagccaaaa atctattgtg gcttatacta tgtctttagg tgctgatagt tcaattgctt   3360
actctaataa caccattgct atacctacta acttttcaat tagcattact acagaagtaa   3420
tgcctgtttc tatggctaaa acctccgtag attgtaatat gtacatctgc ggagattcta   3480
ctgaatgtgc taatttgctt ctccaatatg gtagcttttg cacacaacta aatcgtgcac   3540
tctcaggtat tgctgctgaa caggatcgca acacacgtga agtgttcgct caagtcaaac   3600
aaatgtacaa aaccccaact ttgaaatatt ttggtggttt taatttttca caaatattac   3660
ctgaccctct aaagccaact aagaggtctt ttattgagga cttgctcttt aataaggtga   3720
cactcgctga tgctggcttc atgaagcaat atggcgaatg cctaggtgat attaatgcta   3780
gagatctcat ttgtgcgcag aagttcaatg gacttacagt gttgccacct ctgctcactg   3840
atgatatgat tgctgcctac actgctgctc tagttagtgg tactgccact gctggatgga   3900
catttggtgc tggcgctgct cttcaaatac cttttgctat gcaaatggca tataggttca   3960
atggcattgg agttacccaa aatgttctct atgagaacca aaaacaaatc gccaaccaat   4020
ttaacaaggc gattagtcaa attcaagaat cacttacaac aacatcaact gcattgggca   4080
agctgcaaga cgttgttaac cagaatgctc aagcattaaa cacacttgtt aaacaactta   4140
gctctaattt tggtgcaatt tcaagtgtgc taaatgatat cctttcgcga cttgataaag   4200
tcgaggcgga ggtacaaatt gacaggttaa ttacaggcag acttcaaagc cttcaaacct   4260
atgtaacaca acaactaatc agggctgctg aaatcagggc ttctgctaat cttgctgcta   4320
ctaaaatgtc tgagtgtgtt cttggacaat caaaaagagt tgacttttgt ggaaagggct   4380
accaccttat gtccttccca caagcagccc cgcatggtgt tgtcttccta catgtcacgt   4440
atgtgccatc ccaggagagg aacttcacca cagcgccagc aatttgtcat gaaggcaaag   4500
catacttccc tcgtgaaggt gtttttgtgt ttaatggcac ttcttggttt attacacaga   4560
ggaacttctt ttctccacaa ataattacta cagacaatac atttgtctca ggaaattgtg   4620
atgtcgttat tggcatcatt aacaacacag tttatgatcc tctgcaacct gagcttgact   4680
cattcaaaga agagctggac aagtacttca aaaatcatac atcaccagat gttgattttg   4740
gcgacatttc aggcattaac gcttctgtcg tcaacattca aaaagaaatt gaccgcctca   4800
atgaggtcgc taaaaattta aatgaatcac tcattgacct tcaagaactg ggaaaatatg   4860
agcaatatat taaatggcct ctcgacgaac aaaaactcat ctcagaagag gatctgaatg   4920
ctgtgggcca ggacacgcag gaggtcatcg tggtgccaca ctccttgccc tttaaggtgg   4980
tggtgatctc agccatcctg gccctggtgg tgctcaccat catctccctt atcatcctca   5040
tcatgctttg gcagaagaag ccacgttagg cggccgctcg agtgctagca ccaagggccc   5100
```

```
cagcgtgttc cccctggccc ccagcagcaa gagcaccagc ggcggcacag ccgccctggg   5160
ctgcctggtg aaggactact tccccgagcc cgtgaccgtg agctggaaca gcggcgcctt   5220
gaccagcggc gtgcacacct tccccgccgt gctgcagagc agcggcctgt acagcctgag   5280
cagcgtggtg accgtgccca gcagcagcct gggcacccag acctacatct gcaacgtgaa   5340
ccacaagccc agcaacacca aggtggacaa acgcgtggag cccaagagct gcgacaagac   5400
ccacacctgc ccccctgcc ctgcccccga gctgctgggc ggaccctccg tgttcctgtt    5460
ccccccaag cccaaggaca ccctcatgat cagccggacc cccgaggtga cctgcgtggt    5520
ggtggacgtg agccacgagg accccgaggt gaagttcaac tggtacgtgg acggcgtgga   5580
ggtgcacaac gccaagacca agccccggga ggagcagtac aacagcacct accgggtggt   5640
gagcgtgctc accgtgctgc accaggactg gctgaacggc aaggagtaca agtgcaaggt   5700
gagcaacaag gccctgcctg cccccatcga gaagaccatc agcaaggcca agggccagcc   5760
ccgggagccc caggtgtaca ccctgccccc cagccgggag gagatgacca agaaccaggt   5820
gtccctcacc tgtctggtga agggcttcta ccccagcgac atcgccgtgg agtgggagag   5880
caacggccag cccgagaaca actacaagac cacccccct gtgctggaca gcgacggcag    5940
cttcttcctg tacagcaagc tcaccgtgga caagagccgg tggcagcagg gcaacgtgtt   6000
cagctgcagc gtgatgcacg aggccctgca caaccactac acccagaaga gcctgagcct   6060
gagccccggc aagtgataat ctagagggcc cgtttaaacc cgctgatcag cctcgactgt   6120
gccttctagt tgccagccat ctgttgtttg cccctccccc gtgccttcct tgaccctgga   6180
aggtgccact cccactgtcc tttcctaata aaatgaggaa attgcatcgc attgtctgag   6240
taggtgtcat tctattctgg ggggtggggt ggggcaggac agcaaggggg aggattggga   6300
agacaatagc aggcatgctg gggatgcggt gggctctatg gcttctgagg cggaaagaac   6360
cagctggggc tctagggggt atccccacgc gccctgtagc ggcgcattaa gcgcggcggg   6420
tgtggtggtt acgcgcagcg tgaccgctac acttgccagc gccctagcgc ccgctccttt   6480
cgctttcttc ccttcctttc tcgccacgtt cgccggcttt ccccgtcaag ctctaaatcg   6540
ggggctccct ttagggttcc gatttagtgc tttacggcac ctcgacccca aaaaacttga   6600
ttagggtgat ggttcacgta gtgggccatc gccctgatag acggtttttc gccctttgac   6660
gttggagtcc acgttcttta atagtggact cttgttccaa actggaacaa cactcaaccc   6720
tatctcggtc tattcttttg atttataagg gattttgccg atttcggcct attggttaaa   6780
aaatgagctg atttaacaaa aatttaacgc gaattaattc tgtggaatgt gtgtcagtta   6840
gggtgtggaa agtccccagg ctccccagca ggcagaagta tgcaaagcat gcatctcaat   6900
tagtcagcaa ccaggtgtgg aaagtcccca ggctccccag caggcagaag tatgcaaagc   6960
atgcatctca attagtcagc aaccatagtc ccgcccctaa ctccgcccat cccgccccta   7020
actccgccca gttccgccca ttctccgccc catggctgac taattttttt tatttatgca   7080
gaggccgagg ccgcctctgc ctctgagcta ttccagaagt agtgaggagg cttttttgga   7140
ggcctaggct tttgcaaaaa gctcccggga gcttgtatat ccattttcgg atctgatcaa   7200
gagacaggat gaggatcgtt tcgcatgatt gaacaagatg gattgcacgc aggttctccg   7260
gccgcttggg tggagaggct attcggctat gactgggcac aacagacaat cggctgctct   7320
gatgccgccg tgttccggct gtcagcgcag gggcgcccgg ttctttttgt caagaccgac   7380
ctgtccggtg ccctgaatga actgcaggac gaggcagcgc ggctatcgtg gctggccacg   7440
```

```
acgggcgttc cttgcgcagc tgtgctcgac gttgtcactg aagcgggaag ggactggctg   7500
ctattgggcg aagtgccggg gcaggatctc ctgtcatctc accttgctcc tgccgagaaa   7560
gtatccatca tggctgatgc aatgcggcgg ctgcatacgc ttgatccggc tacctgccca   7620
ttcgaccacc aagcgaaaca tcgcatcgag cgagcacgta ctcggatgga agccggtctt   7680
gtcgatcagg atgatctgga cgaagagcat caggggctcg cgccagccga actgttcgcc   7740
aggctcaagg cgcgcatgcc cgacggcgag gatctcgtcg tgacccatgg cgatgcctgc   7800
ttgccgaata tcatggtgga aaatggccgc ttttctggat tcatcgactg tggccggctg   7860
ggtgtggcgg accgctatca ggacatagcg ttggctaccc gtgatattgc tgaagagctt   7920
ggcggcgaat gggctgaccg cttcctcgtg ctttacggta tcgccgctcc cgattcgcag   7980
cgcatcgcct tctatcgcct tcttgacgag ttcttctgag cgggactctg gggttcgaaa   8040
tgaccgacca agcgacgccc aacctgccat cacgagattt cgattccacc gccgccttct   8100
atgaaaggtt gggcttcgga atcgttttcc gggacgccgg ctggatgatc ctccagcgcg   8160
gggatctcat gctggagttc ttcgcccacc ccaacttgtt tattgcagct tataatggtt   8220
acaaataaag caatagcatc acaaatttca caaataaagc atttttttca ctgcattcta   8280
gttgtggttt gtccaaactc atcaatgtat cttatcatgt ctgtataccg tcgacctcta   8340
gctagagctt ggcgtaatca tggtcatagc tgtttcctgt gtgaaattgt tatccgctca   8400
caattccaca caacatacga gccggaagca taaagtgtaa agcctggggt gcctaatgag   8460
tgagctaact cacattaatt gcgttgcgct cactgcccgc tttccagtcg ggaaacctgt   8520
cgtgccagct gcattaatga atcggccaac gcgcggggag aggcggtttg cgtattgggc   8580
gctcttccgc ttcctcgctc actgactcgc tgcgctcggt cgttcggctg cggcgagcgg   8640
tatcagctca ctcaaaggcg gtaatacggt tatccacaga atcaggggat aacgcaggaa   8700
agaacatgtg agcaaaaggc cagcaaaagg ccaggaaccg taaaaaggcc gcgttgctgg   8760
cgtttttcca taggctccgc ccccctgacg agcatcacaa aaatcgacgc tcaagtcaga   8820
ggtggcgaaa cccgacagga ctataaagat accaggcgtt tccccctgga agctccctcg   8880
tgcgctctcc tgttccgacc ctgccgctta ccggatacct gtccgccttt ctcccttcgg   8940
gaagcgtggc gctttctcat agctcacgct gtaggtatct cagttcggtg taggtcgttc   9000
gctccaagct gggctgtgtg cacgaacccc ccgttcagcc cgaccgctgc gccttatccg   9060
gtaactatcg tcttgagtcc aacccggtaa gacacgactt atcgccactg gcagcagcca   9120
ctggtaacag gattagcaga gcgaggtatg taggcggtgc tacagagttc ttgaagtggt   9180
ggcctaacta cggctacact agaagaacag tatttggtat ctgcgctctg ctgaagccag   9240
ttaccttcgg aaaaagagtt ggtagctctt gatccggcaa acaaaccacc gctggtagcg   9300
gtttttttgt ttgcaagcag cagattacgc gcagaaaaaa aggatctcaa gaagatcctt   9360
tgatcttttc tacggggtct gacgctcagt ggaacgaaaa ctcacgttaa gggattttgg   9420
tcatgagatt atcaaaaagg atcttcacct agatcctttt aaattaaaaa tgaagtttta   9480
aatcaatcta aagtatatat gagtaaactt ggtctgacag ttaccaatgc ttaatcagtg   9540
aggcacctat ctcagcgatc tgtctatttc gttcatccat agttgcctga ctccccgtcg   9600
tgtagataac tacgatacgg gagggcttac catctggccc cagtgctgca atgataccgc   9660
gagacccacg ctcaccggct ccagatttat cagcaataaa ccagccagcc ggaagggccg   9720
agcgcagaag tggtcctgca actttatccg cctccatcca gtctattaat tgttgccggg   9780
aagctagagt aagtagttcg ccagttaata gtttgcgcaa cgttgttgcc attgctacag   9840
```

```
gcatcgtggt gtcacgctcg tcgtttggta tggcttcatt cagctccggt tcccaacgat   9900

caaggcgagt tacatgatcc cccatgttgt gcaaaaaagc ggttagctcc ttcggtcctc   9960

cgatcgttgt cagaagtaag ttggccgcag tgttatcact catggttatg gcagcactgc  10020

ataattctct tactgtcatg ccatccgtaa gatgcttttc tgtgactggt gagtactcaa  10080

ccaagtcatt ctgagaatag tgtatgcggc gaccgagttg ctcttgcccg gcgtcaatac  10140

gggataatac cgcgccacat agcagaactt taaaagtgct catcattgga aaacgttctt  10200

cggggcgaaa actctcaagg atcttaccgc tgttgagatc cagttcgatg taacccactc  10260

gtgcacccaa ctgatcttca gcatctttta ctttcaccag cgtttctggg tgagcaaaaa  10320

caggaaggca aaatgccgca aaaaagggaa taagggcgac acggaaatgt tgaatactca  10380

tactcttcct ttttcaatat tattgaagca tttatcaggg ttattgtctc atgagcggat  10440

acatatttga atgtatttag aaaaataaac aaataggggt tccgcgcaca tttccccgaa  10500

aagtgccacc tgacg                                                   10515
```

```
<210> SEQ ID NO 54
<211> LENGTH: 8777
<212> TYPE: DNA
<213> ORGANISM: Artificial sequence
<220> FEATURE:
<223> OTHER INFORMATION: Vector pIg-C909-Ckappa
<220> FEATURE:
<221> NAME/KEY: misc_feature
<222> LOCATION: (1328)..(3860)
<223> OTHER INFORMATION: Stuffer

<400> SEQUENCE: 54
```

```
tcgacggatc gggagatctc ccgatcccct atggtgcact ctcagtacaa tctgctctga     60

tgccgcatag ttaagccagt atctgctccc tgcttgtgtg ttggaggtcg ctgagtagtg    120

cgcgagcaaa atttaagcta caacaaggca aggcttgacc gacaattgtt aattaacatg    180

aagaatctgc ttagggttag gcgttttgcg ctgcttcgct aggtggtcaa tattggccat    240

tagccatatt attcattggt tatatagcat aaatcaatat tggctattgg ccattgcata    300

cgttgtatcc atatcataat atgtacattt atattggctc atgtccaaca ttaccgccat    360

gttgacattg attattgact agttattaat agtaatcaat tacggggtca ttagttcata    420

gcccatatat ggagttccgc gttacataac ttacggtaaa tggcccgcct ggctgaccgc    480

ccaacgaccc ccgcccattg acgtcaataa tgacgtatgt tcccatagta acgccaatag    540

ggactttcca ttgacgtcaa tgggtggagt atttacggta aactgcccac ttggcagtac    600

atcaagtgta tcatatgcca agtacgcccc ctattgacgt caatgacggt aaatggcccg    660

cctggcatta tgcccagtac atgaccttat gggactttcc tacttggcag tacatctacg    720

tattagtcat cgctattacc atggtgatgc ggttttggca gtacatcaat gggcgtggat    780

agcggtttga ctcacgggga tttccaagtc tccaccccat tgacgtcaat gggagtttgt    840

tttggcacca aaatcaacgg gactttccaa aatgtcgtaa caactccgcc ccattgacgc    900

aaatgggcgg taggcgtgta cggtgggagg tctatataag cagagctcgt ttagtgaacc    960

gtcagatcgc ctggagacgc catccacgct gttttgacct ccatagaaga caccgggacc   1020

gatccagcct ccgcggccgg gaacggtgca ttggaatcga tgactctctt aggtagcctt   1080

gcagaagttg gtcgtgaggc actgggcagg taagtatcaa ggttacaaga caggtttaag   1140

gagatcaata gaaactgggc ttgtcgagac agagaagact cttgcgtttc tgataggcac   1200
```

```
ctattggtct tactgacatc cactttgcct ttctctccac aggtgtccac tcccagttca   1260
attacagctc gccaccatgc ggctgcccgc ccagctgctg ggccttctca tgctgtgggt   1320
gcccgcctcg agatctatcg atgcatgcca tggtaccaag cttgccacca tgagcagcag   1380
ctcttggctg ctgctgagcc tggtggccgt gacagccgcc cagagcacca tcgaggagca   1440
ggccaagacc ttcctggaca agttcaacca cgaggccgag gacctgttct accagagcag   1500
cctggccagc tggaactaca acaccaacat caccgaggag aacgtgcaga acatgaacaa   1560
cgccggcgac aagtggagcg ccttcctgaa ggagcagagc acactggccc agatgtaccc   1620
cctgcaggag atccagaacc tgaccgtgaa gctgcagctg caggccctgc agcagaacgg   1680
cagcagcgtg ctgagcgagg acaagagcaa gcggctgaac accatcctga acaccatgtc   1740
caccatctac agcaccggca aagtgtgcaa ccccgacaac ccccaggagt gcctgctgct   1800
ggagcccggc ctgaacgaga tcatggccaa cagcctggac tacaacgagc ggctgtgggc   1860
ctgggagagc tggcggagcg aagtgggcaa gcagctgcgg cccctgtacg aggagtacgt   1920
ggtgctgaag aacgagatgg ccagggccaa ccactacgag gactacggcg actactggag   1980
aggcgactac gaagtgaacg gcgtggacgg ctacgactac agcagaggcc agctgatcga   2040
ggacgtggag cacaccttcg aggagatcaa gcctctgtac gagcacctgc acgcctacgt   2100
gcgggccaag ctgatgaacg cctaccccag ctacatcagc cccatcggct gcctgcccgc   2160
ccacctgctg ggcgacatgt ggggccggtt ctggaccaac ctgtacagcc tgaccgtgcc   2220
cttcggccag aagcccaaca tcgacgtgac cgacgccatg gtggaccagg cctgggacgc   2280
ccagcggatc ttcaaggagg ccgagaagtt cttcgtgagc gtgggcctgc ccaacatgac   2340
ccagggcttt tgggagaaca gcatgctgac cgaccccggc aatgtgcaga aggccgtgtg   2400
ccaccccacc gcctgggacc tgggcaaggg cgacttccgg atcctgatgt gcaccaaagt   2460
gaccatggac gacttcctga ccgcccacca cgagatgggc cacatccagt acgacatggc   2520
ctacgccgcc cagcccttcc tgctgcggaa cggcgccaac gagggctttc acgaggccgt   2580
gggcgagatc atgagcctga gcgccgccac ccccaagcac ctgaagagca tcggcctgct   2640
gagccccgac ttccaggagg acaacgagac cgagatcaac ttcctgctga agcaggccct   2700
gaccatcgtg ggcaccctgc ccttcaccta catgctggag aagtggcggt ggatggtgtt   2760
taagggcgag atccccaagg accagtggat gaagaagtgg tgggagatga agcgggagat   2820
cgtgggcgtg gtggagcccg tgccccacga cgagacctac tgcgaccccg ccagcctgtt   2880
ccacgtgagc aacgactact ccttcatccg gtactacacc cggaccctgt accagttcca   2940
gttccaggag gccctgtgcc aggccgccaa gcacgagggc cccctgcaca agtgcgacat   3000
cagcaacagc accgaggccg gacagaaact gttcaacatg ctgcggctgg gcaagagcga   3060
gccctggacc ctggccctgg agaatgtggt gggcgccaag aacatgaatg tgcgccccct   3120
gctgaactac ttcgagcccc tgttcacctg gctgaaggac cagaacaaga acagcttcgt   3180
gggctggagc accgactgga gcccctacgc cgaccagagc atcaaagtgc ggatcagcct   3240
gaagagcgcc ctgggcgaca aggcctacga gtggaacgac aacgagatgt acctgttccg   3300
gagcagcgtg gcctatgcca tgcggcagta cttcctgaaa gtgaagaacc agatgatcct   3360
gttcggcgag gaggacgtga gagtggccaa cctgaagccc cggatcagct tcaacttctt   3420
cgtgaccgcc cccaagaacg tgagcgacat catccccggg accgaagtgg agaaggccat   3480
ccggatgagc cggagccgga tcaacgacgc cttccggctg aacgacaact ccctggagtt   3540
cctgggcatc cagcccaccc tgggccctcc caaccagccc cccgtgagca tctggctgat   3600
```

```
cgtgtttggc gtggtgatgg gcgtgatcgt ggtgggaatc gtgatcctga tcttcaccgg   3660
catccgggac cggaagaaga agaacaaggc ccggagcggc gagaacccct acgccagcat   3720
cgatatcagc aagggcgaga acaaccccgg cttccagaac accgacgacg tgcagaccag   3780
cttctgataa tctagaacga gctcgaattc gaagcttctg cagacgcgtc gacgtcatat   3840
ggatccgata tcgccgtggc ggccgcaccc agcgtgttca tcttcccccc ctccgacgag   3900
cagctgaaga gcggcaccgc cagcgtggtg tgcctgctga acaacttcta cccccgggag   3960
gccaaggtgc agtggaaggt ggacaacgcc ctgcagagcg gcaacagcca ggagagcgtg   4020
accgagcagg acagcaagga ctccacctac agcctgagca gcaccctcac cctgagcaag   4080
gccgactacg agaagcacaa ggtgtacgcc tgcgaggtga cccaccaggg cctgagcagc   4140
cccgtgacca agagcttcaa ccggggcgag tgttaataga cttaagttta aaccgctgat   4200
cagcctcgac tgtgccttct agttgccagc catctgttgt ttgcccctcc cccgtgcctt   4260
ccttgaccct ggaaggtgcc actcccactg tcctttccta ataaaatgag gaaattgcat   4320
cgcattgtct gagtaggtgt cattctattc tggggggtgg ggtggggcag gacagcaagg   4380
gggaggattg ggaagacaat agcaggcatg ctggggatgc ggtgggctct atggcttctg   4440
aggcggaaag aaccagctgg ggctctaggg ggtatcccca cgcgccctgt agcggcgcat   4500
taagcgcggc gggtgtggtg gttacgcgca gcgtgaccgc tacacttgcc agcgccctag   4560
cgcccgctcc tttcgctttc ttcccttcct ttctcgccac gttcgccggc tttccccgtc   4620
aagctctaaa tcgggggctc cctttagggt tccgatttag tgctttacgg cacctcgacc   4680
ccaaaaaact tgattagggt gatggttcac gtagtgggcc atcgccctga tagacggttt   4740
ttcgcccttt gacgttggag tccacgttct ttaatagtgg actcttgttc caaactggaa   4800
caacactcaa ccctatctcg gtctattctt ttgatttata agggattttg gccatttcgg   4860
cctattggtt aaaaaatgag ctgatttaac aaaaatttaa cgcgaattaa ttctgtggaa   4920
tgtgtgtcag ttagggtgtg gaaagtcccc aggctcccca gcaggcagaa gtatgcaaag   4980
catgcatctc aattagtcag caaccaggtg tggaaagtcc ccaggctccc cagcaggcag   5040
aagtatgcaa agcatgcatc tcaattagtc agcaaccata gtcccgcccc taactccgcc   5100
catcccgccc ctaactccgc ccagttccgc ccattctccg ccccatggct gactaatttt   5160
ttttatttat gcagaggccg aggccgcctc tgcctctgag ctattccaga agtagtgagg   5220
aggctttttt ggaggcctag gcttttgcaa aaagctcccg ggagcttgta tatccatttt   5280
cggatctgat cagcacgtga tgaaaaagcc tgaactcacc gcgacgtctg tcgagaagtt   5340
tctgatcgaa aagttcgaca gcgtctccga cctgatgcag ctctcggagg gcgaagaatc   5400
tcgtgctttc agcttcgatg taggagggcg tggatatgtc ctgcgggtaa atagctgcgc   5460
cgatggtttc tacaaagatc gttatgttta tcggcacttt gcatcggccg cgctcccgat   5520
tccggaagtg cttgacattg gggaattcag cgagagcctg acctattgca tctcccgccg   5580
tgcacagggt gtcacgttgc aagacctgcc tgaaaccgaa ctgcccgctg ttctgcagcc   5640
ggtcgcggag gccatggatg cgatcgctgc ggccgatctt agccagacga gcgggttcgg   5700
cccattcgga ccacaaggaa tcggtcaata cactacatgg cgtgatttca tatgcgcgat   5760
tgctgatccc catgtgtatc actggcaaac tgtgatggac gacaccgtca gtgcgtccgt   5820
cgcgcaggct ctcgatgagc tgatgctttg ggccgaggac tgccccgaag tccggcacct   5880
cgtgcacgcg gatttcggct ccaacaatgt cctgacggac aatggccgca taacagcggt   5940
```

```
cattgactgg agcgaggcga tgttcgggga ttcccaatac gaggtcgcca acatcttctt   6000
ctggaggccg tggttggctt gtatggagca gcagacgcgc tacttcgagc ggaggcatcc   6060
ggagcttgca ggatcgccgc ggctccgggc gtatatgctc cgcattggtc ttgaccaact   6120
ctatcagagc ttggttgacg gcaatttcga tgatgcagct tgggcgcagg gtcgatgcga   6180
cgcaatcgtc cgatccggag ccgggactgt cgggcgtaca caaatcgccc gcagaagcgc   6240
ggccgtctgg accgatggct gtgtagaagt actcgccgat agtggaaacc gacgccccag   6300
cactcgtccg agggcaaagg aatagcacgt gctacgagat ttcgattcca ccgccgcctt   6360
ctatgaaagg ttgggcttcg gaatcgtttt ccgggacgcc ggctggatga tcctccagcg   6420
cggggatctc atgctggagt tcttcgccca ccccaacttg tttattgcag cttataatgg   6480
ttacaaataa agcaatagca tcacaaattt cacaaataaa gcattttttt cactgcattc   6540
tagttgtggt ttgtccaaac tcatcaatgt atcttatcat gtctgtatac cgtcgacctc   6600
tagctagagc ttggcgtaat catggtcata gctgtttcct gtgtgaaatt gttatccgct   6660
cacaattcca cacaacatac gagccggaag cataaagtgt aaagcctggg gtgcctaatg   6720
agtgagctaa ctcacattaa ttgcgttgcg ctcactgccc gctttccagt cgggaaacct   6780
gtcgtgccag ctgcattaat gaatcggcca acgcgcgggg agaggcggtt tgcgtattgg   6840
gcgctcttcc gcttcctcgc tcactgactc gctgcgctcg gtcgttcggc tgcggcgagc   6900
ggtatcagct cactcaaagg cggtaatacg gttatccaca gaatcagggg ataacgcagg   6960
aaagaacatg tgagcaaaag gccagcaaaa ggccaggaac cgtaaaaagg ccgcgttgct   7020
ggcgtttttc cataggctcc gcccccctga cgagcatcac aaaaatcgac gctcaagtca   7080
gaggtggcga aacccgacag gactataaag ataccaggcg tttccccctg gaagctccct   7140
cgtgcgctct cctgttccga ccctgccgct taccggatac ctgtccgcct ttctcccttc   7200
gggaagcgtg gcgctttctc atagctcacg ctgtaggtat ctcagttcgg tgtaggtcgt   7260
tcgctccaag ctgggctgtg tgcacgaacc ccccgttcag cccgaccgct gcgccttatc   7320
cggtaactat cgtcttgagt ccaacccggt aagacacgac ttatcgccac tggcagcagc   7380
cactggtaac aggattagca gagcgaggta tgtaggcggt gctacagagt tcttgaagtg   7440
gtggcctaac tacggctaca ctagaagaac agtatttggt atctgcgctc tgctgaagcc   7500
agttaccttc ggaaaaagag ttggtagctc ttgatccggc aaacaaacca ccgctggtag   7560
cggttttttt gtttgcaagc agcagattac gcgcagaaaa aaaggatctc aagaagatcc   7620
tttgatcttt tctacggggt ctgacgctca gtggaacgaa aactcacgtt aagggatttt   7680
ggtcatgaga ttatcaaaaa ggatcttcac ctagatcctt ttaaattaaa aatgaagttt   7740
taaatcaatc taaagtatat atgagtaaac ttggtctgac agttaccaat gcttaatcag   7800
tgaggcacct atctcagcga tctgtctatt tcgttcatcc atagttgcct gactccccgt   7860
cgtgtagata actacgatac gggagggctt accatctggc cccagtgctg caatgatacc   7920
gcgagaccca cgctcaccgg ctccagattt atcagcaata aaccagccag ccggaagggc   7980
cgagcgcaga agtggtcctg caactttatc cgcctccatc cagtctatta attgttgccg   8040
ggaagctaga gtaagtagtt cgccagttaa tagtttgcgc aacgttgttg ccattgctac   8100
aggcatcgtg gtgtcacgct cgtcgtttgg tatggcttca ttcagctccg gttcccaacg   8160
atcaaggcga gttacatgat cccccatgtt gtgcaaaaaa gcggttagct ccttcggtcc   8220
tccgatcgtt gtcagaagta agttggccgc agtgttatca ctcatggtta tggcagcact   8280
gcataattct cttactgtca tgccatccgt aagatgcttt tctgtgactg gtgagtactc   8340
```

```
aaccaagtca ttctgagaat agtgtatgcg gcgaccgagt tgctcttgcc cggcgtcaat   8400

acgggataat accgcgccac atagcagaac tttaaaagtg ctcatcattg gaaaacgttc   8460

ttcggggcga aaactctcaa ggatcttacc gctgttgaga tccagttcga tgtaacccac   8520

tcgtgcaccc aactgatctt cagcatcttt tactttcacc agcgtttctg ggtgagcaaa   8580

aacaggaagg caaaatgccg caaaaaaggg aataagggcg acacggaaat gttgaatact   8640

catactcttc ctttttcaat attattgaag catttatcag ggttattgtc tcatgagcgg   8700

atacatattt gaatgtattt agaaaaataa acaaataggg gttccgcgca catttccccg   8760

aaaagtgcca cctgacg                                                  8777
```

<210> SEQ ID NO 55
<211> LENGTH: 47
<212> TYPE: DNA
<213> ORGANISM: Artificial sequence
<220> FEATURE:
<223> OTHER INFORMATION: Oligonucleotide sy3H-C

<400> SEQUENCE: 55

```
gcccttggtg ctagcgctgg agacggtcac ggtggtgccc tggcccc                   47
```

<210> SEQ ID NO 56
<211> LENGTH: 47
<212> TYPE: DNA
<213> ORGANISM: Artificial sequence
<220> FEATURE:
<223> OTHER INFORMATION: Oligonucleotide 5H-C

<400> SEQUENCE: 56

```
acctgtcttg aattctccat ggcccaggtg cagctggtgg agtctgg                   47
```

<210> SEQ ID NO 57
<211> LENGTH: 43
<212> TYPE: DNA
<213> ORGANISM: Artificial sequence
<220> FEATURE:
<223> OTHER INFORMATION: Oligonucleotide sy3L-Amod

<400> SEQUENCE: 57

```
ccagcacggt aagcttcagc acggtcacct tggtgccagt tcc                       43
```

<210> SEQ ID NO 58
<211> LENGTH: 8792
<212> TYPE: DNA
<213> ORGANISM: Artificial sequence
<220> FEATURE:
<223> OTHER INFORMATION: Vector pIg-C910-Clambda
<220> FEATURE:
<221> NAME/KEY: misc_feature
<222> LOCATION: (1330)..(3869)
<223> OTHER INFORMATION: Stuffer

<400> SEQUENCE: 58

```
tcgacggatc gggagatctc ccgatcccct atggtgcact ctcagtacaa tctgctctga     60

tgccgcatag ttaagccagt atctgctccc tgcttgtgtg ttggaggtcg ctgagtagtg    120

cgcgagcaaa atttaagcta caacaaggca aggcttgacc gacaattgtt aattaacatg    180

aagaatctgc ttagggttag gcgttttgcg ctgcttcgct aggtggtcaa tattggccat    240

tagccatatt attcattggt tatatagcat aaatcaatat tggctattgg ccattgcata    300

cgttgtatcc atatcataat atgtacattt atattggctc atgtccaaca ttaccgccat    360
```

```
gttgacattg attattgact agttattaat agtaatcaat tacggggtca ttagttcata    420
gcccatatat ggagttccgc gttacataac ttacggtaaa tggcccgcct ggctgaccgc    480
ccaacgaccc ccgcccattg acgtcaataa tgacgtatgt tcccatagta acgccaatag    540
ggactttcca ttgacgtcaa tgggtggagt atttacggta aactgcccac ttggcagtac    600
atcaagtgta tcatatgcca agtacgcccc ctattgacgt caatgacggt aaatggcccg    660
cctggcatta tgcccagtac atgaccttat gggactttcc tacttggcag tacatctacg    720
tattagtcat cgctattacc atggtgatgc ggttttggca gtacatcaat gggcgtggat    780
agcggtttga ctcacgggga tttccaagtc tccaccccat tgacgtcaat gggagtttgt    840
tttggcacca aaatcaacgg gactttccaa aatgtcgtaa caactccgcc ccattgacgc    900
aaatgggcgg taggcgtgta cggtgggagg tctatataag cagagctcgt ttagtgaacc    960
gtcagatcgc ctggagacgc catccacgct gttttgacct ccatagaaga caccgggacc   1020
gatccagcct ccgcggccgg gaacggtgca ttggaatcga tgactctctt aggtagcctt   1080
gcagaagttg gtcgtgaggc actgggcagg taagtatcaa ggttacaaga caggtttaag   1140
gagatcaata gaaactgggc ttgtcgagac agagaagact cttgcgtttc tgataggcac   1200
ctattggtct tactgacatc cactttgcct ttctctccac aggtgtccac tcccagttca   1260
attacagctc gccaccatgc ggttctccgc tcagctgctg ggccttctgg tgctgtggat   1320
tcccggcgtc tcgagatcta tcgatgcatg ccatggtacc aagcttgcca ccatgagcag   1380
cagctcttgg ctgctgctga gcctggtggc cgtgacagcc gcccagagca ccatcgagga   1440
gcaggccaag accttcctgg acaagttcaa ccacgaggcc gaggacctgt tctaccagag   1500
cagcctggcc agctggaact acaacaccaa catcaccgag gagaacgtgc agaacatgaa   1560
caacgccggc gacaagtgga gcgccttcct gaaggagcag agcacactgg cccagatgta   1620
ccccctgcag gagatccaga acctgaccgt gaagctgcag ctgcaggccc tgcagcagaa   1680
cggcagcagc gtgctgagcg aggacaagag caagcggctg aacaccatcc tgaacaccat   1740
gtccaccatc tacagcaccg gcaaagtgtg caaccccgac aacccccagg agtgcctgct   1800
gctggagccc ggcctgaacg agatcatggc caacagcctg gactacaacg agcggctgtg   1860
ggcctgggag agctggcgga gcgaagtggg caagcagctg cggcccctgt acgaggagta   1920
cgtggtgctg aagaacgaga tggccagggc caaccactac gaggactacg gcgactactg   1980
gagaggcgac tacgaagtga acggcgtgga cggctacgac tacagcagag gccagctgat   2040
cgaggacgtg gagcacacct tcgaggagat caagcctctg tacgagcacc tgcacgccta   2100
cgtgcgggcc aagctgatga acgcctaccc cagctacatc agccccatcg gctgcctgcc   2160
cgcccacctg ctgggcgaca tgtggggccg gttctggacc aacctgtaca gcctgaccgt   2220
gcccttcggc cagaagccca acatcgacgt gaccgacgcc atggtggacc aggcctggga   2280
cgcccagcgg atcttcaagg aggccgagaa gttcttcgtg agcgtgggcc tgcccaacat   2340
gacccagggc ttttgggaga acagcatgct gaccgacccc ggcaatgtgc agaaggccgt   2400
gtgccacccc accgcctggg acctgggcaa gggcgacttc cggatcctga tgtgcaccaa   2460
agtgaccatg gacgacttcc tgaccgccca ccacgagatg ggccacatcc agtacgacat   2520
ggcctacgcc gcccagccct tcctgctgcg gaacggcgcc aacgagggct ttcacgaggc   2580
cgtgggcgag atcatgagcc tgagcgccgc cacccccaag cacctgaaga gcatcggcct   2640
gctgagcccc gacttccagg aggacaacga gaccgagatc aacttcctgc tgaagcaggc   2700
cctgaccatc gtgggcaccc tgcccttcac ctacatgctg gagaagtggc ggtggatggt   2760
```

```
gtttaagggc gagatcccca aggaccagtg gatgaagaag tggtgggaga tgaagcggga   2820
gatcgtgggc gtggtggagc ccgtgcccca cgacgagacc tactgcgacc ccgccagcct   2880
gttccacgtg agcaacgact actccttcat ccggtactac acccggaccc tgtaccagtt   2940
ccagttccag gaggccctgt gccaggccgc caagcacgag ggcccccctgc acaagtgcga   3000
catcagcaac agcaccgagg ccggacagaa actgttcaac atgctgcggc tgggcaagag   3060
cgagccctgg accctggccc tggagaatgt ggtgggcgcc aagaacatga atgtgcgccc   3120
cctgctgaac tacttcgagc ccctgttcac ctggctgaag gaccagaaca agaacagctt   3180
cgtgggctgg agcaccgact ggagccccta cgccgaccag agcatcaaag tgcggatcag   3240
cctgaagagc gccctgggcg acaaggccta cgagtggaac gacaacgaga tgtacctgtt   3300
ccggagcagc gtggcctatg ccatgcggca gtacttcctg aaagtgaaga accagatgat   3360
cctgttcggc gaggaggacg tgagagtggc caacctgaag ccccggatca gcttcaactt   3420
cttcgtgacc gcccccaaga acgtgagcga catcatcccc cggaccgaag tggagaaggc   3480
catccggatg agccggagcc ggatcaacga cgccttccgg ctgaacgaca actccctgga   3540
gttcctgggc atccagccca ccctgggccc tcccaaccag ccccccgtga gcatctggct   3600
gatcgtgttt ggcgtggtga tgggcgtgat cgtggtggga atcgtgatcc tgatcttcac   3660
cggcatccgg gaccggaaga agaagaacaa ggcccggagc ggcgagaacc cctacgccag   3720
catcgatatc agcaagggcg agaacaaccc cggcttccag aacaccgacg acgtgcagac   3780
cagcttctga taatctagaa cgagctcgaa ttcgaagctt ctgcagacgc gtcgacgtca   3840
tatggatccg atatcgccgt ggcggccgca ggccagccca aggccgctcc cagcgtgacc   3900
ctgttccccc cctcctccga ggagctgcag gccaacaagg ccaccctggt gtgcctcatc   3960
agcgacttct accctggcgc cgtgaccgtg gcctggaagg ccgacagcag ccccgtgaag   4020
gccggcgtgg agaccaccac ccccagcaag cagagcaaca acaagtacgc cgccagcagc   4080
tacctgagcc tcacccccga gcagtggaag agccaccgga gctacagctg ccaggtgacc   4140
cacgagggca gcaccgtgga gaagaccgtg gcccccaccg agtgcagcta atagacttaa   4200
gtttaaaccg ctgatcagcc tcgactgtgc cttctagttg ccagccatct gttgtttgcc   4260
cctcccccgt gccttccttg accctggaag gtgccactcc cactgtcctt tcctaataaa   4320
atgaggaaat tgcatcgcat tgtctgagta ggtgtcattc tattctgggg ggtggggtgg   4380
ggcaggacag caagggggag gattgggaag acaatagcag gcatgctggg gatgcggtgg   4440
gctctatggc ttctgaggcg gaaagaacca gctggggctc tagggggtat ccccacgcgc   4500
cctgtagcgg cgcattaagc gcggcgggtg tggtggttac gcgcagcgtg accgctacac   4560
ttgccagcgc cctagcgccc gctcctttcg ctttcttccc ttcctttctc gccacgttcg   4620
ccggctttcc ccgtcaagct ctaaatcggg ggctcccttt agggttccga tttagtgctt   4680
tacggcacct cgaccccaaa aaacttgatt agggtgatgg ttcacgtagt gggccatcgc   4740
cctgatagac ggtttttcgc cctttgacgt tggagtccac gttctttaat agtggactct   4800
tgttccaaac tggaacaaca ctcaacccta tctcggtcta ttcttttgat ttataaggga   4860
ttttggccat ttcggcctat tggttaaaaa atgagctgat ttaacaaaaa tttaacgcga   4920
attaattctg tggaatgtgt gtcagttagg gtgtggaaag tccccaggct ccccagcagg   4980
cagaagtatg caaagcatgc atctcaatta gtcagcaacc aggtgtggaa agtccccagg   5040
ctccccagca ggcagaagta tgcaaagcat gcatctcaat tagtcagcaa ccatagtccc   5100
```

```
gcccctaact ccgcccatcc cgcccctaac tccgcccagt tccgcccatt ctccgcccca   5160
tggctgacta attttttta tttatgcaga ggccgaggcc gcctctgcct ctgagctatt   5220
ccagaagtag tgaggaggct tttttggagg cctaggcttt tgcaaaaagc tcccgggagc   5280
ttgtatatcc attttcggat ctgatcagca cgtgatgaaa aagcctgaac tcaccgcgac   5340
gtctgtcgag aagtttctga tcgaaaagtt cgacagcgtc tccgacctga tgcagctctc   5400
ggagggcgaa gaatctcgtg ctttcagctt cgatgtagga gggcgtggat atgtcctgcg   5460
ggtaaatagc tgcgccgatg gtttctacaa agatcgttat gtttatcggc actttgcatc   5520
ggccgcgctc ccgattccgg aagtgcttga cattggggaa ttcagcgaga gcctgaccta   5580
ttgcatctcc cgccgtgcac agggtgtcac gttgcaagac ctgcctgaaa ccgaactgcc   5640
cgctgttctg cagccggtcg cggaggccat ggatgcgatc gctgcggccg atcttagcca   5700
gacgagcggg ttcggcccat tcggaccgca aggaatcggt caatacacta catggcgtga   5760
tttcatatgc gcgattgctg atccccatgt gtatcactgg caaactgtga tggacgacac   5820
cgtcagtgcg tccgtcgcgc aggctctcga tgagctgatg ctttgggccg aggactgccc   5880
cgaagtccgg cacctcgtgc acgcggattt cggctccaac aatgtcctga cggacaatgg   5940
ccgcataaca gcggtcattg actggagcga ggcgatgttc ggggattccc aatacgaggt   6000
cgccaacatc ttcttctgga ggccgtggtt ggcttgtatg gagcagcaga cgcgctactt   6060
cgagcggagg catccggagc ttgcaggatc gccgcggctc cgggcgtata tgctccgcat   6120
tggtcttgac caactctatc agagcttggt tgacggcaat ttcgatgatg cagcttgggc   6180
gcagggtcga tgcgacgcaa tcgtccgatc cggagccggg actgtcgggc gtacacaaat   6240
cgcccgcaga agcgcggccg tctggaccga tggctgtgta gaagtactcg ccgatagtgg   6300
aaaccgacgc cccagcactc gtccgagggc aaaggaatag cacgtgctac gagatttcga   6360
ttccaccgcc gccttctatg aaaggttggg cttcggaatc gttttccggg acgccggctg   6420
gatgatcctc cagcgcgggg atctcatgct ggagttcttc gcccacccca acttgtttat   6480
tgcagcttat aatggttaca aataaagcaa tagcatcaca aatttcacaa ataaagcatt   6540
tttttcactg cattctagtt gtggtttgtc caaactcatc aatgtatctt atcatgtctg   6600
tataccgtcg acctctagct agagcttggc gtaatcatgg tcatagctgt ttcctgtgtg   6660
aaattgttat ccgctcacaa ttccacacaa catacgagcc ggaagcataa agtgtaaagc   6720
ctggggtgcc taatgagtga gctaactcac attaattgcg ttgcgctcac tgcccgcttt   6780
ccagtcggga aacctgtcgt gccagctgca ttaatgaatc ggccaacgcg cggggagagg   6840
cggtttgcgt attgggcgct cttccgcttc ctcgctcact gactcgctgc gctcggtcgt   6900
tcggctgcgg cgagcggtat cagctcactc aaaggcggta atacggttat ccacagaatc   6960
aggggataac gcaggaaaga acatgtgagc aaaaggccag caaaaggcca ggaaccgtaa   7020
aaaggccgcg ttgctggcgt ttttccatag gctccgcccc cctgacgagc atcacaaaaa   7080
tcgacgctca agtcagaggt ggcgaaaccc gacaggacta taaagatacc aggcgtttcc   7140
ccctggaagc tccctcgtgc gctctcctgt tccgaccctg ccgcttaccg gatacctgtc   7200
cgcctttctc ccttcgggaa gcgtggcgct ttctcatagc tcacgctgta ggtatctcag   7260
ttcggtgtag gtcgttcgct ccaagctggg ctgtgtgcac gaaccccccg ttcagcccga   7320
ccgctgcgcc ttatccggta actatcgtct tgagtccaac ccggtaagac acgacttatc   7380
gccactggca gcagccactg gtaacaggat tagcagagcg aggtatgtag gcggtgctac   7440
agagttcttg aagtggtggc ctaactacgg ctacactaga agaacagtat ttggtatctg   7500
```

```
cgctctgctg aagccagtta ccttcggaaa aagagttggt agctcttgat ccggcaaaca   7560

aaccaccgct ggtagcggtt tttttgtttg caagcagcag attacgcgca gaaaaaaagg   7620

atctcaagaa gatcctttga tcttttctac ggggtctgac gctcagtgga acgaaaactc   7680

acgttaaggg attttggtca tgagattatc aaaaaggatc ttcacctaga tccttttaaa   7740

ttaaaaatga agttttaaat caatctaaag tatatatgag taaacttggt ctgacagtta   7800

ccaatgctta atcagtgagg cacctatctc agcgatctgt ctatttcgtt catccatagt   7860

tgcctgactc cccgtcgtgt agataactac gatacgggag ggcttaccat ctggccccag   7920

tgctgcaatg ataccgcgag acccacgctc accggctcca gatttatcag caataaacca   7980

gccagccgga agggccgagc gcagaagtgg tcctgcaact ttatccgcct ccatccagtc   8040

tattaattgt tgccgggaag ctagagtaag tagttcgcca gttaatagtt tgcgcaacgt   8100

tgttgccatt gctacaggca tcgtggtgtc acgctcgtcg tttggtatgg cttcattcag   8160

ctccggttcc caacgatcaa ggcgagttac atgatccccc atgttgtgca aaaaagcggt   8220

tagctccttc ggtcctccga tcgttgtcag aagtaagttg gccgcagtgt tatcactcat   8280

ggttatggca gcactgcata attctcttac tgtcatgcca tccgtaagat gcttttctgt   8340

gactggtgag tactcaacca agtcattctg agaatagtgt atgcggcgac cgagttgctc   8400

ttgcccggcg tcaatacggg ataataccgc gccacatagc agaactttaa aagtgctcat   8460

cattggaaaa cgttcttcgg ggcgaaaact ctcaaggatc ttaccgctgt tgagatccag   8520

ttcgatgtaa cccactcgtg cacccaactg atcttcagca tcttttactt tcaccagcgt   8580

ttctgggtga gcaaaaacag gaaggcaaaa tgccgcaaaa aagggaataa gggcgacacg   8640

gaaatgttga atactcatac tcttcctttt tcaatattat tgaagcattt atcagggtta   8700

ttgtctcatg agcggataca tatttgaatg tatttagaaa aataaacaaa taggggttcc   8760

gcgcacattt ccccgaaaag tgccacctga cg                                  8792
```

```
<210> SEQ ID NO 59
<211> LENGTH: 1344
<212> TYPE: DNA
<213> ORGANISM: Artificial sequence
<220> FEATURE:
<223> OTHER INFORMATION: Heavy chain CR4261
<220> FEATURE:
<221> NAME/KEY: CDS
<222> LOCATION: (1)..(1344)
<223> OTHER INFORMATION: Heavy chain CR4261

<400> SEQUENCE: 59

cag gtg cag ctg gtg cag tct ggg gtt gag gtg aag agg cct ggg gcc       48
Gln Val Gln Leu Val Gln Ser Gly Val Glu Val Lys Arg Pro Gly Ala
1               5                   10                  15

tca gtg aag gtc tcc tgc aag gct tct gga tac acc ttc acc agt tat       96
Ser Val Lys Val Ser Cys Lys Ala Ser Gly Tyr Thr Phe Thr Ser Tyr
            20                  25                  30

acc tta cat tgg gtg cgc cag gcc ccc gga caa agg cct gag tgg atg      144
Thr Leu His Trp Val Arg Gln Ala Pro Gly Gln Arg Pro Glu Trp Met
        35                  40                  45

gga tgg atc cac cct gtc aat ggt gac aca aaa tat tca cag aag ttc      192
Gly Trp Ile His Pro Val Asn Gly Asp Thr Lys Tyr Ser Gln Lys Phe
    50                  55                  60

cag ggc aga gtc acc att acc agg gac aca tcc gcg agc aca gcc tac      240
Gln Gly Arg Val Thr Ile Thr Arg Asp Thr Ser Ala Ser Thr Ala Tyr
65                  70                  75                  80
```

```
atg gag ctg agc agc ctg aga tct gaa gac acg gct gtg tat tac tgt      288
Met Glu Leu Ser Ser Leu Arg Ser Glu Asp Thr Ala Val Tyr Tyr Cys
                85                  90                  95

gcg agg ggg tac gac agc tgg tct ttt gac tac tgg ggc cag ggc acc      336
Ala Arg Gly Tyr Asp Ser Trp Ser Phe Asp Tyr Trp Gly Gln Gly Thr
            100                 105                 110

ctg gtg acc gtc tcc agc gct agc acc aag ggc ccc agc gtg ttc ccc      384
Leu Val Thr Val Ser Ser Ala Ser Thr Lys Gly Pro Ser Val Phe Pro
        115                 120                 125

ctg gcc ccc agc agc aag agc acc agc ggc ggc aca gcc gcc ctg ggc      432
Leu Ala Pro Ser Ser Lys Ser Thr Ser Gly Gly Thr Ala Ala Leu Gly
    130                 135                 140

tgc ctg gtg aag gac tac ttc ccc gag ccc gtg acc gtg agc tgg aac      480
Cys Leu Val Lys Asp Tyr Phe Pro Glu Pro Val Thr Val Ser Trp Asn
145                 150                 155                 160

agc ggc gcc ttg acc agc ggc gtg cac acc ttc ccc gcc gtg ctg cag      528
Ser Gly Ala Leu Thr Ser Gly Val His Thr Phe Pro Ala Val Leu Gln
                165                 170                 175

agc agc ggc ctg tac agc ctg agc agc gtg gtg acc gtg ccc agc agc      576
Ser Ser Gly Leu Tyr Ser Leu Ser Ser Val Val Thr Val Pro Ser Ser
            180                 185                 190

agc ctg ggc acc cag acc tac atc tgc aac gtg aac cac aag ccc agc      624
Ser Leu Gly Thr Gln Thr Tyr Ile Cys Asn Val Asn His Lys Pro Ser
        195                 200                 205

aac acc aag gtg gac aaa cgc gtg gag ccc aag agc tgc gac aag acc      672
Asn Thr Lys Val Asp Lys Arg Val Glu Pro Lys Ser Cys Asp Lys Thr
    210                 215                 220

cac acc tgc ccc ccc tgc cct gcc ccc gag ctg ctg ggc gga ccc tcc      720
His Thr Cys Pro Pro Cys Pro Ala Pro Glu Leu Leu Gly Gly Pro Ser
225                 230                 235                 240

gtg ttc ctg ttc ccc ccc aag ccc aag gac acc ctc atg atc agc cgg      768
Val Phe Leu Phe Pro Pro Lys Pro Lys Asp Thr Leu Met Ile Ser Arg
                245                 250                 255

acc ccc gag gtg acc tgc gtg gtg gtg gac gtg agc cac gag gac ccc      816
Thr Pro Glu Val Thr Cys Val Val Val Asp Val Ser His Glu Asp Pro
            260                 265                 270

gag gtg aag ttc aac tgg tac gtg gac ggc gtg gag gtg cac aac gcc      864
Glu Val Lys Phe Asn Trp Tyr Val Asp Gly Val Glu Val His Asn Ala
        275                 280                 285

aag acc aag ccc cgg gag gag cag tac aac agc acc tac cgg gtg gtg      912
Lys Thr Lys Pro Arg Glu Glu Gln Tyr Asn Ser Thr Tyr Arg Val Val
    290                 295                 300

agc gtg ctc acc gtg ctg cac cag gac tgg ctg aac ggc aag gag tac      960
Ser Val Leu Thr Val Leu His Gln Asp Trp Leu Asn Gly Lys Glu Tyr
305                 310                 315                 320

aag tgc aag gtg agc aac aag gcc ctg cct gcc ccc atc gag aag acc     1008
Lys Cys Lys Val Ser Asn Lys Ala Leu Pro Ala Pro Ile Glu Lys Thr
                325                 330                 335

atc agc aag gcc aag ggc cag ccc cgg gag ccc cag gtg tac acc ctg     1056
Ile Ser Lys Ala Lys Gly Gln Pro Arg Glu Pro Gln Val Tyr Thr Leu
            340                 345                 350

ccc ccc agc cgg gag gag atg acc aag aac cag gtg tcc ctc acc tgt     1104
Pro Pro Ser Arg Glu Glu Met Thr Lys Asn Gln Val Ser Leu Thr Cys
        355                 360                 365

ctg gtg aag ggc ttc tac ccc agc gac atc gcc gtg gag tgg gag agc     1152
Leu Val Lys Gly Phe Tyr Pro Ser Asp Ile Ala Val Glu Trp Glu Ser
    370                 375                 380

aac ggc cag ccc gag aac aac tac aag acc acc ccc cct gtg ctg gac     1200
Asn Gly Gln Pro Glu Asn Asn Tyr Lys Thr Thr Pro Pro Val Leu Asp
385                 390                 395                 400
```

```
agc gac ggc agc ttc ttc ctg tac agc aag ctc acc gtg gac aag agc      1248
Ser Asp Gly Ser Phe Phe Leu Tyr Ser Lys Leu Thr Val Asp Lys Ser
                405                 410                 415

cgg tgg cag cag ggc aac gtg ttc agc tgc agc gtg atg cac gag gcc      1296
Arg Trp Gln Gln Gly Asn Val Phe Ser Cys Ser Val Met His Glu Ala
            420                 425                 430

ctg cac aac cac tac acc cag aag agc ctg agc ctg agc ccc ggc aag      1344
Leu His Asn His Tyr Thr Gln Lys Ser Leu Ser Leu Ser Pro Gly Lys
        435                 440                 445


<210> SEQ ID NO 60
<211> LENGTH: 448
<212> TYPE: PRT
<213> ORGANISM: Artificial sequence
<220> FEATURE:
<223> OTHER INFORMATION: Heavy chain CR4261

<400> SEQUENCE: 60

Gln Val Gln Leu Val Gln Ser Gly Val Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Thr Leu His Trp Val Arg Gln Ala Pro Gly Gln Arg Pro Glu Trp Met
        35                  40                  45

Gly Trp Ile His Pro Val Asn Gly Asp Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Ser Trp Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300
```

```
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 61
<211> LENGTH: 1377
<212> TYPE: DNA
<213> ORGANISM: Artificial sequence
<220> FEATURE:
<223> OTHER INFORMATION: Heavy chain CR4267
<220> FEATURE:
<221> NAME/KEY: CDS
<222> LOCATION: (1)..(1377)
<223> OTHER INFORMATION: Heavy chain CR4267

<400> SEQUENCE: 61

cag gtg cag ctg gtg cag tct ggg act gag gtg aag aag cct ggg tcc       48
Gln Val Gln Leu Val Gln Ser Gly Thr Glu Val Lys Lys Pro Gly Ser
1               5                   10                  15

tcg gtg aag gtc tcc tgc aag gct tct gga ggc acc ttc agc aac tat       96
Ser Val Lys Val Ser Cys Lys Ala Ser Gly Gly Thr Phe Ser Asn Tyr
            20                  25                  30

gct atc agc tgg gtg cga cag gcc cct gga caa ggg ctt gag tgg atg      144
Ala Ile Ser Trp Val Arg Gln Ala Pro Gly Gln Gly Leu Glu Trp Met
        35                  40                  45

gga ggt atc gtc cct aag ttt gct aca aca agc tac gca cag agg ttc      192
Gly Gly Ile Val Pro Lys Phe Ala Thr Thr Ser Tyr Ala Gln Arg Phe
    50                  55                  60

cag ggc aga gtc acg att acc gcg gac gaa tcc acg agc aca gtc tac      240
Gln Gly Arg Val Thr Ile Thr Ala Asp Glu Ser Thr Ser Thr Val Tyr
65                  70                  75                  80

atg gag ctg agc agc ctg aga tct gag gac acg gcc gtg tat ttt tgt      288
Met Glu Leu Ser Ser Leu Arg Ser Glu Asp Thr Ala Val Tyr Phe Cys
                85                  90                  95

gcg aga ttt gga gtg gtg gta gct gcc gac cgt caa gga gcc tac tac      336
Ala Arg Phe Gly Val Val Val Ala Ala Asp Arg Gln Gly Ala Tyr Tyr
            100                 105                 110

tac tac ggt atg gac gtc tgg ggc cag ggc acc acc gtg acc gtc tcc      384
Tyr Tyr Gly Met Asp Val Trp Gly Gln Gly Thr Thr Val Thr Val Ser
        115                 120                 125

agc gct agc acc aag ggc ccc agc gtg ttc ccc ctg gcc ccc agc agc      432
Ser Ala Ser Thr Lys Gly Pro Ser Val Phe Pro Leu Ala Pro Ser Ser
    130                 135                 140

aag agc acc agc ggc ggc aca gcc gcc ctg ggc tgc ctg gtg aag gac      480
```

```
Lys Ser Thr Ser Gly Gly Thr Ala Ala Leu Gly Cys Leu Val Lys Asp
145                 150                 155                 160

tac ttc ccc gag ccc gtg acc gtg agc tgg aac agc ggc gcc ttg acc      528
Tyr Phe Pro Glu Pro Val Thr Val Ser Trp Asn Ser Gly Ala Leu Thr
                165                 170                 175

agc ggc gtg cac acc ttc ccc gcc gtg ctg cag agc agc ggc ctg tac      576
Ser Gly Val His Thr Phe Pro Ala Val Leu Gln Ser Ser Gly Leu Tyr
            180                 185                 190

agc ctg agc agc gtg gtg acc gtg ccc agc agc agc ctg ggc acc cag      624
Ser Leu Ser Ser Val Val Thr Val Pro Ser Ser Ser Leu Gly Thr Gln
        195                 200                 205

acc tac atc tgc aac gtg aac cac aag ccc agc aac acc aag gtg gac      672
Thr Tyr Ile Cys Asn Val Asn His Lys Pro Ser Asn Thr Lys Val Asp
    210                 215                 220

aaa cgc gtg gag ccc aag agc tgc gac aag acc cac acc tgc ccc ccc      720
Lys Arg Val Glu Pro Lys Ser Cys Asp Lys Thr His Thr Cys Pro Pro
225                 230                 235                 240

tgc cct gcc ccc gag ctg ctg ggc gga ccc tcc gtg ttc ctg ttc ccc      768
Cys Pro Ala Pro Glu Leu Leu Gly Gly Pro Ser Val Phe Leu Phe Pro
                245                 250                 255

ccc aag ccc aag gac acc ctc atg atc agc cgg acc ccc gag gtg acc      816
Pro Lys Pro Lys Asp Thr Leu Met Ile Ser Arg Thr Pro Glu Val Thr
            260                 265                 270

tgc gtg gtg gtg gac gtg agc cac gag gac ccc gag gtg aag ttc aac      864
Cys Val Val Val Asp Val Ser His Glu Asp Pro Glu Val Lys Phe Asn
        275                 280                 285

tgg tac gtg gac ggc gtg gag gtg cac aac gcc aag acc aag ccc cgg      912
Trp Tyr Val Asp Gly Val Glu Val His Asn Ala Lys Thr Lys Pro Arg
    290                 295                 300

gag gag cag tac aac agc acc tac cgg gtg gtg agc gtg ctc acc gtg      960
Glu Glu Gln Tyr Asn Ser Thr Tyr Arg Val Val Ser Val Leu Thr Val
305                 310                 315                 320

ctg cac cag gac tgg ctg aac ggc aag gag tac aag tgc aag gtg agc     1008
Leu His Gln Asp Trp Leu Asn Gly Lys Glu Tyr Lys Cys Lys Val Ser
                325                 330                 335

aac aag gcc ctg cct gcc ccc atc gag aag acc atc agc aag gcc aag     1056
Asn Lys Ala Leu Pro Ala Pro Ile Glu Lys Thr Ile Ser Lys Ala Lys
            340                 345                 350

ggc cag ccc cgg gag ccc cag gtg tac acc ctg ccc ccc agc cgg gag     1104
Gly Gln Pro Arg Glu Pro Gln Val Tyr Thr Leu Pro Pro Ser Arg Glu
        355                 360                 365

gag atg acc aag aac cag gtg tcc ctc acc tgt ctg gtg aag ggc ttc     1152
Glu Met Thr Lys Asn Gln Val Ser Leu Thr Cys Leu Val Lys Gly Phe
    370                 375                 380

tac ccc agc gac atc gcc gtg gag tgg gag agc aac ggc cag ccc gag     1200
Tyr Pro Ser Asp Ile Ala Val Glu Trp Glu Ser Asn Gly Gln Pro Glu
385                 390                 395                 400

aac aac tac aag acc acc ccc cct gtg ctg gac agc gac ggc agc ttc     1248
Asn Asn Tyr Lys Thr Thr Pro Pro Val Leu Asp Ser Asp Gly Ser Phe
                405                 410                 415

ttc ctg tac agc aag ctc acc gtg gac aag agc cgg tgg cag cag ggc     1296
Phe Leu Tyr Ser Lys Leu Thr Val Asp Lys Ser Arg Trp Gln Gln Gly
            420                 425                 430

aac gtg ttc agc tgc agc gtg atg cac gag gcc ctg cac aac cac tac     1344
Asn Val Phe Ser Cys Ser Val Met His Glu Ala Leu His Asn His Tyr
        435                 440                 445

acc cag aag agc ctg agc ctg agc ccc ggc aag                         1377
Thr Gln Lys Ser Leu Ser Leu Ser Pro Gly Lys
    450                 455
```

<210> SEQ ID NO 62
<211> LENGTH: 459
<212> TYPE: PRT
<213> ORGANISM: Artificial sequence
<220> FEATURE:
<223> OTHER INFORMATION: Heavy chain CR4267

<400> SEQUENCE: 62

```
Gln Val Gln Leu Val Gln Ser Gly Thr Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Val Pro Lys Phe Ala Thr Thr Ser Tyr Ala Gln Arg Phe
    50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Val Tyr Phe Cys
                85                  90                  95

Ala Arg Phe Gly Val Val Val Ala Ala Asp Arg Gln Gly Ala Tyr Tyr
            100                 105                 110

Tyr Tyr Gly Met Asp Val Trp Gly Gln Gly Thr Thr Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Arg Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Glu
        355                 360                 365
```

```
Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455


<210> SEQ ID NO 63
<211> LENGTH: 1344
<212> TYPE: DNA
<213> ORGANISM: Artificial sequence
<220> FEATURE:
<223> OTHER INFORMATION: Heavy chain CR4328
<220> FEATURE:
<221> NAME/KEY: CDS
<222> LOCATION: (1)..(1344)
<223> OTHER INFORMATION: Heavy chain CR4328

<400> SEQUENCE: 63

cag gtg cag ctg gtg cag tct ggg gct gaa atg aag aag cct ggg gcc       48
Gln Val Gln Leu Val Gln Ser Gly Ala Glu Met Lys Lys Pro Gly Ala
1               5                   10                  15

tca gtg aag gtc tcc tgc aag gct tct gga tac acc ttc act agc tat       96
Ser Val Lys Val Ser Cys Lys Ala Ser Gly Tyr Thr Phe Thr Ser Tyr
            20                  25                  30

gct atg cat tgg gtg cgc cag gcc ccc gga caa agg ctt gag tgg atg      144
Ala Met His Trp Val Arg Gln Ala Pro Gly Gln Arg Leu Glu Trp Met
        35                  40                  45

gga tgg atc aac gct ggc aat ggt aac aca aaa tat tca cag aag ttc      192
Gly Trp Ile Asn Ala Gly Asn Gly Asn Thr Lys Tyr Ser Gln Lys Phe
    50                  55                  60

cag ggc aga gtc acc att acc agg gac aca tcc gcg agc aca gcc tac      240
Gln Gly Arg Val Thr Ile Thr Arg Asp Thr Ser Ala Ser Thr Ala Tyr
65                  70                  75                  80

atg gag ctg agc agc ctg aga tct gaa gac acg gct gtg tat tac tgt      288
Met Glu Leu Ser Ser Leu Arg Ser Glu Asp Thr Ala Val Tyr Tyr Cys
                85                  90                  95

gcg agg ggg tac gac agc tgg tct ttt gac tac tgg ggc cag ggc acc      336
Ala Arg Gly Tyr Asp Ser Trp Ser Phe Asp Tyr Trp Gly Gln Gly Thr
            100                 105                 110

ctg gtg acc gtc tcc agc gct agc acc aag ggc ccc agc gtg ttc ccc      384
Leu Val Thr Val Ser Ser Ala Ser Thr Lys Gly Pro Ser Val Phe Pro
        115                 120                 125

ctg gcc ccc agc agc aag agc acc agc ggc ggc aca gcc gcc ctg ggc      432
Leu Ala Pro Ser Ser Lys Ser Thr Ser Gly Gly Thr Ala Ala Leu Gly
    130                 135                 140

tgc ctg gtg aag gac tac ttc ccc gag ccc gtg acc gtg agc tgg aac      480
Cys Leu Val Lys Asp Tyr Phe Pro Glu Pro Val Thr Val Ser Trp Asn
145                 150                 155                 160

agc ggc gcc ttg acc agc ggc gtg cac acc ttc ccc gcc gtg ctg cag      528
Ser Gly Ala Leu Thr Ser Gly Val His Thr Phe Pro Ala Val Leu Gln
                165                 170                 175

agc agc ggc ctg tac agc ctg agc agc gtg gtg acc gtg ccc agc agc      576
Ser Ser Gly Leu Tyr Ser Leu Ser Ser Val Val Thr Val Pro Ser Ser
            180                 185                 190
```

```
agc ctg ggc acc cag acc tac atc tgc aac gtg aac cac aag ccc agc      624
Ser Leu Gly Thr Gln Thr Tyr Ile Cys Asn Val Asn His Lys Pro Ser
        195                 200                 205

aac acc aag gtg gac aaa cgc gtg gag ccc aag agc tgc gac aag acc      672
Asn Thr Lys Val Asp Lys Arg Val Glu Pro Lys Ser Cys Asp Lys Thr
    210                 215                 220

cac acc tgc ccc ccc tgc cct gcc ccc gag ctg ctg ggc gga ccc tcc      720
His Thr Cys Pro Pro Cys Pro Ala Pro Glu Leu Leu Gly Gly Pro Ser
225                 230                 235                 240

gtg ttc ctg ttc ccc ccc aag ccc aag gac acc ctc atg atc agc cgg      768
Val Phe Leu Phe Pro Pro Lys Pro Lys Asp Thr Leu Met Ile Ser Arg
                245                 250                 255

acc ccc gag gtg acc tgc gtg gtg gtg gac gtg agc cac gag gac ccc      816
Thr Pro Glu Val Thr Cys Val Val Val Asp Val Ser His Glu Asp Pro
            260                 265                 270

gag gtg aag ttc aac tgg tac gtg gac ggc gtg gag gtg cac aac gcc      864
Glu Val Lys Phe Asn Trp Tyr Val Asp Gly Val Glu Val His Asn Ala
        275                 280                 285

aag acc aag ccc cgg gag gag cag tac aac agc acc tac cgg gtg gtg      912
Lys Thr Lys Pro Arg Glu Glu Gln Tyr Asn Ser Thr Tyr Arg Val Val
    290                 295                 300

agc gtg ctc acc gtg ctg cac cag gac tgg ctg aac ggc aag gag tac      960
Ser Val Leu Thr Val Leu His Gln Asp Trp Leu Asn Gly Lys Glu Tyr
305                 310                 315                 320

aag tgc aag gtg agc aac aag gcc ctg cct gcc ccc atc gag aag acc     1008
Lys Cys Lys Val Ser Asn Lys Ala Leu Pro Ala Pro Ile Glu Lys Thr
                325                 330                 335

atc agc aag gcc aag ggc cag ccc cgg gag ccc cag gtg tac acc ctg     1056
Ile Ser Lys Ala Lys Gly Gln Pro Arg Glu Pro Gln Val Tyr Thr Leu
            340                 345                 350

ccc ccc agc cgg gag gag atg acc aag aac cag gtg tcc ctc acc tgt     1104
Pro Pro Ser Arg Glu Glu Met Thr Lys Asn Gln Val Ser Leu Thr Cys
        355                 360                 365

ctg gtg aag ggc ttc tac ccc agc gac atc gcc gtg gag tgg gag agc     1152
Leu Val Lys Gly Phe Tyr Pro Ser Asp Ile Ala Val Glu Trp Glu Ser
    370                 375                 380

aac ggc cag ccc gag aac aac tac aag acc acc ccc cct gtg ctg gac     1200
Asn Gly Gln Pro Glu Asn Asn Tyr Lys Thr Thr Pro Pro Val Leu Asp
385                 390                 395                 400

agc gac ggc agc ttc ttc ctg tac agc aag ctc acc gtg gac aag agc     1248
Ser Asp Gly Ser Phe Phe Leu Tyr Ser Lys Leu Thr Val Asp Lys Ser
                405                 410                 415

cgg tgg cag cag ggc aac gtg ttc agc tgc agc gtg atg cac gag gcc     1296
Arg Trp Gln Gln Gly Asn Val Phe Ser Cys Ser Val Met His Glu Ala
            420                 425                 430

ctg cac aac cac tac acc cag aag agc ctg agc ctg agc ccc ggc aag     1344
Leu His Asn His Tyr Thr Gln Lys Ser Leu Ser Leu Ser Pro Gly Lys
        435                 440                 445


<210> SEQ ID NO 64
<211> LENGTH: 448
<212> TYPE: PRT
<213> ORGANISM: Artificial sequence
<220> FEATURE:
<223> OTHER INFORMATION: Heavy chain CR4328

<400> SEQUENCE: 64

Gln Val Gln Leu Val Gln Ser Gly Ala Glu Met Lys Lys Pro Gly Ala
1               5                   10                  15

Ser Val Lys Val Ser Cys Lys Ala Ser Gly Tyr Thr Phe Thr Ser Tyr
```

```
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asp Ser Trp Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

```
<210> SEQ ID NO 65
<211> LENGTH: 1347
<212> TYPE: DNA
<213> ORGANISM: Artificial sequence
<220> FEATURE:
<223> OTHER INFORMATION: Heavy chain CR4335
<220> FEATURE:
<221> NAME/KEY: CDS
<222> LOCATION: (1)..(1347)
<223> OTHER INFORMATION: Heavy chain CR4335

<400> SEQUENCE: 65

cag gtg cag ctg gtg gag tct ggg gga ggc gtg gtc cag cct ggc agg       48
Gln Val Gln Leu Val Glu Ser Gly Gly Gly Val Val Gln Pro Gly Arg
1               5                   10                  15

tcc ctg aga ctc tcc tgt gta gcc tct gga ttc acc ttc agt aag gac       96
Ser Leu Arg Leu Ser Cys Val Ala Ser Gly Phe Thr Phe Ser Lys Asp
            20                  25                  30

gct atg cac tgg gtc cgc cag gct cca ggc aag ggg cta gag tgg gtg      144
Ala Met His Trp Val Arg Gln Ala Pro Gly Lys Gly Leu Glu Trp Val
        35                  40                  45

gca gtt ata tca tat gat gga agt gat aaa cac tac gca gac tcc gtg      192
Ala Val Ile Ser Tyr Asp Gly Ser Asp Lys His Tyr Ala Asp Ser Val
    50                  55                  60

aag ggc cga gtc acc atc tcc aga gac aat tcc agg aaa acg ctg cat      240
Lys Gly Arg Val Thr Ile Ser Arg Asp Asn Ser Arg Lys Thr Leu His
65                  70                  75                  80

ctg cga atg gac agc ctg aga gct gag gac acg gct cta tat tac tgt      288
Leu Arg Met Asp Ser Leu Arg Ala Glu Asp Thr Ala Leu Tyr Tyr Cys
                85                  90                  95

gcg aga gga tac aac tct ggt cat tac ttt gac tac tgg ggc cag ggc      336
Ala Arg Gly Tyr Asn Ser Gly His Tyr Phe Asp Tyr Trp Gly Gln Gly
            100                 105                 110

acc ctg gtg acc gtc tcc agc gct agc acc aag ggc ccc agc gtg ttc      384
Thr Leu Val Thr Val Ser Ser Ala Ser Thr Lys Gly Pro Ser Val Phe
        115                 120                 125

ccc ctg gcc ccc agc agc aag agc acc agc ggc ggc aca gcc gcc ctg      432
Pro Leu Ala Pro Ser Ser Lys Ser Thr Ser Gly Gly Thr Ala Ala Leu
    130                 135                 140

ggc tgc ctg gtg aag gac tac ttc ccc gag ccc gtg acc gtg agc tgg      480
Gly Cys Leu Val Lys Asp Tyr Phe Pro Glu Pro Val Thr Val Ser Trp
145                 150                 155                 160

aac agc ggc gcc ttg acc agc ggc gtg cac acc ttc ccc gcc gtg ctg      528
Asn Ser Gly Ala Leu Thr Ser Gly Val His Thr Phe Pro Ala Val Leu
                165                 170                 175

cag agc agc ggc ctg tac agc ctg agc agc gtg gtg acc gtg ccc agc      576
Gln Ser Ser Gly Leu Tyr Ser Leu Ser Ser Val Val Thr Val Pro Ser
            180                 185                 190

agc agc ctg ggc acc cag acc tac atc tgc aac gtg aac cac aag ccc      624
Ser Ser Leu Gly Thr Gln Thr Tyr Ile Cys Asn Val Asn His Lys Pro
        195                 200                 205

agc aac acc aag gtg gac aaa cgc gtg gag ccc aag agc tgc gac aag      672
Ser Asn Thr Lys Val Asp Lys Arg Val Glu Pro Lys Ser Cys Asp Lys
    210                 215                 220

acc cac acc tgc ccc ccc tgc cct gcc ccc gag ctg ctg ggc gga ccc      720
Thr His Thr Cys Pro Pro Cys Pro Ala Pro Glu Leu Leu Gly Gly Pro
225                 230                 235                 240

tcc gtg ttc ctg ttc ccc ccc aag ccc aag gac acc ctc atg atc agc      768
Ser Val Phe Leu Phe Pro Pro Lys Pro Lys Asp Thr Leu Met Ile Ser
                245                 250                 255
```

```
cgg acc ccc gag gtg acc tgc gtg gtg gtg gac gtg agc cac gag gac      816
Arg Thr Pro Glu Val Thr Cys Val Val Val Asp Val Ser His Glu Asp
            260                 265                 270

ccc gag gtg aag ttc aac tgg tac gtg gac ggc gtg gag gtg cac aac      864
Pro Glu Val Lys Phe Asn Trp Tyr Val Asp Gly Val Glu Val His Asn
        275                 280                 285

gcc aag acc aag ccc cgg gag gag cag tac aac agc acc tac cgg gtg      912
Ala Lys Thr Lys Pro Arg Glu Glu Gln Tyr Asn Ser Thr Tyr Arg Val
    290                 295                 300

gtg agc gtg ctc acc gtg ctg cac cag gac tgg ctg aac ggc aag gag      960
Val Ser Val Leu Thr Val Leu His Gln Asp Trp Leu Asn Gly Lys Glu
305                 310                 315                 320

tac aag tgc aag gtg agc aac aag gcc ctg cct gcc ccc atc gag aag     1008
Tyr Lys Cys Lys Val Ser Asn Lys Ala Leu Pro Ala Pro Ile Glu Lys
                325                 330                 335

acc atc agc aag gcc aag ggc cag ccc cgg gag ccc cag gtg tac acc     1056
Thr Ile Ser Lys Ala Lys Gly Gln Pro Arg Glu Pro Gln Val Tyr Thr
            340                 345                 350

ctg ccc ccc agc cgg gag gag atg acc aag aac cag gtg tcc ctc acc     1104
Leu Pro Pro Ser Arg Glu Glu Met Thr Lys Asn Gln Val Ser Leu Thr
        355                 360                 365

tgt ctg gtg aag ggc ttc tac ccc agc gac atc gcc gtg gag tgg gag     1152
Cys Leu Val Lys Gly Phe Tyr Pro Ser Asp Ile Ala Val Glu Trp Glu
    370                 375                 380

agc aac ggc cag ccc gag aac aac tac aag acc acc ccc cct gtg ctg     1200
Ser Asn Gly Gln Pro Glu Asn Asn Tyr Lys Thr Thr Pro Pro Val Leu
385                 390                 395                 400

gac agc gac ggc agc ttc ttc ctg tac agc aag ctc acc gtg gac aag     1248
Asp Ser Asp Gly Ser Phe Phe Leu Tyr Ser Lys Leu Thr Val Asp Lys
                405                 410                 415

agc cgg tgg cag cag ggc aac gtg ttc agc tgc agc gtg atg cac gag     1296
Ser Arg Trp Gln Gln Gly Asn Val Phe Ser Cys Ser Val Met His Glu
            420                 425                 430

gcc ctg cac aac cac tac acc cag aag agc ctg agc ctg agc ccc ggc     1344
Ala Leu His Asn His Tyr Thr Gln Lys Ser Leu Ser Leu Ser Pro Gly
        435                 440                 445

aag                                                                 1347
Lys


<210> SEQ ID NO 66
<211> LENGTH: 449
<212> TYPE: PRT
<213> ORGANISM: Artificial sequence
<220> FEATURE:
<223> OTHER INFORMATION: Heavy chain CR4335

<400> SEQUENCE: 66

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Lys Asp
            20                  25                  30

Ala Met His Trp Val Arg Gln Ala Pro Gly Lys Gly Leu Glu Trp Val
        35                  40                  45

Ala Val Ile Ser Tyr Asp Gly Ser Asp Lys His Tyr Ala Asp Ser Val
    50                  55                  60

Lys Gly Arg Val Thr Ile Ser Arg Asp Asn Ser Arg Lys Thr Leu His
65                  70                  75                  80

Leu Arg Met Asp Ser Leu Arg Ala Glu Asp Thr Ala Leu Tyr Tyr Cys
                85                  90                  95
```

```
Ala Arg Gly Tyr Asn Ser Gly His Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

```
<210> SEQ ID NO 67
<211> LENGTH: 1368
<212> TYPE: DNA
<213> ORGANISM: Artificial sequence
<220> FEATURE:
<223> OTHER INFORMATION: Heavy chain CR4383
<220> FEATURE:
<221> NAME/KEY: CDS
<222> LOCATION: (1)..(1368)
<223> OTHER INFORMATION: Heavy chain CR4383
```

<400> SEQUENCE: 67

```
cag gtg cag ctg gtg cag tct ggg gct gag gtg aag aag cct ggg gcc       48
Gln Val Gln Leu Val Gln Ser Gly Ala Glu Val Lys Lys Pro Gly Ala
1               5                   10                  15

tca gtg aag gtc tcc tgc aag act tct gga tac acc ttc acc gac tac       96
Ser Val Lys Val Ser Cys Lys Thr Ser Gly Tyr Thr Phe Thr Asp Tyr
            20                  25                  30

tat ctg cac tgg gtg cga cac gcc cct gga caa ggg ctt gag tgg atg      144
Tyr Leu His Trp Val Arg His Ala Pro Gly Gln Gly Leu Glu Trp Met
        35                  40                  45

gga tgg atc aac cct aac agt ggt gac aca aac tat gca cag aag ttt      192
Gly Trp Ile Asn Pro Asn Ser Gly Asp Thr Asn Tyr Ala Gln Lys Phe
    50                  55                  60

cag ggc agg gtc acc atg acc agg gac acg tcc atc agc aca gcc tac      240
Gln Gly Arg Val Thr Met Thr Arg Asp Thr Ser Ile Ser Thr Ala Tyr
65                  70                  75                  80

atg gac ctg agc agg ctg aga tct gac gac gcg gcc gtg tat tac tgt      288
Met Asp Leu Ser Arg Leu Arg Ser Asp Asp Ala Ala Val Tyr Tyr Cys
                85                  90                  95

gcg aga gat tgg aat acg gtg act acg tac tac tat tac tac tac ggt      336
Ala Arg Asp Trp Asn Thr Val Thr Thr Tyr Tyr Tyr Tyr Tyr Tyr Gly
            100                 105                 110

atg gac gtc tgg ggc caa ggg acc acg gtc acc gtc tcg agt gct agc      384
Met Asp Val Trp Gly Gln Gly Thr Thr Val Thr Val Ser Ser Ala Ser
        115                 120                 125

acc aag ggc ccc agc gtg ttc ccc ctg gcc ccc agc agc aag agc acc      432
Thr Lys Gly Pro Ser Val Phe Pro Leu Ala Pro Ser Ser Lys Ser Thr
    130                 135                 140

agc ggc ggc aca gcc gcc ctg ggc tgc ctg gtg aag gac tac ttc ccc      480
Ser Gly Gly Thr Ala Ala Leu Gly Cys Leu Val Lys Asp Tyr Phe Pro
145                 150                 155                 160

gag ccc gtg acc gtg agc tgg aac agc ggc gcc ttg acc agc ggc gtg      528
Glu Pro Val Thr Val Ser Trp Asn Ser Gly Ala Leu Thr Ser Gly Val
                165                 170                 175

cac acc ttc ccc gcc gtg ctg cag agc agc ggc ctg tac agc ctg agc      576
His Thr Phe Pro Ala Val Leu Gln Ser Ser Gly Leu Tyr Ser Leu Ser
            180                 185                 190

agc gtg gtg acc gtg ccc agc agc agc ctg ggc acc cag acc tac atc      624
Ser Val Val Thr Val Pro Ser Ser Ser Leu Gly Thr Gln Thr Tyr Ile
        195                 200                 205

tgc aac gtg aac cac aag ccc agc aac acc aag gtg gac aaa cgc gtg      672
Cys Asn Val Asn His Lys Pro Ser Asn Thr Lys Val Asp Lys Arg Val
    210                 215                 220

gag ccc aag agc tgc gac aag acc cac acc tgc ccc ccc tgc cct gcc      720
Glu Pro Lys Ser Cys Asp Lys Thr His Thr Cys Pro Pro Cys Pro Ala
225                 230                 235                 240

ccc gag ctg ctg ggc gga ccc tcc gtg ttc ctg ttc ccc ccc aag ccc      768
Pro Glu Leu Leu Gly Gly Pro Ser Val Phe Leu Phe Pro Pro Lys Pro
                245                 250                 255

aag gac acc ctc atg atc agc cgg acc ccc gag gtg acc tgc gtg gtg      816
Lys Asp Thr Leu Met Ile Ser Arg Thr Pro Glu Val Thr Cys Val Val
            260                 265                 270

gtg gac gtg agc cac gag gac ccc gag gtg aag ttc aac tgg tac gtg      864
Val Asp Val Ser His Glu Asp Pro Glu Val Lys Phe Asn Trp Tyr Val
        275                 280                 285

gac ggc gtg gag gtg cac aac gcc aag acc aag ccc cgg gag gag cag      912
Asp Gly Val Glu Val His Asn Ala Lys Thr Lys Pro Arg Glu Glu Gln
    290                 295                 300
```

```
tac aac agc acc tac cgg gtg gtg agc gtg ctc acc gtg ctg cac cag      960
Tyr Asn Ser Thr Tyr Arg Val Val Ser Val Leu Thr Val Leu His Gln
305                 310                 315                 320

gac tgg ctg aac ggc aag gag tac aag tgc aag gtg agc aac aag gcc     1008
Asp Trp Leu Asn Gly Lys Glu Tyr Lys Cys Lys Val Ser Asn Lys Ala
                325                 330                 335

ctg cct gcc ccc atc gag aag acc atc agc aag gcc aag ggc cag ccc     1056
Leu Pro Ala Pro Ile Glu Lys Thr Ile Ser Lys Ala Lys Gly Gln Pro
            340                 345                 350

cgg gag ccc cag gtg tac acc ctg ccc ccc agc cgg gag gag atg acc     1104
Arg Glu Pro Gln Val Tyr Thr Leu Pro Pro Ser Arg Glu Glu Met Thr
        355                 360                 365

aag aac cag gtg tcc ctc acc tgt ctg gtg aag ggc ttc tac ccc agc     1152
Lys Asn Gln Val Ser Leu Thr Cys Leu Val Lys Gly Phe Tyr Pro Ser
    370                 375                 380

gac atc gcc gtg gag tgg gag agc aac ggc cag ccc gag aac aac tac     1200
Asp Ile Ala Val Glu Trp Glu Ser Asn Gly Gln Pro Glu Asn Asn Tyr
385                 390                 395                 400

aag acc acc ccc cct gtg ctg gac agc gac ggc agc ttc ttc ctg tac     1248
Lys Thr Thr Pro Pro Val Leu Asp Ser Asp Gly Ser Phe Phe Leu Tyr
                405                 410                 415

agc aag ctc acc gtg gac aag agc cgg tgg cag cag ggc aac gtg ttc     1296
Ser Lys Leu Thr Val Asp Lys Ser Arg Trp Gln Gln Gly Asn Val Phe
            420                 425                 430

agc tgc agc gtg atg cac gag gcc ctg cac aac cac tac acc cag aag     1344
Ser Cys Ser Val Met His Glu Ala Leu His Asn His Tyr Thr Gln Lys
        435                 440                 445

agc ctg agc ctg agc ccc ggc aag                                     1368
Ser Leu Ser Leu Ser Pro Gly Lys
    450                 455


<210> SEQ ID NO 68
<211> LENGTH: 456
<212> TYPE: PRT
<213> ORGANISM: Artificial sequence
<220> FEATURE:
<223> OTHER INFORMATION: Heavy chain CR4383

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Asp Tyr
            20                  25                  30

Tyr Leu His Trp Val Arg His Ala Pro Gly Gln Gly Leu Glu Trp Met
        35                  40                  45

Gly Trp Ile Asn Pro Asn Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ser Arg Leu Arg Ser Asp Asp Ala Ala Val Tyr Tyr Cys
                85                  90                  95

Ala Arg Asp Trp Asn Thr Val Thr Thr Tyr Tyr Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160
```

```
Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455


<210> SEQ ID NO 69
<211> LENGTH: 669
<212> TYPE: DNA
<213> ORGANISM: Artificial sequence
<220> FEATURE:
<223> OTHER INFORMATION: Light chain CR4261
<220> FEATURE:
<221> NAME/KEY: CDS
<222> LOCATION: (1)..(669)
<223> OTHER INFORMATION: Light chain CR4261

<400> SEQUENCE: 69

tcg acg cag gct gtg ctg act cag ccg tcc tca gcg tct ggg acc ccc       48
Ser Thr Gln Ala Val Leu Thr Gln Pro Ser Ser Ala Ser Gly Thr Pro
1               5                   10                  15

ggg cag agg gtc acc atc tct tgt tct gga agc agc ccc aac atc gga       96
Gly Gln Arg Val Thr Ile Ser Cys Ser Gly Ser Ser Pro Asn Ile Gly
            20                  25                  30
```

```
agt aat aat gta aac tgg tac cag cag ctc cca gga acg gcc ccc aaa      144
Ser Asn Asn Val Asn Trp Tyr Gln Gln Leu Pro Gly Thr Ala Pro Lys
        35                  40                  45

ctc ctc att tat agt aat aat cag cgg ccc tca ggg gtc cct ggc cga      192
Leu Leu Ile Tyr Ser Asn Asn Gln Arg Pro Ser Gly Val Pro Gly Arg
    50                  55                  60

ttc tct ggc tcc aag tct ggc acc tca gcc tcc ctg gcc atc agt ggg      240
Phe Ser Gly Ser Lys Ser Gly Thr Ser Ala Ser Leu Ala Ile Ser Gly
65                  70                  75                  80

ctc cag tct gag gat gag gct gat tat tac tgt gca gca tgg gat gac      288
Leu Gln Ser Glu Asp Glu Ala Asp Tyr Tyr Cys Ala Ala Trp Asp Asp
                85                  90                  95

ggc cta agt ggt aat tat gtc ttc gga gct ggg acc cag ctc acc gtt      336
Gly Leu Ser Gly Asn Tyr Val Phe Gly Ala Gly Thr Gln Leu Thr Val
            100                 105                 110

tta agt gcg gcc gca ggc cag ccc aag gcc gct ccc agc gtg acc ctg      384
Leu Ser Ala Ala Ala Gly Gln Pro Lys Ala Ala Pro Ser Val Thr Leu
        115                 120                 125

ttc ccc ccc tcc tcc gag gag ctg cag gcc aac aag gcc acc ctg gtg      432
Phe Pro Pro Ser Ser Glu Glu Leu Gln Ala Asn Lys Ala Thr Leu Val
    130                 135                 140

tgc ctc atc agc gac ttc tac cct ggc gcc gtg acc gtg gcc tgg aag      480
Cys Leu Ile Ser Asp Phe Tyr Pro Gly Ala Val Thr Val Ala Trp Lys
145                 150                 155                 160

gcc gac agc agc ccc gtg aag gcc ggc gtg gag acc acc acc ccc agc      528
Ala Asp Ser Ser Pro Val Lys Ala Gly Val Glu Thr Thr Thr Pro Ser
                165                 170                 175

aag cag agc aac aac aag tac gcc gcc agc agc tac ctg agc ctc acc      576
Lys Gln Ser Asn Asn Lys Tyr Ala Ala Ser Ser Tyr Leu Ser Leu Thr
            180                 185                 190

ccc gag cag tgg aag agc cac cgg agc tac agc tgc cag gtg acc cac      624
Pro Glu Gln Trp Lys Ser His Arg Ser Tyr Ser Cys Gln Val Thr His
        195                 200                 205

gag ggc agc acc gtg gag aag acc gtg gcc ccc acc gag tgc agc          669
Glu Gly Ser Thr Val Glu Lys Thr Val Ala Pro Thr Glu Cys Ser
    210                 215                 220


<210> SEQ ID NO 70
<211> LENGTH: 223
<212> TYPE: PRT
<213> ORGANISM: Artificial sequence
<220> FEATURE:
<223> OTHER INFORMATION: Light chain CR4261

<400> SEQUENCE: 70

Ser Thr Gln Ala Val Leu Thr Gln Pro Ser Ser Ala Ser Gly Thr Pro
1               5                   10                  15

Gly Gln Arg Val Thr Ile Ser Cys Ser Gly Ser Ser Pro Asn Ile Gly
            20                  25                  30

Ser Asn Asn Val Asn Trp Tyr Gln Gln Leu Pro Gly Thr Ala Pro Lys
        35                  40                  45

Leu Leu Ile Tyr Ser Asn Asn Gln Arg Pro Ser Gly Val Pro Gly Arg
    50                  55                  60

Phe Ser Gly Ser Lys Ser Gly Thr Ser Ala Ser Leu Ala Ile Ser Gly
65                  70                  75                  80

Leu Gln Ser Glu Asp Glu Ala Asp Tyr Tyr Cys Ala Ala Trp Asp Asp
                85                  90                  95

Gly Leu Ser Gly Asn Tyr Val Phe Gly Ala Gly Thr Gln Leu Thr Val
            100                 105                 110
```

```
Leu Ser Ala Ala Ala Gly Gln Pro Lys Ala Ala Pro Ser Val Thr Leu
        115                 120                 125

Phe Pro Pro Ser Ser Glu Glu Leu Gln Ala Asn Lys Ala Thr Leu Val
    130                 135                 140

Cys Leu Ile Ser Asp Phe Tyr Pro Gly Ala Val Thr Val Ala Trp Lys
145                 150                 155                 160

Ala Asp Ser Ser Pro Val Lys Ala Gly Val Glu Thr Thr Thr Pro Ser
                165                 170                 175

Lys Gln Ser Asn Asn Lys Tyr Ala Ala Ser Ser Tyr Leu Ser Leu Thr
            180                 185                 190

Pro Glu Gln Trp Lys Ser His Arg Ser Tyr Ser Cys Gln Val Thr His
        195                 200                 205

Glu Gly Ser Thr Val Glu Lys Thr Val Ala Pro Thr Glu Cys Ser
    210                 215                 220


<210> SEQ ID NO 71
<211> LENGTH: 648
<212> TYPE: DNA
<213> ORGANISM: Artificial sequence
<220> FEATURE:
<223> OTHER INFORMATION: Light chain CR4267
<220> FEATURE:
<221> NAME/KEY: CDS
<222> LOCATION: (1)..(648)
<223> OTHER INFORMATION: Light chain CR4267

<400> SEQUENCE: 71

cag tcc gtg ctg acc cag cct ccc tca gcg tct ggg acc ccc ggg cag       48
Gln Ser Val Leu Thr Gln Pro Pro Ser Ala Ser Gly Thr Pro Gly Gln
1               5                   10                  15

agg gtc acc atc tct tgt tct gga agc agc tcc aac atc gga agt aat       96
Arg Val Thr Ile Ser Cys Ser Gly Ser Ser Ser Asn Ile Gly Ser Asn
            20                  25                  30

act gta aac tgg tac cag cag ctc cca gga acg gcc ccc aaa ctc ctc      144
Thr Val Asn Trp Tyr Gln Gln Leu Pro Gly Thr Ala Pro Lys Leu Leu
        35                  40                  45

atc tat agt aat aat cag cgg ccc tca ggg gtc cct gac cga ttc tct      192
Ile Tyr Ser Asn Asn Gln Arg Pro Ser Gly Val Pro Asp Arg Phe Ser
    50                  55                  60

ggc tcc aag tct ggc acc tca gcc tcc ctg gcc atc agt ggg ctc cag      240
Gly Ser Lys Ser Gly Thr Ser Ala Ser Leu Ala Ile Ser Gly Leu Gln
65                  70                  75                  80

tct gag gat gag gct gat tat tat tgt gca gct tgg gat gac acc ctg      288
Ser Glu Asp Glu Ala Asp Tyr Tyr Cys Ala Ala Trp Asp Asp Thr Leu
                85                  90                  95

aat ggt tat gtc ttc gga act ggc acc aag ctt acc gtg ctg ggc cag      336
Asn Gly Tyr Val Phe Gly Thr Gly Thr Lys Leu Thr Val Leu Gly Gln
            100                 105                 110

ccc aag gcc gct ccc agc gtg acc ctg ttc ccc ccc tcc tcc gag gag      384
Pro Lys Ala Ala Pro Ser Val Thr Leu Phe Pro Pro Ser Ser Glu Glu
        115                 120                 125

ctg cag gcc aac aag gcc acc ctg gtg tgc ctc atc agc gac ttc tac      432
Leu Gln Ala Asn Lys Ala Thr Leu Val Cys Leu Ile Ser Asp Phe Tyr
    130                 135                 140

cct ggc gcc gtg acc gtg gcc tgg aag gcc gac agc agc ccc gtg aag      480
Pro Gly Ala Val Thr Val Ala Trp Lys Ala Asp Ser Ser Pro Val Lys
145                 150                 155                 160

gcc ggc gtg gag acc acc acc ccc agc aag cag agc aac aac aag tac      528
Ala Gly Val Glu Thr Thr Thr Pro Ser Lys Gln Ser Asn Asn Lys Tyr
                165                 170                 175
```

```
gcc gcc agc agc tac ctg agc ctc acc ccc gag cag tgg aag agc cac      576
Ala Ala Ser Ser Tyr Leu Ser Leu Thr Pro Glu Gln Trp Lys Ser His
            180                 185                 190

cgg agc tac agc tgc cag gtg acc cac gag ggc agc acc gtg gag aag      624
Arg Ser Tyr Ser Cys Gln Val Thr His Glu Gly Ser Thr Val Glu Lys
        195                 200                 205

acc gtg gcc ccc acc gag tgc agc                                      648
Thr Val Ala Pro Thr Glu Cys Ser
    210                 215


<210> SEQ ID NO 72
<211> LENGTH: 216
<212> TYPE: PRT
<213> ORGANISM: Artificial sequence
<220> FEATURE:
<223> OTHER INFORMATION: Light chain CR4267

<400> SEQUENCE: 72

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Thr Leu
                85                  90                  95

Asn Gly Tyr Val Phe Gly Thr Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 73
<211> LENGTH: 666
<212> TYPE: DNA
<213> ORGANISM: Artificial sequence
<220> FEATURE:
<223> OTHER INFORMATION: Light chain CR4328
<220> FEATURE:
<221> NAME/KEY: CDS
<222> LOCATION: (1)..(666)
<223> OTHER INFORMATION: Light chain CR4328

<400> SEQUENCE: 73
```

```
tcg acg cag gct gtg ctg act cag ccg tcc tca gtg tct ggg acc ccc       48
Ser Thr Gln Ala Val Leu Thr Gln Pro Ser Ser Val Ser Gly Thr Pro
1               5                   10                  15

ggg cag agg gtc acc atc tct tgt tct gga agc agc tcc aac atc gga       96
Gly Gln Arg Val Thr Ile Ser Cys Ser Gly Ser Ser Ser Asn Ile Gly
            20                  25                  30

agt aat act gta aac tgg tac cag cag ctt cca gga aca gcc ccc aaa      144
Ser Asn Thr Val Asn Trp Tyr Gln Gln Leu Pro Gly Thr Ala Pro Lys
        35                  40                  45

ctc ctc atc tat ggt aac aac aat cgg ccc tca ggg gtc cct gcc cga      192
Leu Leu Ile Tyr Gly Asn Asn Asn Arg Pro Ser Gly Val Pro Ala Arg
    50                  55                  60

ttc tct ggc tcc agg tct ggc acc tca gcc tcc ctg gcc atc agt ggg      240
Phe Ser Gly Ser Arg Ser Gly Thr Ser Ala Ser Leu Ala Ile Ser Gly
65                  70                  75                  80

ctc cgg tcc gag gat gag gct gat tat tac tgt gca gca tgg gat gac      288
Leu Arg Ser Glu Asp Glu Ala Asp Tyr Tyr Cys Ala Ala Trp Asp Asp
                85                  90                  95

agc ctg aat ggc ccg gtg ttc ggc gga ggg acc aag ctg acc gtc cta      336
Ser Leu Asn Gly Pro Val Phe Gly Gly Gly Thr Lys Leu Thr Val Leu
            100                 105                 110

ggt gcg gcc gca ggc cag ccc aag gcc gct ccc agc gtg acc ctg ttc      384
Gly Ala Ala Ala Gly Gln Pro Lys Ala Ala Pro Ser Val Thr Leu Phe
        115                 120                 125

ccc ccc tcc tcc gag gag ctg cag gcc aac aag gcc acc ctg gtg tgc      432
Pro Pro Ser Ser Glu Glu Leu Gln Ala Asn Lys Ala Thr Leu Val Cys
    130                 135                 140

ctc atc agc gac ttc tac cct ggc gcc gtg acc gtg gcc tgg aag gcc      480
Leu Ile Ser Asp Phe Tyr Pro Gly Ala Val Thr Val Ala Trp Lys Ala
145                 150                 155                 160

gac agc agc ccc gtg aag gcc ggc gtg gag acc acc acc ccc agc aag      528
Asp Ser Ser Pro Val Lys Ala Gly Val Glu Thr Thr Thr Pro Ser Lys
                165                 170                 175

cag agc aac aac aag tac gcc gcc agc agc tac ctg agc ctc acc ccc      576
Gln Ser Asn Asn Lys Tyr Ala Ala Ser Ser Tyr Leu Ser Leu Thr Pro
            180                 185                 190

gag cag tgg aag agc cac cgg agc tac agc tgc cag gtg acc cac gag      624
Glu Gln Trp Lys Ser His Arg Ser Tyr Ser Cys Gln Val Thr His Glu
        195                 200                 205

ggc agc acc gtg gag aag acc gtg gcc ccc acc gag tgc agc              666
Gly Ser Thr Val Glu Lys Thr Val Ala Pro Thr Glu Cys Ser
    210                 215                 220


<210> SEQ ID NO 74
<211> LENGTH: 222
<212> TYPE: PRT
<213> ORGANISM: Artificial sequence
<220> FEATURE:
<223> OTHER INFORMATION: Light chain CR4328

<400> SEQUENCE: 74

Ser Thr Gln Ala Val Leu Thr Gln Pro Ser Ser Val Ser Gly Thr Pro
1               5                   10                  15

Gly Gln Arg Val Thr Ile Ser Cys Ser Gly Ser Ser Ser Asn Ile Gly
            20                  25                  30

Ser Asn Thr Val Asn Trp Tyr Gln Gln Leu Pro Gly Thr Ala Pro Lys
        35                  40                  45

Leu Leu Ile Tyr Gly Asn Asn Asn Arg Pro Ser Gly Val Pro Ala Arg
    50                  55                  60

Phe Ser Gly Ser Arg Ser Gly Thr Ser Ala Ser Leu Ala Ile Ser Gly
```

```
65                  70                  75                  80

Leu Arg Ser Glu Asp Glu Ala Asp Tyr Tyr Cys Ala Ala Trp Asp Asp
                85                  90                  95

Ser Leu Asn Gly Pro Val Phe Gly Gly Gly Thr Lys Leu Thr Val Leu
            100                 105                 110

Gly Ala Ala Ala Gly Gln Pro Lys Ala Ala Pro Ser Val Thr Leu Phe
        115                 120                 125

Pro Pro Ser Ser Glu Glu Leu Gln Ala Asn Lys Ala Thr Leu Val Cys
    130                 135                 140

Leu Ile Ser Asp Phe Tyr Pro Gly Ala Val Thr Val Ala Trp Lys Ala
145                 150                 155                 160

Asp Ser Ser Pro Val Lys Ala Gly Val Glu Thr Thr Thr Pro Ser Lys
                165                 170                 175

Gln Ser Asn Asn Lys Tyr Ala Ala Ser Ser Tyr Leu Ser Leu Thr Pro
            180                 185                 190

Glu Gln Trp Lys Ser His Arg Ser Tyr Ser Cys Gln Val Thr His Glu
        195                 200                 205

Gly Ser Thr Val Glu Lys Thr Val Ala Pro Thr Glu Cys Ser
    210                 215                 220


<210> SEQ ID NO 75
<211> LENGTH: 666
<212> TYPE: DNA
<213> ORGANISM: Artificial sequence
<220> FEATURE:
<223> OTHER INFORMATION: Light chain CR4335
<220> FEATURE:
<221> NAME/KEY: CDS
<222> LOCATION: (1)..(666)
<223> OTHER INFORMATION: Light chain CR4335

<400> SEQUENCE: 75

tcg acg cag tct gtg ctg act cag cca ccc tca acg tct ggg acc ccc       48
Ser Thr Gln Ser Val Leu Thr Gln Pro Pro Ser Thr Ser Gly Thr Pro
1               5                   10                  15

ggg cag agg gtc acc atc tct tgt tct gga agc gac tcc aac atc ggc       96
Gly Gln Arg Val Thr Ile Ser Cys Ser Gly Ser Asp Ser Asn Ile Gly
            20                  25                  30

agt aat act gta aac tgg tac cag cag ctc cca gga atg gcc ccc aaa      144
Ser Asn Thr Val Asn Trp Tyr Gln Gln Leu Pro Gly Met Ala Pro Lys
        35                  40                  45

ctc ctc atc tat agg aat aat cag cgg ccc tca ggg gtc cct gac cga      192
Leu Leu Ile Tyr Arg Asn Asn Gln Arg Pro Ser Gly Val Pro Asp Arg
    50                  55                  60

ttc tct ggc tcc aag tct ggc acc tca gcc tcc ctg gcc atc agt ggt      240
Phe Ser Gly Ser Lys Ser Gly Thr Ser Ala Ser Leu Ala Ile Ser Gly
65                  70                  75                  80

ctc cag tct gaa gat gag gct gac tat ttc tgt gca tca tgg gat gcc      288
Leu Gln Ser Glu Asp Glu Ala Asp Tyr Phe Cys Ala Ser Trp Asp Ala
                85                  90                  95

aat ctg ggt ggt ccg ctg ttc ggt ggg ggg acc aag gtc acc gtc cta      336
Asn Leu Gly Gly Pro Leu Phe Gly Gly Gly Thr Lys Val Thr Val Leu
            100                 105                 110

ggt gcg gcc gca ggc cag ccc aag gcc gct ccc agc gtg acc ctg ttc      384
Gly Ala Ala Ala Gly Gln Pro Lys Ala Ala Pro Ser Val Thr Leu Phe
        115                 120                 125

ccc ccc tcc tcc gag gag ctg cag gcc aac aag gcc acc ctg gtg tgc      432
Pro Pro Ser Ser Glu Glu Leu Gln Ala Asn Lys Ala Thr Leu Val Cys
    130                 135                 140
```

```
ctc atc agc gac ttc tac cct ggc gcc gtg acc gtg gcc tgg aag gcc      480
Leu Ile Ser Asp Phe Tyr Pro Gly Ala Val Thr Val Ala Trp Lys Ala
145                 150                 155                 160

gac agc agc ccc gtg aag gcc ggc gtg gag acc acc acc ccc agc aag      528
Asp Ser Ser Pro Val Lys Ala Gly Val Glu Thr Thr Thr Pro Ser Lys
                165                 170                 175

cag agc aac aac aag tac gcc gcc agc agc tac ctg agc ctc acc ccc      576
Gln Ser Asn Asn Lys Tyr Ala Ala Ser Ser Tyr Leu Ser Leu Thr Pro
            180                 185                 190

gag cag tgg aag agc cac cgg agc tac agc tgc cag gtg acc cac gag      624
Glu Gln Trp Lys Ser His Arg Ser Tyr Ser Cys Gln Val Thr His Glu
        195                 200                 205

ggc agc acc gtg gag aag acc gtg gcc ccc acc gag tgc agc              666
Gly Ser Thr Val Glu Lys Thr Val Ala Pro Thr Glu Cys Ser
    210                 215                 220


<210> SEQ ID NO 76
<211> LENGTH: 222
<212> TYPE: PRT
<213> ORGANISM: Artificial sequence
<220> FEATURE:
<223> OTHER INFORMATION: Light chain CR4335

<400> SEQUENCE: 76

Ser Thr Gln Ser Val Leu Thr Gln Pro Pro Ser Thr Ser Gly Thr Pro
1               5                   10                  15

Gly Gln Arg Val Thr Ile Ser Cys Ser Gly Ser Asp Ser Asn Ile Gly
            20                  25                  30

Ser Asn Thr Val Asn Trp Tyr Gln Gln Leu Pro Gly Met Ala Pro Lys
        35                  40                  45

Leu Leu Ile Tyr Arg Asn Asn Gln Arg Pro Ser Gly Val Pro Asp Arg
    50                  55                  60

Phe Ser Gly Ser Lys Ser Gly Thr Ser Ala Ser Leu Ala Ile Ser Gly
65                  70                  75                  80

Leu Gln Ser Glu Asp Glu Ala Asp Tyr Phe Cys Ala Ser Trp Asp Ala
                85                  90                  95

Asn Leu Gly Gly Pro Leu Phe Gly Gly Gly Thr Lys Val Thr Val Leu
            100                 105                 110

Gly Ala Ala Ala Gly Gln Pro Lys Ala Ala Pro Ser Val Thr Leu Phe
        115                 120                 125

Pro Pro Ser Ser Glu Glu Leu Gln Ala Asn Lys Ala Thr Leu Val Cys
    130                 135                 140

Leu Ile Ser Asp Phe Tyr Pro Gly Ala Val Thr Val Ala Trp Lys Ala
145                 150                 155                 160

Asp Ser Ser Pro Val Lys Ala Gly Val Glu Thr Thr Thr Pro Ser Lys
                165                 170                 175

Gln Ser Asn Asn Lys Tyr Ala Ala Ser Ser Tyr Leu Ser Leu Thr Pro
            180                 185                 190

Glu Gln Trp Lys Ser His Arg Ser Tyr Ser Cys Gln Val Thr His Glu
        195                 200                 205

Gly Ser Thr Val Glu Lys Thr Val Ala Pro Thr Glu Cys Ser
    210                 215                 220


<210> SEQ ID NO 77
<211> LENGTH: 666
<212> TYPE: DNA
<213> ORGANISM: Artificial sequence
<220> FEATURE:
<223> OTHER INFORMATION: Light chain CR4383
```

```
<220> FEATURE:
<221> NAME/KEY: CDS
<222> LOCATION: (1)..(666)
<223> OTHER INFORMATION: Light chain CR4383

<400> SEQUENCE: 77

tcg acg cag tct gtg ctg act cag cca ccc tca gcg tct ggg acc ccc       48
Ser Thr Gln Ser Val Leu Thr Gln Pro Pro Ser Ala Ser Gly Thr Pro
1               5                   10                  15

ggg cag agg gtc acc atc tct tgt tct gga ggc atc tcc aac atc gga       96
Gly Gln Arg Val Thr Ile Ser Cys Ser Gly Gly Ile Ser Asn Ile Gly
            20                  25                  30

agt aat agt gta aat tgg ttc cag caa ctc cca gga acg gcc ccc aaa      144
Ser Asn Ser Val Asn Trp Phe Gln Gln Leu Pro Gly Thr Ala Pro Lys
        35                  40                  45

ctc ctc ctc tac agt aat aat cag cgg gcc tca ggg gtc cct gac cga      192
Leu Leu Leu Tyr Ser Asn Asn Gln Arg Ala Ser Gly Val Pro Asp Arg
    50                  55                  60

ttc tct ggc tcc aag tct ggc acc tca gcc tcc ctg gcc atc agt ggg      240
Phe Ser Gly Ser Lys Ser Gly Thr Ser Ala Ser Leu Ala Ile Ser Gly
65                  70                  75                  80

ctc cag tct gag gat gag gtt gat tat tac tgt gca gca tgg gat gac      288
Leu Gln Ser Glu Asp Glu Val Asp Tyr Tyr Cys Ala Ala Trp Asp Asp
                85                  90                  95

cgc ctg att ggt tat gtc ttc gga acg ggg acc aag gtc acc gtc cta      336
Arg Leu Ile Gly Tyr Val Phe Gly Thr Gly Thr Lys Val Thr Val Leu
            100                 105                 110

ggt gcg gcc gca ggc cag ccc aag gcc gct ccc agc gtg acc ctg ttc      384
Gly Ala Ala Ala Gly Gln Pro Lys Ala Ala Pro Ser Val Thr Leu Phe
        115                 120                 125

ccc ccc tcc tcc gag gag ctg cag gcc aac aag gcc acc ctg gtg tgc      432
Pro Pro Ser Ser Glu Glu Leu Gln Ala Asn Lys Ala Thr Leu Val Cys
    130                 135                 140

ctc atc agc gac ttc tac cct ggc gcc gtg acc gtg gcc tgg aag gcc      480
Leu Ile Ser Asp Phe Tyr Pro Gly Ala Val Thr Val Ala Trp Lys Ala
145                 150                 155                 160

gac agc agc ccc gtg aag gcc ggc gtg gag acc acc acc ccc agc aag      528
Asp Ser Ser Pro Val Lys Ala Gly Val Glu Thr Thr Thr Pro Ser Lys
                165                 170                 175

cag agc aac aac aag tac gcc gcc agc agc tac ctg agc ctc acc ccc      576
Gln Ser Asn Asn Lys Tyr Ala Ala Ser Ser Tyr Leu Ser Leu Thr Pro
            180                 185                 190

gag cag tgg aag agc cac cgg agc tac agc tgc cag gtg acc cac gag      624
Glu Gln Trp Lys Ser His Arg Ser Tyr Ser Cys Gln Val Thr His Glu
        195                 200                 205

ggc agc acc gtg gag aag acc gtg gcc ccc acc gag tgc agc              666
Gly Ser Thr Val Glu Lys Thr Val Ala Pro Thr Glu Cys Ser
    210                 215                 220


<210> SEQ ID NO 78
<211> LENGTH: 222
<212> TYPE: PRT
<213> ORGANISM: Artificial sequence
<220> FEATURE:
<223> OTHER INFORMATION: Light chain CR4383

<400> SEQUENCE: 78

Ser Thr Gln Ser Val Leu Thr Gln Pro Pro Ser Ala Ser Gly Thr Pro
1               5                   10                  15

Gly Gln Arg Val Thr Ile Ser Cys Ser Gly Gly Ile Ser Asn Ile Gly
            20                  25                  30
```

```
Ser Asn Ser Val Asn Trp Phe Gln Gln Leu Pro Gly Thr Ala Pro Lys
        35                  40                  45

Leu Leu Leu Tyr Ser Asn Asn Gln Arg Ala Ser Gly Val Pro Asp Arg
    50                  55                  60

Phe Ser Gly Ser Lys Ser Gly Thr Ser Ala Ser Leu Ala Ile Ser Gly
65                  70                  75                  80

Leu Gln Ser Glu Asp Glu Val Asp Tyr Tyr Cys Ala Ala Trp Asp Asp
                85                  90                  95

Arg Leu Ile Gly Tyr Val Phe Gly Thr Gly Thr Lys Val Thr Val Leu
            100                 105                 110

Gly Ala Ala Ala Gly Gln Pro Lys Ala Ala Pro Ser Val Thr Leu Phe
        115                 120                 125

Pro Pro Ser Ser Glu Glu Leu Gln Ala Asn Lys Ala Thr Leu Val Cys
    130                 135                 140

Leu Ile Ser Asp Phe Tyr Pro Gly Ala Val Thr Val Ala Trp Lys Ala
145                 150                 155                 160

Asp Ser Ser Pro Val Lys Ala Gly Val Glu Thr Thr Thr Pro Ser Lys
                165                 170                 175

Gln Ser Asn Asn Lys Tyr Ala Ala Ser Ser Tyr Leu Ser Leu Thr Pro
            180                 185                 190

Glu Gln Trp Lys Ser His Arg Ser Tyr Ser Cys Gln Val Thr His Glu
        195                 200                 205

Gly Ser Thr Val Glu Lys Thr Val Ala Pro Thr Glu Cys Ser
    210                 215                 220


<210> SEQ ID NO 79
<211> LENGTH: 23
<212> TYPE: DNA
<213> ORGANISM: Artificial sequence
<220> FEATURE:
<223> OTHER INFORMATION: HuVlambda1A

<400> SEQUENCE: 79

cagtctgtgc tgactcagcc acc                                              23


<210> SEQ ID NO 80
<211> LENGTH: 23
<212> TYPE: DNA
<213> ORGANISM: Artificial sequence
<220> FEATURE:
<223> OTHER INFORMATION: HuVlambda1B

<400> SEQUENCE: 80

cagtctgtgy tgacgcagcc gcc                                              23


<210> SEQ ID NO 81
<211> LENGTH: 23
<212> TYPE: DNA
<213> ORGANISM: Artificial sequence
<220> FEATURE:
<223> OTHER INFORMATION: HuVlambda1C

<400> SEQUENCE: 81

cagtctgtcg tgacgcagcc gcc                                              23


<210> SEQ ID NO 82
<211> LENGTH: 21
<212> TYPE: DNA
<213> ORGANISM: Artificial sequence
<220> FEATURE:
<223> OTHER INFORMATION: HuVlambda2
```

<400> SEQUENCE: 82
cartctgccc tgactcagcc t 21

<210> SEQ ID NO 83
<211> LENGTH: 23
<212> TYPE: DNA
<213> ORGANISM: Artificial sequence
<220> FEATURE:
<223> OTHER INFORMATION: HuVlambda3A

<400> SEQUENCE: 83
tcctatgwgc tgactcagcc acc 23

<210> SEQ ID NO 84
<211> LENGTH: 23
<212> TYPE: DNA
<213> ORGANISM: Artificial sequence
<220> FEATURE:
<223> OTHER INFORMATION: HuVlambda3B

<400> SEQUENCE: 84
tcttctgagc tgactcagga ccc 23

<210> SEQ ID NO 85
<211> LENGTH: 23
<212> TYPE: DNA
<213> ORGANISM: Artificial sequence
<220> FEATURE:
<223> OTHER INFORMATION: HuVlambda4

<400> SEQUENCE: 85
cacgttatac tgactcaacc gcc 23

<210> SEQ ID NO 86
<211> LENGTH: 23
<212> TYPE: DNA
<213> ORGANISM: Artificial sequence
<220> FEATURE:
<223> OTHER INFORMATION: HuVlambda5

<400> SEQUENCE: 86
caggctgtgc tgactcagcc gtc 23

<210> SEQ ID NO 87
<211> LENGTH: 23
<212> TYPE: DNA
<213> ORGANISM: Artificial sequence
<220> FEATURE:
<223> OTHER INFORMATION: HuVlambda6

<400> SEQUENCE: 87
aattttatgc tgactcagcc cca 23

<210> SEQ ID NO 88
<211> LENGTH: 23
<212> TYPE: DNA
<213> ORGANISM: Artificial sequence
<220> FEATURE:
<223> OTHER INFORMATION: HuVlambda7/8

<400> SEQUENCE: 88
cagrctgtgg tgacycagga gcc 23

<210> SEQ ID NO 89

<211> LENGTH: 23
<212> TYPE: DNA
<213> ORGANISM: Artificial sequence
<220> FEATURE:
<223> OTHER INFORMATION: HuVlambda9

<400> SEQUENCE: 89
cwgcctgtgc tgactcagcc mcc 23

<210> SEQ ID NO 90
<211> LENGTH: 23
<212> TYPE: DNA
<213> ORGANISM: Artificial sequence
<220> FEATURE:
<223> OTHER INFORMATION: HuVkappa1B

<400> SEQUENCE: 90
gacatccagw tgacccagtc tcc 23

<210> SEQ ID NO 91
<211> LENGTH: 23
<212> TYPE: DNA
<213> ORGANISM: Artificial sequence
<220> FEATURE:
<223> OTHER INFORMATION: HuVkappa2

<400> SEQUENCE: 91
gatgttgtga tgactcagtc tcc 23

<210> SEQ ID NO 92
<211> LENGTH: 23
<212> TYPE: DNA
<213> ORGANISM: Artificial sequence
<220> FEATURE:
<223> OTHER INFORMATION: HuVkappa3

<400> SEQUENCE: 92
gaaattgtgw tgacrcagtc tcc 23

<210> SEQ ID NO 93
<211> LENGTH: 23
<212> TYPE: DNA
<213> ORGANISM: Artificial sequence
<220> FEATURE:
<223> OTHER INFORMATION: HuVkappa4

<400> SEQUENCE: 93
gatattgtga tgacccacac tcc 23

<210> SEQ ID NO 94
<211> LENGTH: 23
<212> TYPE: DNA
<213> ORGANISM: Artificial sequence
<220> FEATURE:
<223> OTHER INFORMATION: HuVkappa5

<400> SEQUENCE: 94
gaaacgacac tcacgcagtc tcc 23

<210> SEQ ID NO 95
<211> LENGTH: 23
<212> TYPE: DNA
<213> ORGANISM: Artificial sequence
<220> FEATURE:
<223> OTHER INFORMATION: HuVkappa6

<400> SEQUENCE: 95
gaaattgtgc tgactcagtc tcc 23

<210> SEQ ID NO 96
<211> LENGTH: 41
<212> TYPE: DNA
<213> ORGANISM: Artificial sequence
<220> FEATURE:
<223> OTHER INFORMATION: HuVkappa1B-SalI

<400> SEQUENCE: 96
tgagcacaca ggtcgacgga catccagwtg acccagtctc c 41

<210> SEQ ID NO 97
<211> LENGTH: 41
<212> TYPE: DNA
<213> ORGANISM: Artificial sequence
<220> FEATURE:
<223> OTHER INFORMATION: HuVkappa2-SalI

<400> SEQUENCE: 97
tgagcacaca ggtcgacgga tgttgtgatg actcagtctc c 41

<210> SEQ ID NO 98
<211> LENGTH: 41
<212> TYPE: DNA
<213> ORGANISM: Artificial sequence
<220> FEATURE:
<223> OTHER INFORMATION: HuVkappa3B-SalI

<400> SEQUENCE: 98
tgagcacaca ggtcgacgga aattgtgwtg acrcagtctc c 41

<210> SEQ ID NO 99
<211> LENGTH: 41
<212> TYPE: DNA
<213> ORGANISM: Artificial sequence
<220> FEATURE:
<223> OTHER INFORMATION: HuVkappa4B-SalI

<400> SEQUENCE: 99
tgagcacaca ggtcgacgga tattgtgatg acccacactc c 41

<210> SEQ ID NO 100
<211> LENGTH: 41
<212> TYPE: DNA
<213> ORGANISM: Artificial sequence
<220> FEATURE:
<223> OTHER INFORMATION: HuVkappa5-SalI

<400> SEQUENCE: 100
tgagcacaca ggtcgacgga aacgacactc acgcagtctc c 41

<210> SEQ ID NO 101
<211> LENGTH: 41
<212> TYPE: DNA
<213> ORGANISM: Artificial sequence
<220> FEATURE:
<223> OTHER INFORMATION: HuVkappa6-SalI

<400> SEQUENCE: 101
tgagcacaca ggtcgacgga aattgtgctg actcagtctc c 41

<210> SEQ ID NO 102
<211> LENGTH: 48
<212> TYPE: DNA

<213> ORGANISM: Artificial sequence
<220> FEATURE:
<223> OTHER INFORMATION: HuJkappa1-NotI

<400> SEQUENCE: 102
gagtcattct cgacttgcgg ccgcacgttt gatttccacc ttggtccc 48

<210> SEQ ID NO 103
<211> LENGTH: 48
<212> TYPE: DNA
<213> ORGANISM: Artificial sequence
<220> FEATURE:
<223> OTHER INFORMATION: HuJkappa2-NotI

<400> SEQUENCE: 103
gagtcattct cgacttgcgg ccgcacgttt gatctccagc ttggtccc 48

<210> SEQ ID NO 104
<211> LENGTH: 48
<212> TYPE: DNA
<213> ORGANISM: Artificial sequence
<220> FEATURE:
<223> OTHER INFORMATION: HuJkappa3-NotI

<400> SEQUENCE: 104
gagtcattct cgacttgcgg ccgcacgttt gatatccact ttggtccc 48

<210> SEQ ID NO 105
<211> LENGTH: 48
<212> TYPE: DNA
<213> ORGANISM: Artificial sequence
<220> FEATURE:
<223> OTHER INFORMATION: HuJkappa4-NotI

<400> SEQUENCE: 105
gagtcattct cgacttgcgg ccgcacgttt gatctccacc ttggtccc 48

<210> SEQ ID NO 106
<211> LENGTH: 48
<212> TYPE: DNA
<213> ORGANISM: Artificial sequence
<220> FEATURE:
<223> OTHER INFORMATION: HuJkappa5-NotI

<400> SEQUENCE: 106
gagtcattct cgacttgcgg ccgcacgttt aatctccagt cgtgtccc 48

<210> SEQ ID NO 107
<211> LENGTH: 41
<212> TYPE: DNA
<213> ORGANISM: Artificial sequence
<220> FEATURE:
<223> OTHER INFORMATION: HuVlambda1A-SalI

<400> SEQUENCE: 107
tgagcacaca ggtcgacgca gtctgtgctg actcagccac c 41

<210> SEQ ID NO 108
<211> LENGTH: 41
<212> TYPE: DNA
<213> ORGANISM: Artificial sequence
<220> FEATURE:
<223> OTHER INFORMATION: HuVlambda1B-SalI

<400> SEQUENCE: 108
tgagcacaca ggtcgacgca gtctgtgytg acgcagccgc c 41

<210> SEQ ID NO 109
<211> LENGTH: 41
<212> TYPE: DNA
<213> ORGANISM: Artificial sequence
<220> FEATURE:
<223> OTHER INFORMATION: HuVlambda1C-SalI

<400> SEQUENCE: 109
tgagcacaca ggtcgacgca gtctgtcgtg acgcagccgc c 41

<210> SEQ ID NO 110
<211> LENGTH: 39
<212> TYPE: DNA
<213> ORGANISM: Artificial sequence
<220> FEATURE:
<223> OTHER INFORMATION: HuVlambda2-SalI

<400> SEQUENCE: 110
tgagcacaca ggtcgacgca rtctgccctg actcagcct 39

<210> SEQ ID NO 111
<211> LENGTH: 41
<212> TYPE: DNA
<213> ORGANISM: Artificial sequence
<220> FEATURE:
<223> OTHER INFORMATION: HuVlambda3A-SalI

<400> SEQUENCE: 111
tgagcacaca ggtcgacgtc ctatgwgctg actcagccac c 41

<210> SEQ ID NO 112
<211> LENGTH: 41
<212> TYPE: DNA
<213> ORGANISM: Artificial sequence
<220> FEATURE:
<223> OTHER INFORMATION: HuVlambda3B-SalI

<400> SEQUENCE: 112
tgagcacaca ggtcgacgtc ttctgagctg actcaggacc c 41

<210> SEQ ID NO 113
<211> LENGTH: 41
<212> TYPE: DNA
<213> ORGANISM: Artificial sequence
<220> FEATURE:
<223> OTHER INFORMATION: HuVlambda4-SalI

<400> SEQUENCE: 113
tgagcacaca ggtcgacgca cgttatactg actcaaccgc c 41

<210> SEQ ID NO 114
<211> LENGTH: 41
<212> TYPE: DNA
<213> ORGANISM: Artificial sequence
<220> FEATURE:
<223> OTHER INFORMATION: HuVlambda5-SalI

<400> SEQUENCE: 114
tgagcacaca ggtcgacgca ggctgtgctg actcagccgt c 41

<210> SEQ ID NO 115
<211> LENGTH: 41
<212> TYPE: DNA
<213> ORGANISM: Artificial sequence
<220> FEATURE:

<223> OTHER INFORMATION: HuVlambda6-SalI

<400> SEQUENCE: 115
tgagcacaca ggtcgacgaa ttttatgctg actcagcccc a 41

<210> SEQ ID NO 116
<211> LENGTH: 41
<212> TYPE: DNA
<213> ORGANISM: Artificial sequence
<220> FEATURE:
<223> OTHER INFORMATION: HuVlambda7/8-SalI

<400> SEQUENCE: 116
tgagcacaca ggtcgacgca grctgtggtg acycaggagc c 41

<210> SEQ ID NO 117
<211> LENGTH: 41
<212> TYPE: DNA
<213> ORGANISM: Artificial sequence
<220> FEATURE:
<223> OTHER INFORMATION: HuVlambda9-SalI

<400> SEQUENCE: 117
tgagcacaca ggtcgacgcw gcctgtgctg actcagccmc c 41

<210> SEQ ID NO 118
<211> LENGTH: 48
<212> TYPE: DNA
<213> ORGANISM: Artificial sequence
<220> FEATURE:
<223> OTHER INFORMATION: HuJlambda1-NotI

<400> SEQUENCE: 118
gagtcattct cgacttgcgg ccgcacctag gacggtgacc ttggtccc 48

<210> SEQ ID NO 119
<211> LENGTH: 48
<212> TYPE: DNA
<213> ORGANISM: Artificial sequence
<220> FEATURE:
<223> OTHER INFORMATION: HuJlambda2/3-NotI

<400> SEQUENCE: 119
gagtcattct cgacttgcgg ccgcacctag gacggtcagc ttggtccc 48

<210> SEQ ID NO 120
<211> LENGTH: 48
<212> TYPE: DNA
<213> ORGANISM: Artificial sequence
<220> FEATURE:
<223> OTHER INFORMATION: HuJlambda4/5-NotI

<400> SEQUENCE: 120
gagtcattct cgacttgcgg ccgcacytaa aacggtgagc tgggtccc 48

<210> SEQ ID NO 121
<211> LENGTH: 23
<212> TYPE: DNA
<213> ORGANISM: Artificial sequence
<220> FEATURE:
<223> OTHER INFORMATION: HuVH1B/7A

<400> SEQUENCE: 121
cagrtgcagc tggtgcartc tgg 23

<210> SEQ ID NO 122
<211> LENGTH: 23
<212> TYPE: DNA
<213> ORGANISM: Artificial sequence
<220> FEATURE:
<223> OTHER INFORMATION: HuVH1C

<400> SEQUENCE: 122
saggtccagc tggtrcagtc tgg 23

<210> SEQ ID NO 123
<211> LENGTH: 23
<212> TYPE: DNA
<213> ORGANISM: Artificial sequence
<220> FEATURE:
<223> OTHER INFORMATION: HuVH2B

<400> SEQUENCE: 123
saggtgcagc tggtggagtc tgg 23

<210> SEQ ID NO 124
<211> LENGTH: 23
<212> TYPE: DNA
<213> ORGANISM: Artificial sequence
<220> FEATURE:
<223> OTHER INFORMATION: HuVH3B

<400> SEQUENCE: 124
saggtgcagc tggtggagtc tgg 23

<210> SEQ ID NO 125
<211> LENGTH: 23
<212> TYPE: DNA
<213> ORGANISM: Artificial sequence
<220> FEATURE:
<223> OTHER INFORMATION: HuVH3C

<400> SEQUENCE: 125
gaggtgcagc tggtggagwc ygg 23

<210> SEQ ID NO 126
<211> LENGTH: 23
<212> TYPE: DNA
<213> ORGANISM: Artificial sequence
<220> FEATURE:
<223> OTHER INFORMATION: HuVH4B

<400> SEQUENCE: 126
caggtgcagc tacagcagtg ggg 23

<210> SEQ ID NO 127
<211> LENGTH: 23
<212> TYPE: DNA
<213> ORGANISM: Artificial sequence
<220> FEATURE:
<223> OTHER INFORMATION: HuVH4C

<400> SEQUENCE: 127
cagstgcagc tgcaggagtc sgg 23

<210> SEQ ID NO 128
<211> LENGTH: 23
<212> TYPE: DNA
<213> ORGANISM: Artificial sequence
<220> FEATURE:
<223> OTHER INFORMATION: HuVH5B

<400> SEQUENCE: 128
gargtgcagc tggtgcagtc tgg 23

<210> SEQ ID NO 129
<211> LENGTH: 23
<212> TYPE: DNA
<213> ORGANISM: Artificial sequence
<220> FEATURE:
<223> OTHER INFORMATION: HuVH6A

<400> SEQUENCE: 129
caggtacagc tgcagcagtc agg 23

<210> SEQ ID NO 130
<211> LENGTH: 56
<212> TYPE: DNA
<213> ORGANISM: Artificial sequence
<220> FEATURE:
<223> OTHER INFORMATION: HuVH1B/7A-SfiI

<400> SEQUENCE: 130
gtcctcgcaa ctgcggccca gccggccatg gcccagrtgc agctggtgca rtctgg 56

<210> SEQ ID NO 131
<211> LENGTH: 56
<212> TYPE: DNA
<213> ORGANISM: Artificial sequence
<220> FEATURE:
<223> OTHER INFORMATION: HuVH1C-SfiI

<400> SEQUENCE: 131
gtcctcgcaa ctgcggccca gccggccatg gccsaggtcc agctggtrca gtctgg 56

<210> SEQ ID NO 132
<211> LENGTH: 56
<212> TYPE: DNA
<213> ORGANISM: Artificial sequence
<220> FEATURE:
<223> OTHER INFORMATION: HuVH2B-SfiI

<400> SEQUENCE: 132
gtcctcgcaa ctgcggccca gccggccatg gcccagrtca ccttgaagga gtctgg 56

<210> SEQ ID NO 133
<211> LENGTH: 56
<212> TYPE: DNA
<213> ORGANISM: Artificial sequence
<220> FEATURE:
<223> OTHER INFORMATION: HuVH3B-SfiI

<400> SEQUENCE: 133
gtcctcgcaa ctgcggccca gccggccatg gccsaggtgc agctggtgga gtctgg 56

<210> SEQ ID NO 134
<211> LENGTH: 56
<212> TYPE: DNA
<213> ORGANISM: Artificial sequence
<220> FEATURE:
<223> OTHER INFORMATION: HuVH3C-SfiI

<400> SEQUENCE: 134
gtcctcgcaa ctgcggccca gccggccatg gccgaggtgc agctggtgga gwcygg 56

<210> SEQ ID NO 135
<211> LENGTH: 56

<212> TYPE: DNA
<213> ORGANISM: Artificial sequence
<220> FEATURE:
<223> OTHER INFORMATION: HuVH4B-SfiI

<400> SEQUENCE: 135
gtcctcgcaa ctgcggccca gccggccatg gcccaggtgc agctacagca gtgggg 56

<210> SEQ ID NO 136
<211> LENGTH: 56
<212> TYPE: DNA
<213> ORGANISM: Artificial sequence
<220> FEATURE:
<223> OTHER INFORMATION: HuVH4C-SfiI

<400> SEQUENCE: 136
gtcctcgcaa ctgcggccca gccggccatg gcccagstgc agctgcagga gtcsgg 56

<210> SEQ ID NO 137
<211> LENGTH: 56
<212> TYPE: DNA
<213> ORGANISM: Artificial sequence
<220> FEATURE:
<223> OTHER INFORMATION: HuVH5B-SfiI

<400> SEQUENCE: 137
gtcctcgcaa ctgcggccca gccggccatg gccgargtgc agctggtgca gtctgg 56

<210> SEQ ID NO 138
<211> LENGTH: 56
<212> TYPE: DNA
<213> ORGANISM: Artificial sequence
<220> FEATURE:
<223> OTHER INFORMATION: HuVH6A-SfiI

<400> SEQUENCE: 138
gtcctcgcaa ctgcggccca gccggccatg gcccaggtac agctgcagca gtcagg 56

<210> SEQ ID NO 139
<211> LENGTH: 36
<212> TYPE: DNA
<213> ORGANISM: Artificial sequence
<220> FEATURE:
<223> OTHER INFORMATION: HuJH1/2-XhoI

<400> SEQUENCE: 139
gagtcattct cgactcgaga cggtgaccag ggtgcc 36

<210> SEQ ID NO 140
<211> LENGTH: 36
<212> TYPE: DNA
<213> ORGANISM: Artificial sequence
<220> FEATURE:
<223> OTHER INFORMATION: HuJH3-XhoI

<400> SEQUENCE: 140
gagtcattct cgactcgaga cggtgaccat tgtccc 36

<210> SEQ ID NO 141
<211> LENGTH: 36
<212> TYPE: DNA
<213> ORGANISM: Artificial sequence
<220> FEATURE:
<223> OTHER INFORMATION: HuJH4/5-XhoI

<400> SEQUENCE: 141
gagtcattct cgactcgaga cggtgaccag ggttcc 36

<210> SEQ ID NO 142
<211> LENGTH: 36
<212> TYPE: DNA
<213> ORGANISM: Artificial sequence
<220> FEATURE:
<223> OTHER INFORMATION: HuJH6-XhoI

<400> SEQUENCE: 142
gagtcattct cgactcgaga cggtgaccgt ggtccc 36

<210> SEQ ID NO 143
<211> LENGTH: 13
<212> TYPE: PRT
<213> ORGANISM: Artificial sequence
<220> FEATURE:
<223> OTHER INFORMATION: LCDR1

<400> SEQUENCE: 143

Ser Gly Ser Ser Ser Asn Ile Gly Ser Asn Thr Val Asn
1 5 10

<210> SEQ ID NO 144
<211> LENGTH: 7
<212> TYPE: PRT
<213> ORGANISM: Artificial sequence
<220> FEATURE:
<223> OTHER INFORMATION: LCDR2

<400> SEQUENCE: 144

Gly Asn Asn Asn Arg Pro Ser
1 5

<210> SEQ ID NO 145
<211> LENGTH: 11
<212> TYPE: PRT
<213> ORGANISM: Artificial sequence
<220> FEATURE:
<223> OTHER INFORMATION: LCDR3

<400> SEQUENCE: 145

Ala Ala Trp Asp Asp Ser Leu Asn Gly Pro Val
1 5 10

<210> SEQ ID NO 146
<211> LENGTH: 5855
<212> TYPE: DNA
<213> ORGANISM: Artificial sequence
<220> FEATURE:
<223> OTHER INFORMATION: Vector pCR-IgM

<400> SEQUENCE: 146
gttctttcct gcgttatccc ctgattctgt ggataaccgt attaccgcct ttgagtgagc 60
tgataccgct cgccgcagcc gaacgaccga gcgcagcgag tcagtgagcg aggaagcgga 120
agagcgccca atacgcaaac cgcctctccc cgcgcgttgg ccgattcatt aatgcagctg 180
gcacgacagg tttcccgact ggaaagcggg cagtgagcgc aacgcaatta atgtgagtta 240
gctcactcat taggcacccc aggctttaca ctttatgctt ccggctcgta tgttgtgtgg 300
aattgtgagc ggataacaat ttcacacagg aaacagctat gaccatgatt acgccaagct 360
cagaattaac cctcactaaa gggactagtc ctgcaggttt aaacgaattc gcccttcagg 420
gagtgctagc gccccaaccc ttttccccct cgtctcctgt gagaattccc cgtcggatac 480

```
gagcagcgtg gccgttggct gcctcgcaca ggacttcctt cccgactcca tcactttctc    540
ctggaaatac aagaacaact ctgacatcag cagcacccgg ggcttcccat cagtcctgag    600
agggggcaag tacgcagcca cctcacaggt gctgctgcct tccaaggacg tcatgcaggg    660
cacagacgaa cacgtggtgt gcaaagtcca gcaccccaac ggcaacaaag aaaagaacgt    720
gcctcttcca ggtgagggcc gggcccagcc accgggacag agagggagcc gaagggggcg    780
ggagtggcgg gcaccgggct gacacgtgtc cctcactgca gtgattgctg agctgcctcc    840
caaagtgagc gtcttcgtcc caccccgcga cggcttcttc ggcaaccccc gcaagtccaa    900
gctcatctgc caggccacgg gtttcagtcc ccggcagatt caggtgtcct ggctgcgcga    960
ggggaagcag gtggggtctg gcgtcaccac ggaccaggtg caggctgagg ccaaagagtc   1020
tgggcccacg acctacaagg tgaccagcac actgaccatc aaagagagcg actggctcag   1080
ccagagcatg ttcacctgcc gcgtggatca caggggcctg accttccagc agaatgcgtc   1140
ctccatgtgt gtccccggtg agtgacctgt ccccaggggc agcacccacc gacacacagg   1200
ggtccactcg ggtctggcat tcgccacccc ggatgcagcc atctactccc tgagccttgg   1260
cttcccagag cggccaaggg caggggctcg ggcggcagga cccctgggct cggcagaggc   1320
agttgctact ctttgggtgg gaaccatgcc tccgcccaca tccacacctg ccccacctct   1380
gactcccttc tcttgactcc agatcaagac acagccatcc gggtcttcgc catcccccca   1440
tcctttgcca gcatcttcct caccaagtcc accaagttga cctgcctggt cacagacctg   1500
accacctatg acagcgtgac catctcctgg acccgccaga atggcgaagc tgtgaaaacc   1560
cacaccaaca tctccgagag ccaccccaat gccactttca gcgccgtggg tgaggccagc   1620
atctgcgagg atgactggaa ttccggggag aggttcacgt gcaccgtgac ccacacagac   1680
ctgccctcgc cactgaagca gaccatctcc cggcccaagg gtaggcccca ctcttgcccc   1740
tcttcctgca ctccctggga cctcccttgg cctctggggc atggtggaaa gcacccctca   1800
ctcccccgtt gtctgggcaa ctggggaaaa ggggactcaa ccccagccca caggctggtc   1860
cccccactgc cccgccctca ccaccatctc tgttcacagg ggtggccctg cacaggcccg   1920
atgtctactt gctgccacca gcccgggagc agctgaacct gcgggagtcg gccaccatca   1980
cgtgcctggt gacgggcttc tctcccgcgg acgtcttcgt gcagtggatg cagagggggc   2040
agcccttgtc cccggagaag tatgtgacca gcgccccaat gcctgagccc caggccccag   2100
gccggtactt cgcccacagc atcctgaccg tgtccgaaga ggaatggaac acgggggaga   2160
cctacacctg cgtggtggcc catgaggccc tgcccaacag ggtcaccgag aggaccgtgg   2220
acaagtccac cggtaaaccc accctgtaca acgtgtccct ggtcatgtcc gacacagctg   2280
gcacctgcta ctgatgatct agatctagaa cacaaagggc gaattcgcgg ccgctaaatt   2340
caattcgccc tatagtgagt cgtattacaa ttcactggcc gtcgttttac aacgtcgtga   2400
ctgggaaaac cctggcgtta cccaacttaa tcgccttgca gcacatcccc ctttcgccag   2460
ctggcgtaat agcgaagagg cccgcaccga tcgcccttcc caacagttgc gcagcctata   2520
cgtacggcag tttaaggttt acacctataa aagagagagc cgttatcgtc tgtttgtgga   2580
tgtacagagt gatattattg acacgccggg gcgacggatg gtgatccccc tggccagtgc   2640
acgtctgctg tcagataaag tctcccgtga actttacccg gtggtgcata tcggggatga   2700
aagctggcgc atgatgacca ccgatatggc cagtgtgccg gtctccgtta tcggggaaga   2760
agtggctgat ctcagccacc gcgaaaatga catcaaaaac gccattaacc tgatgttctg   2820
gggaatataa atgtcaggca tgagattatc aaaaaggatc ttcacctaga tccttttcac   2880
```

```
gtagaaagcc agtccgcaga aacggtgctg accccggatg aatgtcagct actgggctat   2940
ctggacaagg gaaaacgcaa gcgcaaagag aaagcaggta gcttgcagtg ggcttacatg   3000
gcgatagcta gactgggcgg ttttatggac agcaagcgaa ccggaattgc cagctggggc   3060
gccctctggt aaggttggga agccctgcaa agtaaactgg atggctttct cgccgccaag   3120
gatctgatgg cgcaggggat caagctctga tcaagagaca ggatgaggat cgtttcgcat   3180
gattgaacaa gatggattgc acgcaggttc tccggccgct tgggtggaga ggctattcgg   3240
ctatgactgg gcacaacaga caatcggctg ctctgatgcc gccgtgttcc ggctgtcagc   3300
gcaggggcgc ccggttcttt ttgtcaagac cgacctgtcc ggtgccctga atgaactgca   3360
agacgaggca gcgcggctat cgtggctggc cacgacgggc gttccttgcg cagctgtgct   3420
cgacgttgtc actgaagcgg gaagggactg gctgctattg ggcgaagtgc cggggcagga   3480
tctcctgtca tctcaccttg ctcctgccga gaaagtatcc atcatggctg atgcaatgcg   3540
gcggctgcat acgcttgatc cggctacctg cccattcgac caccaagcga aacatcgcat   3600
cgagcgagca cgtactcgga tggaagccgg tcttgtcgat caggatgatc tggacgaaga   3660
gcatcagggg ctcgcgccag ccgaactgtt cgccaggctc aaggcgagca tgcccgacgg   3720
cgaggatctc gtcgtgaccc atggcgatgc ctgcttgccg aatatcatgg tggaaaatgg   3780
ccgcttttct ggattcatcg actgtggccg gctgggtgtg gcggaccgct atcaggacat   3840
agcgttggct acccgtgata ttgctgaaga gcttggcggc gaatgggctg accgcttcct   3900
cgtgctttac ggtatcgccg ctcccgattc gcagcgcatc gccttctatc gccttcttga   3960
cgagttcttc tgaattatta acgcttacaa tttcctgatg cggtattttc tccttacgca   4020
tctgtgcggt atttcacacc gcatacaggt ggcacttttc ggggaaatgt gcgcggaacc   4080
cctatttgtt tatttttcta aatacattca aatatgtatc cgctcatgag acaataaccc   4140
tgataaatgc ttcaataata ttgaaaaagg aagagtatga gtattcaaca tttccgtgtc   4200
gcccttattc cctttttgc ggcattttgc cttcctgttt ttgctcaccc agaaacgctg   4260
gtgaaagtaa aagatgctga agatcagttg ggtgcacgag tgggttacat cgaactggat   4320
ctcaacagcg gtaagatcct tgagagtttt cgccccgaag aacgttttcc aatgatgagc   4380
acttttaaag ttctgctatg tggcgcggta ttatcccgta ttgacgccgg gcaagagcaa   4440
ctcggtcgcc gcatacacta ttctcagaat gacttggttg agtactcacc agtcacagaa   4500
aagcatctta cggatggcat gacagtaaga gaattatgca gtgctgccat aaccatgagt   4560
gataacactg cggccaactt acttctgaca acgatcggag gaccgaagga gctaaccgct   4620
tttttgcaca acatggggga tcatgtaact cgccttgatc gttgggaacc ggagctgaat   4680
gaagccatac caaacgacga gcgtgacacc acgatgcctg tagcaatggc aacaacgttg   4740
cgcaaactat taactggcga actacttact ctagcttccc ggcaacaatt aatagactgg   4800
atggaggcgg ataaagttgc aggaccactt ctgcgctcgg cccttccggc tggctggttt   4860
attgctgata aatctggagc cggtgagcgt gggtctcgcg gtatcattgc agcactgggg   4920
ccagatggta agccctcccg tatcgtagtt atctacacga cggggagtca ggcaactatg   4980
gatgaacgaa atagacagat cgctgagata ggtgcctcac tgattaagca ttggtaactg   5040
tcagaccaag tttactcata tatactttag attgatttaa aacttcattt ttaatttaaa   5100
aggatctagg tgaagatcct ttttgataat ctcatgacca aaatccctta acgtgagttt   5160
tcgttccact gagcgtcaga ccccgtagaa aagatcaaag gatcttcttg agatcctttt   5220
```

```
tttctgcgcg taatctgctg cttgcaaaca aaaaaaccac cgctaccagc ggtggtttgt   5280
ttgccggatc aagagctacc aactcttttt ccgaaggtaa ctggcttcag cagagcgcag   5340
ataccaaata ctgtccttct agtgtagccg tagttaggcc accacttcaa gaactctgta   5400
gcaccgccta catacctcgc tctgctaatc ctgttaccag tggctgctgc cagtggcgat   5460
aagtcgtgtc ttaccgggtt ggactcaaga cgatagttac cggataaggc gcagcggtcg   5520
ggctgaacgg ggggttcgtg cacacagccc agcttggagc gaacgaccta caccgaactg   5580
agatacctac agcgtgagct atgagaaagc gccacgcttc ccgaagggag aaaggcggac   5640
aggtatccgg taagcggcag ggtcggaaca ggagagcgca cgagggagct tccaggggga   5700
aacgcctggt atctttatag tcctgtcggg tttcgccacc tctgacttga gcgtcgattt   5760
ttgtgatgct cgtcaggggg gcggagccta tggaaaaacg ccagcaacgc ggccttttta   5820
cggttcctgg gcttttgctg gccttttgct cacat                              5855
```

```
<210> SEQ ID NO 147
<211> LENGTH: 2235
<212> TYPE: DNA
<213> ORGANISM: Artificial sequence
<220> FEATURE:
<223> OTHER INFORMATION: pgM104-354C899
<220> FEATURE:
<221> NAME/KEY: Intron
<222> LOCATION: (681)..(764)
<223> OTHER INFORMATION: pgM104-354C899
<220> FEATURE:
<221> NAME/KEY: Intron
<222> LOCATION: (1667)..(1845)
<223> OTHER INFORMATION: pgM104-354C899
<220> FEATURE:
<221> NAME/KEY: Intron
<222> LOCATION: (1101)..(1345)
<223> OTHER INFORMATION: pgM104-354C899

<400> SEQUENCE: 147
```

```
caggtgcagc tggtgcagtc tggggctgag gtgaggaagc ctggggcctc agtgaaggtt     60
tcctgcaagg catctggata caccttcacc cactattata tgcactgggt gcgacaggcc    120
cctggacaag ggcttgagtg gatgggaata atcaacccta gtggtggtag cacaacctac    180
gcacagaagc tccagggcag agtcaccatg accagggaca cgtccacgag cacagtctac    240
atggagctga gcagcctgag atctgaggac acggccgtgt attactgtgc gagagattgg    300
ggctccaatt acgtttgggg gagttatccc aagtactggg gccagggcac cctggtgacc    360
gtctccagcg ctagcgcccc aacccttttc cccctcgtct cctgtgagaa ttccccgtcg    420
gatacgagca gcgtggccgt tggctgcctc gcacaggact tccttcccga ctccatcact    480
ttctcctgga aatacaagaa caactctgac atcagcagca cccggggctt cccatcagtc    540
ctgagagggg gcaagtacgc agccacctca caggtgctgc tgccttccaa ggacgtcatg    600
cagggcacag acgaacacgt ggtgtgcaaa gtccagcacc ccaacggcaa caaagaaaag    660
aacgtgcctc ttccaggtga gggccgggcc cagccaccgg gacagagagg gagccgaagg    720
gggcgggagt ggcgggcacc gggctgacac gtgtccctca ctgcagtgat tgctgagctg    780
cctcccaaag tgagcgtctt cgtcccaccc cgcgacggct tcttcggcaa cccccgcaag    840
tccaagctca tctgccaggc cacgggtttc agtccccggc agattcaggt gtcctggctg    900
cgcgagggga agcaggtggg gtctggcgtc accacggacc aggtgcaggc tgaggccaaa    960
gagtctgggc ccacgaccta caaggtgacc agcacactga ccatcaaaga gagcgactgg   1020
ctcagccaga gcatgttcac ctgccgcgtg gatcacaggg gcctgacctt ccagcagaat   1080
```

```
gcgtcctcca tgtgtgtccc cggtgagtga cctgtcccca ggggcagcac ccaccgacac   1140

acaggggtcc actcgggtct ggcattcgcc accccggatg cagccatcta ctccctgagc   1200

cttggcttcc cagagcggcc aagggcaggg gctcgggcgg caggacccct gggctcggca   1260

gaggcagttg ctactctttg ggtgggaacc atgcctccgc ccacatccac acctgcccca   1320

cctctgactc ccttctcttg actccagatc aagacacagc catccgggtc ttcgccatcc   1380

ccccatcctt tgccagcatc ttcctcacca agtccaccaa gttgacctgc ctggtcacag   1440

acctgaccac ctatgacagc gtgaccatct cctggacccg ccagaatggc gaagctgtga   1500

aaacccacac caacatctcc gagagccacc ccaatgccac tttcagcgcc gtgggtgagg   1560

ccagcatctg cgaggatgac tggaattccg gggagaggtt cacgtgcacc gtgacccaca   1620

cagacctgcc ctcgccactg aagcagacca tctcccggcc caagggtagg ccccactctt   1680

gcccctcttc ctgcactccc tgggacctcc cttggcctct ggggcatggt ggaaagcacc   1740

cctcactccc ccgttgtctg ggcaactggg gaaaagggga ctcaacccca gcccacaggc   1800

tggtcccccc actgccccgc cctcaccacc atctctgttc acaggggtgg ccctgcacag   1860

gcccgatgtc tacttgctgc caccagcccg ggagcagctg aacctgcggg agtcggccac   1920

catcacgtgc ctggtgacgg gcttctctcc cgcggacgtc ttcgtgcagt ggatgcagag   1980

gggcagccc ttgtccccgg agaagtatgt gaccagcgcc ccaatgcctg agccccaggc    2040

cccaggccgg tacttcgccc acagcatcct gaccgtgtcc gaagaggaat ggaacacggg   2100

ggagacctac acctgcgtgg tggcccatga ggccctgccc aacagggtca ccgagaggac   2160

cgtggacaag tccaccggta aacccaccct gtacaacgtg tccctggtca tgtccgacac   2220

agctggcacc tgcta                                                    2235
```

<210> SEQ ID NO 148
<211> LENGTH: 576
<212> TYPE: PRT
<213> ORGANISM: Artificial sequence
<220> FEATURE:
<223> OTHER INFORMATION: Heavy chain CRM4354

<400> SEQUENCE: 148

```
Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr His Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Thr Tyr Ala Gln Lys Leu
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Trp Gly Ser Asn Tyr Val Trp Gly Ser Tyr Pro Lys Tyr
            100                 105                 110

Trp Gly Gln Gly Thr Leu Val Thr Val Ser Ser Ala Ser Ala Pro Thr
        115                 120                 125

Leu Phe Pro Leu Val Ser Cys Glu Asn Ser Pro Ser Asp Thr Ser Ser
    130                 135                 140

Val Ala Val Gly Cys Leu Ala Gln Asp Phe Leu Pro Asp Ser Ile Thr
```

-continued

```
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
            180                 185                 190

Leu Leu Pro Ser Lys Asp Val Met Gln Gly Thr Asp Glu His Val Val
        195                 200                 205

Cys Lys Val Gln His Pro Asn Gly Asn Lys Glu Lys Asn Val Pro Leu
    210                 215                 220

Pro Gly Glu Val Ile Ala Glu Leu Pro Pro Lys Val Ser Val Phe Val
225                 230                 235                 240

Pro Pro Arg Asp Gly Phe Phe Gly Asn Pro Arg Lys Ser Lys Leu Ile
                245                 250                 255

Cys Gln Ala Thr Gly Phe Ser Pro Arg Gln Ile Gln Val Ser Trp Leu
            260                 265                 270

Arg Glu Gly Lys Gln Val Gly Ser Gly Val Thr Thr Asp Gln Val Gln
        275                 280                 285

Ala Glu Ala Lys Glu Ser Gly Pro Thr Thr Tyr Lys Val Thr Ser Thr
    290                 295                 300

Leu Thr Ile Lys Glu Ser Asp Trp Leu Ser Gln Ser Met Phe Thr Cys
305                 310                 315                 320

Arg Val Asp His Arg Gly Leu Thr Phe Gln Gln Asn Ala Ser Ser Met
                325                 330                 335

Cys Val Pro Asp Gln Asp Thr Ala Ile Arg Val Phe Ala Ile Pro Pro
            340                 345                 350

Ser Phe Ala Ser Ile Phe Leu Thr Lys Ser Thr Lys Leu Thr Cys Leu
        355                 360                 365

Val Thr Asp Leu Thr Thr Tyr Asp Ser Val Thr Ile Ser Trp Thr Arg
    370                 375                 380

Gln Asn Gly Glu Ala Val Lys Thr His Thr Asn Ile Ser Glu Ser His
385                 390                 395                 400

Pro Asn Ala Thr Phe Ser Ala Val Gly Glu Ala Ser Ile Cys Glu Asp
                405                 410                 415

Asp Trp Asn Ser Gly Glu Arg Phe Thr Cys Thr Val Thr His Thr Asp
            420                 425                 430

Leu Pro Ser Pro Leu Lys Gln Thr Ile Ser Arg Pro Lys Gly Val Ala
        435                 440                 445

Leu His Arg Pro Asp Val Tyr Leu Leu Pro Pro Ala Arg Glu Gln Leu
    450                 455                 460

Asn Leu Arg Glu Ser Ala Thr Ile Thr Cys Leu Val Thr Gly Phe Ser
465                 470                 475                 480

Pro Ala Asp Val Phe Val Gln Trp Met Gln Arg Gly Gln Pro Leu Ser
                485                 490                 495

Pro Glu Lys Tyr Val Thr Ser Ala Pro Met Pro Glu Pro Gln Ala Pro
            500                 505                 510

Gly Arg Tyr Phe Ala His Ser Ile Leu Thr Val Ser Glu Glu Glu Trp
        515                 520                 525

Asn Thr Gly Glu Thr Tyr Thr Cys Val Val Ala His Glu Ala Leu Pro
    530                 535                 540

Asn Arg Val Thr Glu Arg Thr Val Asp Lys Ser Thr Gly Lys Pro Thr
545                 550                 555                 560

Leu Tyr Asn Val Ser Leu Val Met Ser Asp Thr Ala Gly Thr Cys Tyr
                565                 570                 575
```

<210> SEQ ID NO 149
<211> LENGTH: 60
<212> TYPE: DNA
<213> ORGANISM: Artificial sequence
<220> FEATURE:
<223> OTHER INFORMATION: Leader peptide heavy chain
<220> FEATURE:
<221> NAME/KEY: CDS
<222> LOCATION: (1)..(60)
<223> OTHER INFORMATION: Leader peptide heavy chain

<400> SEQUENCE: 149

```
atg gga tgg agc tgt atc atc ctc ttc ttg gta ctg ctg ctg gcc cag       48
Met Gly Trp Ser Cys Ile Ile Leu Phe Leu Val Leu Leu Leu Ala Gln
1               5                   10                  15

ccg gcc atg gcc                                                       60
Pro Ala Met Ala
            20
```

<210> SEQ ID NO 150
<211> LENGTH: 20
<212> TYPE: PRT
<213> ORGANISM: Artificial sequence
<220> FEATURE:
<223> OTHER INFORMATION: Leader peptide heavy chain

<400> SEQUENCE: 150

```
Met Gly Trp Ser Cys Ile Ile Leu Phe Leu Val Leu Leu Leu Ala Gln
1               5                   10                  15

Pro Ala Met Ala
            20
```

<210> SEQ ID NO 151
<211> LENGTH: 57
<212> TYPE: DNA
<213> ORGANISM: Artificial sequence
<220> FEATURE:
<223> OTHER INFORMATION: Leader peptide kappa light chain
<220> FEATURE:
<221> NAME/KEY: CDS
<222> LOCATION: (1)..(57)
<223> OTHER INFORMATION: Leader peptide kappa light chain

<400> SEQUENCE: 151

```
atg cgg ctg ccc gcc cag ctg ctg ggc ctt ctc atg ctg tgg gtg ccc       48
Met Arg Leu Pro Ala Gln Leu Leu Gly Leu Leu Met Leu Trp Val Pro
1               5                   10                  15

gcc tcg acg                                                           57
Ala Ser Thr
```

<210> SEQ ID NO 152
<211> LENGTH: 19
<212> TYPE: PRT
<213> ORGANISM: Artificial sequence
<220> FEATURE:
<223> OTHER INFORMATION: Leader peptide kappa light chain

<400> SEQUENCE: 152

```
Met Arg Leu Pro Ala Gln Leu Leu Gly Leu Leu Met Leu Trp Val Pro
1               5                   10                  15

Ala Ser Thr
```

<210> SEQ ID NO 153
<211> LENGTH: 60
<212> TYPE: DNA

<213> ORGANISM: Artificial sequence
<220> FEATURE:
<223> OTHER INFORMATION: Leader peptide lambda light chain
<220> FEATURE:
<221> NAME/KEY: CDS
<222> LOCATION: (1)..(60)
<223> OTHER INFORMATION: Leader peptide lambda light chain

<400> SEQUENCE: 153

```
atg cgg ttc tcc gct cag ctg ctg ggc ctt ctg gtg ctg tgg att ccc      48
Met Arg Phe Ser Ala Gln Leu Leu Gly Leu Leu Val Leu Trp Ile Pro
1               5                   10                  15

ggc gtc tcg acg                                                      60
Gly Val Ser Thr
            20
```

<210> SEQ ID NO 154
<211> LENGTH: 20
<212> TYPE: PRT
<213> ORGANISM: Artificial sequence
<220> FEATURE:
<223> OTHER INFORMATION: Leader peptide lambda light chain

<400> SEQUENCE: 154

```
Met Arg Phe Ser Ala Gln Leu Leu Gly Leu Leu Val Leu Trp Ile Pro
1               5                   10                  15

Gly Val Ser Thr
            20
```

<210> SEQ ID NO 155
<211> LENGTH: 54
<212> TYPE: DNA
<213> ORGANISM: Artificial sequence
<220> FEATURE:
<223> OTHER INFORMATION: leader peptide heavy chain

<400> SEQUENCE: 155

```
atgggatgga gctgtatcat cctcttcttg gtactgctgc tggcccagcc ggcc          54
```

<210> SEQ ID NO 156
<211> LENGTH: 56
<212> TYPE: DNA
<213> ORGANISM: Artificial sequence
<220> FEATURE:
<223> OTHER INFORMATION: Leader peptide kappa light chain

<400> SEQUENCE: 156

```
atgcggctgc ccgcccagct gctgggcctt ctcatgctgt gggtgcccgc ctcgag        56
```

<210> SEQ ID NO 157
<211> LENGTH: 59
<212> TYPE: DNA
<213> ORGANISM: Artificial sequence
<220> FEATURE:
<223> OTHER INFORMATION: Leader peptide lambda light chain

<400> SEQUENCE: 157

```
atgcggttct ccgctcagct gctgggcctt ctggtgctgt ggattcccgg cgtctcgag     59
```

<210> SEQ ID NO 158
<211> LENGTH: 13
<212> TYPE: DNA
<213> ORGANISM: Artificial sequence
<220> FEATURE:
<223> OTHER INFORMATION: SfiI-site

<400> SEQUENCE: 158
ggcccagccg gcc 13

<210> SEQ ID NO 159
<211> LENGTH: 5
<212> TYPE: DNA
<213> ORGANISM: Artificial sequence
<220> FEATURE:
<223> OTHER INFORMATION: Combined XhoI/SalI-site

<400> SEQUENCE: 159 tcgac 5

<210> SEQ ID NO 160
<211> LENGTH: 24
<212> TYPE: DNA
<213> ORGANISM: Artificial sequence
<220> FEATURE:
<223> OTHER INFORMATION: Forward primer

<400> SEQUENCE: 160
atgaaggtga cagcgtgagg tgac 24

<210> SEQ ID NO 161
<211> LENGTH: 24
<212> TYPE: DNA
<213> ORGANISM: Artificial sequence
<220> FEATURE:
<223> OTHER INFORMATION: Reverse primer

<400> SEQUENCE: 161
acatggatag acgcaggaca gcag 24

<210> SEQ ID NO 162
<211> LENGTH: 68
<212> TYPE: DNA
<213> ORGANISM: Artificial sequence
<220> FEATURE:
<223> OTHER INFORMATION: Forward primer

<400> SEQUENCE: 162
aagcttagca tggaacaaaa acttatttct gaagaagatc tgctggcaac acggcggctg 60
ctcggctg 68

<210> SEQ ID NO 163
<211> LENGTH: 27
<212> TYPE: DNA
<213> ORGANISM: Artificial sequence
<220> FEATURE:
<223> OTHER INFORMATION: Reverse primer

<400> SEQUENCE: 163
gatatccttt attgtccagc attccac 27